US008815942B2

(12) United States Patent
Gros et al.

(10) Patent No.: US 8,815,942 B2
(45) Date of Patent: Aug. 26, 2014

(54) COMBINATION THERAPY AND USES THEREOF FOR TREATMENT AND PREVENTION OF PARASITIC INFECTION AND DISEASE

(75) Inventors: Philippe Gros, St-Lambert (CA); Gundula Min-Oo, San Francisco, CA (US); Anny Fortin, Montreal (CA)

(73) Assignee: The Royal Institution for the Advancement of Learning/McGill University, Montreal, Quebec (CA)

( * ) Notice: Subject to any disclaimer, the term of this patent is extended or adjusted under 35 U.S.C. 154(b) by 341 days.

(21) Appl. No.: 13/277,942

(22) Filed: Oct. 20, 2011

(65) Prior Publication Data

US 2012/0101151 A1 Apr. 26, 2012

Related U.S. Application Data

(60) Provisional application No. 61/394,958, filed on Oct. 20, 2010.

(51) Int. Cl.
*A61K 31/365* (2006.01)
*A61K 31/145* (2006.01)

(52) U.S. Cl.
USPC .......................................... 514/468; 514/665

(58) Field of Classification Search
USPC ................................................ 514/468, 665
See application file for complete search history.

(56) References Cited

U.S. PATENT DOCUMENTS

| | | | |
|---|---|---|---|
| 4,868,116 | A | 9/1989 | Morgan et al. |
| 4,980,286 | A | 12/1990 | Morgan et al. |
| 5,166,320 | A | 11/1992 | Wu et al. |
| 5,399,346 | A | 3/1995 | Anderson et al. |
| 5,554,655 | A | 9/1996 | Thoene |
| 5,714,519 | A | 2/1998 | Cincotta et al. |
| 6,340,746 | B1 | 1/2002 | Roberts et al. |
| 6,468,522 | B1 | 10/2002 | Stein et al. |
| 6,521,266 | B1 | 2/2003 | Mann |
| 2009/0082426 | A1 | 3/2009 | Commercon et al. |
| 2009/0298881 | A1 | 12/2009 | Li et al. |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 91/14689 | 10/1991 |
| WO | WO 92/07573 | 5/1992 |
| WO | WO 95/05452 | 2/1995 |
| WO | WO 99/65914 | 12/1999 |
| WO | WO/00/04024 | 1/2000 |
| WO | WO 00/04025 | 1/2000 |
| WO | WO/00/42046 | 7/2000 |
| WO | WO 03/076446 | 9/2003 |
| WO | WO 2007/009388 | 1/2007 |
| WO | WO 2007/083228 | 7/2007 |
| WO | WO 2007/089670 | 8/2007 |
| WO | WO 2007/116135 | 10/2007 |
| WO | WO 2008/046109 | 4/2008 |
| WO | WO 2008/092262 | 8/2008 |
| WO | WO 2008/127381 | 10/2008 |

OTHER PUBLICATIONS

"The Use of Artemisinin & Its Derivatives as Anti-Malarial Drugs," World Health Organization, Malaria Unit, Report of Joint CTD/DMP/TDR, Informal Consultation, Geneva, Jun. 10-12, 1998, pp. 1-33.

Dias et al., "Evaluation and intermethod comparison of the Bio-Rad high-performance liquid chromatographic method for plasma total homocysteine," *Clin Chem*, 44: 2199-2201, 1998.

Dunay et al., "Artemisone and artemiside control acute and reactivated toxoplasmosis in a murine model," *Antimicrob Agents Chemother*, 53: 4450-4456, 2009.

Eastman et al., "Artemisinin-based combination therapies: a vital tool in efforts to eliminate malaria," *Nature*, 7: 864-847, 2009.

Fidler et al., "Pharmacokinetics of cysteamine bitartrate following gastrointestinal infusion," *Br J Clin Pharmacol*, 63: 36-40, 2007.

Fortin et al. "Identification of a new malaria susceptibility locus (Char4) in recombinant congenic strains of mice," *Proc Natl Acad Sci* USA, 98: 10793-10798, 2001.

Fortin et al., "Complex genetic control of susceptibility to malaria in mice," *Genes and Immunity* 3: 177-186, 2002.

Fortin et al., "Recombinant congenic strains derived from A/J and C57BL/6J: A tool for genetic dissection of complex traits," *Genomics*, 74: 21-35, 2001.

Hunt et al., "Immunopathogenesis of cerebral malaria," International Journal for Parasitology, 36: 569-582, 2006.

Keiser et al., "Artemisinins and synthetic trioxolanes in the treatment of helminth infections,"*Curr Opin Infect Dis*, 20: 605-612, 2007.

Kleta et al., "Pharmacological treatment of nephropathic cystinosis with cysteamine," *Expert Opin. Pharmacother*. 5(11): 2255-2262, 2004.

Lebo et al., "Inactivation of Human y-Glutamylcysteine Synthetase by Cystamine," *Journal of Biol Chem*, 253(8): 2615-2623, 1978.

Li et al., "Artemisinin derivatives bearing Mannich base group: synthesis and antimalarial activity," *Bioorganic & Medicinal Chemistry*, 11(20): 4363-4368, 2003.

Li et al., "Synthesis and antimalarial activity of artemisinin derivatives containing an amino group," *J. Med. Chem*, 43(8): 1635-1640, 2000.

Lüersen et al., "Plasmodium falciparum-infected red blood cells depend on a functional glutathione de novo synthesis attributable to an enhanced loss of glutathione," *Biochem J*, 346: 545-552, 2000.

Min-Oo et al., "Complex genetic control of susceptibility to malaria: positional cloning of the Char9 locus," *The Journ of Exp. Medicine*, 204(3): 511-524, 2007.

(Continued)

*Primary Examiner* — Raymond Henley, III

(74) *Attorney, Agent, or Firm* — Klarquist Sparkman, LLP

(57) ABSTRACT

The invention relates to compounds, methods, uses, compositions, combinations, kits and packages for the prevention and/or treatment of parasite infection (e.g., *Plasmodium* parasites) and/or disease (e.g., malaria) based on uses of (a) cystamine, cysteamine, and analogs, derivatives, prodrugs, precursors thereof; an agent capable of inducing their production; and/or salts thereof, and (b) artemisinin and functional derivative, analog, conjugate, metabolite, prodrug or precursor thereof, and/or salts thereof.

41 Claims, 43 Drawing Sheets

(56) References Cited

OTHER PUBLICATIONS

Min-Oo et al., "Cysteamine, the molecule used to treat cystinosis, potentiates the antimalarial efficacy of artemisinin," *Antimicrobial Agents and Chemotherapy*, 54(8): 3262-3270, 2010.

Min-Oo et al., "Genetic analysis in mice identifies cysteamine as a novel partner for artemisinin in the treatment of malaria," *Mamm Genome*, 22: 486-494, 2011.

Patel et al., "The association of the glycophorin C exon 3 deletion with ovalocytosis and malaria susceptibility in the Wosera, Papua New Guinea," *Blood*, 98: 3489-3491, 2001.

Penet et al., "Protection against cerebral malaria by the low-molecular-weight thiol pantethine," *PNAS*, 105(4) :1321-1326, 2008.

Ploypradith, "Development of artemisinin and its structurally simplified trioxane derivatives as antimalarial drugs," *Acta Trop*, 89: 329-342, 2004.

Posner et al., "Orally active, hydrolytically stable, semisynthetic, antimalarial trioxanes in the artemisinin family," *J. Med. Chem*, 42(2): 300-304, 1999.

Sissoko et al., "Efficacy of Artesunate + Sulfamethoxypyrazine/Pyrimethamine versus Praziquantel in the Treatment of *Schistosoma haematobium* in Children," *PLos One* 4(10): e6732, 2009.

Tallarida, "Drug synergism: its detection and applications," *J Pharmacol Exp Ther*, 298: 865-872, 2001.

Mus musculus vanin 1 (Vnn1) nucleotide sequence (SEQ ID NO:1)
gi|6755978|ref|NM_011704.1
Coding Sequence = 22-1560

```
   1 ttgctgtcgt tggacttcag catgggcacg tcttggtggc tggcgtgtgc tgcagcgttt
  61 tctgccctct gtgtcttaaa agccagctcg ctggatactt tcctcgcggc tgtttacgag
 121 catgctgtga tcctgcctaa ggacaccctg ttgccagtgt ctcacggtga ggctctggca
 181 ttaatgaacc agaatctgga cctlctggaa ggagcgatcg tatctgcagc gaagcagggt
 241 gcgcacatta tcgtgactcc agaagatggc atatacggtg tgcgtttcac cagggatacg
 301 atctacacat acctggagga gatcccagac cctcaagtaa actggatacc ctgtgataac
 361 cctaaaagat ttggctctac ccaggtgcag gagagactca gctgcctggc caagaacaac
 421 tccatctatg ttgtggcgaa catgggagac aagaagccct gtaacaccag cgactctcac
 481 tgtcccactg acggcagatt ccagtacaac accgatgtgg tgtttgattc ccagggtaaa
 541 ctggttgcga gatacatcaa gcaaaacatt ttcatgggag aagatcagtt caatgtcccc
 601 atggagccta agtttgtgac tttcgacacc ccctttggaa agtttggcgt cttcacctgt
 661 ttcgatattc tcttccatga tcccgctgtc accctggtga cagaattcca ggtggacacc
 721 atactgttcc caacccgctg gatggacgtc cttcctcatt tggcagccat tgaattccac
 781 tcagcctggg ctatgggcat gggggtcaat ttcctagcag ctaatctaca taatccctcg
 841 aggagaatga caggaagtgg tatctatgca cccgattctc caagggtctt tcactacgac
 901 aggaagaccc aagaaggaaa actcctcttc gctcagctga aatcccaccc aattcactcc
 961 ccggtgaact ggacttccta tgctagcagt gtagaatcaa cccaacccaa aacccaggaa
1021 tttcagagta ttgtcttttt tgatgagttt acctttgtgg agctcaaagg gatcaaagga
1081 aattacactg tttgccagaa tgaactctgc tgtcacctaa gctaccagat gtctgagaag
1141 cgagcagatg aggtttatgc cttgggagcc tttgatgggc tgcacacagt ggaagggcag
1201 tactacctac agatctgcat cctgctaaaa tgtaaaacta ccaatttacg cacctgtggt
1261 agttcagtgg acacggcttt taccaggttc gaaatgttct cgctcagcgg cactttggga
1321 acccggtatg tcttccctga agtgttgctg agtgaggtca agctcgcacc tggggagttt
1381 caggtgtcaa gtgatgggcg cctggttagc ctgaagccaa cctcgggacc tgtgttaacc
1441 atcgggctct ttgggaggtt gtatgggaag gactgggcat ccaatgcttc ctcagacttc
1501 atagcacact cgctgataat aatgctgatt gtgacgccta ttatacatta cttgtgctga
1561 tggaattttt acatttttta ttttatttag aaaatttaaa attggtggat gcagaaaaaa
1621 taactgtttg tcaacagtgg actcgggtgt aagcaaataa agtgcctctt cttagaaaaa
1681 acatatgtac accagatacc tttcaggaaa attaataaaa ctttgagcat tggaacgaga
1741 tggagggcca agtaaaggtc gcatgtgttt tatttcagag aaataaaaat tacagttaaa
1801 aggcacttca aaccatcata agatagattt acaagaggtg taaatctatc atacatctta
1861 ctcagttatg cttagaattt ccaatgtgtc tgttcatctg ggctattaag tatttatctc
1921 aacatttcag ttctctcatg gaccagatcc tgtagtttta attcttcagt tcaagtccca
1981 gttcccacaa cctcagaacg tgactgcctt ggtgtctttg gcaatgaaga catagaggc
2041 atcattagca tggactttaa ttcaatatga ctgatctcct cagaagaaat caggacaagg
2101 acttgcatca agtgaagccc ttgtgaacac aggaaaagat ggtcatgtac aacaagaaaa
2161 ggggcctcag gagaacgcaa acctgctaac gtgtcaaact tccaggtctc cagaatcatg
2221 aggcaataaa tttctgtttt aaatgaaaaa aaaaa
```

Mus musculus vanin 3 (Vnn3) nucleotide sequence (SEQ ID NO:3)
gi|6755980|ref|NM_011979.1
Coding sequence = 113-1615

```
   1 atatattcac aggcagctgg ctggcatcac gacttgcgtc tgaatacttt ttttccccac
  61 tgagatacag tagaagaacc ttccgatttc cagagatcac tctattttaa ctatggcttc
 121 attacattct cctcaatggg cagtgagttt tgtcttcttt gcccaggctg tgggttcaat
 181 ggaccctttt attgctgctg tgtatgaaca tgctgttata ctgcccaaca aaactgaaag
 241 tcctgtttcc actgaagagg cttgctcctt gataaacaag aacatagaca ttttggagag
 301 tgcaatcaag ctggcagcca gacagggtgc acatatcatt gtgacgccag aagatggaat
 361 ctatggttgg atcttcacca gggagaccat ttaccctcac ctagaggata taccagaccc
 421 tgaagtgaac tggattccct gtagagaccc taggaggttt ggctacacac cagtacagga
 481 gagactgagc tgccttgcca aggagaactc tatctatatt atggcaaata ttggggacaa
 541 gaagccatgc aatgctactg atcctcattg tcccagggat ggcagttacc aatataatac
 601 caatgtggtc tttgattcta agggtaggct aacagccagc taccataagt acaatctttt
 661 tgaaccagag attcagtttg atttccccaa agattcagag ctggtgacct ttgaaacccc
 721 gtttgggaag tttggcatct tcacttgctt tgacattttc tcttatgacc cagctgtggt
 781 ggttgtgaag gacacccagg tcgacagtgt tcttcttacc aggcgctggt acaacaccct
 841 gcccctgctt tcagcagttc cattccattc ggtgtgggcc agagccatgg gggtcaacgt
```

FIG. 7A

```
 901 gcttgctgca aacacccaca acaccagcat gcatatgaca gggagtggaa tctacagccc
 961 ggaagctgtc cgagtgtacc actatgacat ggagacagag agtggccaac tgctgctttc
1021 agagctgagg tctggcccta gccagcacgc cacccctgca gaggttaact ggagcgctta

1081 tgccaggact gtgaagccgt tctcatcggg gcaggcagcc ttcccaggaa agatttattt
1141 tgacgaattt agcttcacca agcttacagg aagtgctggc aattacacag tttgccaaaa
1201 ggacctgtgc tgtcacctga cttacaagat gtctgaaagc cgaatggacg aggtgtatgt
1261 tctgggtgcc tttgatggac tccatacagg ggaaggccag tattacctac agatatgtac
1321 attgctgaag tgtcaaacca ccaacctcag aacttgtggg gaaccegtgg ggtcagcttt
1381 tacaaagttt gaagaattct ctctcagtgg cacctttggg acaaaatatg ttttcccaca
1441 gatcgtgcta agtggagagc aacttgcccc ggaaagatat tatgaagtct caaggagatgg
1501 aggtctgagg agtcgaggtg gagccccttt gcctatctta gtgatggcca tgtatggaag
1561 agtgtttgag agagaccctc cgcgcttagg gcagggacct gggaagctgc agtgatccct
1621 tcattgggga cccccaccgc ctgccctgac acaagggggc gggtctgcac aggattagcc
1681 tggcagagag cggggctcta agagcaagaa caaggagctg cagggttcca ttaggagata
1741 cgatgtaagc tgctgaaaag gcaaagcaag tgagaggaaa caataaagta aaaaagcaaa
1801 aaaaaaaaaa aaaaaaaa
```

Homo sapiens vanin 1 (VNN1) nucleotide sequence (SEQ ID NO:5)

gi|47593111|ref|NM_004666.1

Coding Sequence = 15-1556

```
   1 cattggactt cagcatgact actcagttgc cagcttacgt ggcaatttig ctttictatg
  61 tctcaagagc cagctgccag gacactttca ttgcagctgt ttatgagcat gcagcgatat
 121 tgcccaatgc caccctaaca ccagtgtctc gtgaggaggc tttggcatta atgaatcgga
 181 atctggacat tttggaagga gcgatcacat cagcagcaga tcagggtgcg catattattg
 241 tgactccaga agatgctatt tatggctgga acttcaacag ggactctctc taccoatatt
 301 tggaggacat cccagaccct gaagtaaact ggatccctg taataatcgt aacagatttg
 361 gccagacccc agtacaagaa agactcagct gcctggccaa gaacaactct atctatgttg
 421 tggcaaatat tggggacaag aagccatgcg atacccagtga tcctcagtgt ccccctgatg
 481 gccgttacca atacaacact gatgtggtat ttgattctca aggaaaactg gtggcacgct
 541 accataagca aaaccctttc atgggtgaaa atcaattcaa tgtacccaag gagcctgaga
 601 ttgtgacttt caataccacc tttggaagtt ttggcatttt cacatgcttt gatatactct
 661 tccatgatcc tgctgttacc ttggtgaaag atttccacgt ggacaccata gtattcccaa
 721 cagcttggat gaatgttttg ccacatttgt cagctgttga attccactca gcttgggcta
 781 tgggcatgag ggtcaatttc cttgcatcca acatacatta cccctcaaag aaaatgacag
 841 gaagtggcat ctatgcaccc aattcttcaa gagcatttca ttatgatatg aagacagaag
 901 agggaaaact cctcctctcg caactggatt cccacccatc ccattctgca gtggtgaact
 961 ggacttccta tgccagcagt atagaagcgc tctcatcagg aaacaaggaa tttaaaggca
1021 ctgtcttttt cgatgaattc actttgtga agctcacagg agttgcagga aattatacag
1081 tttgtcagaa agatctctgc tgtcatttaa gctacaaaat gtctgagaac ataccaaatg
1141 aagtgtacgc tctaggggca tttgacggac tgcacactgt ggaagggcgc tattatctac
1201 agatttgtac cctgttgaaa tgtaaaacga ctaatttaaa cacttgcggt gactcagctg
1261 aaacagcttc taccaggttt gaaatgttct ccctcagtgg cactttcgga acccagtatg
1321 tctttcctga ggtgttgctg agtgaaaatc agcttgcacc tggagaattt caggtgtcaa
1381 ctgacgggcg cttgtttagt ctgaagccaa catccggacc tgtcttaaca gtaactctgt
1441 ttgggagggt gtatgagaag gactgggcat caaatgcttc atcaggcctc acagcacaag
1501 caagaataat aatgctaata gttatagcac ctattgtatg ctcattaagt tggtagaata
1561 ttgacttttt ctcttttttca tttgggataa tttaaaaaat gatggatgag aaagaaagga
1621 ttggtccggg ttaatattat cctctagtat aagtgaatta ctagtttctc tttatttaga
1681 caaacacaca cacaccagat aatataaact taataaatta tctgttaatg tagattttat
1741 ttaaaaaact atatttgaac attggtcttt cttggacgtg agctaattat atcaaataag
1801 tatcaacaat ctttacgca gaagaaataa aacctacggg tagaaaacat aaggacctatc
1861 ataaaattta cttacaagga ggctgctctt gttaccactt ttattatatt acgtatcact
1921 tattcagctc tgctgaaaat ttccaatgac tttgattgtt tgctctttta gttttttacc
1981 taaacaatac atttgattc tcttgtgggt tgataatgtc tccccaaaat ttacatgttg
2041 aagcacctca gaatgtgact gtatttggag acagggtctt taaagaggta aaataaggtc
2101 attaggatag acccctaatc aatatgactg atgatcatca aagaagaggc gagtaggcca
2161 caacaggcac aaagggagac cataaggaga cacagaggaa ggacaactct ttacaagcta
2221 agaagagagg gcctcagaag aaacccaacc tgccaacacc ttgatcttgg acttccagcc
```

FIG. 7B

```
2281 tccaaaacta tggagaataa attttcattg tttaagtaac ccagtcaatg gtactttgtt
2341 aggcagcctt ggcaaatgaa tcaaagaccc attcctgttc ctctcccaac cactactgtt
2401 ttctactgta atctgaagct tcaacaaaag gcttacctgg taagaatatt cagctggtct
2461 gggtcctcaa gactccaata gacacttcta aagaaggatt gctgatggat tgatagtgaa
2521 accattagat cattgaattc ctctggaatt agaaaaccag agagtcccat tttaagaaat
2581 tagatattta atatagcatt gtgtgttcta ttttagtaac agcagaatct cttgaaatta
2641 cacaactcag tgaaacaaca tcatttaagc caaaatatct cccaactgac tgatagactc
2701 tgagcactaa tatcatagtg ctgtgatgat ggacaattac atagtactga taacagccat
2761 gcactgtgca aagcatgccc ttctgaacag gagagaaagg caccttgcag agtgatctac
2821 gccagcaaaa catcatttcg agccaaacat ttttgtggca gatgttttcc ctaaaaagta
2881 ctatatcatc caagaaatat ttgagtaaaa tcctttgttc ttttgggtga cattaactga
2941 catttgcttt ttttcaagac ctaatagaaa ataagaaagc ccataatgta tttagaaaca
3001 ggaatcctca gagcaattct ctgtacctcc atataatttc aatgtaaaac agaaaacata
3061 ttgatgtgtt ggtgataggc ttgaattatt aaaaacttca aaaacaaaa
```

Homo sapiens vanin 2 (VNN2), transcript variant 1, nucleotide sequence (SEQ ID NO:7)

gi|17865813|ref|NM_004665.2

Coding Sequence = 12-1574

```
   1 aaaccttggc catggtcacc tcctcttttc caatctctgt ggcagttttc gccctaataa
  61 ccctgcaggt tggtactcag gacagtttta tagctgcagt gtatgaacat gctgtcattt
 121 tgccaaataa aacagaaaca ccagtttctc aggaggatgc cttgaatctc atgaacgaga
 181 atatagacat tctggagaca gcgatcaagc aggcagctga gcagggtgct cgaatcattg
 241 tgactccaga agatgcactt tatggatgga atttcaccag ggaaactgtt ttccctatcc
 301 tggaggatat cccagacccc caggtgaact ggattccctg tcaagacccc cacagatttg
 361 gtcacacacc agtacaagca agcctcagct gcctggccaa ggacaacatt atctatgcct
 421 tggcaaattc gggggacaaa aagccatgta attccgtgaa ctccacatgt cctctaaatg
 481 gctaccttca atacaatacc aatgtggtgt ataatacaga aggaaaactc gtggcacggt
 541 accataagta ccaactgtac tctgagcctc agtttaatgt ccctgaaaag ccggagttgg
 601 tgactttcaa caccgcattc ggaaggtttg gcatttttac gtgctttgac atattcttct
 661 atgatcctgg tgttaccctg gtgaaagatt tccatgtgga caccatactg tttcccacag
 721 cttggatgaa cgttttgccc cttttgacag ctattgaatt ccattcagct tgggcaatgg
 781 gaatgggagt taatcttctt gtggccaaca cacatcatgt cagcctaaat atgacaggaa
 841 gtggtattta tgcaccaaat ggtcccaaag tgtatcatta tgacatgaag acagagttgg
 901 gaaaacttct cctttcagag gtggattcac atccccatcc cccgcttgcc tacccaacag
 961 ctgttaattg gaatgcctac gcacacaaca tcaaaccatt tccagtacag aaaaacactt
1021 tcaggggatt tattttcagg gatgggttca actttacaga actttttgaa aatgcaggaa
1081 accttacagt ctgtcaaaag gagcttgtct gtcattaaag ctacagaatg ttacaaaaag
1141 aagagaatga agtatacgtt ctaggagctt ttacaggatt acatggccga aggagaagag
1201 agtactggca ggtcctgacc atgctgaagt gcaaaactac taatttgaca actgtggac
1261 ggccagtaga aacgcttcct acaagatttg aaatgttctc catcagtggc acatttggaa
1321 cagagtatgt ttttcctgaa gtgctactta accgaaattca tatgtcacct ggaaaatttg
1381 aggtgctgaa agatgggcgt ttggtaaaca agaatggatc atctggacct atactaaaag
1441 tgtcaacctt tgggaggtgg tacacaaagg actcacttta cagctcatgt gggaccagca
1501 attcagcaat aacttaactg ctaatattca tattatcaat gatcatagct ttgcaaaata
1561 atgtaatgtt atagggcgtc tctttatcac ccagccttcg catcatacgc ttggctgaat
1621 gtgtttatcg gctttccaag tttactaaga aacttggaag ggctatttca gtagtataga
1681 ccagtgagtc ctaaatattt tttctcatca ataatttatt tttaagtatt atgataatgt
1741 tgtcccattt tttggctacc ctgaaatgtt gcagtgtgga acaatggaaa gagcctgggt
1801 gtttgggtca gataaatgaa gatcaaacct cagctccagc ctcatttgct tgagactttg
1861 tgtgtatggg ggacttgtat gtatgggacc gaggagtttc aggccattcg caaacatagc
1921 tgtgcccttg aagagaatag taatgatggg aatttagagg tttatgactg aattcccttt
1981 gacattaaag actatttgaa ttcaaaaaaa aaaaaaaaaa aaaaaaaaaa aaaa
```

Homo sapiens vanin 2 (VNN2), transcript variant 2, nucleotide sequence (SEQ ID NO:9)

gi|17865815|ref|NM_078488.1

Coding Sequence = 113-1516

```
   1 gactggagga gcaaaggcct tggaaaggaa agcagctgag attcagagga gtggaaggct
```

FIG. 7C

```
  61 cccccttgac taaagctaaa caccagtttc tcaggaggat gccttgaatc tcatgaacga
 121 gaatatagac atttctggaga cagcgatcaa gcagcgcagct gagcaggggtg ctcgaatcac
 181 tgtgactcca gaagatgcac tttatggatg gaatttttacc agggaaactg tttcccttta
 241 tctgggggat atcccagacc ctccaggtgaa ctggattccg tgtcaagacc cccacagacc
 301 tggtcacaca ccagtacaag caagactcag ctgcctggcc aaggacaact ctatctatgt
 361 cttggcaaat ttggggggaca aaaagccctg taatttcctgt gactccacat gtcctcctaa
 421 tggcctcttc caataccaata ccaatgtggt gtatatatacta gaaggaaaac ccgtggcacg
 481 ttacccataag taccaccctgt actctgagcc tcagtttaat gtcccggaaa agccggagtt
 541 ggtgactttc aaacccgcat ttggaaggtt tggcattttc acgtgctttg atatattctt
 601 ctatgatccc ggtgttaccc tggtgaaaga tttccatgtg gacaccatac tgttcccca
 661 agcttggatg aacgttttgc ccctttgac agcatttgaa ttccatttcag cttgggcaat
 721 gggaatggga gttaatcttc ttgtggccaa cacacatcat gtcagcctaa atatgacagg
 781 aagtggtatt tatgcaccaa atggtcccaa agtgtatcat tatgacatga agacagagct
 841 gggaaaactt ctccttttcag aggtggattc acatcccctta tcctcgcttg accacacaac
 901 agctgttaat tggaatggcct acgccaccac catcaaacca tttccagtac agaaaaacac
 961 tttcaggggga ttttatttcca gggatgggtt caacttcaca gaacttttttg aaaatgcagg
1021 aaaccttaca gtctgtcaaa aggagctttg ctgtcattta agttacagaa tgttacaaaa
1081 agaagagaat gaagtataccg ttctaggagc ttttacaggga ttacatggcc gaaggagaag
1141 agagtactgg caggtcctgca caatgctgaa gtgcaaaact actaatttga caacttgtgg
1201 acggccagta gaaactgctt ctacaagatt tgaaatgttc tccctcagtg gcacatttgg
1261 aacagagtat gtttttcctg aagtgctact tacctgaaat catctgtcac ctggaaaatt
1321 tgaggtgctg aaagatggggc gtttggtaaa caagaatgga tcatctgggc ctatactaac
1381 agtgtcactc tttgggaggt ggtacacaaa ggactcactt tacagctcat gtgggaccag
1441 caattcagca ataactttacc tgctaatatt catattatta atgatcatag ctttgcaaaa
1501 tattgtaatg ttatagggcg tctctttatc actcagccctc tgcatcatat gccttggctga
1561 atgtgtttac cggctttccca agtttactaa gaaactttga aggctatttt cagtagtata
1621 gaccagtgag tcctaaatat ttttttctcat caataatttat ttttttaagta ttatgataat
1681 gttgatccatc tttttggtcta ctctgaaatg ttgcagtgtg gaacaatgga aagagcctgg
1741 gtgtttgggc cagataaatg aagatcaaac tccagctcca gactcacttg cttgagactt
1801 tgtgtgtatg ggggacttgt atgtatggga gtgaggagtt tcagggccat tgcaaacata
1861 gctgtgcccc tgaagagaat agtaatgatg ggaatttaga ggtttatgac tgaattcccc
1921 ttgacattaa agactatttg aattcaaaaa aaaaaaaaaa aaaaaaaaaa aaaaaa
```

Homo sapiens vanin 3 (VNN3), transcript variant 1, nucleotide sequence (SEQ ID NO:11)

gi|66932887|ref|NM_018399.3

Coding Sequence = 73-897

```
   1 atgtaaagtt tttccagtga aacaaaacgt aagaaatgta gtttgctttt caaagatcac
  61 taaattttag ttatgatcat atcacatttt ccaaaatgtg tggcagtttt tgccctcctt
 121 gctctgagtg ttggggcact ggacactttt attgctgtag tatatgagca tgcggtgata
 181 ttaccaaatg gaacagaaac acctgtttca aaagagaagg ctttgctcct gatgaacaag
 241 aacatagatg ttttggagaa agcagtaaag ctggcagcga agcaggggtgc acatatcatt
 301 gtgacccctg aagatggaat ctatggcttgg atcctcacca gggagaggat ttaccctat
 361 ctagaggata taccagaccc tggagtgaac tggatcccat gtagagaccc ctggagattc
 421 ggcaacacac cagtgcaaca aagactcagc tgcctggcca aggacaactc tatctatgtc
 481 gtggctaata ttgggggacaa gaagccatgc aatgccagtg actctcagtg tccccctgac
 541 ggccgttacc aatacaacac tgatgtggtg tttgattctc aggggaaact ggtggcacgc
 601 taccataagc aaaatctttt tgcacctgaa attcagtttg atttcccaa ggattcagaa
 661 cttgtgactt ttgacactcc ctttgggaag tttggcattt ttacctgctt tgacattttc
 721 tctcatgacc cagccgtggt ggtggtggat gagttcaaat tgacagcatt cctctaccca
 781 cagcatggta caacacggtg ccccctcctc aggcctgttcc cttccattca gcatgggcca
 841 aggccatggg agtcaatcta cttgctgcaa atacccaaac caccagcatg caatgacaag
 901 ggagtggaat ctacgcccca gaagcagtca aggtgtacca ctatgacatg gaaacagaga
 961 gtggtcagct gttgctatca gaactgaagt ctaggccccg ccgtgagccc actcacccctg
1021 cagctgctga ctggcatcgg tatgccagca gtgtcaagcc atttttcctct gaacagtcag
1081 atttctcggg gatgatttat tttgatgagt ttaccctcac caagcttaag aggaaatacag
1141 gaaattacac agctttgcag aaagatctgt gttgtcactt aacttacaag atgtctgaga
1201 agcgagacga cgagatctat gccctaggtg ctttcgatgg actgcacaca gtagaaggcc
1261 aatattactc acagatatgt gcattactga agtgtcaaac caatgaccttg gaaacgtgtg
1321 gagaacctgc ggggtcagct tttaccaagt ttgaaagactt ctccctcagt ggcacatttg
1381 gaacgcgtta tgttttccca caggtcattc taagtggggag tcagcttgcc cctgaaagac
```

FIG. 7D

```
1441 attatgagat ttaaagagat ggacgcttga ggagaagaag tggagacact ttgaatgtat
1501 tagtatggc cctgtatgga agagtgcttg agaaggaacc tcaacgttta gggcaggat
1561 ctgggaaatt ccagtgaatt cctttagcag agcccttta ggattagcct ggctaagaaa
1621 gggagaaaaa aaagagaacc gttagtgtat gtttagaaaa gatgttatas acttacagaa
1681 acaaatataa taaactgaag cagatttgaa aagcaaaaaa aaaaaaaaaa aaa
```

Homo sapiens vanin 3 (VNN3), transcript variant 2, nucleotide sequence (SEQ ID NO:13)

gi|66932886|ref|NM_078625.2

Coding Sequence = 73-516

```
   1 atgtaaagtt tttccagtga aacaaaaagt aagaactgga gtttgttttt caaagatcac
  61 taaatttcag ttatgattat atcacatttt ccaaaatgtg tggcagtttt tgccctccc
 121 gctctgagtg ttggtgcact ggacactttt attgctgcag tatatgagca tgcggtgata
 181 ttacccaaca gaacagaaac acctgtttca aaagaagaag ctttgctcct gatgaacaag
 241 aacatagatg ttttggagaa agcagttaag ctggcagcga agcagggtgc acatatcatt
 301 gtgaccccag aagatggaat ctatggttgg atttaacca gggagagcat ttacccctat
 361 ctagaggata tcccagaccc tggagtgaac tggattccat gtagagaccc ctggaggaag
 421 agtaaaaaga tgaatgagc tgtttcaaa gagctttgct atacactgca ttcagaatgc
 481 aatcaaatgg gcaaatggaa attgtatagg acttgaaaaa ggaagaccta cttcgggac
 541 aacattttac gacaaactag ccgagtgata aatcactaaa atatagtaag tttgaggaaa
 601 tgtcttttga attagatttg gcaacacacc agtgaaacaa agactcagct gcctggcaaa
 661 ggacaactct atctacgtcg tggcctaatt tggggacaag aagccatgca atgccagtga
 721 ctctcagtgt caccctgatg gcggttacca atacaaact gatgtggtgt ttgattctaa
 781 gggaaaactg ttggcacggt acataaagta caatcttttt gaacctgaaa ttcagtttga
 841 ttcccccaag gattcagaac tcgtgacttt tgacactcc cttgggaagt ttggaattcc
 901 tacttgcttt gacattttct ctcatgaccc agctgtggtg gtggtggatg agtttcaatt
 961 gacagcattc ctaccccaac agcatggtac aaacacgtgc ccctctctc ggctgttccc
1021 tcccattcag catgggccaa ggccatggga gtcaatctac ttgctgcaaa taccccaaac
1081 accagcatgc acatgacagg gagtggaatc tacggccaag aagcagtcaa ggtgtaccac
1141 tatgacatgg aaacagagag tggtcagctg ttgctatcag aactgaagtc tcggccccgc
1201 agtgagccca cctaccccgc agctgtggac tggcatggt atgccagcag tgtcaagccc
1261 ttctcctctg aacagtcaga ccttctgggg atgatctatt ttgatgagtt tacctcacc
1321 aagcttaaga gaaatacagg aaattacaca gcttgcaga aagatctgtg ttgtcactta
1381 acctacaaga tgtctgagaa gcgaacagac gagatctatg cactaggtgc ctttgatgga
1441 ctgcacacag tagaaggcca atattactta cagatatgtg cattactgaa ggtgcaaacc
1501 actgacctgg aaacgtgtgg agaacctgtg gggtcagctt ttacccagtt tgaagacttc
1561 tccctcagtg gcacattgg aacgcgtat gtttttaccac agatcattct aagtgggagt
1621 cagcttgccc ctgaaagacc tcatgagatt tcaagagatg gacgcttgag gagccgaagt
1681 ggagaccact tgaatgtatt agtatggcc ctgtatggaa gagtgcttga aaggaacccc
1741 ctacgctcag ggcaggggatc tgggaaattc cagtgaattc ctttagcagc gcccttttag
1801 gattagcctg gctaagaaag gagagaaaaa aagagaatcg ttagtgtatg tttagaaaag
1861 atgttataaa cttacagaaa caaatataat aaactgaagc agatttgaaa agcaaaaaaa
1921 aaaaaaaaaa aa
```

Homo sapiens vanin 3 (VNN3), transcript variant 3, nucleotide sequence (SEQ ID NO:15)

gi| 66932889|ref|NM_ 001024460

Coding Sequence = 73-426

```
   1 atgtaaagtt tttccagtga aacaaaaagt aagaactgga gtttgttttt caaagatcac
  61 taaatttcag ttatgattat atcacatttt ccaaaatgtg tggcagtttt tgccctcctt
 121 gctctgagtg ttggtgcact ggacactttt attgctgcag tatatgagca tgcggtgata
 181 ttacccaaca gaacagaaac acctgtttca aaagaagaag ctttgctcct gatgaacaag
 241 aacatagatg ttttggagaa agcagttaag ctggcagcga agcagggtgc acatatcatt
 301 gtgaccccag aagatggaat ctatggttgg atttaacca gggagagcat ttacccctat
 361 ctagaggata tcccagaccc tggagtgaac tggattccat gtagagaccc ctggagaaat
 421 cactaaaata tagtaagttt gaggaaatgt cttttgaatt agattggca acacaccagt
 481 gaaacaaaga ctcagctgcc tggcaaagga caactctatc tatgtcgtgg cctaatttgg
 541 ggacaagaag ccatgcaatg ccagtgactc tcagtgtcac cctgatggcc gttaccaata
 601 caaactgat gtggtgtttg attctaaggg aaaactgttg gcacggtaca ataaagtaca
 661 tcttttgaa cctgaaattc agtttgattc cccaaggat tcagaactcg tgacttttga
 721 cactcccctt gggaagtttg gaatttctac ttgctttgac attttcttc atgacccagc
 781 tgtggtggtg gtggatgagt ttcaattgac agcattcctat acccccaacagc atggtacaaac
```

FIG. 7E

```
 841 acgctgcccc tccctctggc tgttcccttc cattcagcat gggccaaggc catggggctc
 901 aatctacttg ctggaaatac ccacaacacc agcatgcaca tgacaggggg tggaatctac
 961 gccccagaag cagtcaaggt gtaccactat gacatggaaa cagagagtgg tcagctgctg
1021 ctatcagaac tgaagtcccg gcccgcccgt gagcccacct accctgcagc tgttgactgg
1081 catgcgtatg ccagcagtgt caagccattt tcctctgaac agtcagattt tctggggatg
1141 atttattttg atgagttcac cttcaccaag cttaagagaa atacaggaaa ttacacagct
1201 tgccagaaag atctgtgttg tcacttaact tacaagatgt ctgagaagcg aacagacgag
1261 atctatgcca taggtgcttt tgatgggctg cacacagtag aaggccaata ttacttacag
1321 atatgtgcat tactgaagtg tcaaaccact gacctggaaa cgtgtggaga accgtggggg
1381 ccagctttta ccaagttcga agacttctcc ctcagtggca cattggaaac gcgtttatgc
1441 ttcccacaga tcattctaag tgggagtcag cttgccccctg aaagacatta tgagattctc
1501 agagatggac gcttgaggag ccgaagtgga gccccttgc ctgtcctagc taiggcctcg
1561 tatgggaagg tgtttgagaa ggaccctcca cgtttaggc aggaatctgg gaaattccag
1621 tgatctcctt tagcagagcc ctttcaggat tagctggct aagaaaggaa gaaaaaaag
1681 agatccgtta gtgcctgctt agaaaagatg ttataaactt acagaaacaa atataataaa
1741 ctgaagcaga tttgaaaagc aaaaaaaaaa aaaaaaaaa
```

Homo sapiens vanin 1 (VNN1) gene, complete cds (SEQ ID NO:17)

gi|68248545|gb|DQ100297.1

Coding Sequence = join (1959..2168, 4155..4278, 21806..22005, 22680..22971, 23411..23772, 31490..31660, 32673..32855)

```
   1 gttaccttgg caattgcaga ataaatgcat tatagttact aaagtaaaaa attagatatg
  61 cctgtttgca gattgaacta taaaaatacc attcaaagac aaatagatcc aaaaataaaa
 121 tggaaaaaca taaacactaa ttctgtaaat attatactta atgcacaact gaaacaaaat
 181 ttgccagctt actcaatatc aaaatccatg aacagttttt ctattttata taatttccct
 241 ctcctctctc tggatctcgc tccccagctc atttttttatt ttctttgcta tgatttctta
 301 taaacctctg ttgcccatgt gataagcagc ttcaaagatg gttcctaatg cttcctttga
 361 tagaataaca caaaagcgat gaggtgttgc ttcccaaatt acattacgaa gcacccgtgg
 421 cttcaatcta cagtggttcc acttgctgtc tggctcaag gggatccaga tacatatatg
 481 cgggctgccc tatggtgagg tttgcatcac taggaaccca tgtcctctggg caacaaccaa
 541 tgaggtcttg atcccctgccg ccagccacat gagggagctt ggagctcgga agtgaatccc
 601 cctgggagtca agccttgata tagccagccc tggcagcgc ctgactgcag cctcgtgaaa
 661 gagacctggg gccagaggca ccagctaaac tgcccctgga ctcctgaccc agagaaagcg
 721 ggagatgatg tatttctgct ttttgaagct gctgaatttg gggataattc gttatatagc
 781 aatagaaaat gagtaactct tttgtattcc tctttgtcct ggcttcccca tttgaggaa
 841 aataaagtaa atcaaagcgt agagctgaaa tattcacatg aaaataatac taaagcttta
 901 aaattatttg aatgtcttgt gctgacattc caaaatatat gaattccaaa aatttatatg
 961 ttgaagtcct aactgtcagt actttagaat gtaacttttt tggaaaaggg gtcatttcag
1021 atctaattag ttaagatgaa gttatactgg agtacagtgg gcactaaatc gaattggtcc
1081 tatgattgag tctcagtctt tcagtgagcc tgtacccctg ggtttatgac ctccagttgg
1141 cttttttctc ctgcccctat ttggcataaa aacaaagcag gtggatcacc tgaggtcagc
1201 aatttgagac cagcctgccc aacacgggga aacccctgtct ctactaaaaa tacaaaaat
1261 tagcctggcg tggtggcggg cgcctgtaat cccagctact tgggaggctg aggcaggaga
1321 atcacctgaa cccgagaggc ggaggttgca gtgagccaag atttcgccac tgcactccag
1381 cctgggtgac aagagtgaaa ctccatctca aacaacaaca acaataaaca aacaacaacg
1441 atgacaaaaa aagctagagc tgggattttc cctttccctg tgttaaagat tagagtgggtg
1501 tcctcacaaa aaggggaaac ctggatcacg gcacacacat ggggagaata gcatatgaag
1561 agacacaggg agaaggcagc catctatggg taaaggagag aggcctggaa cacatcttc
1621 cttcacccgc ctcaggagga acccactctg ctgacacctt catccgggac tcccaccccc
1681 cagaactgca aagcaataaa tttttaattc tttacaccac ccagcttatc gtatttgct
1741 aggcagccct agcgaactaa tgtacataga gttcttgagt caatctttcac aaattactgc
1801 aataaagggg ggtctttcgt tatgtaaaca tgctatgaaa tcatagcgtt tcctttaatta
1861 acttcctgtag ttcaaggcac taagtctggg aaacccagtg tctcttttct atacatacca
1921 ggacatgctc tgcttttcag cactcattgg acttcagcat gactactcag ttgcagctt
1981 acgtggcaat tttgctttc tatgtcccaa gagccagctg ccaggaccct ttcattgcag
2041 ctgtttatga gcatgcagcg atattgccca atgccaccct aacaccagtg tctgtgagg
2101 aggctatggc attaatgaat cggaactcgg acattttgga aggagcgatc acatcagcag
2161 cagaccaggc accatcctca ccatcctccc agtgtactgg attctatgag aaaggagggg
2221 gtcctagggg acagggccac tgtcagggtc agttacactt ttagatgata tatgtatcag
2281 agtagccaag aacctttatt ttacagttag aattctactt tcctatcaaa attagagcaa
2341 ggacttccct aaaagtaaga acaaagttaa gaaagagaca atttgctcac tatcaagaag
```

FIG. 7F

```
2401 cagcagacct ttgaggaact ggccataaat tcaacatctt tgttcccatt ttctggtaca
2461 gatggaggat ggaggataaa tgggtcaggg actaggtgct atttcagag tattagtggc
2521 cttcatgtac tcatgtgcta ttaaggcttt gcaggtttc gaataaattt ataatctgaa
2581 aacaaattta agtttcaat tccttgccag catgcattat atacttcaca cttcattcta
2641 attacaagat aaaagtatat gtaatgcatt gtgagtcctt aagtttagtg aaggtttcag
2701 tttgaagtta atcatacagt ataaattgtg gtttacacaa atattatttt aaaagctatt
2761 gatcgattag gtgtagacca ggaatacatg aagtgtgata aaagtcatgg ataaatgtgt
2821 attacatata tctataaata tatattcttt tgtgttgttg agttaaggtc tcactctgtc
2881 acccaggatg gagtatagtg gtgtgatcac gtctcactgc agccttgact tcccgggctc
2941 aggtgattct cccacctcag tctccagagt agctgggacc acagatgcat gccaccgtgc
3001 ccagctaagt tttgtatttt ttgtagagat gggatttgc catgttgccc acgctggact
3061 tgaactcctg acctcaggtg atccacctgc cttgggctcc caaagtgctg ggattacagg
3121 catgagctac cgtgactgcc ctatattctt atatatacta atatttaaaa ggttatcagg
3181 agttcctgatg ttcttttca tccttagtcc aactatttcc ttgaaggtca cagagctttt
3241 taaggtgact ctctaattgg aaggtgccca ggttagctca ggcagtactt gtaggcatgg
3301 gacaagttcaa gtaaccagtt tgtggctcct cttttctga gaagcaggaa tcatgtttgc
3361 aggggaaagc tagggcagag gaggaaataa acagaatatt taagttatta atcagtcttg
3421 acacaggcac agtcatcagc gaaagttcaa gggaggctt ggttccagga taagctaggt
3481 ttatagttaa cgactgccat aggaaacaac aatggcagga ttagaaaatt aaaatgcttg
3541 actaagccag gtgcggtggc tcatgtctgt aattccaaca ctttgggagg ctgaagcagg
3601 cggatcacct gaggttggga gttcaagacc atcctggcca atatggagaa accccatctc
3661 tactaaaaat acaaaaatta gccaggcgtg gtggcagatg cctgtgatcc tagctactta
3721 tgaggctgag gcgggagaat cgcttgaacc cgggaggtgg agattgtggt aagccgagat
3781 ctagccattg cactccagcc tgggcagcag agcgaaactc catctgaaaa aaaaaaaaaa
3841 gagagaaaaa aaaatgcttg actagaagcc caaaactcac cattatgtaa catatccatg
3901 caacaaacct gcatttgtac ccttgaatc taaaattaga aataaagaaa agaaaagaaa
3961 aagaaaaaga agtgacagtg cactgaaaaa aaaggaaatt aaaatgcttt ggaaaagaaa
4021 ataaattata aaaatataga aaacaaaata agatttaagg ggtgtggggg aagcccaaat
4081 agttgttact cagccactca gctcctcagc tcctcttgca ggccccctt tggattaagt
4141 tgcatttta acagggtgcg catattattg tgactccaga agatgctatt tatggctgga
4201 acttcaacag ggactctcc taccctattt tggaggacat cccagaccct gaagtaaact
4261 ggatccctg taataatcgt aacaggtaaa gaaacaactt gtgaaaaatt cactagtaaa
4321 catcaacttg atttacctgg gaaaacttg ttgatgatca ttgcatagat cccagatcaa
4381 ttcttaagtt tcagtatagc ttattttca tctactatgg gtatatttac tgggagagca
4441 aatatgaatt atgaagtcac agaaatcaga gctagaaagt agcttagaaa tcatcacatt
4501 cagtgtgaac atctctggtc tctgactcct caccagtgaa cagaaaaata tttccctgtg
4561 taggtctgtg atttgaaaac tatatgagta aatggcaaaa gagagtcaca tcagtttaag
4621 attaatagtt ttcctttctc attgctaaga tagctgatga ggttaatgta gtaaaagtcc
4681 ttaaagtgta agctgattgc aatctaagag gtgatatggc aggattttaa gtggtttaag
4741 tcaggtctcg gctacagaga tattaagtgt ggtgaaagca gcactattaa ttttaatgta
4801 aggaaaccaa tatcttatac acctaagaaa atcatgtcga ttcacatact tctttctgaa
4861 tacacatggc taaattatt ttaggaattc ctctttgga actattctca aaaccgcaca
4921 acgccagtta gaatggtgat cattaaaag tcaggaaaca acagatgctg gagaggatgt
4981 ggagaaaggg gaactcttt acactgttgg tgggagtata aattagttca accattgtgg
5041 aagacagtgt ggtgattcct caaggatcta gaaccagaaa taccatttga ccccacaatc
5101 ccattactgg gtatatacca aaggatcata aatcatttta ctataaagac acatgcatgc
5161 atatgtttat tgcagcactg ttcacaatag caaagacttg gaaccaaccc aaatacccat
5221 caatggtaga ctggataaag aaaatgtggc acatatatac cacagaacac tacacagctg
5281 taaaaaagga taagttcatg tcctttgcag ggacatggat aaagctggaa accatcattc
5341 tcagcaaact aaacacagaa cagaaaacaa aacactgcat gttctcgctc ataagtggga
5401 gttgaacaac gagaatacat ggacacaagg aggggaacat cacacaccgg ggcctgtcgg
5461 ggagtcgggg gctaagggag ggatggcatt aggagaaata cctaatgtag atgatgggtt
5521 ggtgggtgca gcaaaccacc atggcacgtg tatacctatg taacaagcct gcatgttctg
5581 cacatgtatc tcagaactta aagtataata ataataataa taaattaaa aatcccacag
5641 aaactggctg ggtgtggtga ctcatgcctg taattccaac actttgggag gccgaggcag
5701 gaggatcacc tgaggtcagg agtttgagac cagcctggcc aatttggcaa aaccccatct
5761 ctactaaaaa tacaaaaatt agtgggggcgt ggtggtgggc acctataatc ccagctactt
5821 ggaaggctga ggcagggaga actgcttgaa cctgggaggc agaggttgca gtgagccaag
5881 atagtgacac tgcactccag cctgggtaac agagctagac tctgtctcaa aaacaaacaa
5941 acaaacaaac ccacaaaac tacttacaga gacaccttga ttttgacaag gtggattttg
6001 ataaattcca gtgttattta tcgtaatcat ttactctatt cttatttaat tgtaccataa
6061 ttatttctta tttaatcatg tcatatgtca gtgcttcagt ttctaaaagg caagcactct
6121 attatcactt ccactatgaa ttgaattgac ttatttctga atggcctttc cctagaacct
```

FIG. 7G

```
6181 catctccaag ggcctcctga acatccccac aaggatgtcc cattcacttc atttcaagga
6241 acacggttgc ccatttatgt tttccatcaa ctaatgatgt ctgaatgtct tgccttaact
6301 ctctctgtct ctctctctct tttttttttt tttgagagag agactctgtg tcgcccaggc
6361 tggagtgcag tggcgtgatc tcagctcact gcaacctcta tcccccaggt ccaagcaatc
6421 cttgtgcctc agcctcccga agatgacaag tgtgagccac aacacccagc tagttttttg
6481 tatttttagt agagatgggt ttcaccatgt tggccaggct ggtcttgaac tcctggcctc
6541 aagtgatcca cctgcctcgg cctcccaagt gctgggatta caggtatgag tcatcacgcc
6601 cagctgcctt aatttattaa ctctgcaaat tttttttgag tacctattat gtctaaacat
6661 tgttctgggc aatgaagtga acaaaacaga ttaaaaattc ctgtcccctt gaatttcata
6721 ttctagtgtg gggaggtaat aaatgtttta aaaagataat tatctatcta tctatcatct
6781 atctatcatc tatctattat ctatctacct atctttatat aggtatcttt catctgtcta
6841 cctatctatg atatgaggtg gaagtaaatg ttatggaaaa aataaagtgg ggaaggtgaa
6901 tagggtggca agcgtggggc tgaaatttta aaaggtcgtc tgagggcatc acagtgagat
6961 ttcagcaaag acctgaaaga aatgaggcaa tagatcatgt gagtatctga aaaaagtgca
7021 ttccaggctg aaggaattct aaattccaag atcctgtggt cagagtatgt gtctaaccta
7081 tggaacagaa aaagggttag tgtggttaca gtgatgtgac agaagaggag aaaagtagga
7141 aatggaggca gaagggcagg aggagcgcaa tgttgagaat agactccagg gtataggtca
7201 ccaaagaagc agagggcagt tcaaaagctg ttgtgatcat tatggcatag agatgatggg
7261 tctgagacca agaaatggta gaagtttagg tattgagaag tggacagatt ccgaataaag
7321 tttgaaagta gcactggcag gttttgttga aagactggat gtaggatgtg agagaaaagg
7381 aggactcaat atccttccct gctctcatag aatcagatct catcttattg agtatgtttg
7441 aagtatgcac atagttgatt gctttctctt ctcatattca ccaaactttt gggacctaca
7501 tcacctctta gactgagcgt taaaggaaca ggctctcatc actttttctt ttatttaaat
7561 ttatttagca tttatatgtc atatcgttcc aggaaggatt gaagtttcta attatatcta
7621 atataattaa aaataggata ctttagttct aacaacaaac tagaacccat atgaatagag
7681 gaagcagttg ttatgaggca tcatggtaaa gagctgctca ttacaactgg atgttaagta
7741 tagttctaag agtttctgag cagctaagag aagtacaatt ttgttcagac actttgattg
7801 catcatagaa gaaagcttgc atatttcttc agagacaaac tatgtctaat aacctaactt
7861 aaagatgaat ttacttattc aactgttttt gttaattatt ttatttttaa ctttcatggg
7921 tacatagtag atgtatatat ttatagggta catgagatgt tttgatgttt gtacacaagc
7981 atgcaatggt aacaatcaca tcatgaagaa tggggtttcc atcccctcaa gcatttatcc
8041 tttgtattac aaaccattca attatgctct tttaggtatt taaaaatgta caattaagtt
8101 attattgatt atagtcaccc tgttgtgcta ttgaatacta gaccttattc attcattcta
8161 actatttttt tgtacccatt aatctcctca ctttctcccc actcctcccc taactaccct
8221 tcccagcctc tggtaaccat ctttctattc tctatctcta tctccatgag ttcaattgtt
8281 ttgattttca gatcccacaa ataagtgaga acatgtgatg tttgcctttc tgtgcctaac
8341 ttacgttatt tcacataacc taatgatctc cagttccatt catattgttg caaatgactg
8401 gatctcattc tttttgtagc tgaatagtac tttattgtgt acatgtacca caggtttgct
8461 tccaaatttt ggctattgtg aacagagttg caataaacat gaaagtgcag atatcttttc
8521 tatatactga ttttcttttt gaggagtata tacccagcag tgggattgct ggatcgtatg
8581 gtggctctat ttttagtttt ttgagaaacc ttcaaactgt tctctacagt ggctgtacta
8641 atttgcattc ccactaacag tgtatgaggg ttcccttttc tcccatccct caccagcatt
8701 tgttataagt cattttaaca ggtgtgagat gatatcattg tacttttgat ttgctttttc
8761 ttttttttga gacagagcct ccctcttgtt gcccaggctg aagtgcaatg gtgccatctt
8821 ggctcactgc aacctctgcc tcctgggttc aagcaattct cctgcctcag cctcacgagt
8881 agctgggatt acaggtgcct gccactacac ccagctattt ttgtattttt ggtagagacg
8941 gggtttcacc atgttgtcca ggctgatctc aaactcctga cctcaggtga tcctcctgcc
9001 tcagcctcca gaaatgctgg gattacaggt gtgaaccacc atgcccggtt gatttgcagt
9061 tttctgatga tcagtgatgt tgagcaactt ttcacatgcc tgtttgccat ttgtataact
9121 tcttttgaga aatgtctgtt caaatctttt gcccattttt ggattggatt attagatttt
9181 ttttcctata gagttgtttg gactccttac atattcaggt tatgaatccc ttatcagatg
9241 gatagtttgc aaatattttc tcccaacctg tgggttgtct ctttcacttc ttgatagttt
9301 cccctgctgt gcagaagctt tttaacttga tgtgattcca tttgtcaatt tttgctttgg
9361 ttgcctgtgc ctgtggggta ttactcaaga aatctttgtc cagaccaatg tcctggagag
9421 tttccccaaa gttttctttt agtagtttca tagtttgagg tcaaatattt aagtatataa
9481 ttcattttta tttgattttt gtatatggtg aggatagggg gtctactttc attcttcagc
9541 atatgggtat ctggttttcc cagcaccatt tattgaaaaa actgtccttt ccccaatata
9601 tgctcttggc atctttgttg aagaccgagt cactgtagat atttgggttt atttctgggt
9661 tctctcttct gtttcattgg tctatgtgtc tgtttttatg ccagtaccat gcagttttgg
9721 ttactagagc tctgtagtat aatttaaagt caggtaatgt gatttctcca gttttttttc
9781 tttttgctta ggagggcttc tggatcttct gtgttcccac gtaaattcca gaatttcttt
9841 ttctatgtct gtgaagaatg acattggtat tttgatggag attgcattga atctgtagaa
9901 tgctttggat agtatgggca tttaacaaat attgattctt ccaatctatg aacatggaat
```

FIG. 7H 9961 atctttccat gttttgtgtc ctcttcaatt tcttacatca atgttttaca gacttcattg
10021 tagagagctt tctctttctt ggataaatta attcctaggt attgtatttt atttatagct
10081 ataacaaatg ctattccttt cttgatttct ttttcagatt gcttgctgtt ggcacagaaa
10141 tgctactgat tttttatgtt gattttgtat cctgcaactt tactgaattt gtttgtcagt
10201 tctattagtt ttttggtgga gtctttaggg ttttccaagt ataagataat aacatctgca
10261 aacaaaaata attttcctcc tttccaattt ggatgcattt tattttcttc tcttgtctga
10321 ttactttagt gagaacctcc actactatgt tgaataatag tggtgaaaat ggacattctt
10381 gtcttttcta gatcttagag aaaagctttc agttttccct cattcagtat gataccagcc
10441 atgggtctgt cataaatggc tattattgtg ttgaggtatg ttccttctat atccagtcat
10501 tgagggtttt tattatgaag ggatgttgaa ttttaccaaa tattttttca gtgtcaattg
10561 aaatgaccat ttggtttttg ttcttcattc tgttgatatg atgtgccaca tcaattgatt
10621 tgtgcatgtt gaaccatcct tgcacccttg ggataaatcc gacttggtca tgatgaataa
10681 tttttaaatg tgtcgttgca tttggtttgc tagtattttg ttgaggtttt tttgcatcaa
10741 tgttcatcag ggatgctggg ctgtagtttt cttttttatg tgtctttgcc tggttttggt
10801 atagtataat actagcctca ttgaatgagt ttggaagcat tcctttctct attttttgga
10861 atagtttgaa taggatttgt attagttctt taattgtttg gtaaaattca gcactgaagc
10921 ctttaagtcc tgggcttttt tttgctggga gatcttttat tacagcttca atcttactat
10981 ttgttatctg tctattcagg ttttggattt ctttgtggtt caatcttggt aggctgtatg
11041 tgtctaggaa tttatccatg tcttttaggt tttccaattt atggcatagt agttgctcat
11101 agtaatctct aatgatcttt tgaatttctg cagtattggt tataatgtct catttttcat
11161 ctctgagttt atttttcttc tatctttttt tcttagtctc actaaaagtc aattttatct
11221 tttcaaaaag aaactttta gttttttttg gatgtttttt atttcaattt catttatttc
11281 tgttcagatg tttattattt ttcttctact aatttcaggt ttggtttgct cttccttttc
11341 tagtttaaaa aaatatatca ttaggctgtt tacttgaagg ttttcttctt tgttagtgta
11401 ggcacttata gctataaact ttcctcttag aacgattttg ctgtatccca taagttttga
11461 tatgttgcat atccattttc atttgtttca ataaaaattt taaatttctt cttaatttct
11521 tcattaacct gctggtaatt caggagcaca ttgtttaaat tctgtatgtt tgtatagttt
11581 tcaaaattcc ctttgctatt gatttctagt actatttcat tgtggtcaga gaagatactt
11641 gatatgatct caattttttt taatgtttta agatttgttt tgtgacctaa catatggtct
11701 ctccttgaga atgatccatg tgctggggag aagaatgttt attctgtagc cattggatga
11761 aattttctgt aactatctat taagcccact tggtctgtaa tgcagattaa gtccaatgtt
11821 tctttatttt ttttttcctt ctggatgatc tgtccaatgc tgaaagtagg atgttgaaat
11881 ctccagctat tattgcattg ggatctatct ctctctttag ctctagtaat atgtccttta
11941 tatatctgtg tgctcaagtg ttaggcacat tgtgtgctca attgttatat cctctgacag
12001 aattgacctc tttatcatta tataattaat ttctttgtct ccttttatgg tttttgtcct
12061 gaaatctatt ctgtctgata aaaatatagc tacccctgct ccttttgttt tccatttgca
12121 tggaaatctt tgctatccct ttattttctg tctgtgtgtg tctttataag tgaagtgtgt
12181 ttcttgtaca caatcgacca ttgccattga ttttttttct ttttatacca tttagccact
12241 ctatgtcttt tgattggaga gtttagacca tttacattca atgttttatt gttaagtaag
12301 gacatactcc tgccattttg tttttttgtt ttctggttgt tttgtggtgt tgtcttcctt
12361 tcttcctgtc ttcctttttg tgaaggtgtt tttctctgat ggtatgtttt aatttttgct
12421 tttcattttt tgtgtatctg ttgtaggttt tttgatttga tgttatgcag cttgtaaata
12481 acaacttata gttcattatt ttaaagtgat gacaacttaa cattgattgt ataaactaac
12541 aagcaaagag aaagctaata aaagcttcat actttaactt catcccccat actttaattt
12601 tttaatactt tctatttata tctttacttg tctatgtctt aaaaagcttt tataattatt
12661 atttttgatt ggttcatctt ttagtttttc tactcaagat atgagaagtt tacaccacaa
12721 ttacagagtt atacacactc atgtttgtct gtgtacttac tagtgagttt tgtaccttaa
12781 gatgctttct tattggttat tgatgtcttt ttctttcaga ttgaagaaat ttctttagca
12841 tttcttataa gagaaggcag tgggttcttt tctggctcag ggtgggtcta gaaatgccat
12901 ccaggagcta agtcctggaa ttgaggactt taggagtctg cttggtgctt catgttactg
12961 tggctaagtt ggtacccaat ttgtaagaca aagtcctctt actcttccct ctcctttcct
13021 ccccatgcct ccccatggct acaacagctg ggaatgtgct gggtcacacc tgaaaccagc
13081 atggtactgg gtcccaccca agcctcgtgg tggatactgc ctggctatca ctgatgttta
13141 ttcaaagccc aagggctctt tagttagcag gtggtgattc ttgccaggac tgggtccttc
13201 catttaaggc aagaagttcc cttatagcct agtgtatgtc tagaaatatc atcagggagc
13261 tagggcctgg gttgggggat tcagtactct acttggtgct ttattttact gtggttgagc
13321 tgttatccaa gttgcaagac aaagtcctct ttatgctcct gtctcctttc ttaaggcaga
13381 gggacggagt ctctcaaagc tgtgagctgt gctgcctgga gttggaggag ggttgatgca
13441 accactcctt tgactactcc agctggtgtc tcactaggtt atgtgcgctc caaggctact
13501 ggttctgagc tcagtacagc actaggactt gcctaggaat tgtagtcctt gtggcctaaa
13561 tcagctgtcc ccaaagtttt tggcaccagg gactggtttt gtggaagaca attttttaat
13621 ggacagggtg gagtatgctt tctggataaa actgttccac cttagatcat caggcattag

FIG. 7I

```
13681 ttaaattctc ataaggaaca tgcaacctag attcctcaga tgcacagttc acaacaggct
13741 tccattccta tgagaatcta atgctgcaac tgatctgaca ggaggcagag ctcaggcagt
13801 aatgtcactc atctcctact gtgcagccag tttctaacag gccatggact ggtactgcag
13861 tgcagcccaa ttcctaacag gccacagtcc atggcatagg gattgggaac ccctggccta
13921 gactgccttt caagtttact tagaacccca gagaacttta tcccacattg gtgatccttg
13981 gtagaactca ggttctgact gctgggtagg acaattcctc tctgacaaga gctgttctaa
14041 atgtgccctc tgtgggcact ggctgaattc tgtgccatgt tgctttctgc tgttacatgg
14101 caaacctgac ttccaatgta aagtcccaca atcactgtac tttccttccc ccaagggcac
14161 aaattttctc tccacaccat gtggtaacct ggaggatggg ggagagtggt attggcaatt
14221 aaagactttc tttcttacct ccttcagtgc ctctttcctt gatatgattt taaaacaagg
14281 tactgtgatt actcttctga ttttggtttc ttatgaaggt tcattcttgt tgtggatggt
14341 tgttcagttt ggtgatcctg caggaagaca attgctggaa ggttctattt ggccatcttc
14401 ctctgcttcc tcctcatctt ttatttcttc ctcttgcctg attgctctgg ctaggacttc
14461 cagtatgatg ttgaatagaa gtggtgaagg tgggccttcc tgtcttgtta cagttcctag
14521 aacaaaggct ttcagctttt ccccattcca caggatgtta gctgtaggtg ctgacatata
14581 cgccatctat agcctttatt atgttgaggt atattccttc tgtataataa agtgcacatg
14641 tctgaattat atattacttg ccttgagggt gccaagaaac tatttatact gcctagaata
14701 ttaaccttta ttatgcctaa agagttcatt agtcaaatgt tggttttgat gtagacctca
14761 tagtttaaaa cttaacattt aaattaaatg ggttataatt tttaatacca cctaaataca
14821 atatattgat ccaatataga aagttagatc aatgttagaa ataaagagtc acagtgtacc
14881 tttccagact tgtcattagc atttcatatt tatagtttta gcttgatttt gaatgtctca
14941 cagatgaact taaatcaaca cataattcca ccatagcata atagtaatta ggcagtttcc
15001 ctaaatttga gaacattgcc ttaatgtagt tgtgatgttt tgaggcttca tagcttaaat
15061 ccattatacc attatggaat ctatagagca gggctatgga gaaaggcttc agagaagttt
15121 tttttgctac tataacctta tttaaagaaa caaacagaaa aaaacccaaa cgtatttgaa
15181 gtctgcttaa atattactgt taaatgtgaa gtgtttatat ctaacattca taatcatatg
15241 aatgtcaaca tttagtttgg agtagaaaaa gataaatcat tactgtgagt taagaaattt
15301 aaatggagat gtgtgaggga gcatgtccat ttcatccttc ccatctccac cctccccaga
15361 gtttcatccc cagggtgccc ttcttggttt cccagcctctg gtgttctgct tggggtcttg
15421 acttcttccc atgccactca ggctcagccc cagacctaga cagggtttgg gaagcagtgg
15481 ggatagccaa gatgggtgtc agtgggtggc ccagcagttt ctgtcccagg agtggccaca
15541 ggccaggggt agtggtggct gtgcatgtgg ccagcctgct gccattgtcc catccctgtc
15601 agggccctct ctttcacctt acagcatctg aggggcagag ctctagagtg tttgggcaga
15661 caatgcctct gaaaatttct ttttaaataa aatttagatg acaagtatat atcatatatg
15721 cagtgaccaa gcatataact actttacagt catctaactg ctgtagcaat gatatgtaac
15781 tacagtgtca aaacaccctg acagttttca gaaacccaat gtggagacca tctgccatat
15841 cttacttttt ctttaggtac aatattcaaa ttcatattga ttttgcttac atatgaatag
15901 tttcaaattt gttcacatat ggtttaaact ttttgtccct attgtcttac tcaggcttgt
15961 gtaacttaaa atgagcctga gcatgggtct acacacagca agatgtgtaa taaaaacaca
16021 attttagtgc tactttcaaa attcatgcta ttaagaaaga tgctgttttc aaagctgaaa
16081 agatcatgaa atggctaact tacatatcag aggttggata attccttact attgaggtgt
16141 tatattttct gtgtagtaaa tgccttcaaa tattaactga aagatcagtg aagtcatttt
16201 cccctttgtg attccaactt catttgtttt attttgaaga taattaatat tttaattgca
16261 aaagaaaatt atagcattgg aaaattttct gtatatggag aataacaatg aaccaaattt
16321 accaattagg gaaccatttc aggaattgtt ggatggtgaa tttttcttca gtaactatgc
16381 tttagttgca atgcagtatg cccagaaaca atccatttca acttctgaat gcttgatttg
16441 gaacatttgt ttgatgagta ttcagttaaa cacttggata caaactcttt ccagaaggtc
16501 acatctctac catttatctt ggaatgtttc tgaagacatt ctactcattt tattaactgt
16561 atacacttct gtttttggat ctccaatatg attatagaca atatcaacat agaaggcttt
16621 gatttagact ccaaagttta gagcatttga tcttgacatg ccttaaattg ggcttccagt
16681 caaaattgag gccacttctc ctttcaaatg gcaagttctc ttgaatgagt gaatagtgga
16741 gttgtagaaa ttgaaaggca gtagtagctt tcactttaca ttacaacttc tccaatgcaa
16801 tcttttccat tctcatcaag tctgaaaccg tgaacctata ttcacctatt tggaacacat
16861 cagttgccaa tgggacatcc ctttcctctt ctattgattt tacagccgaa tagaagaagc
16921 tcagttcaac acatccaagg tgcttgggct gcaccttcat ttaacacagg aatctgtcca
16981 gtaaattcac agagaaaatg cctttgtgtt aaagccaaag aacagaatta gactaacatc
17041 ttgtacttca aagtcctgta gccttgcagt catttctggg ctattgtcta tcatgtgcaa
17101 actcaattag tctcaaacca cagatcttta actgacatat agacttcagt tccaacaagg
17161 cattcagctg gtgtagcagt ttctgacagt caggtttcag tacctctatc atcttgatag
17221 tgattgagcc tcagtggtaa ccacccttct tgggcctgca ctcacctcac cccacgaaat
17281 ccaatctcag aggcctagga aacaaagcaa acagagaggc ccagggaggg gaagccttcc
17341 tgggtggatg tctctgcaga gccacccaga tcatattgcc ctcatcaggg tcagcttgga
```

FIG. 7J

```
17401 gctgaagggc tgaaaaggca ttttgatatt tgattgcata ttatttcata ctgttatttc
17461 agagttttgt gtgcacacat tgtttcttca gtaagcctaa tgctttataa gcatagcaac
17521 cacatctgac atttcctatg ctctcacatt gtatgcttgg acagctctgc ctggaatatt
17581 cttcccccag ttgcccacat gtccaatata gtgctttgtg ttgtgtcaaa acctaatgca
17641 tatttgttga atatttaaca tgtgctgatt ttagattagt aaatatcttt ccgataattg
17701 atgatttttg ttatacctaa agattgaaca ctttgaaagc agccttagaa aatgcatttc
17761 aattattctc tttcacctcc tccttctgtg cccagggcaa aactctgcat ggattaagga
17821 ctcagcaaat atcatggatg aagcaacagg cagatttcag gcaccataag caaactgaat
17881 tcttaaaccc caatttagga catgtggtct aattttggag cattttatgt gtacgccaaa
17941 cagcctgaga aatgtagctt gaattgaaat atattagaat acatgaagac taatagagtc
18001 agtaggaaaa tatgtttgtc atcagaactg tttcagaaat ccaaaaaacc aacctactta
18061 ttccaccact caaggtgatc caaaaagact gggggtaaac atgtttcaag tggttcaatg
18121 tgttgtaatt tatatctatg catttcagat atcaattgaa gcaaaggtgg gttaaactat
18181 tgaacggttg ttctttctta caaacacatt gaaataataa ttttctatat gtattattat
18241 atccttttcc aatctttttc aaggatatgt tttatagatg attgctatgg cttcctttat
18301 attcattata caaatttgtt tgtagatcta gtagccaata tttgatgtca ccaaattttt
18361 attcatacaa cagttatctc agccttctca gctattcttc aataaccatt tatcatttca
18421 gagttgtgca atagaggata aatatagcaa tatgttaaat attattttca aaattgtatt
18481 ttaattgctt tactgggaca attattggta actttgtaaa agaataaaaa aatcaggcat
18541 taacaaatgc tccaggattt ccatttgttc atactagctg gtactgccct agccaatcct
18601 tgttacctct tatttgaaca atggcaacag cttcctaatg aatcccctgc atttagtctc
18661 tcactgttcc agtacattct acactccgtg ttctatttat ctttatgaag aaaattttga
18721 ccaggttgct tctgtcttca aaggctttaa tagtacctat ttattactaa atttggaaca
18781 aatcttagcc tcttgtgcaa agctcaatat ccatcctctc ttccttcctt cctccctgcc
18841 tcccttcttt ctttcctttt ttaaaatatt tttaaacttt ttattttttt gagacagagt
18901 ctcactctgt cacccaggct ggagtgcagg ggcgcaatct cagctcactg caagctccac
18961 ctcccgagtt cacgccattc tgctgcctca gcctcctgag tagctggaac tacaggcacc
19021 tgccaccacg cctggctaat tttttgtatt tttagtggag acggggtttc accgtgttag
19081 ccaggatggt ctcgatctcc tgacctcagg tgttccactg gcctcagtct tgcaaagtgc
19141 taggattaca ggcgtgagcc actgtgccct ctcctctcct ctcctcccct cccctcctct
19201 cccctcccct cccttctctc tttccttcct tctcaaatct gagaatgtct tcactttctc
19261 ctcccttttg aagggcagtt ctgatggata tagaattctt ggttgtcaga tttttttttc
19321 tttcagtact ttaaatatat cagctcaatg ctttgtggtc tccaaagtta ttgatgagaa
19381 atctgccgat aatcttattg gggatccctt gtatgtatga gtcacttctg tcttgctgct
19441 ttcaagattc tcattttgtc tttggctctc tacaatttga ttatagtgtg tcttagtgtg
19501 agtctctttg aattcattct cttggagttt gttgagcttc ttggatcttt atattcatat
19561 cttccttcaa gtttgggaag ttttcagcca ttatttcttc aaataatctc tcttctcctt
19621 ctgagactcc cacagtgcat gtgttggaca ctcaatggtg ttcctaaggc tctgttcaat
19681 ttcttttaat attttttgtt gttgttctgc agacttaata atttcaatgg ttctgtcttc
19741 cagttcactg ttttcttttt ctacatgcct gaattggtct tcgaatcctc ctataaaata
19801 ttcatttcag ttattgtaat tttcagctcc agattctttt taggttttct atctttttat
19861 tgatatttct actttgtttt gttttttgat tttctccaca tcttccttta ttttcttaag
19921 cttctgtaaa accattgttt taaagtctgt gtttagtagg tctgtcatgt ggtccttttc
19981 agggatgatt ttcgttggtt tatttttcct ttcttttgag tgagtcatac tttcctgttt
20041 ctttgtatga tttgtgattt ttttggttga taactagaca tttgaatctt atcacatggt
20101 tactctggga atcagattct ctgggtttgc tatgtttgtt tgtttgtttg ttttgttgtt
20161 gtaggatgtt tgtgttgagg atcagcttga gatgtaaatt taaggtcttc ttagaccttt
20221 tatgagtctg tacctttccc tgggcatgta tgggcacttt ctaaatttcc ctgtatattt
20281 aattgcttat tccttaaatg tctcactatc caaaggagaa aaagagaaaa taaataaata
20341 aataagacac tggttcttta aatctcctgg aagccacttc agccagaaag agggcctgca
20401 aaaatggtgt gtctgtatgt atacacaaca atagctgctt gcctttgcat ttgtacctcc
20461 atgatcagaa gcaacaatta gtgatcagaa tgcagatctc gtatatttga aagacaaggt
20521 cattattgtc cacactgctc ccataaggtg cctgcaagct gctttaggaa cacagacatg
20581 gcagcctgtc acagggacag gggatgagga attggtaacc actattgagc taagagctaa
20641 aatggactga aattaactgc aagttaacct ccaagcattc ttctggaagt tgcaagcact
20701 agagctccaa aatagtaata ttagacagat tccaacagtg caattgttat ctaggtgggg
20761 agaaaaattc cctgctctgc tatcttccca gcatccctct acctctaaat ttttgttaac
20821 tcattcaaaa aaattttttt ttgagatgga gtctcactct tgttgcctag gatggagtgc
20881 aatggcatga tctcagctca ccacaacctc tgcctcccaa gatcaagcaa ttctcccacc
20941 tcagcctctt gagtagctgg gattataggc gcacgccacc aggcccagct aattttgtat
21001 ttttagtaga gacggggttt cttcatgttg gtctggctgg tctcgaactc ctgacctcag
21061 ctgatccacc cacctcggcc tcccaaaatg ttgggattac aggcatgagc taccacacct
```

FIG. 7K

```
21121 ggccccccaa aatttgtttt ttgagacagg gttttgctct gttgcccagg ttggaatgca
21181 gtggaactca ctgtagcctc aaaatcccaa gttcaagcaa tcatcccacc tcagtctccc
21241 aaatatctga gactacaggc acacaccact atgcctggct attttttttt ttcttcattt
21301 tttgtagaga gacagtcttg ctttgttgcc caggctggtc tcaaactcct gggctcaagc
21361 aatccttcct ccttggactc ccaaagtgct gggattacag gcatgagcaa ccacacccac
21421 cccaagatat tttttaatgc ctctcttctg ttagacataa ttttagtaaa cgggatatgt
21481 aagtcattga tctatgatat ccacaggatg ctgcagacat tataagacaa acacgtaagt
21541 gaaaatatga ctatagatta cgataaatgc tatgaagaaa aaatacgtgg tctggaatct
21601 tatcctacag taggttccta caaccaattt tactcaagca tgggcttcct ctgaactcct
21661 ttcttgtctt aatacttctc ttctaattat tgttatttag aattactttt tgcatatatc
21721 aaataatagg tttaggcaac tatcattcag gattttgttg agagttaaga ttgatttaca
21781 aagatttttt tcctccaata aacatgtatc agatttggcc agaccccagt acaagaaaga
21841 ctcagctgcc tggccaagaa caactctatc tatgttgtgg caaatattgg ggacaagaag
21901 ccatgcgata ccagtgatcc tcagtgtccc cctgatggcc gttaccaata caacactgat
21961 gtggtatttg atttctaagg aaaactgggg gcacgctacc ataaggtaaa attaatttgc
22021 aaataatcca attagttaat gcctaatgaa ataaagtggg caaggagaaa aatatgttat
22081 tgataatgat aagcacactt tagaaatcga gtaggggcaa agcatagaaa gtaatgataa
22141 agtgtggaaa gctcctataa agaggcttaa ggggttccgt gtacatataa gaacacagga
22201 gtgtgttttc aggagtgtgt agcagtcaga aagtgccgca tgcattatgt tgcctaatgt
22261 tgccttttgg actttgtcct tttaaaggca taccctggca atgggtcaag gctagaatga
22321 aaaactgctt accacataga ctctgtcttg aggagaatgg aacaaacaaa gttccttgcc
22381 aaggaaaaca gttaagtcta cttggcaaac agaagtaatc tattttatgt cttataagat
22441 tccagtgggt ctttatagat aaagataccc atgtacatat ttgtaatgtg gagactgaac
22501 taaaggccca atttagctag aatggcctct gattctctaa agcaaactca tttcccatga
22561 aaacactgat catagatgaa attggcacta agatgtgagc ttgtactttt tcccacactg
22621 tgatgtccag atcaacttcc taaaataatt tttttctctt tatcttctgt ttattgcagc
22681 aaaacctttt catgggtgaa aatcaattca atgtacccaa ggagcctgag attgtgactt
22741 tcaataccac ctttggaagt tttggcattt tcacatgctt tgatatactc ttccatgatc
22801 ctgctgttac cttggtgaaa gatttccaag tggacaccat agtattccca acagcttgga
22861 tgaatgtttt gccacatttg tcagctgttg aattccactc agcttgggct atgggcatga
22921 gggtcaattt ccttgcatcc aacataactt acccctcaaa gaaaatgaca ggtaatgtgt
22981 gatcttaaag atatgcaggc tgatgtaatc agaaaagaaa agaaaaaaaa aacatgtttt
23041 tctagctaac gcatactcct taatacaatg ttttccagct cttaattttc gaacatctag
23101 ctgttaatat gctatagaat caatctcagt ctaaattgtt ttgtagattt atttggtttt
23161 atttaacttg attttttttt caaaatatat gacttcttac atacaactct cccttcttgg
23221 cttcttggtt tcatacttta attgatttcc tctcacttct cctgtcttat cagcatgctt
23281 tactgaaatt aataaaacat ataacttaga gagagtaaaa tgtgaatatg aggttaaaat
23341 agtaataaca attatgaaat ccctttttac tttccaattt caaatgatgt tttaaactta
23401 ttacttccag gaagtggcat ctatgcaccc aattcttcaa gagcatttca ttatgatatg
23461 aagacagaag agggaaaact cctcctctcg caactggatt cccacccatc ccattctgca
23521 gtggtgaact ggacttccta tgccagcagt atagaagcgc tctcatcagg aaacaaggaa
23581 tttaaaggca ctgtcctttt cgatgaattc actttgtgga agctcacagg agttgcagga
23641 aattatacag tttgtcagaa agatctctgc tgtcatttaa gctacaaaat gtctgagaac
23701 ataccaaatg aagtgtacgc tctaggggca tttgacggac tgcacactgt ggaagggcgc
23761 tattatctac aggtaatatt ttgatgtcag aagagttact ggataaaata aagacactca
23821 gttaaatata cagtttagat aaataatgaa tgatttttta gtataagcat atcacacttt
23881 tggggattta tgtatgctaa aaattttgtt gtttatttga aattcaactt tagctgggaa
23941 gcctacaaat acaggctaaa tttatttgct aaatcttttt tttttttttt tgagacagag
24001 tctcactctg tagcccaggc tggagtgcag tggtgcgatc gctcactgca acctctgcct
24061 cctcggccaa gcaattctca cgcctcagcc tcccaagtag ctgggactac aggcgagtgc
24121 caccacgcct ggctaatttt tttgttgttg ttgtatttta gtagagacag agtttcacca
24181 tattggccag ggtggtctca aactcccgga gctcaggtga tccgcccacc tcagcctccc
24241 aaagtgttga gattataggc atgagccacc gtgcctggcc tatttgctaa accttgaaac
24301 cttagatgtc agttcaattt taagctgatt gggaaaaggc aggacattta cttgcagtag
24361 cagtattaaa aataaatatt caaattacag atcattataa caggagttca ttgaaaaccc
24421 attttatttc ctgcctgaac aaattaagcc attttcctta tatgttcaca aatgcctatc
24481 ttgctttata aagagtttga cactaagtat atcctggata tgaatggggt tgaccaccaa
24541 gatagttcaa tggaatggct tattgctgca aagatccaat ctctcactgc tcgcaagtgg
24601 cctccatggt cctctcattc ttctcttctc ttccttggcc tggcccccat cttatctcac
24661 ttaacagggc ttcctattga cagtctgaca atctcagctc catccagtca gttctccata
24721 ttgtagttac agaaatcaca aaaagctgtt tttgattata atactgtctg gcttaaaatt
24781 cttcactgac ttctaattga caaatcaaat tctttaacat gaaagacaca caaagtctag
```

FIG. 7L

```
24841 atgtgtggtc cattcctatc ctctatcctc taatctcact tctacttaca aatacctggg
24901 gctttctgcaa tattgaaata ttttccaatc tcctatttgc tagcatatgc aggaacctaa
24961 ggtgtttgca cagattgttt ggtcctttat ccgtggcgag ccccacctac taatctttca
25021 tagcactttt ctggtgttac cgtcaccaag aggggttcct ggatatttcc cacagagcca
25081 ctcctacctc tccagatgag ttaagtacat cctttatgtg ctcccaggac accctatgct
25141 tagctttatc aaagacatat tatgtcatag tattcactta cttatttgag actgagaacc
25201 ccttgagtgc tgaaattatg ccaactgcac agtatttgt ttgctctatg ataactaccc
25261 taacaatact ttttcgtttt agcaaatgaa ggcctactat atgccaggta ttatttagt
25321 gttaatgata tgaagataaa taagcataga tcctcctctt gaagaattca gtctttagta
25381 atggagaaag acatttgaac agataatttc agcataggtt ggcatgtgat tgtccgtaga
25441 atgcacattt tgctggagga gcactaaaga gctctactta gattaatttg ggaatgcagg
25501 gaagtttctg gagctgatgc tattatccag gtgaaaaaga gtaggagggg attccttgcg
25561 gtgtgaagag catgaacaag ggtgtggatg caggcaggag caggctctgc agggaacagc
25621 aacaggtcag tgctactaag gcaactgggg catggcttgc gaagcctgggt ttggtgggaa
25681 ataagcctgg aagcaacatc ctgtcctgca ggatcttacc tagcaacctt aagattcagc
25741 ctttatttctg tgggtgatgg tcagctggtg gaagtggtcc agtgaaggaa tgatgtggtc
25801 agatctacct ttgaatatat catttttact actctgtaga tgatggagca aagacccaaa
25861 agactagatt attaaaatag tcttattaag ggtctggacc aagactgtgt ttgttggaat
25921 aaaagcaggg catggagtct agacatattt agaaaatgga actcagtggc caatttgatg
25981 tggaacagga aaacggaatg gagagtccag aatgtggcag atttctggca agaatggctg
26041 ggtgggtgag atgcatctga cagatcagga ggcaagagag gagcagacc actgacagcg
26101 ggtagaggct gagttcagct acagatgtgc tggttttgaa gcagttatga gacattcagc
26161 tggacccagc cagttgtctg ttgaatactt tggtctgatg cttaaggag atactagaat
26221 tagaaatatt gtttcaaaaa tcagcaagat acaaggggca atttagcaaa caacagtgaa
26281 tgatacgaca aaggagactg tactgacagt aaagaactat tgacaaagta gaaccttgg
26341 gagcttcggt atttggggca ggaaaggaca gaggacaaga aacctgcaaa tacaattaag
26401 aaataaagga aaatttaaaa agagaacatc tggtagatgc caaggaagta gagactcttg
26461 gaggaaagaa atcaatgaggt gcattaacac aataggttga ccattattag catttttgag
26521 tataatttg gcagaatttt ctgagctcat aatgatagga tgatggcag atttatttgg
26581 gttgaaaagt caaagggaag tgaatgcact tttttccca agaaatctta tctgagacaa
26641 gaagaagaga agcaagacaa tggtttaaca gagacccatg gccaggagaa atgtgcgtgt
26701 atgtgcgtat gtgtgtgtgt gtgtttctca acaaacgaga gagccttgat tgcctttgta
26761 ggtctaagag aaagagctac aaaaggaaaa aatacataaa atatgagagg aatcaggtcc
26821 agtgcagtgg cctgtaatcc cagcactttg ggaggtcaag gcgggcagat catctgagat
26881 caggagtttg tgaacctggt caaacatggt gaaacctgtc tctactaaaa atacaaaaat
26941 tagccaggca tggtggcagg cgcctgcaat cccagctact tggaaggctg agacaggaga
27001 attgcttgat cctgggagat agaggttgca gtgagctgaa attgtgccac tgcactccag
27061 cctaggcaac agagtgagac tctgtctcaa aataaaataa aatatacaag gaatcattac
27121 tcctactcag tgttccaagg tgctggagga aagagggaaa aatagtatca tgaacacagg
27181 tacaaaatgt ccaacaactg gaaattaaat gaatcatatt gtagaagaac atttatttgcc
27241 ataaaattac taccatatac catatgttat attaacatat atagccttat atatgtgaca
27301 ttcatatggt attatattgc tatataaatt tttaaaatta aaatataaat tgtgatgtat
27361 tattttttaag ttaaaaaaag ttggtcacaa aacaagagag taatctctta gctcttcttc
27421 cctcctcttc cttcctgcct cctcaatctt ttcctacctt tttacctcct ccagagtctt
27481 ggctctacct aaagagagct gcggaagct ctttcttagt gctgtgaggt aggttagctt
27541 tgtcaagtaa aaccaagctt tctgtttatc ttgctagacg gtgatatttc atctaaacga
27601 ttggtaccag atatgtttg gaatcttcct atttaaagat aataatacat attacttgat
27661 attacccagca gagtctggga aaataccccag aatcaaacat attaatatat ctattggaaa
27721 acatgggatt attcacctta aatagcttga ataaaaatgt tatagcctta tgttaattca
27781 agttaggtct taatgccaat gtgccagtgg gttacaaaaa tcctttattt tcagaagatt
27841 ttggatttt gcattgaaga taaggaattt tggtatcata ttatatttat aatttttcat
27901 agtctaactg tgatgatata ttatgcttga aaaatctcga ttatcaccaa aagctaccc
27961 caaaccaagg gaagagacac aaagagaggt aaaagtgaaa taaaccccta tcttgccaca
28021 cagatttccc aagcatttta tagcaaatat gcataatttt gtttatatca gtatgtcatt
28081 gcaaacatca ctcagagttt tgcttttata gtttttcttt gttttccta aagttattaa
28141 ttgccttatt ttttttaaatt tcgttaattt tctttgactt tttgttaaaa ccccatatct
28201 tccaacagca tctcagaata atttttccac aatatcattt tcataagttt atcttgagct
28261 aaaaataata accttttctcc gcactggttt ccctctagtc attccgcaca gttgtcatat
28321 tgagatttcc tttactgtca tcctaggaat gctcttttag ctatttcctt gttttaggtt
28381 ctctgctttt ctcctttctac ctttatttgc tccttgttc tgttgtagtc aacgctgtct
28441 agtcacattg ctctaatctg aactggctgc tctccatgcc ttgtatacga taggagtcat
28501 cctggaatct cccttatcc tcatggtgaa gatttttctt taccacttcc ctgtgtggat
```

FIG. 7M

```
28561 ttcctgtttt ctgttccccg tcttccttgt tttgggcttg tgccctcttt cctgttgtta
28621 acagtttccg gaaagagagt gatcgggatg caagattttt gagactcact ggtctgaaac
28681 tgcctttcct cttaaattta gttaagtatt tccctgggca tggaattcaa aggtggttat
28741 gacttttctt caggattgtg aatgtattta tatcctccca tcttacgttg ctattgagaa
28801 ttctgaagtt cttctgattc ctgattcttt gtatgtgtat tcctcattcc acacctttcc
28861 cagaatgcat gcagaatttc ttcctttcta tttctttttc tctttttctg aaactcttat
28921 tactgggatc tcctgccctc tggattaggg ctctaatttt ccgacatttt ctctgctatt
28981 ttttactact ttatttttct cctctacttt ctgagagatt tcctcctctt gatcttccaa
29041 atcttgtact gaatctttta tttttgttaa catgttctta atttccaaga actctttttt
29101 cttgtcttcg gagtttcaac acttattgtt gttttgtgca tgtattattt tttcttttct
29161 ctctgaggct atttaggaaa ttttttattg aagctcctcc ccctgctttc cttcaagttg
29221 cttttatctg cttttttatt tgcttttcca tgcaataagt ttttctcaca tgtctggtaa
29281 ctcttgggga ttaccaaaaa ctcatagaaa attctgacca tgtgagtaac acttgccaat
29341 tttgagcttc atgatagaat gatctagctg gaccttttgc tgcggggaaa tcggaggtaa
29401 gtgtctttgg agacttcctc ttgggatggt caggtctccc aggtttcaag attcttctaa
29461 tttccttctt gaatcagttg cctaatttag gaaataaaaa tacaggatct ccaggtaaat
29521 ttgaagttca gataaacttt gtttttcttg agagagtctc tttctgttgc caaggctgga
29581 gtgcagtggc atgatttcgg ctcactgcaa cctctgcctc ccgggttcaa gcaattctcc
29641 tgcctcagcc tcccgagtag ctgggattac aggttcatgc caccactccc agctaatttt
29701 ttatattttt ggtacagatg gggtttcccc atgttggcca ggctggtctc gaactcctga
29761 cctcaagtga tccgcctgcc tcggcctccc aaagtgctgg gattacaggt gggagccact
29821 gctcccagcc cagataaaca ttttttttaa aaagtgtaag tatgtcccat tcaatattta
29881 agacatactt atactaaaaa attatttgtt gtgtatctga acttcacatt taactgggag
29941 tcttgtcctg tgtttaacct ggcaacccta ttcctgaaag ataaatcctt gctgacagca
30001 ttagggatcc aagtgaggaa aatggccttg caggtgtggg gtgggggtgg aggggaaacg
30061 ttttcaacat tcagtgttat ttattcaggt aatccccttc aactatgtct cttaaacttt
30121 catctaaaga ccatccactt taccctctct ggaaacattc tccgttattt actggagtag
30181 gggaggatca gtctatctgg tttttggagg acttagtatc caaggcatcc ttcacaactt
30241 tctgctcatt tactttcctt tgactgccac aacttactc ctagctctag gtatagagca
30301 gtcccagtga ttaatttgag tgctttgcag tgtagatagg gattcttggc tctttctact
30361 gctagtttag gacctggttt tcttgggtct gctgaatcaa ttactacttt ttgtatcaac
30421 atcctagttt ttaaaactgt gttgtggtct atcctcctat tttcctacct ttgtgggtta
30481 aaaaaaatag tgttcttttg aaggattgta ggaaataaaa ttgaagcata tgttcattct
30541 acctttacct gaaagttact tctatccact cttaatacac ttgcactgaa gtgattactt
30601 tccacctgca aagtggaaac aataagacca gttagggcct gctgctttag tcaagcaaga
30661 gatgaaggtg acctggaata tgctgtacag atggcattaa atgaatatgg atctcctttt
30721 ggaaactttt catctgcatg gtgagatgac tcacatactt agattttata ttcaaatagc
30781 tacgtactat agtggaagaa aaacttaatg gagaagtgtt tcagttcttg cgcagtatag
30841 aggatatgac ttttccagat tacaggggtt gcctctaggt caactctagg gctcattaca
30901 actctgaagc tcttttattg tgtgaaacag gcaataagat atgatttaca caggtgccta
30961 aattaaacct ttaaacacat tttaaattct tgataattaa aatcattagt aacttgagaa
31021 caatgaagat atagctgttc atggctatag gccaaggatc tgattgcttt tacagggcta
31081 atcttttgga cagtgaattg caggaggcac tggggcttaa agccctttat ttttattatt
31141 agttgtatta attattcagt gataaactgg atgactctaa tgaagaagta acattatttt
31201 accaaataaa gtggcatagg catttttcta gatcaagaga gtatttcagt tgactttctc
31261 atgtttttct tttaagagca tctagcagtt tatttaatta ttttattcta ttttttatct
31321 ttaaaattta tcctagcttt actgtcatta acaaatgaaa attgtatatc tttacagtgt
31381 atgatgtgac gttttgatat gtgtacaaac cgtgaaatga ttaaatcaag caaattcaac
31441 tatcccacat gactttctta tgacttactg gttttcatga cttccctaga tttgtaccct
31501 gttgaaatgt aaaacgacta atttaaacac ttgcggtgac tcagctgaaa cagcttctac
31561 caggtttgaa atgttctccc tcagtggcac tttcggaacc cagtatgtct ttcctgaggt
31621 gttgctgagt gaaaatcagc ttgcaactgg agaatttcag gtaagaatct tcggaatatg
31681 ccaattagtt tcatgtaaga ggaagcactt tttgatataa aaatctgctc aagtgcttac
31741 aaatatcata aaatttccat ttagaaaggt taagattatc cttggggatc atgaaggaca
31801 ttgagcaggc tgcatttctt gtctggaaat tcttaacata ataattactg tgtccttcag
31861 aataaaaaaa tatatatctt attttgggga ttatagggag tttaaagtct tccaagtaga
31921 aagaagattc aacgagagta gtttcagaac cagtgccatt ggagcccctt aggaccactg
31981 gggagtgatg gcctagggaa gttgaaagga gtccctcttg tcgagtgagt caaggctctg
32041 tgtgatggta gaaggaaaag agacaaggaa aagctgaaga agagagaatt tgacagtggc
32101 ggatgttagc aaaaagcaaa aaacttttta aagttcagaa ataatccctt gcttcacatg
32161 tgctctgccc agccacattc tttcgctgac ttcctgcaag ttctcctccc actccccgtt
32221 cctggtagaa accactgctg gggtgtggga ggacaatgga atggtgagga ggttgtggtg
32281 agcaagagac aggagatgac agatgctcag ttcaaatccc tgttagtcaa ttgcttcggg
```

FIG. 7N

```
32341 ccattgtggg gagtctttat cttgtctgag aggactaggt ttctcttctg tatactgcca
32401 aatccactgg tttgtgttta ttaactctta cggcgcttcc acaggtaagt aaattagaag
32461 acattgatta cgggcatctc actaataaat gaatcagtgc cagtttcata gctccaattt
32521 ttcttgtact tggcaacatt tcaaattttt ctgatagaat ggaatttggc cagtattttt
32581 gtttctttat tctgttatag taaattttaa aagtgattta tgggatgtga aaacttgaag
32641 gtagcctttg cctacttttt tgttttaatc aggtgtcaac tgacggacgc ttgtttagtc
32701 tgaagccaac atccggacct gtcttaacag taactctgtt tggggaggtg tatgagaagg
32761 actgggcatc aaatgcttca tcaggcctca cagcacaagc aagaataata atgctaatag
32821 ttatagcacc tattgtatgc tcattaagtt ggtagaatat tgactttttc tcttttttat
32881 ttgggataat ttaaaaaatg atggatgaga aaagaaagat tggtccgggt taatattatc
32941 ctctagtata agtgaattac tagtttctct ttatttagac aaacacacac acaccagata
33001 atataaactt aataaattat ctgttaatgt agattttatt taaaaaacta tatttgaaca
33061 ttggtctttc ttggacgtga gctaattata tcaaataagt atcacaaatc ttttacgcag
33121 aagaaataaa aactacgggt agaaaacata agaactatca taaaatttac ttacaaggag
33181 gctgctcttg ttaccacttt tattatatta cgtatcactt atttcagctc gctgaaaatt
33241 tcccatgact ttgtttgttt gctctttttg ttttttacct aaacaataca ttttgattct
33301 cttgtgggtt gataatgtct ccccaaaatt tacatgttga agcacctcag aatgtgactg
33361 tatttggaga cagggtcttt aaagaggtaa aataaggtca ttaggataga ccctaattca
33421 atatgactga tgatcataaa agaagaggag agtagggcac aacaggcaca aagggagacc
33481 ataaggagac acagaggaag gacaactctt taccagctaa gaagagaggg cctcagaaga
33541 aaccaacact gccaacacct tgatcttgga cttccagcct ccaaaactat gagaaataaa
33601 tttctattgt ttaagtcacc cagtccatgg tacttgttta ggcagccctg gcaaatgaat
33661 caaagaccca ttcctgttcc tctccccacc actactgttt tctactgtaa tctgaagctt
33721 caacaaaagg cttacctggt aagaatattc agctggtctg ggtcctcaag actccaatag
33781 acactcttag agaaggattg ctgatggatt gatagtgaaa ccattagatc attgaattcc
33841 tctggaatta gaaaaccaga gagtcccatt ttaagaattt agatatttaa tatagcattg
33901 tgtgttctat tttagtaaca gcagaatctc ttgacattac acaactcagt gaaacaacat
33961 catttaagcc aaaatatctc ccaactgact gatagactct gagcactaat atcatagtgc
34021 tgtgatgatg gacaattaca tagtaccgat aacagccatg cactgtgcaa agcatgccct
34081 tctgcacagg agagcaaggc acttgcagta gtgatctatg ccagcaaaac atcatttgga
34141 gacaaacatt tttgtggcag atgtttttcc taaaaagtac tatatcatcc aagaaatatt
34201 tgagtaaaat cccttgttct tttgggtgac attaactgac atttgctttt tttcaagacc
34261 taatagaaaa taagaaagcc cataatgtat ttagaaacag gaatcctcag agcaattctc
34321 tgtattctca tataatttca atgtaaaaca gaaaacatat tgatgtgttg gtgataggct
34381 tgaattatta aaaacttcaa aaacatccta agtgtttctt ttttgctcaa cgttgtcaac
34441 tatagtaggt ctcccttgtg gtgtaatgaa ttgcccccaa actattatct taaaacaaca
34501 aacatttatt atcttatagc atttctgagg gtcaggatct gggactggct tagtggagtt
34561 gttctggatc agggcctttg gaaagttgta gttaacttgt cccaagggct gccatcatct
34621 caaggctagg gtggggctgg agaaaatctg cttctcagct cactcacggc ggttgccagg
34681 cctccattct ttaggatgct agaaaaactt tcataaaatg tcatctggct tctcctagag
34741 caatgatact gagagagaaa gcacatgaga gaaagagcga gggaacttgg atgtaagcca
34801 cagtctttga aaacctaatc acagaagtga catctcttct tccacatgat gttggtcaca
34861 tggaccaaca atggcacaac gtggacagaa tcaaacagag ttgagaatat caggaggtgg
34921 ggcttcatgg gggccatttt ggatgctatc atagtgaata tatgtattta tatttatatc
34981 tgtatatatt gcaatgtaat ttaaaaaata ggattgtttt cctttccttt ttgctatatg
35041 tgatatgtat ttcaaaatac actcccaata gttacgtctg aaaagcacta cactaaaaaa
35101 ctttctatac attgaataat taaattaaat aatctaataa tctctacttt tggtccatag
35161 taaatttaag ttaactgttt gccttaacta cagtttgtgg caaaaccatc tccttttaat
35221 atacacaagg gacttttttt tttttttttg agacggagtt ttgctcttgt tgcccaggct
35281 ggaatgcgat ggtgtgatct cagctcactg caacctctgt ctcctgggtt taagcgattc
35341 tcctgccaga gcctcctgtg tagctgggat tacaggctgg gattacaggc atgcgccacc
35401 atgcctgcct aattttgtat ttttagtaga gatggggttt ctccatgttg gtcaggttgg
35461 tctcgaaacc cgagctcagg tgatccaccc gtctaggcct cccaaagtgc tgggattaca
35521 ggcgtgagcc accatgcccg gcccgtggga cttttgcatt catttttcag aagctcactt
35581 tgtaggggaa catacattaa aaggtaacaa aataaacagc ataagttcca gaattattaa
35641 ttcatgaagt gcaaccacta ggaaaagggg tcttaaaaac atcaccctct ttactggatt
35701 ctttgaagaa accaagattt ttttcctaat aatctgtttt atacacaata tataccaaaa
35761 atatataaat atataagtat ataacaaaag tgaaagaaac tgactcttaa tcaaatgttt
35821 ctgaatagca agaggaatac taaaaaagtc aactagaaag tcatgtcaac gtcaaaatct
35881 gttctgaaac acatcacttt gattttatac tgaaagccga tacctcgaat ttcctctgct
35941 tcgctgtcct gtggttgtac tgggcatgtt ccaaatgtat cactttcatt tttatttcaa
36001 taatttcaag tgttatttta gattcaggag gcccatgtgc aggtttgtta catgggtata
```

FIG. 7O

```
36061 ttcagtaatg ctgaggtttg gggtacaaat gatcctgtca cccaggtgat aagcataata
36121 cccaaaaggt agttttcagc ccttccccc tccctgtttc ccagctgtag tagccgctag
36181 tgtctgttgt tacccatcttt atatctatgt gtaccaaatg tttagcttcc atttaaaagt
36241 gagaatatgc agtatttggt ttctgttcc tgccttaact tgcttaggat aatggcctcc
36301 agctgcatcc atgttgctgc aaaagacatg attttgttct ctttatggc tctgtggtat
36361 tctatggtg
```

Homo sapiens vanin 2 (VNN2) gene, complete cds (SEQ ID NO:18)

gi|82399141|gb|DQ249347.1|[82399141]

Coding Sequence = join (2009..2221, 2346..2476, 3857..4049, 7144..7432, 8375..8748, 10028..10198, 15403..15594)

```
    1 atactaacag tctattatac aatctgctaa aaattcataa aaatatctat cccttacat
   61 tttccacaaa agggcttgac catttttcct gaattatttt tagtttttctg ctctatagag
  121 ataagaaaag ttattccttt aatagaaact tctattcaaa gcagaaata tgagcagatc
  181 ttatttatag ccctaggcc caattcttaa caaacattt atctcagtaa gaaggaagc
  241 acagaataaa atttgtttaa tcgtacctac tcttctatgc tgtctaaaag catttccgtg
  301 actttttacca aaggctgga taaaataaa acaaatcctt tatttggcag gattgggcct
  361 ggggaaggga gaatatgaat gcctaagaa ggcatctgag atcacatcct gtattgttg
  421 ttattattgt tttttttttt tttttttttt ttgagacgga gtttcgctct gtcgcccagc
  481 ctggaggcga atggtgtgat ctcagctcac tgcagcctct gcctcctggg ttccagcgat
  541 tctcctgcct cagcctcccg agtagctggg attacaggcg cccaccacca cgacccagcta
  601 cttttgtgt ttttggtaga gatggggggt tccactatgt tggccaggct ggtcttgaac
  661 tcctgacctc aggtgatctg cctgcctcgg cctcccaaag tgctaggatt acaggcatga
  721 gccactgcac ctggcctgtt agcattgctt ttaaactcat tgttgttatt tgctgctaac
  781 aaaaatgtaa gttacatctt ctccttatta caacacagat gatctttatc accaatcctg
  841 gactcttccc cttccctggc atcttcctcc aaagcagggg gtggggaggg aggaaaaaga
  901 aggggggagaa ggagtagggg gagaaggaga agtaggggga ggatggggag ggaggggtga
  961 aagagagaaa gaaggaaaga agcggagtat cctgaggcct ggggccccct gagctgagat
 1021 tcctcctctg gcctaggtgc ctcggggtat tgttgctgta ggcactaact atacagcagt
 1081 gaacaaacca gacacaaaat cctgctttc tggagcaact gttttcagtc cttaatagca
 1141 ataagtaagt cagagtgtag atttgggtaa atttgttat caatattgtc ctgtgttaca
 1201 tttttcttagt agtaagtatt taatatttc ccccccgtct aaaaataaac acaatgtaag
 1261 tgaatcaaca gaacaaaaaa aattgttgtc aatttttaaa tttaataaat gagatatttg
 1321 ttgggatgtg atttttttac acgagagtta gttatgagtt tctattaaca aaagctggaa
 1381 ttgtttctata tttgaatttg ggtgtctttt ggaaattcaa tattaaatct tagtactaat
 1441 agtacatgct gttcaatccc tgtaatactt tctgattgtc ttaaatggac tgcaactttt
 1501 cttttcttaa aagtggtcag atatattgcg ttcttaagat tataaagtag gccaagtgca
 1561 gtggcccacg cctgtaatcc cagcactttg agaggctgag gtggatggat cacaagatca
 1621 ggagtttgag accagcctgg ccaatatgt gaaaccccat ctctactaaa aatacaaaaa
 1681 ttagctggac gtggtggcgc gcacctgtag tcctagctgt ttcagaggct gaagaaggac
 1741 aatcgcttga acctgggagg tggaagttgt agtgagctga gcttgcgcca ctgcattcca
 1801 gcctgggtga cagagcaaac tccgcctcaa aaaaaaaaaa aaaaaaaaaa aagaagaaga
 1861 agaagaagaa gaagaagaag aagaagaaga aaaaagatga taaagtaaaa ggccagtaac
 1921 tggcagccac atgttatgca aacattctcc cctctgtaaa tactacatga atgttatttt
 1981 tgctttcagg aatcactaaa cctggccat ggtcacttcc tctttccaa tctctgtggc
 2041 agtttttgcc ctaataaccc tgcaggttgg tactcaggac agtttatag ctgcagtgta
 2101 tgaacatgct gtcatttgc caaataaaac agaaacacca gtttctcagg aggatgcctt
 2161 gaatctcatg aacgagaata tagacattct ggagacagcg atcaagcagg cagctgagca
 2221 ggtatctct tatttctgtt aatcataatg tacacgaggg gcatgggagc tggtggaaga
 2281 cgagagagct gaattgtctg tgttgtacat ggaaaaatca ttttatttt gcttgcttg
 2341 aacagggtgc tcgaatcatt gtgactccag aagatgcact ttatggatgg aaatttacca
 2401 gggaaactgt tttccctat ctggaggata tcccagaccc tcaggtgaac tggattccgt
 2461 gtcaagaccc ccacaggtat tttaactatc ttagtcttt gtgcaaaagt aactctctaa
 2521 aatgggcacg ttcaccaaag caaaatgatt gctcttgaat taccatatat gtggtatatg
 2581 ttatggttat atttatctca acatttgtca gatttaaaa aattgtactt agatactatt
 2641 taaaaatctt ttgtgattga aaatctttat taaatttga gaaaatgtgt aaatagggta
 2701 ttcctgcaag aaaaactaag ggaagagatc tcatagatac aagtagtaac ttaatttctg
 2761 aagtagacag tggattgtgt taggaataca ttccaaagcc tctgctgaag ggacaccctt
 2821 tcaatgttat agagtctctc cattccagag ttgcttctta ggcagaaaga cttcaccatg
 2881 tattttcaag tgaatcataa gacctttatgc tttgaaactg catttccta ggctcacaaa
 2941 tctaattttc ctgggaaaag gttatctaga aacctttcaa tatatattaa aaatctgggt
```

FIG. 7P

```
3001 cctactgtca tcctggaggt gtcaacgtgg cagttgcatg gacaagtctg gcatgaaaag
3061 acaaaattat atctggagat agaaaatcaa atgtcagcat atagatggtg ttaaacacca
3121 tgatgagttc acctgtggag tgagttagag aagagtttag gtataaggct tgagcactag
3181 gaaattctag tgtttagact cggaagaaaa cgaggaatca gcagaagagt cgaagaagag
3241 caaccaataa ataggaaaat gagagggtgg gtccaataga gaagtgaggt gtttccagaa
3301 ggaggtgtaa ttaactgtgc caactgctgt tgaaaagtta agatgagatc aggtaaaatg
3361 tgggggtcac tgctggcatt agtaagagtt tgggtgatag agatacaagt tggagtgctc
3421 tgaaagggaa tgggagagga ggaactggca acagcaagag gggctgatct tttgaggagt
3481 tttgctttaa gagagagatg aggattaaag caatatttgg aagggcatgt ttggaaaggt
3541 caaaagaggt tttaacttta tttttaaaag atgggaggta ctagaggata tttcattgct
3601 gatgggatgt ttcagtagag aggagaccct tgatgaggca ggagaccgaa taatgaattt
3661 ctggagcaat agatacogtg tgggaagcat tcatcaagtg tataatcatc tgtggctttt
3721 aaagtatgat atttttaggc atagtttttg tattaactta agttccactt aagtggttac
3781 agttgctatc gtttccatat aaagtgacta aaatattttt ttaaaattga aatttcttaa
3841 ttataatttg gtttagattt ggtcacacac cagtacaagc aagactcagc tgcctggcca
3901 aggacaactc tatctatgtc ttggcaaatt tgggggacaa aaagccatgt aattcccgtg
3961 actccacatg tctccctaat ggctactttc aatacaatac caatgtggtg tataatacag
4021 aaggaaaact cgtggcacgt taccataagg taagagagag tgacggacgt gtaaaatgga
4081 gcgtgctgtg agtggtcaat gctgggttta ggagtttgaa tttcattccc tatatgatac
4141 aatattacta gagggttttt ttgttttgtt ttgttttttg ttttttgaaa gtgggcaata
4201 aagaaaatga cacttttggc tgggcgtgga ggcttatgcc tgtaagccca gcactttggg
4261 aggctgaggc aggtggatca cttgaggcca ggaatttgag accagtctgg ccaacattgt
4321 gaaaccccgt ctctactaaa aaatacaaaa attagcgggg cgtgatggca catgcctgta
4381 gtcccagcta tgtgggagct gaagcaggag acttgcttga acccaggagg tggaggctgc
4441 agtgagccga gattgtgtca ctgcactcca gcctgggtga cagagggaga ctctcaaaaa
4501 aaaaaaaaga aaaaaaagaa aaagaaaaaa gaaaatgaca cgttgtaaaa aactactcag
4561 aaaaacatgt aggcagagaa ctgttaaaaa aaaaaaaaag tagcatgatg gtccaggatt
4621 gagataaact ttttgcacat ataaaacaaa taattttaac ataaaaaaag atactaaggt
4681 gactacaatc tgggcactgt ttcaataatt ttatattttt ttagagacag ggtctcactg
4741 ttgcccaggc tggagtgcag tggagccatc atggctcact gttaacctca aactcctggg
4801 ctctagtgat cctcctgcct cagcctccca agtagctgag actgtaggca tgtgccacca
4861 tgctaatttt taaatatttt tttggaaaca gagtctcact acattgccca ggctgtcttt
4921 gaactcttca cctcaagcag tcctcccacc ttggcctccc aaaatgctga gattaggggc
4981 atgagccact gagcacagcc ataatctaaa tactatttaa tattgaaatg gtagaaagat
5041 gtttcaaaat tgtatgaatc agctttgcat aagttaattt gctatcaaac cacaaaatac
5101 cttattttct acaccagcta atttaattac catcttatag atttaagatc aaaccataaa
5161 atgtttactt taaattctga attgaaaaaa ggaatcaaat aacctttaag tcataatttt
5221 atactaaact aggtagagaa agaagcctgg ccttttaaat ggtatgtgt gatgtacagg
5281 cagtatgaat gtcccttctc cacacccaga tattttgtaa gcatcttaaa ctgtagcctc
5341 agaatctttg gagtggagaa actatctcct ggcagtctca gttaaaatat aaatattaat
5401 taagaggagg gatgttaaac caatggtttt caaatgattt cgatcatgga cccctattgg
5461 aaaaaatcgt taacataagt cctcaatata tgtatttttg tgtgtgtatt tataaagtgc
5521 aacaatttca aaatgctttc ttcataattt tgtggatttt gacagcttct tttcatatat
5581 atcactgcac ttcactttct tcttaaaatg tgtctcatag taaaaataga aaggtcagtg
5641 cttccatttt cttgcttggg agattgtttg cattatttgt attatctttc aatgcagttt
5701 atttgcagta atcatttgaa gctattctgc cattctgtaa atatgcagga tggcacagtg
5761 cactgaatgt ggacaaacta gcaaggaacc tgcagtcacc ctgtctaagt tgaaaggctc
5821 tcactcttcc ctgagggtac ctcagggacc gtttgtaacc catgacctct gacatatgtg
5881 aacctaatga gaataccttt gtcgatcaat tccttttttt tttttttttt tttttttttt
5941 aggcagagtc tggctctgtc atccaggctg gagtgcaatg gcacgatctc agctcactgc
6001 aacctctgac tcccaggttc aaccgattct cctgcctcag cctcctgagt agctgggatt
6061 acaggtgcat accaccacac ccggctaatt tttggatttt ttagtagaga tggggtttct
6121 ccatgttggc caggctggtc ttgagctcct ggcctcaagt tatctgcctg ccttggcctc
6181 ccaaagtgct tggattacag gcatgagcca ccttgcctgg cctgtcaatt cttaaaatag
6241 tagtaaagcc caatttcttt tctatttttt agatattttt tctacactgc agaccatttt
6301 attaactgtt gattccattt attatattag actaagtttt tttttagttt acctagaagg
6361 aatcggggaa ttaaatacat ttcctatggta atttgaaag gtgggcaaga gtcactgaga
6421 ttactttgga tgggacacta aagagagaga tgacatctct cacctgactt acaggtattt
6481 attatgcatc tattaatatt acgtttctag gcaccaagga ttcaaagaag aataatgcat
6541 gttttttaac ttttaagaag cctatagggc caggtgctgt ggttcattcc tgtaatccca
6601 gcactttggg aggcccaggt gggtggatca tgaggtcagg agattgagat catcctggct
6661 gacacggtga aaccccgact ctactaaaaa tacgaaaaaa ttagccgggc atagtggcac
```

FIG. 7Q

```
 6721 gtgcctgtaa tcccagctac tcgcttgaac tcaggaggtg gagattgcag tgagccgaaa
 6781 tcatgccact gcactccagc ctgggtgata gagcgaggct ccgtctcaga aaaataaaat
 6841 taaattaaat ttaaaaaaag cttacggact ttggggttta tggggggggt atttggctct
 6901 taactgagag agagggaaag agagagaagg gagagagagg agatggagga tgctatggac
 6961 gtatgttaca tattcctcca cattttcctt agaaatttac ttccaattgc cagatttatc
 7021 cgcttcctag gagattccct gcagttgacc atagccaaat ctgttaccaa cttagagggt
 7081 ttttatgagt catttcttca acaaataagg ttttactggt ttctcctat ccatttgttg
 7141 tagtaccacc tgtactctga gcctcagttt aatgtccctg aaaagccgga gttggtgact
 7201 ttcaacaccg catttggaag gtttggcatt ttcacgtgct ttgatatatt cttctatgat
 7261 cctggtgtta ccctggtgaa agatttccat gtggacacca tactgtttcc cacagcttgg
 7321 atgaacgttt tgcccctttt gaaagctatt gaattccatt cagcttgggc aatgggaatg
 7381 ggagttaatc ttcttgtggc caacacacat catgtcagcc taaatatgac aggtaattca
 7441 tgaccaggtt aggtttcatc ttatattttt aagtgcagag aaatgaatgc ctcagttatg
 7501 acttgcatta atttcttgct tattggaaat tcttactgtg tttgtcatag tttcacaata
 7561 gaaaaaaaaa gctagcactt gattataagc tatggttata ctaagacctt tatgtgtatt
 7621 attcatttaa ttattacaat aattatatga gatagatagt gtcatcccaa ctttgcagat
 7681 gagaaaattg acatacagag agtgcaagta atttgcccaa tgctacccag ctactacttt
 7741 cctcagtggc catggaagcc tctatatctt gcccttgtc tcctcctatg gctgcatggc
 7801 atatcctcgt gacatggctg ctgtcttcct ctagagcaat taatgagagg ggacaagaga
 7861 gaaaaggaaa gaagccacat tgctatttat gactagttac ccaccatcac ttctgccatg
 7921 ttctattcat tggaagtgag tcactaagtc cagccctctct tcaaggggaa aggaattaga
 7981 tcctcccacc agaaagaaga attttaagga atttttggat atatttgaaa accaccacaa
 8041 tgaggaatag gggagaattt ttattccctt tccccacctt tcaggaactc ctgactacaa
 8101 agatttttgt agttggttta atttccata atgctaataa ataatgctat tatatttaag
 8161 gtttaattga aatgagacca aggaatgttt atttaatct cttccattag agaatagaag
 8221 tagttaggtg ttcagtgcaa ttagaagcat gtatcctctc tcatcgtgac taatatggtg
 8281 gcgtgatcac atgcccaatt ctgatgggga aattggcagt tttggttttt ttgtgtgtgg
 8341 tgttgtttt agaagacttg tctttcattc acaggaagtg gtatttatgc accaaatggt
 8401 cccaaagtgt atcatttatga catgaagaca gagttgggaa aacttctcct ttcagaggtg
 8461 gattcacatc ccctatcctc gcttgcctac ccaacagctg ttaattggaa tgcctacgcc
 8521 accaccatca aaccattcc agtacaggaa aacactttca gggggatttat ttccagggat
 8581 gggttcaact tcacagaact ttttgaaaat gcaggaaacc ttacagtctg tcaaaaggag
 8641 ctttgctgtc atttaagcta cagaatgtta caaaaagaag agaatgaagt atacgttcta
 8701 ggagctttta caggattaca tggccgaagg agaagagagt actggcaggt aatttcagtt
 8761 caaatgaaag ggcatttcaag tgaaaggtaa atttccaggtt aactttttat atttgttcca
 8821 gaaaaccagg tgcttttcct tggcttgact ccatgcattg atggcaacac acacacacac
 8881 aacacacaca cacacacgtg catttatgca cgtacataca ctgggataaa atatttacaa
 8941 tgggaattaa gtataatctt attgcttgct ttaagcatat ttaaaaaatt attaacctaa
 9001 ccatgatgag tttcgatttg actaataaac cagcctactg tggagaacat caagaagact
 9061 tccttaagtg ggtttgccaa catatctaaa ttataaacag tcttattttc acttgcaaaa
 9121 ctaacagtaa atagagatac tactttattt ttagtttctc ttctaatcag atgtcccggg
 9181 ttttgtatag cttctctttt ccttttcttt cttttctttt tttttttttt tgagacaatc
 9241 tcactctgtc accctggcta gagtgcagta gcatgatctc ggctcactac aacctctgcc
 9301 tcccaggttc aagcgattct catgcctcag cctcctgagt agctgggact acaggcatgt
 9361 gccaccacac ctggaaaaat atatatatat atatacacat atacaaaata tttttagtag
 9421 agacagggtt tcaccatgtt ggccaggctg gtctcaaact cctcacctct gctgatccga
 9481 ctgcctcggc ctcccaaatt gctgggataa catgtgtgaa ccaccacacc tggccttgta
 9541 ttgctcttcaa atgacaaact ttaaagactga aactttttat agaatgttgg ctctgaattt
 9601 gtatttttcct atttatactcc atgtcccact gccttcttct aaagaaaagg attgggaaga
 9661 gaggtgagat taaaggtgg aaaaaatttt aatatccttt cagcttcagt actcctcagt
 9721 actattgttg ccccaaagatc tccacttcat tggagctgat gccatcatct gacatacccaa
 9781 actaatggtt taactctaat tctaaactga cttctttctc ttaatccgct tgttatttag
 9841 gaagtgggtt gattctcaag tcactggcca ttttaataa agcagttaat tataagacac
 9901 atgatccaaa tccctttca gagaaagata atgtttgctt cgctgtagtt aaaaactaag
 9961 gcaacattc tggtatgagt aacttcaatg taaggcattg cgtttatact gcgttgttc
10021 cacatagggtc tgcacaatgc tgaagtgcaa aactactaat ttgccaactt gtggacggcc
10081 agtagaaact gcttctcaa gatttgaaat gttctcccttc agtggcacat ttggaacaga
10141 gcatgcttt cctgaagtgc tacttaccga aattcatctg tcacctggaa aatttgaggt
10201 aagaggactt ttataagagt attttcattt tatatgttct ctgaagtcaa gtaaaacaag
10261 ctatagccac tctgccagtt aactttctgct gtgtaacaaa tttcctcaaa aacatttctt
10321 tagccctggt tctgtgggtt ggcaatttga acttggggta ggtaggctgt tttctcggtc
10381 tgagatagc tcagttgacg ttggctgggc tcattgtgtc tgccattggc tagtgggttg
10441 attaggactg accagtttgt gattgccttg tcctggacag ctgggattat taaggccatc
```

FIG. 7R

```
10501 tctccccgtg gtctctcatc tttcagcaaa cctgagcttg ttcacatgtt agctgaatga
10561 gtccaggagc atcagagaaa aaacaaatct ttgcaagttc tttgcaaatc tctgcttgca
10621 ccgtgtttgc aaacgttgca tcaacacagg aagttacatg agcagtggtg acttcaatgg
10681 tagagaaatg aagaactcag acctctcaat gggaagagct ataaaatcac acggcaaaag
10741 gacatgggtc aaggagggga aaatattgtg atcattttt caattataa caactaatta
10801 taaaatgatg atactccatt ggaagaacat aataaagaac atacctagaa ctgtgagtct
10861 gagataccat tcattgaaga atgtttgttt atagatttt aatttccttt tgtcactagt
10921 gaagacaaac agaaaatcag atgtttattt cacatttttt tttaaacaga gtcttgctct
10981 gtcacccagg ttagagtgca gtggcatgat catagctcac tgaagcctca aactcctggg
11041 ctcaagcaat cctcctgcct cagcctcctg agtagctagg atttaaaggc atgtgccact
11101 gcacccagca tttgttcata aattacagtg gctgtagcta attaattcac aaattaagct
11161 ggcttcaaat tagaattatg actctgcagg cttatatctg ctaatataca acacttgcac
11221 acatgcacat aaacgcatac atacacatat tccagtggtt tgaatattaa tgtctctctc
11281 gaattgtggc aaacagtggc aggttttcag taactagggt gaaatcattg catattctat
11341 aaaatagggt ccaagttaac tcaatcaagg catcaagtaa ggaagtcttt aaaattgcag
11401 attgcttatg gtcatgtatc tgtatctgct gtgttatcag agtggaatat atcatactta
11461 taaaaatgct taattctatg aaaccaacaa tttaacatac agtgtaacct taaggccata
11521 aaatccaaag atcaggaatg ctttgccgcc atagaacctg tttaggcaga atctcatgag
11581 caaattgagg ctggaataaa agctgaagtg ccaactacag aaaatcatga ttaaatctac
11641 agcaaggagt ctggggctaa aatccagtag ctaaaaggtg gctggactga cataaatatc
11701 tatctgagat cacttcaagg aagtgagaga gagaaatcag ggtcacccaag gtaaacttag
11761 gaggacatag ggtctagcca tattgatgca ttatattctg taagcctgaa gatttaaact
11821 gagcacacaa tctaatttcc tcgtactaat ttgccacttt ttccatgtct tgtactcata
11881 gaaatctatc tctttgagga attgtcccat agtaggactg aacatttacc tgatgaaact
11941 acttcatcca tgggagaagg acaaaaaaat gctagagttt tccaaactag gttaaaggtc
12001 caaagccaga aataccattt cactcttact ctgaaccaca taagtgtttg aaggtggatg
12061 gtgatagtgc atgaagagtt ggagaacgta aataatttat tccattacta cttccttctc
12121 ttgttttaaa aatttcatcc caaatgtctt caggcagtta agaagagtta gagaatgata
12181 caagagaata catgtttaaa tgcttaactc catagtattt gtacatctca actcttaaac
12241 atttttttaa atcattttta attattatta ttatttgaga tggcgtctcg ctgtgttgcc
12301 cagactggag tgcagtggtg caatctcagc tcactgcaaa cctgcctct tgggttcaag
12361 cgattctcct gcctcagcct cataagtagc tgggactaca ggtgcatgcc accacgccca
12421 gctactttttt gtatttttag tggagatggg gtttcaccat attggccagg ctggtctcga
12481 actcctaaca tctagtgatc tgcccacctcg acctcccaaa gttctggaat tacaggcatg
12541 agccaccatg cctggccttg ttttaattt ttgtgggtac atagtaggtg tatatattta
12601 tgggttacag gagatatttt gatacagaca tgcaatgtgt aatcatcaca ttagggtaaa
12661 tatggtatca gtaggtctca actttaatg attctgtgaa cttgtcatgc tgtatcccat
12721 ctctggttcc ttcttagatg gaaggaagga gggaaggggg catagcacct acagtttaaa
12781 ttgggcacct gtaatcatta tttggatctt gtcttacctg ctccagacca tttgcagaag
12841 aaggaaatga gatatagatt gtattacacc aaaaaagata tgaaagagcc atgtgacagc
12901 tggcagggag ggtctttgga attgtagtcc cttggaggga gcatcatgat gagggtgagg
12961 caggtcttta ttttgtaagt gtagattctc tgtggcatga ctttcactga agttcatcag
13021 gttctaagga acagatacta atcaaatttg caagatagat aagcgagaac accaacttgt
13081 tatttttaaaa aataggttcc cttagctggg aacaatgaac tgtatgtcaa ggagactctt
13141 cattggcaaa tcctctcaaa agtacaaatg atagatcagt ttgttttgtg agtgcagaat
13201 taaaacaaaa ggagtttggc attcttggaa aagatttcca agaacccacg gaagcctgag
13261 gcaatgtgat tcttctcttt agggctggtg atctgaagac catgtaggat caaggtgccc
13321 actttcctca aaaagagcca aaaaaaaagt ccaataaccc attcttggtt ttttagtgc
13381 ttctttctc tagagacctt gcagggcatg gcccttctgt gaatatgttg tttctagaaa
13441 cagcagtcat aatattgaag atgacaaatg tttacaatca gtcatgctca ttatggcttc
13501 ttgagtagct tctcagttct gttgatggat gcacactctc tccatagata tttacacgtt
13561 atcttagagg atcaatattg cagagattte aacacacttg ttgtgtatcc tcaaccccca
13621 ccaccacctt agttttatgt taaaagggtg gtgttactca ccatgcccac aaatgtggaa
13681 acatcttgct ttagcacctt aggcaactct ggtgtattgt cagaagcact ggcagagtct
13741 gttctctgta actaactagt tagataacct tgggaaagtc acttaacctc tgaattttcct
13801 actcatagaa gagaatattt tcctcactga tttggtgagg atcaaatatg ataatgcatg
13861 tgaagacact ttgtgaatgg tgaagtacaa tcattatctt ctaggatatt tagtcatttt
13921 ctcctcccag ttgtaaagca tctgtttttcc taatttttcaa ttcttctcc actccaacta
13981 attccccaat tttcaatttc ttctccattc caactccatt tccacaacta atgggtcat
14041 tttcttttat tcttgtttcttg tttattgact gtctatgcat gcttccttct gttcttgttc
14101 aattgctttg tacatattcc tctcttatga aaactccact gtggcttcag gctagatcta
14161 gtcattaatg cctttcacag tctgatctcc accttcctct gatcatattc cttcttctct
14221 tcttcactaa tctttcagcgc tagccagtgg tgtgatgtaa ctttaaacaa ttccttctct
```

FIG. 7S

```
14281 gaggtagaaa acaaaaagcc ctgacttatg gaatttgcca gttttcattg tgtcaatatt
14341 cccgccatga tcccaccagc ttcaagaatg gatctgttgg cagagtttga tagctcacgc
14401 ctgtaatccc agcactttgg gaggctgagt tgggaggacc atttgaggcc aggagttcga
14461 gaacagcctg ggcaacatgg tgaagccctg tctctactaa aaatacaaaa attagctggg
14521 cttggtggca cgcccctgta atcccagcta ctggggagct tgaggcagga gaatcacttg
14581 aacccaggag gcggaggttg cagtgagcca agatcatgcc actgcactcc agcctgggtg
14641 acagagcgag actccatctc aaaaaagggg gaaaaaaaga atggctgtgt ttaacagcca
14701 gctgtcccat tccctggaaa tttaacaatc tgttctcatg agcctgtgca ccactagctc
14761 cagcacacca ctggttttaa ccaatctaga atgagaactc acattgcctt gatctgtcac
14821 acacacttct gtctcagaat gagcctttgc tggttcaatg tccacttccc acaatgtctt
14881 ccaccatacc gcccttgaaa gaaattccta acagcttgag tttttggcag cttgtgtccc
14941 actccgtgaa acagaccagt tcagtttttt ttttctcaga cctcctagca cttacctgtt
15001 ctcttctctg atacactgat aaactgattt ctctctttat gtttagaatc cgctccattt
15061 caccattagc tctttagctt cttgagggaa ggatgtgatg tataactctc tggttcctga
15121 ttgtcttgca cataatcgaa ctcaatgaat tgctgctgct gattttgact ttccattaat
15181 ggttacattt gattgttgaa actaaaatct tgggccctcc tgaattgctc tagtcttcat
15241 tatgtagtaa atggctgtcc cctgcctggc ctacttgctg catcctccta aatcagaaat
15301 gatttgacta tacattatat ctaggatggt ttcaaaatga ttaatttgct tttaacttct
15361 atgttaagaa agctgactgt actttttcca cctttctttt aggtgctgaa agatgggcgt
15421 ttggtaaaca agaatggatc atctgggcct atactaacag tgtcactctt tgggaggtgg
15481 tacacaaagg actcacttta cagctcatgt gggaccagca attcagcaat aacttacctg
15541 ctaatattca tattattaat gatcatagct ttgcaaaata ttgtaatgtt atagggcgtc
15601 tctttatcac tcagcttctg catcatatgc ttggctgaat gtgtttatcg gcttcccaag
15661 tttactaaga aactttgaag ggctattcca gtagtataga ccagtgagtc ctaaatattt
15721 tttctcatca ataattattt tttaagtact atgtaaatgt tgtccatttt tttggctact
15781 ctgaaatgtt gcagtgtgga acaatggaaa gagcctgggt gtttgggtca gataaatgaa
15841 gatcaaactc cagctccagc ctcatttgct tgagactttg tgtgtatggg ggacttgtat
15901 gtatgggagt gaggagtttc aggccatttg caaacatagc tgtgcccttg aagagaatag
15961 taatgatggg aatttagagg tttatgactg aattcccttt gacattaaag actatttgaa
16021 ttcacctagt ttctgtgctt aatgtttatc aggagattta cttcccaatc aaaaggcaat
16081 gtcgacattt atttctacag tgaacgtagt tttgagtgct agaagaattg atggctattc
16141 caagttcata tcaaaggaga cctgacccag ggcactcata gcccagcttg tcccacctta
16201 aggctatggc gtaatttaac aggcagaaat ctcatacaac aaagaccatg acagttaaaa
16261 gttacactat tttcagcatt tggttgactt tttacaaaat acacatattc catgctactt
16321 gaagtaaact agtatatttg ttattgatca tttaattcag atactcttaa aattaaagaa
16381 ctgattttga attttcagat ttattttctg atttttatct cccaaagtat ttttaagttc
16441 aatactttta catataaaaa cacaattgaa gcatttatct ttgtttttta catattgtca
16501 taaacctact tatggatttg atttcaaaat tctacaaaaa tacactagaa aagtaagatt
16561 ccttttataa tctcgtggtt agtattaaga gaagaaatat ggaagttaag ccacactttg
16621 tatttaattt tgagaagagc atacatattc cctatgttca gcattgggac atcaaagatg
16681 gcaatcttaa agctgtaatg aacgtgcatt tgtgtatata gtccaaatca tataatcatc
16741 aaagttttat gctctttttt ctttttcttt ttcttttttt ttttttgaga cagagtctca
16801 ctctgtcacc caagctggag tgcaatggtg ggagttcagc tcattgcaac ctccgcctcc
16861 tgggttcaag tgcttctcct gcctcaacct cccaagtagc tggaattaca ggcacccacc
16921 accatgcccg gctaattttt gtatttttag tagagatgga gtttcgccat gttggccagg
16981 ctggtctcga actcctgacc aggtgatcca cccactttgg cctcccgatg tgctgggatt
17041 acaggcatga gccaccatgc ctggcttctt tttccttttc ataaagtatg ggacatttaa
17101 aatttgccaa gttttgcttg aggaagttag atgttgtgca gtggttttgc agcatgtatt
17161 ttggctctgg ggcaatgaag tttcatttgc agaagtttag atgttgattg aaaatcaaca
17221 gctgacgtta aacaaactgg tttgagtaag atacaagcaa ggagctcctt tcacagaaag
17281 ggacagttct gattcaagct tggagctctc agctgtacct cagtttgtta aaaataaaaa
17341 caaaaaacga aagcaccaag tgccaaggaa attaaagagc acttaatgct ctactgtaaa
17401 attgcctgca ccacatttta acccatctcc acagtggttt ctcacataca ttttatttta
17461 tcaaacaacc caagcatagt ttcatttggc ctttatattt ctttgataac tatctttcat
17521 ccccatttat ttttatttta cttatttatt tatttatttt ttgagataga gtctcgctct
17581 gttgcccagg ctggagtgca gtggtgcgat ctcggctcac ttcaagctcc gcctcccggg
17641 ttcacgccat tctcctgcct cagcctcctg agtagctggg actacaggcg cccgccacca
17701 cgcctggcta atttttgtat ttttagtag agacggggtt tcaccatgtt agccaggatg
17761 gtctcgaact cctgacctca tgatccgccc acctcggcct cccaaagtgc tgggattaca
17821 ggcgtgagcc accgcgcccg gcctcatccc atttctaaat ttcatgttag ttcttgagtc
17881 ccttgtggtt ctggagatag taaacaaagc tcttattttc tcctatttgg ccttcattag
17941 gcttttttcc tgaaatgctc ttttacaact tcctggttac agccccctgt attacaaagt
18001 cacatgctca gcagcagcct tct
```

FIG. 7T

Homo sapiens vanin 3 (VNN3) gene, complete cds (SEQ ID NO:19)

gi|77022115|gb|DQ220706.1|[77022115]

Coding Sequence = join (1814..2026,2123..2253,7573..7765,9494..9781)

```
   1 cgccttatac acctaggaag caaagacatt actaacaaca ttgggtaatc aaatatttaa
  61 ctcaagtttc tattgatttc aacacacaaa aaaagctggt acatttcctg gaactagggg
 121 ctgggagaat gaaggggaat tcccatatgt ttccttttga ttctattcag aaagtcaggt
 181 gaaccaagaa aagagttaga atttcaactt gaaatatgaa aattattttc ttctcatccc
 241 agatcaatcc atctgtttta catagtttcc ctcttctcct cagaaatttt tttggaaaag
 301 aacttatgtc tgatgtctga tgaaaacaat ttatgtcaga cataaactca gaatttaggg
 361 ctgaatttat gttcatatgt ccttatttcc tgaaatggta tcagggcata aggacatatg
 421 gaaacactgt ggggtatctg ggagcagaaa tatttggata atggaaaagt ttattgaaac
 481 caagggactt tgaattatag aaacaaacca aacccaaaat agacacaaat ctccataact
 541 tacaattttc cttagatctt agaaagaatc tcaagaggga gaagcagtgt taattgttct
 601 agaatcagag atttaaacct taaaaaatat tctacatttt aaattaactg atattcaaac
 661 aaggagattc aatccaaaat tgggcgaggg aagtgaattt aactaatcaa aaaacattta
 721 cagagcttag cacagtataa aattctatag aagcagcaga gaattataat gtgaccctgc
 781 ccttaaggga cttataagga tgatatgttt aaaaaataaa agaattaaag gagaacttaa
 841 cactttttga attattgatt agtcttcata tggaagcggg tttaaactgt agaagacagg
 901 taaagtaaat tgcatctcaa taacaagaat gttcttaaaa ttggcaatgt tcaaaggtgg
 961 aatagactgg cccatcaggt agtagattcc gtcattcaac attcattcat atattgagct
1021 ttcaccatct gtcacacatg tgctggggtg atgaggttca acagtgagca ggacacttcc
1081 cttaccctcc aggggcaaca tcccaggata catcatctct gtctagatgt ttattggaca
1141 tggatgttct gaaagaaaac agcaagtttc tctttaatct ctttaagaag acaaaacata
1201 catatataat attaagtatt ggtataatac ttaaattaaa ggtcaagaca acagcaagga
1261 gtgagagaca ttcagcagca cagaaaaaaa tgctatagga gttcagaaat atcacttagg
1321 actggagtgg atttgggagg actctagggg gagctggaac ttagacggat ggagaacaag
1381 ggctttcaa atagaaatgg ccatacaaat atgtaagtag agtgctcaac aaactgttgc
1441 tatgatgact accttccaat attggcccta ttaatagaaa tgttggctta ccaggaaaat
1501 tttttttat tagaaaagac ttcaactgcc agtgtgtttt ggactggggt gaattcatct
1561 ggttggctca atcttttagt gttgacttga ctctgaacaa tgtcaacaac tgcactgtac
1621 acttgaatca atccaattac gtcctggctg tcagttttct tgcacaacat cctttctcaa
1681 tgctgtgttg tgtaatatat gtgcaagaaa atataaacag ctgattgcca ggagggattt
1741 aatgtaaagt ttttccagtg aaacaaaacg taagaatctg agtttgtttt tcaaagatca
1801 ctaaatttta gttatgatta tatcacattt tccaaaatgt gtggcagttt ttgccctcct
1861 tgctctgagt gttggtgcac tggacacttt tattgctgca gtatatgagc atgcggtgat
1921 attaccaaac agaacagaaa caccctgttc aaaagaagaa gctttgctcc tgatgaacaa
1981 gaacatagat gtttgggaga aagcagttaa gctggcagcg aagcaggtat taccatttta
2041 cacttgtaaa ggagacttgc agtttggtca aagagtattt ggaattcatg acaaactttt
2101 ttgccccact tgtttcgagc agggtgcaca tatcatgtgg accccagaag atggaatcta
2161 tggttggatc ttcaccaggg agagcattta cccctatcta gaggatatac cagaccctgg
2221 agtgaactgg attccatgta gagatccctg gaggtaatat catatcatta atttctaaac
2281 aaaaagttgt gatttggtaa aacaccaaca gtaaactcac tgaatttgac tggtaattgt
2341 gttgataaat agtcaatctg tggcatagga tgtagatgct ttttttcccc tgtaattcaa
2401 acttttagtt tagattgagg gagtacatgt gcaggtttgt tacatgggca aattgcatga
2461 cgctgaggat tgggttacaa tgattgcacc acccagcata gtatacaaca ggaaggtttt
2521 cagcccttgc cctcctctct ctctctcccc tctattagtt cccagtgtct attgctgtca
2581 tctttatggc catgagttcc caatgcttag ctcccactta taagtgagaa catgcagtat
2641 ttggttttct gttcctgtgt taacttgctg aggataatgt cctttggtgc tgcaaaagac
2701 atgattttgt tccttcttgt gggcacctag gttaattcca tatcttgcct gttgtgaaaa
2761 gtgctgcgat gaacatacaa gtgcacgagt ctttttggta gaatgatttc ctttcctttg
2821 ggtatatacc tagtaatggg attgtgagtc gaatggttgc tgtgttttaa gttctctgag
2881 aaatctccaa actgctttcc acaatggctg aactaattta catttccaac aatagtgtgt
2941 aagtgttccc cttttctcat agcatctttt attatttgac ttttagttaa cagtcattct
3001 gactggtgtg agatgatatc tcattgtggt tttgctttgc atttctctga tgataagtga
3061 tgttgagtgt ttgttcacgt gtttttggc cacttgtatg tcctcttttg agaagtgtct
3121 gttcatgtct tttgcccact ttttaatggg gttatttgtt ttgtttttgc ttattgattt
3181 aagttcctta tggattctag atagtagacc tttgttagat gcctagtttg caaatatttt
3241 ctcccattct gtaggttgtc tatttactct gttgatagtt gctttgcctg tacagagctc
3301 tttagttaaa ttaggtccca catgtcaagt tttgtttttg ttgcaattgc ttttgaggac
3361 ttagtcataa attattttcc aaggttcatg tccagaatgg tgctttctag attttcttct
3421 aggattctta tagtttgagg tcatacattt aaatctttaa tccatcctga gttaattttt
3481 gtacatggtg aaagataggg gtccagtttc aatctcctgc atatggctag ccagatattc
```

FIG. 7U

```
3541 cagcaccttt tgttgaataa ggagtccttt ccccatactt atttttgtga actttgcttg
3601 agctacagat ggctgtaggt gtgcggcttt gtttctaggc tctctattct gttctattgg
3661 tctatgtgtc tgttttttcta acagtaccat gttgttttga ttactgtagc cttgggtaat
3721 gtgatgcctc aggctttgct ctttttgttt aggattggtt tggcgattca ggctcttttt
3781 tggttccata tgaattttag aatttttgtt tataatctcg tgaaaaaatg acattggtag
3841 tttgttagaa atagtgttga ggctgggtgc tgtggctcat gcctataatc ccagcacttt
3901 gggaggccaa ggcaggtgga ttacttgaga ttaggagttt gagaccagcc tggccaacgt
3961 ggtaaaaccc catctctacc aaaatacaaa aattagctgg gtgtggtggt gtgtgcctgt
4021 aatcccagct actcgggagg ctaaggcatg agaattgctt gaacgataga gtgagactct
4081 gtctcaaaaa aaaaaaaaaa aaaaaaagaa gaaaagaaat agtgttgaat ctgcagatac
4141 tgcttatgtt tcatagtgta tatcatctgg catatctcct gtttggtaaa tgacttgaga
4201 tactgatgac tagttggtta tttgttgcaa ttgtctttca acaatagtag gtgtgaccag
4261 gcgtggtggc tcacacttgt aatcccatca ctgtgggaag ccaaagcagg aggactgctt
4321 gaagccagaa gtttgagacc agcctgcgca gcaaagccag accctatttc ggcaaataaa
4381 aaatttagcc aggtgtggtg gctcacacct ataatcccag ctactcgaga ggctgaagca
4441 ggaggatcac tggggccaag gagtttgagg ctgcagtgag ctatgattgc accactgcac
4501 tccagcctgg gtgacagtaa gaccttgtct caaaaaaata gtaggtatag gccgggtgtg
4561 gtggctcacg cctgtaatcc cggaacttta ggaggtggag gtgggcaaat cacctgaggt
4621 caggagttcg agaccagcct ggccaacatg gtgaaacccc atctctacta aaaatacaaa
4681 acattagctg ggtgtggttg tgcatgccta taatcccagc tactcgggag actgaggcag
4741 gagaactact tgaacccagg aggcagaggt tgcagtgagc cgagatcacg ccactgcact
4801 ccagcctggg caacagagtg agactccatc tcgaaaaaaa aatagtaggt atatacacaa
4861 tttttatagt aaatgtgttt aattgggttt gaacaaagtg aaaaagttgg aatatctaga
4921 acctgtgtcc caaataccag taagttggtt catccatgga cacctgcctc cttcacagga
4981 agagtaaaaa gatgaatgag cctgtttcca aagagctttg ctatcactat cattcagaat
5041 gcaatcaata tggccaatgg aaattgtata ggacttgaaa aaggaagccc tacttctggg
5101 accacatttt acgaccacct agctgagtga tgtaagcgta taacctaaat gcttaacatt
5161 tctgtttcat tatctgtaaa acaggataa tagagtccct taatttctt acagatcaga
5221 caagagtaat gaagtaatac acatggaatt tgtacattgt aatgcactct ccaatgctag
5281 ctgtcactat tccttttttt ttttgttaa cagaagggac tgagtctgaa cttctttgtg
5341 ttcttgtcct ttgagagact ttagtaatta ttagtagatg taatttaggc ataacttct
5401 taaagaaaat atgcataata aatatgatat ctgtgaaata gattatttta gttgtattaa
5461 ctttaaaaaa tagtttaaga ttatttcttt aaatggcaaa attgatgggt taagaagtca
5521 tttaacttgc taattttaaa tttacatgca cctgtttaga actacaccta ttgtgcaaaa
5581 agagaaactt ctttgataat tttacctatg tgaaattaag tggaaagtca tgcttaatgg
5641 tacaacattc aggctcagct atgtgagtca aacctcactc tgggatttg cctttggaa
5701 aaatattctc taaacattgc atggtctgtg tttacagaaa ccatgtcact atgattcaac
5761 atctacttgc ttatgaggcg tttcccagaa caggaaggaa tcattatttg ctgcagttga
5821 tgaggcttac acgaaaatgt actgtatttg actgggctaa tgaaactgac tttttcaggg
5881 aaaagatatc cataaatttg ataattagct atcgataaat tattttaagt tgggaaagta
5941 ggtgactgat gaaatgtcaa cattatgaac tctttacacct acttattcaa atgacaacct
6001 ttcagttttg tgttacaaaa aggagaaatc cagtatttaa tatastgata atattggaaa
6061 agaaagtcag tttctccct ggtgatattt atccctgaag agaatagtag agaggcatgc
6121 ggtcatcctt gtgcatttaa atatttagaa tgctgacatg tcaaacagtt ccatgggctt
6181 tttttcatgag taactagtag gaaatattaa ataactcaaa ttatttagtc aagaaaagaa
6241 aaattaaaca aagtacatga taaagttatt aaaggtctta atgaatatga atattaatag
6301 tacttctctg tttttttag aagaaaataa aaagaaaagg tctaaaccag taggccatta
6361 atctgtcctt tttatttcaaa ggttagttta acctcaattg cagaggggct gtgagttcat
6421 agagagacat ggaatggcct ctaatcacac aatccataat agcaattttc atttactgag
6481 cacttacttg gtccccagaa ctgtacctgg tatactatac ccattattac atttcaattta
6541 tgtagttggc attactattt gcattacaaa tatgtgaaaa aaggaaggct tatgatctca
6601 tgattgatca ttagattggc tggaattaaa acagctatgt cattaactg tgctaacgga
6661 atggactcta agggcctaga tgaaccatat tataataaaa ttttagtga ctagcaaatc
6721 cacttattta acagagtgag ctggttgcta aacattttt gtcttatttt ctgctgaaat
6781 ctgcctcact ttaacttcct ttcgtctttt tcctgcattc tatgctatgt tcacacatat
6841 gaccccatctc ctataaatta agcctttcaa atatttgaag ccagcatatca ccatgctaca
6901 ttctcttctt atacaagga taaatatcct taatatggat ggacttggta aaacaatttc
6961 atgtctgtac ttatcccagg atttctcatg tggatccact aaggcagaaa ggaagctatt
7021 gtttacactt tgacagatga agaaactgag tcagtacagt gaagtgcttt ttattttta
7081 ttttaatttc taacattcc actacttaca gctatatttg tttttttata gagacaatct
7141 ggagggtaca aactatttac tgtcacctgg catttctgtt tccaaccaca tctgtatca
7201 gcaaccttgt acaaattatg gcttggatta tagaaaaggt cctctccatt agcagaatct
7261 gctaaatttc aagtgcttca tatatcttcc tgggagcact tcataagaga atgtgctgct
```

FIG. 7V

```
7321 tcttttcatc ctcctcttcc tcttccatct ttcttttcct tcagtcttgt actgtaatct
7381 ggagtttggc atagtaaatt aggttagctt tcaggaagat aaacactgta tcacatgaga
7441 gttttaaaat attttctgtt gattcttgac ctagagctgt tgtgttatgg gcaatgggca
7501 aataaagtat cactttggta tttcagaaat cactaaaata tagtaagttt gaggaaatgt
7561 ctattgaatt agattgggca acacatcagt gcaacaaaga ctcagctgcc tggccaagga
7621 caacctctac tatgtcgtgg ctaatattgg gggacaagag ccatgcaatg ccagtgactc
7681 tcagtgtccc cctgatggcc gttaccaata caacactgat gtggtgtttg attctcaggg
7741 aaaactgttg gcacgctacc ataaggtgag catcacttgt gccttagctc aacttgttac
7801 ttcttctgtg tgcttgtggt atgtatgtgt gtttgtttgt tgaatgttgg ggagagaact
7861 gttatagatg catcttatca ttattacatc atagttgaaa aggagattta attcagttcc
7921 atataacogt tctgggtttg catttatcat aaaacagaat atggtagagt atttaaatgg
7981 atgtgacaat agccacacaa agctttaaat gttctctgaa aaagaagtaa acattctgtt
8041 tcattcatga tttaatatca ggttcatttt ttagcccaat ttgttagcat ttcatactaa
8101 gctaccatgt attccattag gacttttttg attgcaatga aacaaaaacc tcaaatgaaa
8161 atggctttaa aaagatggaa atttccttgc ttatgcacat gtaaaaatgt gtatcataga
8221 aaggacaggt ctcatttcag tgcagtctga cactcagagg ctccaaagtt atcatcccac
8281 cctctagctc tcctagccct ttgttacagc ttctttctca gggaactct cctttagaa
8341 gccacattgc tggagcaaca cgaaattcac atctttatca acaaaatcta caggaagggt
8401 gtatttctcc ctcctagaac cttgcaaagg ccttatcgct cctgattca attaggtgac
8461 gtgcctttcc tgagctaatc accaaaggat gagggatagg ctgccacatg ggaggagaaa
8521 ggaggagcaa gaggcctcca tggaccacag aggtgggaag tagctctccc caggagcacac
8581 acatgcacac aacaggccaa acaaaaacct gagcaaaaca tatgctgtac tcctgagccc
8641 aggttaagtg gagtttggca aaaagaatca ggctgaaaaa taaaataaaa ttatgaatgg
8701 cttactaatt aataatatgt agcaactgca ttgtctaaat taatttcaa tggacttcac
8761 ttctataaac ctggcagtat cattgggaca catgacaaag tttatttat taacatagta
8821 gtgctgttga aatttaaaga atatagtgga aaacaatctg agaagtgtag gatttcagat
8881 ttcaacctgt gatttaaaga tacacatttt cacattttaa atatcatttg tacatgtggt
8941 ttcattcatt ggttgtaaaa aaaataaagt tttttattta atgtcacagt aagaaaatgt
9001 atagatggtg gtatagtggg gatgattttt acaaatgtat gtgtaacagt tttatttgt
9061 tgttgttgtt gattttggaa atggaatctt gctctgttgc ccaggctgga gtgcagtggc
9121 gcgatctcgg ctcactgcaa cctcggcctc ctgggttcag gggctcccc tgcctcagcc
9181 tatgagtagc tgggattaca ggcatatgcc atcatgcctg gctaattttt tttgatattt
9241 gtagtagaga cagggtttta ccacattggc caggctggtc tcgaactcct gacctcaagt
9301 gatccacccg cctcagcctc ctaacatgct gggattacag gcgtaagcca ccacacctgg
9361 cctatgtgta acactttaa acctgcatgt caacatacat gagaggaaag atttaacggg
9421 gaaagactta attgatcaca tctatttggc agtttttctta ttaattttct tcttctttgc
9481 tttttattaa cagtacaatc ttttgcacc tgaaattcag tttgatttcc ccaaggattc
9541 agaacttgtg actttgaca ctcccttgg gaagtttggc atttttactt gctttgacat
9601 tttttctcat gacccagctg tggtggtggt ggatgagttt caattgacag cattctctac
9661 cccacagcat ggtacaacac gctgccctc ctctcggctg ttcccttcca ttcagcatgg
9721 gccaaggcca tgggagtcaa tctacttgct gcaaataccc acaacaccag catgcacatg
9781 acaggtaact cacgcgggcc tgcaccaagt gggagtgaca gtcttaggaa ggcttcattg
9841 atttccaagc cacaaacttt tgtttaataa ctttattacc aatttaaca tcacaaatt
9901 aataatagca ttgtttccta cttaaggaac gttcattgtc cttgtgaata aaagaggcaa
9961 acattattat ctcaatttta cttgaaagga aattggagct ggaggaagtc atgtaaaaaa
10021 atcaaagaga gttctaagaa acttcctagc caatgtgcat tagtaatatc gaaatcagtc
10081 tggttgttta aagagataac ctacagagca gaagaaaata tttgcaaact atgcatttca
10141 taaaaatcta atatctagaa tccataagga acttaaacaa atcaacaaac aaaaaacaaa
10201 ctatccccatt aaaaaatgga caaaggacat gaacagacac ttctcaaaag aagacataca
10261 tgtggccaac aagcatgtaa aaatgcttaa catcactaat cattacagaa atgcaaatca
10321 aaaccacaat gagataccac ctcgctccag tcagaatggc tatgattaaa aaataaaaaa
10381 caaacagatg ctggcgaggt tgtgaagaaa aaggaaacac ctatacactg ctggtgaaaa
10441 tgtaaattag ttcagccaca gtggaaagca gtttggcgat ttctcagaga acttaaaaca
10501 gaactgccat tcgactcagc aatcccatta ataggtatat acccagaagga atataaatca
10561 ttctaccata aagacacatg cacttgtatg ttaatrgcag cagtttagc aatagcaata
10621 acgtggaatc aacccaggtg ctcatcaacg gtgaagtgga taaagaaaat gtgatacata
10681 tacaccatag aatactacat agccataaca aagaatgaaa taatgtcctt tgcaacaaga
10741 tggatgcaac tggaggtcat tatcctcagc gaatgaacac aggaacagaa aatcaaatac
10801 ctcgtgttct cacgagttga agttaaacat tgagtacaca tgaacacaaa gaggggaaca
10861 atagacacca gggtttactt gaggggggat ggtgggagga gggtgaggat tgaaaaacta
10921 cctattggat actgtgctca ctacctgggt gacaaaatcg tttgcacacc aaaccccagc
10981 aacatgcaat ttacccatgt aacaaacctt cacacgttcc cctctatac ctaaaataac
11041 agttggaaga aaaaaataca aacaaataaa aatatttcaa gcattaaaaa aaaacttgtt
```

FIG. 7W

```
11101 gaagtgataa aaatctcttt tgacttaatc aggtttttag agtttctcct ttatcatatc
11161 catgttcaaa gtaatgcagg cttcctttt aactgttctg ttatttgttg aataacaaat
11221 ccccaaacaca aataaactaa atcgtcagtg gagagctaaa attattcttc acgttggggg
11281 atttttctagt ttgttgctaa gttagcttaa aactatgccc cccaagtcaa atgataattt
11341 cagtgcaagt agtaccttat ggaggacaca gagtcaaatt ggaacttagg ccaatgtaac
11401 agctatctcc ttaactatct tgaaaatatg ctttaataac tttgtattta acttcacatg
11461 ggaatattct attagttggt caccataaca aatctgaaac caatgtttgt atttatgttg
11521 cttgtaggga gtggaatcta cgccccagaa gcagtcaagg tgtaccacta tgacatggaa
11581 acagagagtg gtcagctgtt gctatcagaa ctgaagtctc ggccccgccg tgagccccacc
11641 taccctgcag ctgttgactg gcatgcgtat gccagccagtg tcaagccatt ttcctctgaa
11701 cagtcagatt ttctggggat gatttatttt gatgagttta ccttcaccaa gcttaagaga
11761 aatacaggaa attacacagc ttgccagaaa gatctgtgtt gtcacttaac ttacaagatg
11821 tctgagaagc gaacagacga gatcctatgcc ctaggtgctt ttgatggact gcacacagta
11881 gaaggccaat attacttaca ggtagaaatg ctttaatatg ttaaagtggc cttattatca
11941 gtttttcttc taggtcatca ttgcctttct ttgaaaattg ggctggattt agctaatttt
12001 ataattagta atgttatatt tatctctgaa ttttgtcccc agaaacacatt atttgttcag
12061 tctttagcaag aacagaatta gttctttttag ttgaaaggca aaaacataaa gcaaattgat
12121 tagttctcag caggccaggt tcaggtttca aaagctgcaa tttctgtgta ttcctctttc
12181 ccgtcaggtt actttagagc agtgttttc aaattgtctt caactaaatc cagagaaaga
12241 aggatatttt acctcataac ccagtgtagc caagtggatg tgtgactgaa taaaaaaaaa
12301 gatattttaat tgaaatagtt tatgaaataa tttaaaatag aattagaaat agctattatt
12361 atgtgcaatg cactctgatt tttaaaatcc tagtctattc tatttgactt cagtataaaa
12421 agtgttaatc ctgacccact atattgattt taggattcat taatcagttg ttacctgcag
12481 tttgaaaaat actttcttatg aggcaattta aatatgcatt tatagtttga aattgcatta
12541 tttagctgag aaaatatttg caagtttttct gactccttct cttttctttt cttccataga
12601 tatgtgcatt actgaagtgt caaacccactg acctggaaac gtgtggagaa cctgtggggt
12661 cagcttttac caagtttgaa gacttctccc tcagtggcac atttggaacg cgttatgttt
12721 tccccacagat cattctaagt gggagtcagc ttgcccctga aagacattat gaggtaggag
12781 gtgtgcagga tgataaattc ctttgagcag agtagatggg tagagcagca taatgaaaat
12841 ctttgaaata atgagagtat agcaatatcg tggttcacat tctacaagaa acaccttaaa
12901 tatgtggaaa ctatgatatg gaatataaat tgtggtttta gattgccatt aggctgtgat
12961 ggagaatttg gggttccattt ttttaacata aatgtgatgt tgatattcaa ggcaacagga
13021 aattcacaga gaagctaaaa taaaaatgtt gactgctgat aatggcaata atgttgtcat
13081 ttgcatggtg tagaaggtgc aaattaaata cattaaataa tgcatctaca acttattttc
13141 tgggtatact atttgagaa gttgttataa tttatagtaat aactaatatt ttgtatagtg
13201 tttcatgagt ttgaagaaca tatttttata catattatct gaccacctgt gcaacaaatt
13261 tgttggctgc actttcgcac aaagtccctc tactttcaga cttgaaacat gaacctggt
13321 cttccaacac caaatcctgt gtgatttttta ccattctaca ctgctttagg agggagtgat
13381 cttgcctgag aagggctcta ggttgtaacc taaactctgc actgaagtta accctttgct
13441 ttctttgacc agatttcaag agatggacgc ttgaggagcc gaagtggagc cccttttgcct
13501 gtccttagtta tggccctgta tggaagagtg tttgagaagg accctccaag cttagggcag
13561 ggatctggga aattccagtg atctccttta gcagagccct tttaggatta gcctggctaa
13621 gaaaggaaga aaaaaaagag atccgttagt gtctgtttag aaaagatgtt ataaacttac
13681 agaaacaaat ataataaact gaagcagatt tgaaaagcaa caagtgtgtg tgcaaatttc
13741 acatttttaca tgtttggtat agcacaggtt catttatggg agccgcattc atcctccatg
13801 tatgtgagtt taagtatatg taagtatgta tatgtatagt ggagcgtata tttaaatagg
13861 aggaggtcct agaaaaatcc ttttgcagta actgcactaa tgtatgcaag tgttgtttcc
13921 atcatatgat ggttaatttt atgtgttgat ttgactgggt catgagatgc ccagatagct
13981 ggttaaccat tgtttctggg tgtgtctgtg agggtgtttc aaggaagaga acagcatttg
14041 aattggtgga ctgagtaaag cagacggtcc tccccagtgt ggatggtcat cgtccagtcc
14101 cttgagggcc tgcagagaaa aacaagaagg aggaggtttg aattcatttt ctgccagact
14161 acttgagctg gatagagatc ttctcctgcc ttcatgtgct cctggttctc aggcctcag
14221 gcctggactg gaattgacac catcaactct tcagctctca ggccttcgaa tgacaccccct
14281 ggctttcctg catctccagc ttgcaaatgg cagaccagac tgtgggattt ctcagccttc
14341 ataactgtct gagccaatac cttatcataa atcctcttct ctctcctct cctgttggtt
14401 ctctttctct gggagaaccct gactaatgca cttcatttgt aaatacatag gatgaacttt
14461 gaatatgcag agggtatttg attccagcca actaagatac aggaaattaa agaataagga
14521 catctttttaa agtaactatg aacaactttt tagctagtat tgtcccttta gtcatgacta
14581 atttgactcc taagttctat ttatatggaa attgga
```

FIG. 7X

Mus musculus vanin 1 (Vnn1), amino acid sequence (NP_ 035834.1) (SEQ ID NO:2)

```
  1 mqtswvlaca afsalcvlk assldtflaa vyehavilpk dtllpvshge alalmnqnld
 61 llegaivsas kqgahiivtp edgiygvrft rdtiypylee ipdpqvnwip cdnpkrfgst
121 pvqerlscla knnsiyvvan mgdkkpcnts dshcppdgrf qyntdvvfds qgklvaryhk
181 qnifmgedqf nvpmepefvt fdtpfgkfgv ftcfdilfhd pavtlvtefq vdtilfptaw
241 mdvlphlaai efhsawamgm gvnflasnlh npsrrmtgsg iyapdsprvf hydrktqegk
301 llfaqlkshp ihspvnwtsy assvestptk tqefqsivff deftfvelkg ikgnytvcqn
361 dlcchlsyqm sekradevya fgafdglhtv egqyylqicl llkckttnlr tcgssvdtaf
421 trfemfslsg tfgtryvfpe vllsevklap gefqvssdgr lvslkptsgp vltiglfgrl
481 ygkdwasnas sdfiahslil mlivtpilhy lc
```

Mus musculus vanin 3 (Vnn3), amino acid sequence (NP_ 036109.2) (SEQ ID NO:4)

```
  1 maslhfpqwa vsfvffaqav gqmdtflaav yehavilpnk tespvsteea llinknldil
 61 lesaikklasr qgahiivtpe dgiygwiftr etiypyledi pdpevnwipc rdprrfgytp
121 vqerlsclak ensiyimanl gdkkpcnstd phcppdgryq yntnvvfdsk grltaryhky
181 nlfepeiqfd fpkdselvtf dtpfgkfglf tcfdifsydp avvvvkdrqv dsvllptawy
241 ntlpllsavp fhsvwaramg vnvlasnthn tsmhmtgsgl yspeavrvyh ydmetesgql
301 llselrsrpr qhatpsevnw saystvkpf seggadfpgk iyfdefsftk ltgsagnytv
361 cqkdlcchlt ykmseerwde vyvlgafdgl htgegqyylq icsllkcqtt nsrtcgspvg
421 saftkfeefs lsgtfrtkyv fpqivlsgsq lsleryyevs rdgrlrsrgg aplpilvmal
481 ygrvferdpp rlgqgpgklq
```

Homo sapiens vanin 1 (VNN1), amino acid sequence (NP_004657.1) (SEQ ID NO:6)

```
  1 mttqlpayva lllfyvsras cqdtflaavy ehaailpnat ltpvsreeal almnrnldil
 61 egaitsaadq gahiivtped aiygwnford slypyledip dpevnwipcn nrnrfgqtpv
121 qerlsclakn nslyvvanig dkkpcdtsdp qcppdgryqy ntdvvfdsqg klvaryhkqn
181 lfmgenqfnv pkepeivtfn ttfgsfglft cfdilfhdpa vtlvkdfhvd tivfptawmn
241 vlphlsavef hsawamgmrv nflasnihyp skkmtgsgly apnssraihy dmktesgkll
301 lsqldshpsh savvnwtsya sslealssgn kefkgtvffd eftfvkltgv agnytvcqkd
361 lcchlsykms enipnevyal gafdglhtve grayylqicl lkckttnlnt cgdsaetasr
421 rfemfslsgt fgtqyvfpev llsenqlapg efqvstdgrl fslkptsgpv ltvtlfgrly
481 ekdwasnass gltaqarlim llviapivcs lsw
```

Homo sapiens vanin 2 (VNN2), isoform 1, amino acid sequence (NP_004656.2) (SEQ ID NO:8)

```
  1 mvtssfpisv avfallitlqv gtqdsflaav yehavilpnk tetpvsqeda lnlmnenidi
 61 letaikqaae qgarilvtpe dalygwkftr etvfpyledi pdpqvnwipc qdphrfghtp
121 vqarlsclak dnslyvlanl gdkkpcnsrd stcppngyfq ynthvvyntq gklvaryhky
181 hlysepqfnv pekpelvtfn tafgrfglft cfdiffydpg vtlvkdfhvd tllfptawmn
241 vlpllltaief hsawamgmgv nllvanthhv slnmtgsgly apngpkvyhy dmktelgkll
301 lsevdshpls slayptavnw nayattikpf pvqkntfrgf isrdgfnftе lfenagnltv
361 cqkelcchls yrmlqkeene vyvlgaftgl hgrrrreywq vctmlkcktt nlttcgrpve
421 tastrfemfs lsgtfgtsyv fpevllteih lspgkfevlk dgrlvnkngs sgpiltvslf
481 grwytkdsly sscgtsnsai tylllfillm liialqnivml
```

Homo sapiens vanin 2 (VNN2), isoform 2, amino acid sequence (NP_511043) (SEQ ID NO:10)

```
  1 mnenidilet aikqaaeqga rilvtpedal ygwkftretv fpyledipdp qvnwipcqdp
 61 hrfghtpvqa rlsclakdns lyvlanlgdk kpcnsrdstc ppngyfqynt nvvyntqgkl
121 varyhkyhly sepqfnvpek pelvtfntaf grfglftcfd iffydpgvtl vkdfhvdtll
181 fptawmnvlp lltaiefhsa wamgmgvnll vanthhvsln mtgsglyapn gpkvyhydmk
241 telgkllise vdshplssla yptavnwnay attikpfpvq kntfrgflsr dgfnftelfe
301 nagnltvcqk elcchlsyrm lqkeenevyv lgaftglhgr rrreywqvct mlkckttnlt
361 tcgrpvetas trfemfslsg tfgtsyvfpe vllteihlsp gkfevlkdgr lvnkngssgp
421 iltvslfgrw ytkdslyssc gtsnsaitylllfillmlia lqnivml
```

FIG. 7Y

Homo sapiens vanin 3 (VNN3), isoform 1, amino acid sequence (NP_060869) (SEQ ID NO:12)

```
      1 miishfpkcv avfallalsv qaldtfiaav yehavilpnr tetpvskeea illmnknidv
     61 lekavklaak qqahiivtpe dgiyqwiftr esiypyledi pdpgvnwipc rdpwrfgntp
    121 vqqrlsclak dnsiyvvani gdkkpcnasd sqcppdgryq yntdvvfdsq gkliaryhky
    181 nlfapeiqfd fpkdselvtf dtpfgkfgif tcfdifshdp avvvvdefqi tafatpqhgt
    241 vrcpasrlfp siqhgqrpwe siyllqiptt pact
```

Homo sapiens vanin 3 (VNN3), isoform 2, amino acid sequence (NP_ 523239.1) (SEQ ID NO:14)

```
      1 miishfpkcv avfallalsv qaldtfiaav yehavilpnr tetpvskeea illmnknidv
     61 lekavklaak qqahiivtpe dgiyqwiftr esiypyledi pdpgvnwipc rdpwrkskkm
    121 nepvskelcy hchsecnqyg qwklyrt
```

Homo sapiens vanin 3 (VNN3), isoform 3, amino acid sequence (NP_ 001019631) (SEQ ID NO:16)

```
      1 miishfpkcv avfallalsv qaldtfiaav yehavilpnr tetpvskeea illmnknidv
     61 lekavklaak qqahiivtpe dgiyqwiftr esiypyledi pdpgvnwipc rdpwrnh
```

FIG. 7Z

COMBINATION THERAPY AND USES THEREOF FOR TREATMENT AND PREVENTION OF PARASITIC INFECTION AND DISEASE

CROSS REFERENCE TO RELATED APPLICATIONS

This application claims the benefit of U.S. provisional application Ser. No. 61/394,958, filed on Oct. 20, 2010, which is incorporated herein by reference in its entirety.

FIELD OF THE INVENTION

The present invention relates to the prevention and/or treatment of infectious diseases, and more particularly parasitic infection and disease, such as *Plasmodium* infection and associated disease such as malaria.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Oct. 19, 2011, and having a size of 169 kilobytes, as permitted under 37 CFR 1.821(c). The material is the aforementioned file is hereby incorporated by reference in its entirety.

BACKGROUND OF THE INVENTION

Parasites are organisms that live on or within another organism (the host) and harm the host. Diseases caused by parasites such as protozoa and helminths are among the leading causes of death and disease in tropical and subtropical regions of the world.

Malaria is an infectious disease that causes severe morbidity and mortality with an estimated 300-500 million cases worldwide and more than 1 million deaths annually in sub-Saharan Africa alone. The disease is caused by protozoan parasites of the genus *Plasmodium*, transmitted by mosquitoes. The most serious forms of malaria are caused by *Plasmodium falciparum* and *Plasmodium vivax*, but other species (e.g., *Plasmodium ovale, Plasmodium malariae*, and *Plasmodium knowlesi*) can also infect humans.

Among the murine malarial parasites, *Plasmodium chabaudi* (*P. chabaudi*) AS provides a unique experimental model to study the erythroid stage of the disease (Li, C. et al., 2001. *Med. Microbiol. Immunol.* (*Berl*) 189:115-126). *P. chabaudi* AS produces an infection in mice that shares many similarities with *P. falciparum* malaria in humans, including anemia, splenomegaly, hepatomegaly, renal alterations, hypoglycemia, and parasite sequestration (Cox, J. et al., 1987. *Parasite Immunol.* 9:543-561; Landau, I. and Gautret, P. 1998. Animal models: rodents. In *Malaria, Parasite Biology, Pathogenesis, and Protection*. I. W. Sherman, editor ASM Press, Washington D.C., pages 401-417). Among the murine malarial parasites, *Plasmodium berghei* (*P. berghei*) ANKA provides a unique model to study the cerebral stage of the disease (Hunt, N. H. et al., 2006 *Int. J. Parasitol* 36: 569-582). *P. berghei* ANKA produces an infection in mice that shares many similarities with cerebral malaria in humans, including sequestration of infected erythrocytes at the blood brain barrier, and appearance of cerebral symptoms such as fever, tremors, paralysis, coma and death.

In humans, malaria provides a clear example of host genetic factors influencing onset, progression, type of disease developed and ultimate outcome of infection (Hill, A. V. 1998. *Annu. Rev. Immunol.* 16: 593-617). Epidemiological data, together with linkage and association studies have shown that selection pressure from the parasite has caused retention of disease-associated but malaria-protective alleles in the human population, suggesting co-evolution of the host and parasite. Such otherwise deleterious alleles include those causing sickle cell anemia (Allison, A. C. 1954. *Br. Med. J.* 1(4857): 290-294; Willcox, M. A. et al., 1983. *Ann. Trop. Med. Parasitol.* 77: 239-246), thalassemias (Weatherall, D. J. 2001. *Nat. Rev. Genet.* 2: 245-255), and glucose-6-phosphate dehydrogenase deficiency (Ruwende, C. et al., 1995. *Nature* 376: 246-249). Polymorphisms in other erythroid proteins, including common variants of the Duffy antigen (Miller, L. H. et al., 1976. *N. Engl. J. Med.* 295: 302-304), the erythrocyte band 3 (anion exchanger) (Allen, S. J. et al., 1999. *Am. J. Trop. Med. Hyg.* 60: 1056-1060), and glycophorin C (Patel, S. S., et al., 2001. *Blood* 98:3489-3491), as well as variants in the TNF-α cytokine (McGuire, W. et al., 1994. *Nature* 371: 508-510) and the CD36 scavenger receptor (Aitman, T. J. et al., 2000. *Nature* 405: 1015-1016) are also associated with protection against malaria. Additional linkage studies in Burkina Faso have suggested a complex genetic component of susceptibility showing blood parasitemia levels linked to the 5q31-q33 region (Rihet, P. et al., 1998. *Am. J. Hum. Genet.* 63: 498-505). The genetic component of malaria susceptibility is further modified by environmental factors (Kwiatkowski, D. 2000. *Curr. Opin. Genet. Dev.* 10: 320-324).

No efficacious vaccines are currently available to prevent or control the spread of parasitic diseases such as malaria, and most existing therapeutics are either not completely effective or toxic to the human host. Also, drugs often fail as a result of the selection and spread of drug resistant variants of the parasites. Notably, control of malaria has been hampered by the spread of drug resistance in both the *Plasmodium* parasites and the *Anopheles* insect vector, and by the lack of an efficacious vaccine (Moorthy, V. S. et al., 2004. *Lancet* 363: 150-156).

Therefore, there is a need to develop new approaches for the prevention and/or treatment of parasitic diseases such as malaria.

The present description refers to a number of documents, the content of which is herein incorporated by reference in their entirety.

SUMMARY OF THE INVENTION

The present invention relates to decreasing susceptibility to parasite infection or disease or to preventing or treating parasite infection or disease.

Accordingly, in a first aspect, the present invention provides a method for decreasing susceptibility to parasite infection or disease or for preventing or treating parasite infection or disease, in a subject, said method comprising administering to said subject an effective amount of (i) (a) cystamine; (b) cysteamine; (c) an agent capable of inducing the production of (a) or (b); (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound.

In another aspect, the present invention provides a method for decreasing susceptibility to parasite infection or disease or for preventing or treating parasite infection or disease, in a subject, said method comprising administering to said subject an effective amount of (i) (a) a compound of formula I: $NH_2—CH_2—CH_2—S—R$ (I), wherein R is H or $S—CH_2—$ $CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In an embodiment, the above-mentioned method comprises administering to said subject an effective amount of (i) (a) cystamine; (b) cysteamine; (c) a pharmaceutically acceptable salt of (a) or (b); or (d) any combination of (a) to (c); and (ii) an artemisinin-related compound.

In an embodiment, the above-mentioned method comprises administering to said subject an effective amount of (i) cysteamine or a pharmaceutically acceptable salt thereof and (ii) (a) an artemisinin-related compound.

In various embodiments, the method results in reduced levels of parisitemia, delay in peak levels of parasitemia, or reduced severity of infection compared to treatment with cystamine, cysteamine, a derivative or pharmaceutically acceptable salt thereof or an artemisinin-related compound alone.

In another aspect, the present invention provides a use of (i) (a) cystamine; (b) cysteamine; (c) an agent capable of inducing the production of (a) or (b); (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound, for decreasing susceptibility to parasite infection or disease or for preventing or treating parasite infection or disease.

In another aspect, the present invention provides a use of (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound, for the preparation of a medicament for decreasing susceptibility to parasite infection or disease or for preventing or treating parasite infection or disease.

In another aspect, the present invention provides a use of (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound, for decreasing susceptibility to parasite infection or disease or for preventing or treating parasite infection or disease.

In another aspect, the present invention provides a use of (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound, for the preparation of a medicament for decreasing susceptibility to parasite infection or disease or for preventing or treating parasite infection or disease.

In an embodiment, the above-mentioned use is of (i) (a) cystamine; (b) cysteamine; (c) a pharmaceutically acceptable salt of any of (a) or (b); or (d) any combination of (a) to (c); and (ii) (a) artemisinin, (b) a functional derivative, analog, conjugate, metabolite, prodrug or precursor of artemisinin, (c) a pharmaceutically acceptable salt of (a) or (b), or (d) any combination of (a) to (c).

In another embodiment, the above-mentioned use is of (i) cysteamine or a pharmaceutically acceptable salt thereof; and (ii) an artemisinin-related compound.

In another aspect, the present invention provides a package for decreasing susceptibility to parasite infection or disease or for preventing or treating parasite infection or disease, said package comprising (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound.

In another aspect, the present invention provides a package for decreasing susceptibility to parasite infection or disease or for preventing or treating parasite infection or disease, said package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In another aspect, the present invention provides a package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) an artemisinin-related compound, for decreasing susceptibility to parasite infection or disease or for preventing or treating parasite infection or disease in a subject.

In an embodiment, the above-mentioned i) and ii) are packaged separately.

In another embodiment, the above-mentioned i) and ii) are packaged in the same formulation.

In an embodiment, the above-mentioned compound i) is present in a delayed release composition.

In another embodiment, the above-mentioned package further comprises labels and instructions for use.

In another aspect, the present invention provides a package comprising (i) a plurality of doses of a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) a plurality of doses of an artemisinin-related compound, for decreasing susceptibility to parasite infection or disease or for preventing or treating parasite infection or disease in a subject.

In an embodiment, the above-mentioned (i) and (ii) are packaged separately.

In another embodiment, the above-mentioned (i) and (ii) are packaged together.

In an embodiment, the above-mentioned package comprises (i) (a) cystamine; (b) cysteamine; (c) a pharmaceutically acceptable salt of (a) or (b); or (d) any combination of (a) to (c) and (ii) an artemisinin-related compound.

In a further embodiment, the above-mentioned package comprises (i) cysteamine or a pharmaceutically acceptable salt thereof; and (ii) an artemisinin-related compound.

In another embodiment, the above-mentioned package further comprises instructions for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) instructions for using (i) in combination with an artemisinin-related compound, for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) instructions for using (i) in combination with an artemisinin-related compound, for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) an artemisinin-related compound; and (ii) instructions for using (i) in combination with (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) an artemisinin-related compound; and (ii) instructions for using (i) in combination with (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); for decreasing susceptibility to parasite infection or disease or for preventing or treating parasite infection or disease.

In another aspect, the present invention provides a composition for decreasing susceptibility to parasite infection or disease or for preventing or treating parasite infection or disease, said composition comprising: (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound.

In another aspect, the present invention provides a composition for decreasing susceptibility to parasite infection or disease or for preventing or treating parasite infection or disease, in a subject, said composition comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In an embodiment, the above-mentioned composition comprises (i) (a) cystamine; (b) cysteamine; (c) a pharmaceutically acceptable salt of (a) or (b); or (d) any combination of (a) to (c); and (ii) an artemisinin-related compound.

In a further embodiment, the above-mentioned composition comprises (i) cysteamine or a pharmaceutically acceptable salt thereof; and (ii) an artemisinin-related compound.

In an embodiment, the above-mentioned composition further comprises a pharmaceutically acceptable carrier or excipient.

In another aspect, the present invention provides a combination comprising: (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); and (ii) (a) an artemisinin-related compound; for decreasing susceptibility to parasite infection or disease or for preventing or treating parasite infection or disease.

In another aspect, the present invention provides a combination comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound; for decreasing susceptibility to parasite infection or disease or for preventing or treating parasite infection or disease.

In another aspect, the present invention provides (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); or (ii) a composition comprising (i) and a pharmaceutically acceptable carrier; for use in combination with (iii) an artemisinin-related compound; or (iv) a composition comprising (iii) and a pharmaceutically acceptable carrier; for decreasing susceptibility to parasite infection or disease or for preventing or treating parasite infection or disease.

In another aspect, the present invention provides (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); or (ii) a composition comprising (i) and a pharmaceutically acceptable carrier; for use in combination with (iii) an artemisinin-related compound; or (iv) a composition comprising (iii) and a pharmaceutically acceptable carrier; for decreasing susceptibility to parasite infection or disease or for preventing or treating parasite infection or disease.

In another aspect, the present invention provides (i) an artemisinin-related compound; or (ii) a composition comprising (i) and a pharmaceutically acceptable carrier; for use in combination with (iii) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e) or (iv) a composition comprising (iii) and a pharmaceutically acceptable carrier; for decreasing susceptibility to parasite infection or disease or for preventing or treating parasite infection or disease.

In another aspect, the present invention provides (i) an artemisinin-related compound; or (ii) a composition comprising (i) and a pharmaceutically acceptable carrier; for use in combination with (iii) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); or (iv) a composition comprising (iii) and a pharmaceutically acceptable carrier; for decreasing susceptibility to parasite infection or disease or for preventing or treating parasite infection or disease.

The present invention further provides a combination for decreasing susceptibility to parasite infection or disease or for preventing or treating parasite infection or disease, said combination comprising: (i) (a) cystamine; (b) cysteamine; (c) an agent capable of inducing the production of cysteamine; (d) a functional derivative, analog, conjugate, prodrug or precursor of any of (i) to (iii); (e) a pharmaceutically acceptable salt of any of (a) to (d); or (f) any combination of (a) to (e); and (ii) an artemisinin-related compound.

The present invention further provides a combination for decreasing susceptibility to parasite infection or disease or for preventing or treating parasite infection or disease, in a subject, said combination comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) (a) an artemisinin-related compound.

In embodiments, the above-mentioned combination comprises: (i) (a) cystamine; (b) cysteamine; (c) a pharmaceutically acceptable salt of (a) or (b); or (d) any combination of (a) to (c); and (ii) an artemisinin-related compound.

In embodiments, the above-mentioned combination comprises: (a) cysteamine or a pharmaceutically acceptable salt thereof; and (b) an artemisinin-related compound.

In an embodiment, the above-mentioned artemisinin-related compound is (a) artemisinin, (b) a functional derivative, analog, conjugate, metabolite, prodrug or precursor of artemisinin, (c) a pharmaceutically acceptable salt of (a) or (b), or (d) any combination of (a) to (c).

In an embodiment, the above-mentioned artemisinin derivative is artesunate. In another embodiment, the above-mentioned artemisinin metabolite is dihydroartemisinin.

In another embodiment, the above-mentioned agent capable of inducing the production of cystamine or cysteamine is (a) a pantetheinase polypeptide, (b) a fragment or variant of (a) having pantetheinase activity; (c) a nucleic acid encoding the polypeptide of (a) or (b), (d) an agent capable of increasing pantetheinase activity or expression, or (e) any combination of (a) to (d).

In an embodiment, the above-mentioned polypeptide comprises the amino acid sequence of SEQ ID NO: 6, 8, 10, 12, 14 or 16.

In another embodiment, the above-mentioned nucleic acid comprises a nucleotide sequence which encodes a polypeptide comprising the amino acid sequence of SEQ ID NO: 6, 8, 10, 12, 14 or 16. In a further embodiment, the above-mentioned nucleic acid comprises the coding sequence of SEQ ID NO: 5, 7, 9, 11, 13, 15, 17, 18 or 19.

In an embodiment, the above-mentioned (i) and (ii) are packaged separately.

In another embodiment, the above-mentioned (i) and (ii) are packaged together.

In an embodiment, the above-mentioned compounds i) and ii) act synergistically.

In an embodiment, the above-mentioned synergy results in use of effective doses of compound i) and/or ii) that are lower than doses administered when the compounds are administered in the absence of the other composition.

In an embodiment, the above-mentioned effective dose of compound (i) is lower than a dose of (i) administered in the absence of compound (ii).

In an embodiment, the above-mentioned effective dose of compound (ii) is lower than a dose of (ii) administered in the absence of compound (i).

In an embodiment, the above-mentioned effective dose of (i) and (ii) are lower than a dose of compound (i) or compound (ii) administered in the absence of the other composition.

In an embodiment, the dose of compound (i) and/or (ii) is suboptimal.

In an embodiment, the above-mentioned effective dose of compound (i) is in the range of 1 to 500 mg/kg.

In an embodiment, the above-mentioned compound (i) is present in a delayed release composition.

In an embodiment, the peak level of parisitemia is reduced.

In an embodiment, the above-mentioned administering prevents parisitemia.

In an embodiment, the above-mentioned compound (i) is administered less than four times a day.

In an embodiment, the above-mentioned compound (i) is administered twice daily.

In an embodiment, the above-mentioned compounds (i) and (ii) are administered coextensively.

In an embodiment, the above-mentioned parasite is of the genus *Plasmodium*. In a further embodiment, the above-mentioned parasite is *Plasmodium falciparum, Plasmodium vivax, Plasmodium ovale, Plasmodium malariae*, or *Plasmodium knowlesi*.

In another embodiment, the above-mentioned disease is malaria. In a further embodiment, the above-mentioned malaria is blood-stage malaria or cerebral malaria.

In an embodiment, the above-mentioned subject is a mammal. In a further embodiment, the above-mentioned mammal is a human.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A: plasma levels of cysteamine-free base (measured by HPLC) following either intraperitoneal (i.p.) or subcutaneous (s.c.) injections (120 mg/kg) were measured in 3 mice and used to calculate $C_{max}$ and AUC pharmacokinetic parameters (see text). Error bars indicate standard deviation from the mean.

FIG. 1B: A/J female mice were infected with *P. chabaudi* ($10^5$ pRBC i.v.) and treated daily (either s.c. or i.p.) with cysteamine (120 mg/kg) starting at day 1 to day 10. Blood parasitemia was monitored on days 5, 6, and 7 and is plotted. The % inhibition of parasite replication was calculated by comparison to the blood parasitemia measured in PBS-treated controls and is indicated below the graphs. Each dot represents a mouse. Levels of statistical significance are represented by asterisks; *, P<0.01; , P<0.05 (compared to PBS control group);

FIG. 2A: the plasma levels of cysteamine-free base (measured by HPLC) following subcutaneous (s.c.) injection (50 mg/kg) were measured in 3 mice and used to calculate $C_{max}$ and AUC pharmacokinetic parameters (see text). Error bars indicate standard deviation from the mean. FIG. 2B: A/J female mice were infected with *P. chabaudi* ($10^5$ pRBC i.v.) and treated daily with cysteamine (s.c.) from day 1 to day 10, with the indicated dosing: 1×150 mg/kg, 3×50 mg/kg, or 4×50 mg/kg, given at 1 or 2 h intervals. Blood parasitemia was monitored on days 5, 6, and 7 and is plotted. The % inhibition of parasite replication was calculated by comparison to the blood parasitemia measured in PBS-treated controls and is indicated below the graphs. Each dot represents a mouse. Levels of statistical significance are represented by asterisks; ***, P<0.01 (compared to PBS control group);

FIG. 5C: Kaplan-Meier survival plot for experimental treatment groups for which lethality was observed. Depiction of artesunate doses and dashed versus solid lines are as described for FIG. 5B. FIG. 5D: Parasitemia levels at day 6 post-infection for all experimental groups are shown, with each dot representing a mouse. Mean levels are shown as bars;

FIG. 6B: Parasitemia levels at day 6 post-infection for all experimental groups are shown, with each dot representing a mouse. Mean levels are shown as bars;

FIGS. 7A to 7Z show the nucleotide and amino acid sequences of murine and human pantetheinase (Vanin, Vnn) genes and polypeptides;

DISCLOSURE OF THE INVENTION

Described herein are studies using the mouse model system of *Plasmodium* infection which show that treatment of mice with a combination of cysteamine and artemisinin-related compounds (e.g., the artemisinin derivative artesunate and the artemisinin metabolite dihydroartemisinin) leads to a synergistic reduction in parasitemia in these mice and to an increase in survival.

Cysteamine ($C_2H_7NS$, CAS#60-23-1) has the following chemical formula: $NH_2—CH_2—CH_2—SH$ It is often used as a salt, such as the hydrochloride salt, $C_2H_8ClNS$ (CAS#156-57-0), which has the following formula: $^-Cl^+NH_3—CH_2—CH_2—SH$ Cystamine ($C_4H_{12}N_2S_2$) is the oxidized form of cysteamine (i.e., a dimer of cysteamine) and has the following chemical formula: $NH_2—CH_2—CH_2—S—S—CH_2—CH_2—NH_2$ Cystamine may also be in the form of a salt, such as a dihydrochloride salt (CAS #56-17-7) or phosphate salt (CAS#3724-89-8).

As such, a compound of formula I: $NH_2—CH_2—CH_2—S—R$ (I) wherein R is H or $S—CH_2—CH_2—NH_2$; an agent capable of inducing the production of the compound of formula I; a functional derivative, analog, conjugate, prodrug or precursor of the compound of formula I; or salts (e.g., pharmaceutically acceptable salts) thereof, are also useful in the methods, uses, and compositions of the present invention.

Cysteamine, and more particularly the bitartrate salt thereof (commercialized under the trade name Cystagon™) has been approved for the pharmacological management of cystinosis, an autosomal recessive disorder caused by mutations in the lysosomal cystine carrier cystinosin (encoded by the CTNS gene), whose absence leads to intracellular cystine crystals, widespread cellular destruction, renal Fanconi syndrome in infancy, renal glomerular failure in later childhood and other systemic complications (Kleta R. and Gahl W. A., 2004. *Expert Opin. Pharmacother.* 5(11): 2255-2262).

Figure 3A:
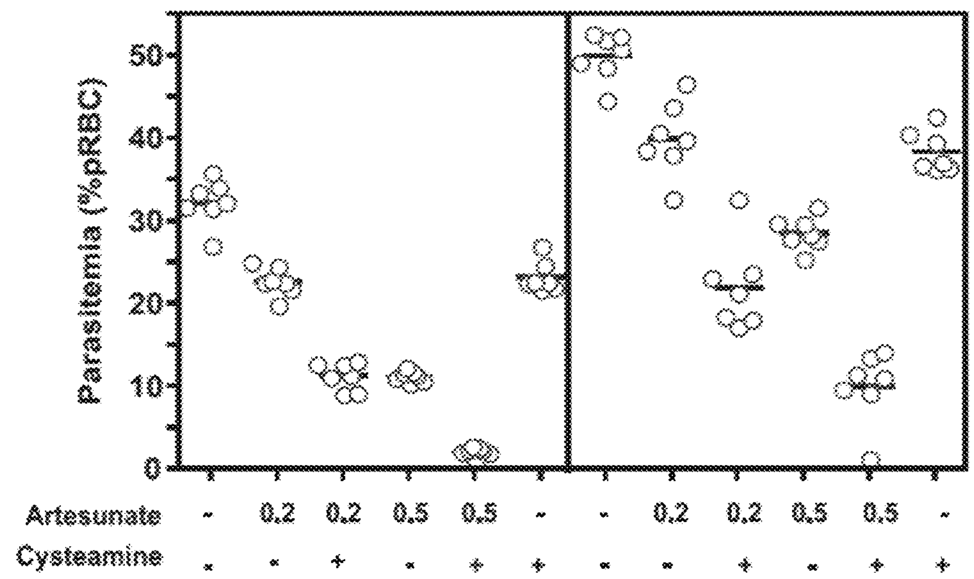
FIGS. 3A to 3C show the synergistic effect of cysteamine on artemisinin efficacy against replication of *Plasmodium chabaudi* in vivo. Groups (n=6) of female A/J (FIGS. 3A and B) or C57BL/6 (FIG. 3C) mice were infected with *P. chabaudi* ($10^7$ pRBC, i.v.) and treated for 4 days (days 0, 1, 2, and 3) with indicated doses (in mg/kg) of artesunate (FIGS. 3A and C) or dihydro-artemisinin (DHA) (FIG. 3B) and/or cysteamine (170 mg/kg, i.p.), and blood parasitemia (expressed as percentage of parasitized erythrocytes) was determined at days 4 (left) and 5 (right) postinfection. In all experiments, control groups were treated with PBS. The presence or absence of cysteamine is indicated by a plus or a minus, respectively, and doses of artemisinin derivatives in mg/kg are indicated below the plots. Each dot represents a mouse and bars indicate the mean of the group.
Figure 3B:
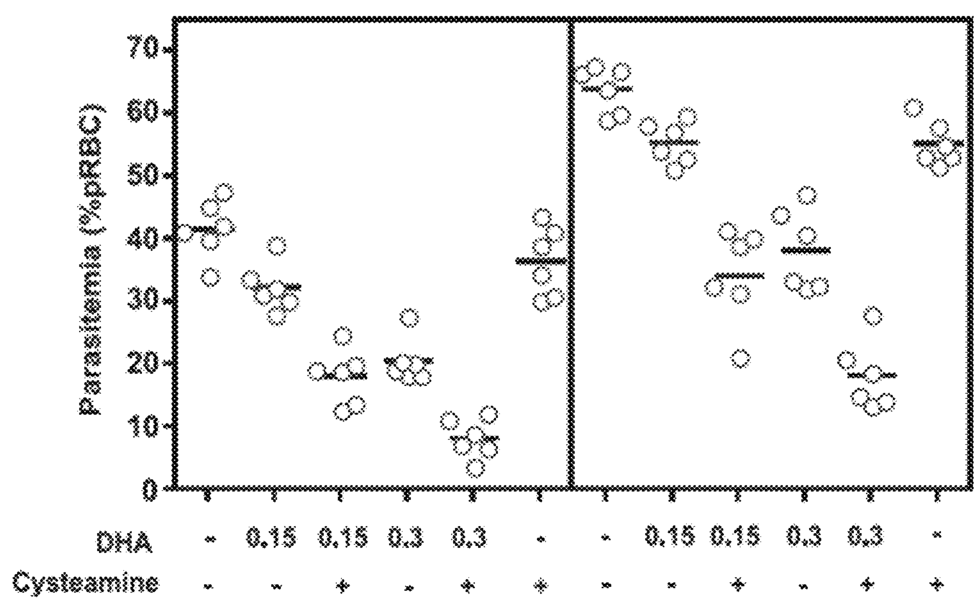

Cysteamine is a metabolite (product) generated by pantetheinase enzymatic activity. Pantetheinase (EC 3.5.1.92) is a ubiquitous enzyme encoded by the Vanin genes (FIG. 3, SEQ ID NOs:1, 3, 5, 7, 9, 11, 13, 15, and 17-19); 2 genes in mice (Vanin-1 and -3) and 3 genes in human (Vanin-1, -2 and -3). It is an amidohydrolase that hydrolyzes pantetheine (which is a metabolic product of Coenzyme A (CoA) degradation) to pantothenic acid (also called pantothenate or vitamin B5) and cysteamine.

Artemisinin (CAS#63968-64-9) is a sesquiterpene lactone which was first isolated from the plant *Artemisia annua*, and has the following formula:

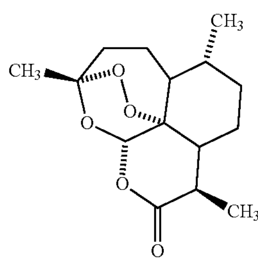

An active metabolite of artemisinin and artemisinin-related compounds is dihydroartemisinin (CAS#71939-50-9), which has the following formula:

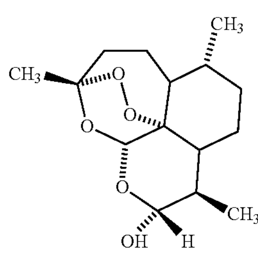

Accordingly, in an aspect, the present invention provides a method for decreasing susceptibility to parasite infection or disease or for preventing or treating parasite infection or disease, in a subject, said method comprising administering to said subject an effective amount of (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound.

The present invention further provides a method for decreasing susceptibility to parasite infection or disease or for preventing or treating parasite infection or disease in a subject (an animal such as a mammal, in a further embodiment a human), said method comprising administering to said subject an effective amount of (i) (a) a compound of formula I: $NH_2—CH_2—CH_2—S—R$ (I) wherein R is H or $S—CH_2—CH_2—NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d) and (ii) an artemisinin-related compound.

In another aspect, the invention provides a use of (i) (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, for decreasing susceptibility to parasite infection or disease or for preventing or treating parasite infection or disease; or for the preparation of a medicament for decreasing susceptibility to parasitic infection or disease or for preventing or treating parasite infection or disease.

In another aspect, the invention provides a combination of (i) (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, for use in decreasing susceptibility to parasite infection or disease or for use in preventing or treating parasite infection or disease; or for use in the preparation of a medicament for decreasing susceptibility to parasitic infection or disease or for use in preventing or treating parasite infection or disease.

In an embodiment, the above-mentioned parasite infection is an infection of a parasite of the genus *Plasmodium*. In an embodiment, the above-mentioned *Plasmodium* parasite is an artemisinin-resistant human *Plasmodium* parasite.

In an embodiment, the above-mentioned disease is malaria. In a further embodiment, the above-mentioned malaria is blood-stage malaria. In another embodiment, the above-mentioned malaria is cerebral malaria.

Accordingly, the invention further provides a method for treating or preventing malaria in an animal, comprising administering to the animal (i) a cysteamine-related compound and (ii) an artemisinin-related compound.

As used herein, the term "cysteamine-related compound" refers to cysteamine and functional derivatives, analogs, conjugates, prodrugs or precursors of cysteamine and various cysteamine salts (such as cysteamine hydrochloride, cysteamine salicylate, cysteamine phosphate and cysteamine bitartrate [Cystagon™]). Also included within the scope of the subject invention are analogs, derivatives, conjugates, metabolites, prodrugs and precursors of cysteamine (such as cystamine, the oxidized form of cysteamine, cysteine, and the like), which have the ability, as described herein, to prevent and/or treat and/or decrease the susceptibility to parasite infections, such as infection by a *Plasmodium* parasite (e.g., *P. falciparum* infection) and/or to prevent and/or treat associated disease (e.g., malaria), and more particularly to act synergistically with artemisinin and artemisinin-related compounds. Various analogs, derivatives, conjugates, prodrugs and metabolites of cysteamine are known and include, for example, compounds, compositions, formulations and methods of delivery as set forth in U.S. Pat. Nos. 6,521,266; 6,468,522; 6,340,746; 5,714,519 and 5,554,655 and PCT publication No. WO 2007/089670.

As used herein, the term "artemisinin-related compound" refers to artemisinin and to functional derivatives, analogs, conjugates, metabolites, prodrugs or precursors of artemisinin, as well as salts thereof, and includes the artemisinin derivatives/analogs artesunate, artemether, arteether, artelinic acid, artenimol and artemotil, the artemisinin precursor artemisinic acid (Ro D K, et al., *Nature* 440:940-943), as well as the artemisinin metabolite dihydroartemisinin. Also included within the scope of the subject invention are analogs, derivatives, conjugates, metabolites, prodrugs and precursors of artemisinin which have the ability, as described herein, to prevent and/or treat and/or decrease the susceptibility to parasite infections, such as infection by a *Plasmodium* parasite (e.g., *P. falciparum* infection) and/or to prevent and/or treat associated disease (e.g., malaria), and more particularly to act synergistically with cysteamine and cysteamine-related compounds. Also included within the scope of the subject invention are analogs, derivatives, conjugates, metabolites, prodrugs and precursors of artemisinin which have the ability which may be metabolized into a biologically active metabolite of artemisinin (e.g., dihydroartemisinin), as well as synthetic trioxolanes (mimicking the trioxolane structure of artemisinin) such as those described in Vennerstrom et al., 2004, *Nature* 430, 900-904 (Arterolane) and O'Neill et al., *Angewandte Chemie International Edition,* 2010, 49(33): 5693-97. Various functional analogs, derivatives, conjugates, prodrugs and metabolites of artemisinin, as well as methods to produce them, are described, for example, in Posner et al., 1999*, J. Med. Chem.* 42(2): 300-304, Li et al., 2000*, J. Med. Chem.* 43(8): 1635-1640, Li et al., 2003*, Bioorganic & Medicinal Chemistry* 11(20): 4363-4368, Ploypradith P, 2004. *Acta Trop* 89:329-342, PCT publications No. WO/2008/127381, WO/2008/046109, WO/2007/116135, WO/2007/009388, WO/2003/076446, WO/2000/042046, WO/2000/004025, WO/2000/004024, WO/1999/065914 and WO/1991/014689. Artemisinin-related compounds have been shown to be active against a variety of parasites including *Plasmodium* parasites, *Toxoplasma parasites, Schistosoma* parasites and helminths and (Dunay I R, et al., 2009*, Antimicrob Agents Chemother* 53:4450-4456; Keiser J, Utzinger J (2007) *Curr Opin Infect Dis* 20:605-612; Sissoko M S et al., (2009) *PLoS One* 4:e6732)

Methods to isolate and/or produce artemisinin and/or artemisinin-related compounds are well known in the art. Methods to produce/isolate artemisinin from tissue culture or whole plant of *Artemisia annua* are described, for example, in Liu et al., 2006*, Appl Microbiol Biotechnol.* 72(1):11-20, Epub 2006 Jun. 3. The synthesis of artemisinin may also be performed using basic organic reagents, for example using the methods described in Schmid and Hofheinz, *J. Am. Chem. Soc.* (1983) 105(3): 624-625. The precursor of artemisinin, artemisinic acid, may for example be produced at high levels in an engineered *Saccharomyces cerevisiae* system (Ro D K et al., 2006*, Nature* 440(7086): 940-943). Methods to produce/synthesize various functional analogs, derivatives, conjugates, prodrugs and metabolites of artemisinin, are described, for example, in Posner et al., 1999*, J. Med. Chem.* 42(2): 300-304, Li et al., 2000*, J. Med. Chem.* 43(8): 1635-1640, Li et al., 2003*, Bioorganic & Medicinal Chemistry* 11(20): 4363-4368, PCT publications No. WO/2008/127381, WO/2008/046109, WO/2007/116135, WO/2007/009388, WO/2003/076446, WO/2000/042046, WO/2000/004025, WO/2000/004024, WO/1999/065914 and WO/1991/014689.

In an embodiment, the above-mentioned agent capable of inducing the production of cystamine, cysteamine, or a compound of formula I is (a) a pantetheinase polypeptide, (b) a fragment or variant of (a) having pantetheinase activity; (c) a nucleic acid encoding the polypeptide of (a) or (b), (d) an agent capable of increasing pantetheinase activity or expression, or (e) any combination of (a) to (d).

In an embodiment, the above-mentioned pantetheinase polypeptide comprises the amino acid sequence of SEQ ID NO: 2, 4, 6, 8, 10, 12, 14 or 16 (FIG. 7), or a variant/fragment thereof having pantetheinase activity.

In an embodiment, the above-mentioned pantetheinase nucleic acid comprises (a) the coding sequence of SEQ ID NO: 1, 3, 5, 7, 9, 11, 13, 15, 17, 18 or 19 (FIG. 7); (b) a nucleotide sequence which encodes a polypeptide comprising the amino acid sequence of SEQ ID NO: 2, 4, 6, 8, 10, 12, 14 or 16; or (c) a fragment, variant or complement of (a) or (b) encoding a pantotheinase polypeptide.

The above-mentioned coding sequences correspond to: (a) nucleotides 22 to 1560 for SEQ ID NO: 1, (b) nucleotides 113-1615 for SEQ ID NO: 3, (c) nucleotides 15-1556 for SEQ ID NO: 5, (d) nucleotides 12-1574 for SEQ ID NO: 7, (e) nucleotides 113-1516 for SEQ ID NO: 9, (f) nucleotides 73-897 for SEQ ID NO: 11, (g) nucleotides 73-516 for SEQ ID NO: 13, (h) nucleotides 73-426 for SEQ ID NO: 15, (i) the junction of nucleotides 1959-2168, 4155-4278, 21806-22005, 22680-22971, 23411-23772, 31490-31660 and 32673-32855 for SEQ ID NO: 17, (j) the junction of nucleotides 2009-2221, 2346-2476, 3857-4049, 7144-7432, 8375-8748, 10028-10198 and 15403-15594 for SEQ ID NO: 18, and (k) the junction of nucleotides 1814-2026, 2123-2253, 7573-7765 and 9494-9781 for SEQ ID NO: 19 (FIGS. 7A to Z).

In another embodiment, the above-mentioned nucleic acid fragment or variant encodes a polypeptide having pantetheinase activity.

In an embodiment, the above-mentioned pantetheinase nucleic acid comprises the nucleotide sequence of SEQ ID NO: 1, 3, 5, 7, 9, 11, 13, 15, 17, 18 or 19 (FIGS. 7A to Z).

The increase of expression of a pantetheinase nucleic acid or encoded polypeptide or pantetheinase activity in cell or tissue of said subject may be achieved, for example, by administrating to a subject: (a) a polypeptide comprising the amino acid sequence of SEQ ID NO: 2, 4, 6, 8, 10, 12, 14 or 16, or a variant or fragment thereof having pantetheinase activity; (b) a nucleic acid molecule encoding pantetheinase or a functional variant thereof (e.g., a nucleic acid which encodes the polypeptide of SEQ ID NO: 2, 4, 6, 8, 10, 12, 14 or 16, or a variant or fragment thereof having pantetheinase activity) or (c) a composition (e.g., a pharmaceutical composition) comprising the above-mentioned polypeptide or nucleic acid and, for example, a pharmaceutically acceptable carrier/excipient.

A variant and/or fragment of pantetheinase which retains activity (e.g., having a domain conferring pantetheinase activity) may also be used in the uses and methods of the invention. Variants or homologs include protein sequences, which are substantially identical to the amino acid sequence of a pantetheinase (e.g., SEQ ID NO: 2, 4, 6, 8, 10, 12, 14 or 16), sharing significant structural and functional homology with a pantetheinase (e.g., SEQ ID NO: 2, 4, 6, 8, 10, 12, 14 or 16). Variants include, but are not limited to, proteins or peptides, which differ from a pantetheinase (e.g., SEQ ID NO: 2, 4, 6, 8, 10, 12, 14 or 16) by any modifications, and/or amino acid substitutions, deletions or additions. Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of a pantetheinase or a fragment or a portion of a homolog or variant of a pantetheinase which retains pantetheinase activity. The pantetheinase polypeptide (or a variant or fragment thereof having pantetheinase activity) may also be fused with another polypeptide or conjugated to one or more molecules.

"Homology", "homologous" and "homolog" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to or is a "homolog" of another sequence if the two sequences are substantially identical and the functional activity of the sequences is conserved (as used herein, the term 'homologous' does not infer evolutionary relatedness). Two nucleic acids or amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 96%, 97%, 98% or 99%, e.g., with any of SEQ ID NOs: 1-19. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs: 1-19.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 97%, at least 98% or at least 99%, e.g., with any of SEQ ID NOs: 1-19. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, more preferably highly stringent conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

The above-mentioned nucleic acid may be delivered to cells in vivo using methods well known in the art such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) *Nature* 332: 815-818; Wolff et al. (1990) *Science* 247: 1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126).

Defective retroviruses are well characterized for use as gene therapy vectors (for a review see Miller, A. D. (1990) *Blood* 76: 271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85: 6460-6464; Wilson et al. (1988) *Proc. Natl. Acad. Sci. USA* 85: 3014-3018; Armentano et al. (1990) *Proc. Natl. Acad. Sci. USA* 87: 6141-6145; Huber et al. (1991) *Proc. Natl. Acad. Sci. USA* 88: 8039-8043; Ferry et al. (1991) *Proc. Natl. Acad. Sci. USA* 88: 8377-8381; Chowdhury et al. (1991) *Science* 254: 1802-1805; van Beusechem et al. (1992) *Proc. Natl. Acad. Sci. USA* 89: 7640-7644; Kay et al. (1992) *Human Gene Therapy* 3: 641-647; Dai et al. (1992) *Proc. Natl. Acad. Sci. USA* 89: 10892-10895; Hwu et al. (1993) *J. Immunol.* 150: 4104-4115; U.S. Pat. No. 4,868,116; U.S. Pat. No. 4,980,286; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a nucleic acid compound of the invention (e.g., a pantetheinase nucleic acid), but is inactivated in terms of its ability to replicate in a normal lytic viral life cycle. See for example Berkner et al. (1988) *BioTechniques* 6: 616; Rosenfeld et al. (1991) *Science* 252: 431-434; and Rosenfeld et al. (1992) *Cell* 68: 143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89: 6482-6486), hepatocytes (Herz and Gerard (1993) *Proc. Natl. Acad. Sci. USA* 90: 2812-2816) and muscle cells (Quantin et al. (1992) *Proc. Natl. Acad. Sci. USA* 89: 2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. *Curr. Topics in Micro. and Immunol.* (1992) 158:97-129). AAV may be used to integrate DNA into non-dividing cells (see for example Flotte et al. (1992) *Am. J. Respir. Cell. Mol. Biol.* 7: 349-356; Samulski et al. (1989) *J. Virol.* 63: 3822-3828; and McLaughlin et al. (1989) *J. Virol.* 62: 1963-1973). An AAV vector such as that described in Tratschin et al. (1985) *Mol. Cell. Biol.* 5: 3251-3260 may be used to introduce DNA into cells (see for example Hermonat et al. (1984) *Proc. Natl. Acad. Sci. USA* 81: 6466-6470; Tratschin et al. (1985) *Mol. Cell. Biol.* 4: 2072-2081; Wondisford et al. (1988) *Mol. Endocrinol.* 2: 32-39; Tratschin et al. (1984) *J. Virol.* 51: 611-619; and Flotte et al. (1993) *J. Biol. Chem.* 268: 3781-3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., *Blood* 78: 1132-1139 (1991); Anderson, *Science* 288: 627-9 (2000); and Cavazzana-Calvo et al., *Science* 288: 669-72 (2000)).

The present invention relates to the administration of (i) (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, to elicit any of the effects discussed above. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound may be administered alone or in combination with at least one other agent, such as stabilizing compound, which may be administered in any sterile, biocompatible pharmaceutical carrier, including, but not limited to, saline, buffered saline, dextrose, and water. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound may be administered alone or in combination with other agents, drugs or hormones. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and artemisinin-related compound may be administered separately or together (e.g., together in a composition). The combination of therapeutic agents and compositions of the present invention may be administered or co-administered in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, the (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e) may be administered to a patient before, concomitantly, before and after, or after the artemisinin-related compound is administered.

As such, in embodiments, the invention further provides:

(1) a composition (e.g., a pharmaceutical composition or medicament) comprising (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e)) and a pharmaceutically acceptable diluent or carrier;

(2) a composition comprising (a) an artemisinin-related compound and a pharmaceutically acceptable diluent or carrier;

(3) a composition comprising (i) (a) cystamine; (b) cysteamine; (c) an agent capable of inducing the production of cysteamine and/or cystamine; (d) a functional derivative, analog, conjugate, prodrug or precursor of (a) to (c); (e) a pharmaceutically acceptable salt of any of (a) to (d); or (f) any combination of (a) to (e); and (ii) an artemisinin-related compound; or (4) a composition comprising (i) (a) cystamine; (b) cysteamine; (c) an agent capable of inducing the production of cysteamine and/or cystamine; (d) a functional derivative, analog, conjugate, prodrug or precursor of (a) to (c); (e) a pharmaceutically acceptable salt of any of (a) to (d); or (f) any combination of (a) to (e); and (ii) an artemisinin-related compound; and (iii) a pharmaceutically acceptable diluent or carrier.

As such, in an embodiment, the present invention further provides a combination of compositions (1) and (2) mentioned above for decreasing susceptibility to parasite infection or disease or for preventing or treating parasite infection or disease (e.g., malaria). The present invention further provides composition (3) or composition (4) mentioned above for decreasing susceptibility to parasite infection or disease or for preventing or treating parasite infection or disease (e.g., malaria). In an embodiment, components (i) and (ii) of the composition of (3) are formulated together. In an embodiment, components (i) and (ii) of the composition of (3) are formulated separately.

As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. Formulations may be in the form of liquid solutions or suspension; for oral administration, formulations may be in the form of tablets or capsules; and for intranasal formulations, in the form of powders, nasal drops, or aerosols.

Formulations suitable for oral administration can consist of (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin (e.g., unit dose); (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art. The oral formulation may further contain one or more coatings, such as an enteric coating. Enterically coated formulations of cystamine, cysteamine and derivatives thereof are described, for example, in PCT publication No. WO 2007/089670.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use are prepared by dissolving the active compound(s)/composition(s) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (Rowe et al., *Handbook of pharmaceutical excipients,* 2003, 4$^{th}$ edition, Pharmaceutical Press, London UK). Except insofar as any conventional media or agent is incompatible with the active compound, use thereof in the pharmaceutical compositions of the invention is contemplated.

It is further contemplated that the cystamine, cysteamine, a derivative or pharmaceutically acceptable salt thereof can be administered orally in a delayed release formulation. Exemplary delayed release formulations are disclosed in U.S. Pat. No. 8,026,284.

The composition may also contain a combination of active compounds for the particular indication being treated, preferably those with complementary activities that do not adversely affect each other. It may be desirable to use the above-mentioned composition in addition to one or more agents currently used to prevent or treat the disorder in question (e.g., an antimalarial such as sulfadoxine-pyrimethamine [Fansidar®], mefloquine [Lariam®], atovaquone, proguanil, atovaquone-proguanil [Malarone®], quinine, doxycycline, primaquine), Lumefantrine (or benflumetol). The above-mentioned agents may be formulated in a single composition or in several individual compositions which may be co-administered in the course of the treatment.

Formulations to be used for in vivo administration are preferably sterile. This is readily accomplished, for example, by filtration through sterile filtration membranes.

The amount of the pharmaceutical composition which is effective in the prevention and/or treatment of a particular disease, disorder or condition (e.g., parasite infection and/or parasite-related disease) will depend on the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect a beneficial prophylactic and/or therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

The cystamine, cysteamine, a derivative or pharmaceutically acceptable salt thereof or any combination thereof may be administered one, two or three or four times per day. In various embodiments, an effective dosage of cystamine, cysteamine, or derivative of a pharmaceutically acceptable salt thereof may be within the range of 0.01 mg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. In some embodiments, the cystamine, cysteamine, a derivative or pharmaceutically acceptable salt thereof is administered at a total daily dose of from approximately 0.25 g/m$^2$ to 4.0 g/m$^2$ body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$. In some embodiments, the cystamine, cysteamine, a derivative or pharmaceutically acceptable salt thereof may be administered at a total daily dose of about 1-1.5 g/m$^2$ body surface area, or 0.5-1 g/m2 body surface area, or about 0.7-0.8 g/m$^2$ body surface area, or about 1.35 g/m$^2$ body surface area.

Examples of treatment regimens for artemisinin, artesunate and artemether recommended by the World Health Organization (WHO) (The use of Artemisinin and its derivatives as anti-malarial drugs, Report of a Joint CTD/DMP/TDR Informal Consultation, Geneva, 10-12 Jun. 1998) for the treatment of parasitic disease (malaria) are provided below:

Artemisinin may be administered at 20 mg/kg in a divided dose (loading dose) on the first day, followed by 10 mg/kg once a day for 6 days. Artesunate may be administered at 4 mg/kg in a divided dose on the first day, followed by 2 mg/kg once a day for 6 days. Artemether may be administered at 4 mg/kg in a divided dose on the first day, followed by 2 mg/kg once a day for 6 days.

In an embodiment, the dose of (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e) and/or (a) an artemisinin-related compound that is used/administered in the methods, uses, compositions, packages and combinations of the invention is a suboptimal dose. "Suboptimal dose" as used herein refers to a dose of one of the compounds of the combination described herein, which, when used in the absence of another compound of the combination, results in a biological effect of 50% or less (e.g., inhibition of parasitemia of 50% or less), in an embodiment of 40% or less, in a further embodiment of 30% or less, in a further embodiment of 20% or less, in a further embodiment of 10% or less. As such, use of a combination of the compounds described herein, where one or more compounds in the combination is used at a suboptimal dose, may achieve increased efficacy/biological effect (e.g., inhibition of parasitemia) relative to using the compound(s) in the absence of the other(s), at a comparable suboptimal dose.

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in parasite load (parasitemia), an amelioration of symptoms and parasite-related effects, and increased survival time of the affected host animal, following administration of (a) cysteamine, cystamine, a compound of formula I, an agent capable of increasing expression of pantetheinase or pantetheinase activity, an agent capable of inducing the production of cysteamine, a functional derivative, analog, metabolite, prodrug or precursor thereof, or salts thereof, and (b) an artemisinin-related compound. In embodiments, the decrease in parasite load or parasitemia induced by the treatment may be, for example, a 10%, 20%, 30%, 40%, 50%, 60%, 70%, 80%, 90%, 95%, 98%, 99% or 100% (i.e., complete elimination of the parasite) decrease in parasitemia. In accordance with the invention, a prophylactic effect may comprise a decrease in the onset of or of the severity of one or more of parasite load or parasitemia, symptoms and parasite-related effects, and increased survival time of the affected host animal, following administration of (a) cysteamine, cystamine, a compound of formula I, an agent capable of increasing expression of pantetheinase or pantetheinase activity, an agent capable of inducing the production of cysteamine, a functional derivative, analog, prodrug or precursor thereof, or salts thereof and (b) an artemisinin-related compound.

As such, a "therapeutically effective" or "prophylactically effective" amount of (a) cysteamine, cystamine, a compound of formula I, an agent capable of inducing expression of pantetheinase, an agent capable of inducing the production of cysteamine, a functional derivative, analog or precursor thereof, or salts thereof, or any combinations thereof, and (b) an artemisinin-related compound, may be administered to an animal, in the context of the methods of treatment and prevention, respectively, described herein.

In an embodiment, the above-mentioned subject is a mammal. A mammal, including for purposes of treatment and prevention, refers to any animal classified as a mammal, including humans, domestic and farm animals, and zoo, sports or pet animals such as dogs, horses, cats, cows etc. In an embodiment, the mammal is human.

Parasitic or parasite infection refers to an infection by an organism that lives on or inside another organism (host) and typically causes harm to the host. Parasite disease or parasitic disease refers to a disease or condition associated with parasite infection of a host. In an embodiment, the above-mentioned parasite is a protozoa. In an embodiment, the above-mentioned parasite is of the *Plasmodium* genus. In a further embodiment, the parasite is *Plasmodium falciparum, Plasmodium vivax, Plasmodium ovale*, or *Plasmodium malariae.*

The invention further provides kits or packages (e.g., commercial packages) comprising the above-mentioned compositions or agents together with instructions for their use for decreasing susceptibility to parasite infection or disease or for preventing or treating parasite infection or disease such as malaria (e.g., blood-stage malaria or cerebral malaria).

The arrangement and construction of such kits is conventionally known to one of skill in the art. Such kits may include, for example, container(s) (e.g., syringe and/or vial and/or ampoule) for containing the agent or combination of agents or compositions, other apparatus for administering the therapeutic agent(s) and/or composition(s) and/or diluent(s). The kit may optionally further include instructions. The instructions may describe how the agent(s) and the diluent should be mixed to form a pharmaceutical formulation. The instructions may also describe how to administer the resulting pharmaceutical formulation to a subject.

As used herein, a synergistic effect (e.g., reduction in parasitemia, increase in survival time) is achieved when the effect of the combined drugs is greater than the theoretical sum of the effect of each agent in the absence of the other. One potential advantage of combination therapy with a synergistic effect is that lower dosages (e.g., a suboptimal dose) of one or both of the drugs or therapies may be used in order to achieve high therapeutic activity with low toxicity. In an embodiment, the combination therapy results in at least a 5% increase in the effect as compared to the predicted theoretical additive effect of the agents. In a further embodiment, the combination therapy results in at least a 10% increase in the effect as compared to the predicted theoretical additive effect of the agents. In a further embodiment, the combination therapy results in at least a 20% increase in the effect as compared to the predicted theoretical additive effect of the agents. In a further embodiment, the combination therapy results in at least a 30% increase in the effect as compared to the predicted theoretical additive effect of the agents. In a further embodiment, the combination therapy results in at least a 50% increase in the effect as compared to the predicted theoretical additive effect of the agents.

A further advantage of using the drugs in combination is that efficacy may be achieved in situations where either drug alone would not have an effect. For example, in a case where the parasite is resistant to a drug when used alone but is affected by the drugs when used in combination.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The articles "a" and "an" are used herein to refer to one or to more than one (i.e., to at least one) of the grammatical object of the article. The term "such as" is used herein to mean, and is used interchangeably, with the phrase "such as but not limited to". The following examples are illustrative of various aspects of the invention, and do not limit the broad aspects of the invention as disclosed herein.

MODE(S) FOR CARRYING OUT THE INVENTION

The present invention is illustrated in further details by the following non-limiting examples.

Example 1

Materials and Methods

Mice. A/J and C57BL/6 (B6) mice were purchased from the Jackson Laboratories (Bar Harbor, Me.) and were housed at McGill University according to the guidelines of the Canadian Council on Animal Care. An LDH virus-free isolate of *P. chabaudi* AS was maintained by weekly passage in NJ mice. Mice were infected intravenously into the tail vein (i.v.) with $10^6$ or $10^7$ pRBC suspended in pyrogen-free saline. Following infection, the percentage of pRBC was determined daily on thin blood smears stained with Dif-Quik™ (Dade Behring, Newark, Del.), as described (Fortin A, et al. (2001) *Proc Natl Acad Sci USA* 98: 10793-10798).

Pharmacokinetic studies of cysteamine hydrochloride in vivo. Cysteamine was detected in plasma by high performance liquid chromatography analysis with ultraviolet detection (Dias V C, et al. (1998) *Clin Chem* 44: 2199-2201). Briefly, blood was collected in EDTA/heparin-containing tubes, and plasma was obtained by centrifugation. Plasma thiols were reduced by treatment with Tris(2-carboxyethyl)

phosphine (0.05M final concentration, 20 min. at 20° C.), and proteins were precipitated with tri-chloroacetic acid (TCA, 10% final concentration). Free thiols from the protein-free supernatant were derivatized using SBD-F (7-benzo-2-oxa-1,3-diazole-4-sulfonic acid), used at a final concentration of 0.2 mg/ml (1 hr at 60° C.) in 0.05 M borate buffer (pH 9.5). The mixture was then analyzed by HPLC: the mobile phase consisted of an aqueous solvent (0.1M acetic acid, 0.1 sodium acetate, pH 4.3) running on a Supelco™ LC-8 column, and elution of plasma analytes was with a 0-10% acetonitrile gradient. Detection of SBD-F derivatized analytes was by reading fluorescence at 515 nm (excitation at 385 nm). Cysteamine elution peaks were quantified (surface area), and plasma concentrations were calculated using a set of internal cysteamine standards processed at the same time. Area under the curve ($AUC_{t0\text{-}tlast}$) as calculated using the trapezoid approximation method.

Cysteamine, Chloroquine, Artesunate and Dihydroartemisinin administration in vivo. Cysteamine hydrochloride (Sigma, Burlington ON) was prepared in PBS. Chloroquine hydrochloride, artesunate and dihydroartemisinin were provided by Dafra Pharmaceuticals; chloroquine was prepared in PBS, artesunate and DHA were prepared in 5% sodium bicarbonate and diluted in water to appropriate concentrations. All solutions were prepared fresh daily, filter sterilized and injections were performed intra-peritoneally (i.p) or sub-cutaneously (s.c.) for 4 days or according to treatment regimen. Mice were weighed prior to treatment to determine appropriate doses and injection volumes ranged from 100-400 μL per mouse. In the case of animals treated with two drugs, artemisinin derivatives were administered first (due to the short half life of cysteamine), followed by cysteamine 5-10 minutes later on alternate sides. Untreated control animals were injected with PBS alone.

Statistical Tests. Groups with normally distributed data points were compared using parametric unpaired t-tests, while groups with non-Gaussian distributions were compared using non-parametric Mann-Whitney tests. Survival differences were analyzed using the Log-Rank test. Synergistic effects were defined as: the percent inhibition of the combination therapy was >10% greater than the sum of the percent inhibition of the individual mice. Standard error of percent inhibition was calculated from individual mice compared to the mean parasitemia level of the control group.

Example 2

Figure 1A:
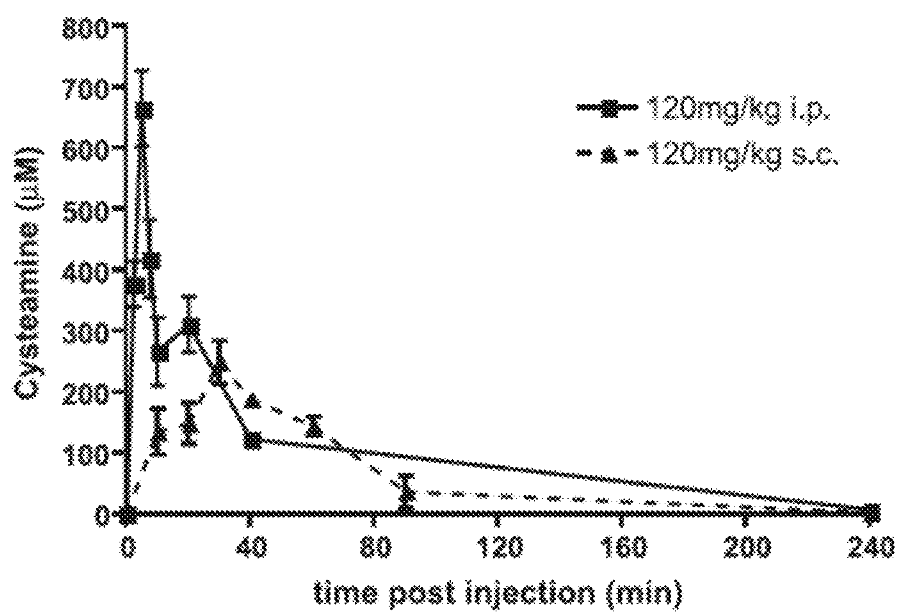
FIGS. 1A and 1B show the effect of cysteamine on replication of *Plasmodium chabaudi* in vivo.
Figure 1B:
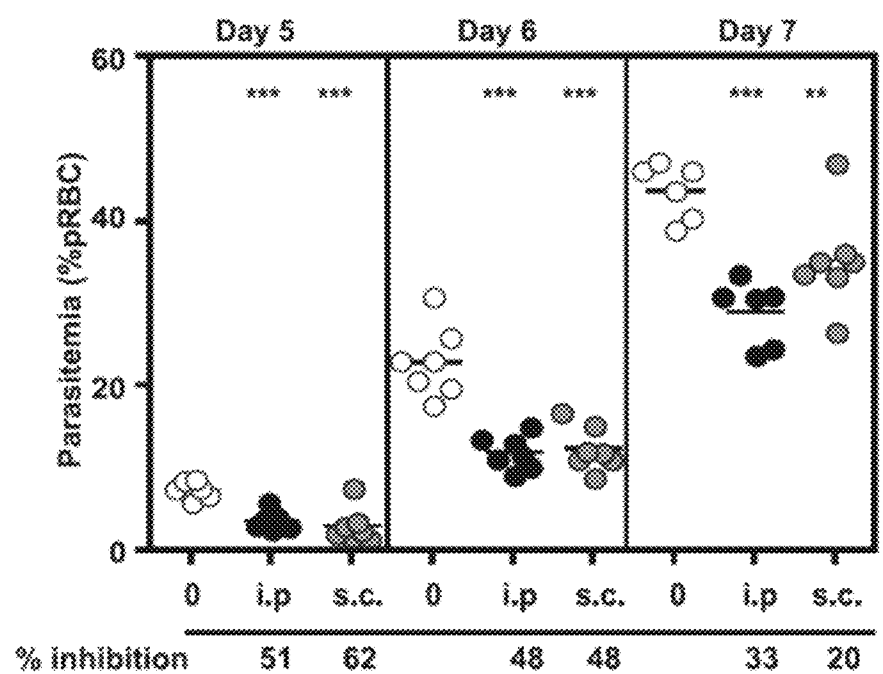

Characteristics of Cysteamine Activity Against *Plasmodium chabaudi* Infection In Vivo To gain more insight into the anti-malarial effect of cysteamine (Cys) in vivo, the pharmacokinetic characteristics (plasma level) of Cys administered through the sub-cutaneous (s.c.) and intra-peritoneal (i.p) routes was compared. Peak plasma concentration ($C_{max}$) and total bioavailability (area under the curve, AUC) after administration of a single dose of 120 mg/kg of Cys hydrochloride (FIG. 1A) was measured. The $C_{max}$ was higher (665 μM) and reached more rapidly ($T_{max}$<5 min) following i.p injection, compared to the s.c. route, where a $C_{max}$ of 250 μM was attained with a $T_{max}$ of 30 min. On the other hand, total Cys bioavailability ($AUC_{T0\text{-}Tlast}$) was comparable for both routes (24282 vs 15277 min×μM for i.p. and s.c., respectively). To determine which pharmacokinetic parameter (AUC vs. $C_{max}$) is important for efficacy against *Plasmodium*, the i.p. and s.c. routes of injection were compared in a continuous treatment regimen, starting one day prior to infection ($10^5$ pRBC of *P. chabaudi*, i.v.) and continuing daily for 7 days. Parasitemia was monitored on thin blood smears at days 5, 6 and 7 following infection (FIG. 1B). Treatment of infected animals with 120 mg/kg of Cys administered either s.c. or i.p. caused a highly significant ($p<0.01$) 50% reduction in parasitemia at day 5 and 6, relative to saline injected controls. These results suggest that total Cys exposure ($AUC_{T0\text{-}Tlast}$) is a pharmacokinetic parameter influencing the anti-malarial effect of Cys.

Example 3

Figure 2A:
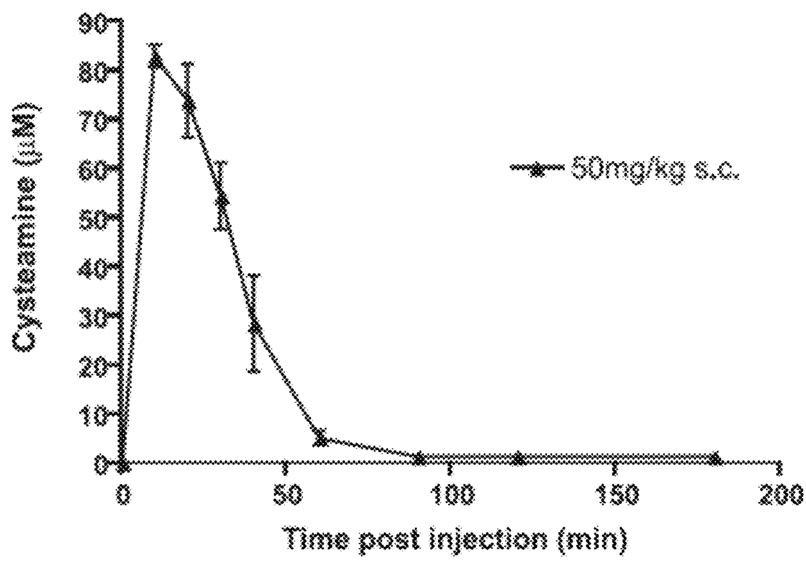
FIGS. 2A and 2B show the effect of cysteamine dosing used for treatment of cystinosis on replication of *Plasmodium chabaudi* in vivo.
Figure 2B:
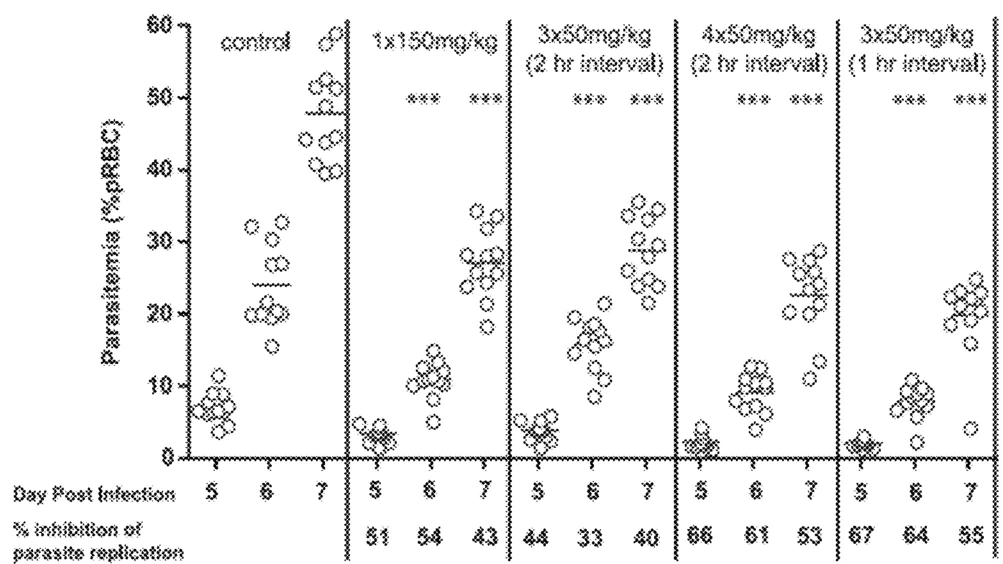

Cysteamine Dosing Used in the Treatment of Cystinosis Reduces Parasitemia During *P. chabaudi* Infection In Vivo It was next determined whether Cys at equivalent dosing to that used in the clinical treatment of nephropathic cystinosis in humans has an effect on the course and severity of *P. chabaudi* infection in mice. In cystinosis patients, Cys is given orally as Cys bitartrate (Cystagon®). The PK profile of an oral dose of 1475 mg of Cys bitartrate (500 mg cysteamine base), includes a peak plasma concentration of 39 μM ($C_{max}$) with a concomitant AUCT0-Tlast of 3613 min×μM (Fidler M C, et al. (2007) *Br J Clin Pharmacol* 63: 36-40). Results depicted in FIG. 2A show that a single s.c. injection of 50 mg/kg Cys hydrochloride in mice has a PK profile comparable to that of one oral dose of Cystagon® in humans, including a $C_{max}$ of ~80 μM and an AUC of 2845 min×μM. The efficacy of different regimens of 50 mg/kg Cys s.c (number of injections, interval between injections) on replication of *P. chabaudi* in vivo was evaluated. *P. chabaudi*-infected mice were treated daily, starting at day −1 and continuing to day 10, with either 1×150 mg/kg, 3×50 mg/kg given at 2 hr intervals, 4×50 mg/kg given at 2 hr intervals or 3×50 mg/kg given at 1 hr intervals of Cys, and blood parasitemia was monitored at days 5, 6 and 7 (FIG. 2B). Significant reduction (40-67%) of blood parasitemia was seen for all treatment regimens, with the strongest effect achieved with 3×50 mg/kg given at 1 hr intervals. All 50 mg/kg repeated dosing regimens (s.c.) showed inhibitory effects on parasitemia that were similar to that produced by a single s.c. injection of 150 mg/kg Cys, in agreement with data from FIGS. 1A and 1B showing that is a pharmacokinetic parameter influencing the anti-malarial effect of Cys. These results suggest that multiple Cys treatments at doses similar to those used in humans for cystinosis, can significantly reduce blood-stage replication of *Plasmodium* parasites in mice.

Example 4

Figure 3C:
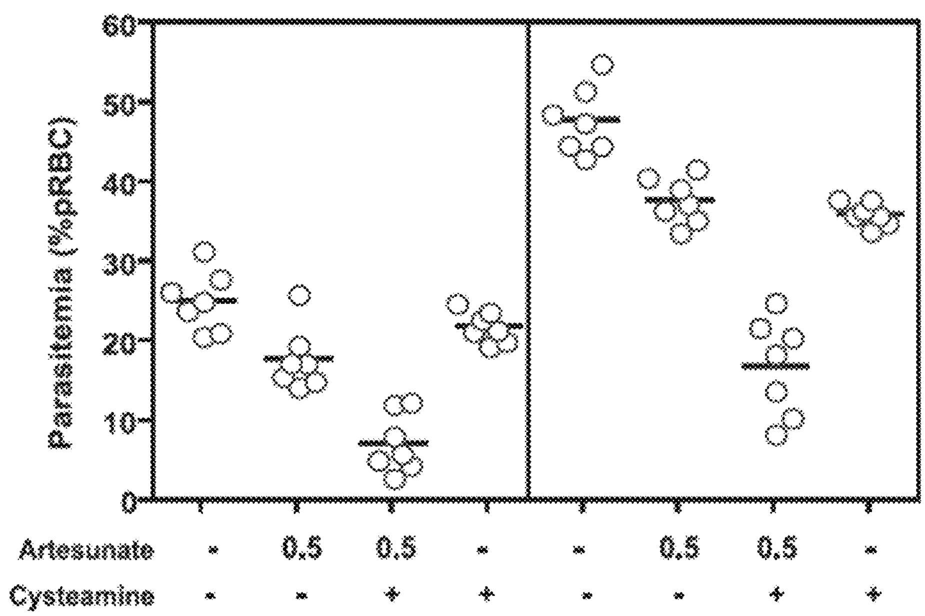

Cysteamine and Artemisinin Derivatives Show Synergistic Effects Against *Plasmodium* In Vivo The effect of Cys on the potency and efficacy of the anti-malarial artemisinin derivatives was tested. In these studies, artemisinin derivatives were given at sub-optimal concentrations to distinguish between the lack of an effect and additive or synergistic effects of Cys addition. Synergy (Tallarida R J (2001) *J Pharmacol Exp Ther* 298: 865-872) is defined as a total anti-malarial activity (reduction in blood parasitemia compared to untreated controls in a standard 4-day test) of the two compounds administered together being greater than the sum of the independent activities of the two compounds given alone. We tested combinations of Cys and either artesunate (ART) or dihydroartemisinin (DHA), the bioactive form of artemisinin. Pantetheinase-deficient A/J mice were infected with *P. chabaudi* ($10^7$ pRBC, i.v.) and treated with Cys (170 mg/kg) and/or sub-optimal doses of ART (0.2 or 0.5 mg/kg) (FIG. 3A) or DHA (0.15 or 0.3 mg/kg) (FIG. 3B) from day 0-3 and parasitemia was monitored on days 4 and 5. Sub-optimal doses of the artemisinin derivatives alone resulted in parasitemia inhibition ranging from 20-30%, while higher doses of these drugs could inhibit parasitemia 40-60%, compared to controls (FIG. 3A/B; TABLE 1). However, addition of Cys to either ART or DHA resulted in stronger inhibition of parasitemia than the additive effect of the two compounds, indicating a synergistic effect (TABLE 1; stars). Synergy was observed at all concentrations of ART and DHA tested. Mice receiving both Cys and ART/DHA also showed fewer symptoms of disease (ruffled fur, lethargy), compared to mice receiving either PBS or only one compound. To assess whether the synergistic effect between Cys and ART was restricted to NJ mice deficient in pantetheinase, the experiment were repeated in pantetheinase sufficient and malaria-resistant C57BL/6 mice (FIG. 3C). Potentiation of the anti-malarial activity of ART (0.5 mg/kg) by Cys was also clearly evident in these C57BL/6 mice at both days 4 and 5 post-infection, with combined treatment causing a 65-71% reduction in parasitemia compared to PBS controls, greater than either compound tested alone (13-29%) (TABLE 1).

TABLE 1

Effect of cysteamine and artemisinin derivative combinations on blood-stage replication of *Plasmodium chabaudi* in vivo

| Mouse type and drug | Dose (mg/kg) | Cysteamine (170 mg/kg) | Inhibition of parasitemia (% PBS control)[a] Day 4 | Day 5 |
|---|---|---|---|---|
| Pantetheinase-deficient A/J | | | | |
| Artesunate | 0.2 | − | 30 | 20 |
| Artesunate | 0.2 | + | 65* | 56* |
| Artesunate | 0.5 | − | 65 | 43 |
| Artesunate | 0.5 | + | 93 | 80* |
| DHA | 0.15 | − | 22 | 13 |
| DHA | 0.15 | + | 56* | 46* |
| DHA | 0.3 | − | 50 | 40 |
| DHA | 0.3 | + | 80 | 71* |
| NA[b] | 0 | + | 28 | 23 |
| Pantetheinase-sufficient C57BL/6 | | | | |
| Artesunate | 0.5 | − | 29 | 21 |
| Artesunate | 0.5 | + | 71* | 65* |
| NA | 0 | + | 13 | 25 |

[a]*indicates synergy between the compounds.

[b]NA, no drug administered.

Example 5

Figure 4A:
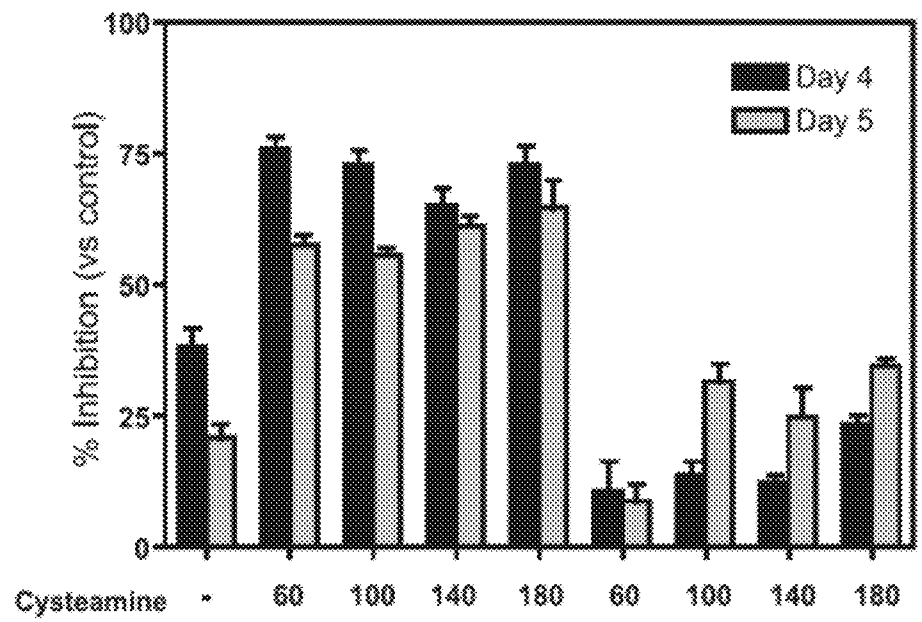
FIGS. 4A to 4C show the dose-dependent synergistic effect of cysteamine on artemisinin efficacy against replication of *Plasmodium chabaudi* in vivo. Groups (n=6) of female NJ mice were infected with *P. chabaudi* ($10^7$ pRBC, i.v.) and treated for 4 days (days 0, 1, 2, and 3) with increasing doses (indicated) of artesunate (FIG. 4C) and/or cysteamine (FIGS. 4A and B) given i.p. Blood parasitemia was determined at days 4 and 5 post-infection, and the inhibitory effects of the different drug treatments on blood-stage *P. chabaudi* replication were calculated for each animal compared to the mean of PBS-treated controls (expressed as a percentage). The presence or absence of drug is indicated by a plus or minus, respectively, and all doses are in mg/kg. Error bars represent standard error of the mean.
Figure 4B:
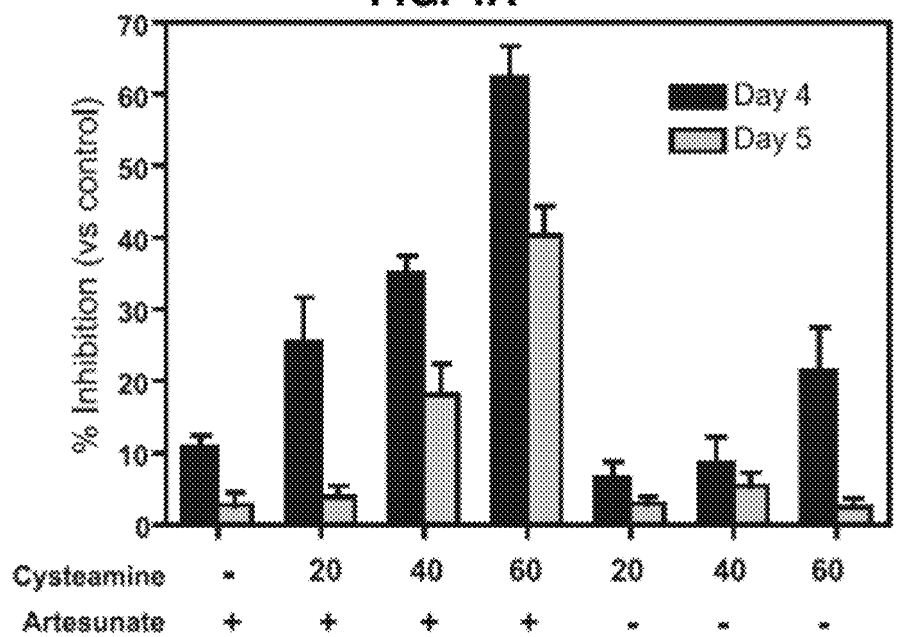
Figure 4C:
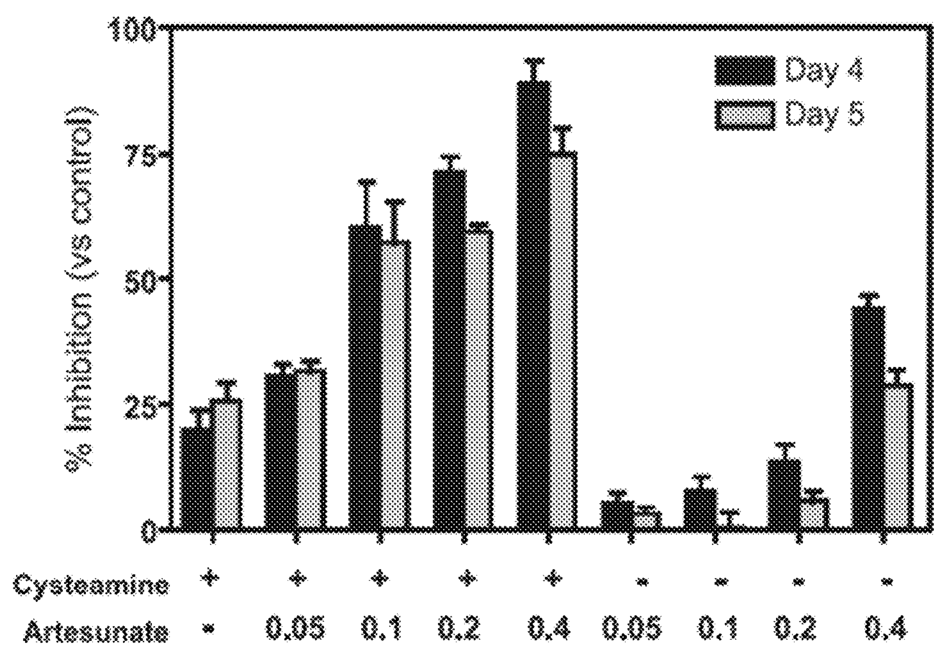

Synergistic Inhibition of *Plasmodium* Replication by Artesunate and Cysteamine is Dose-Dependent It was subsequently examined whether Cys potentiation of ART was dose dependent. Initially, Cys doses of 60, 100, 140 and 180 mg/kg were tested with a sub-optimal ART dose of 0.2 mg/kg. The drugs were administered from day 0-3 post infection, parasitemia was counted at day 4 and day 5 and the percent inhibition was calculated compared to PBS-treated controls (FIG. 4A). At 0.2 mg/kg, ART alone inhibits parasitemia by ~20% (day 4) and 40% (day 5) while inhibition by Cys alone was partially dose dependent (varying between 10% and 25%). Synergy was observed for all Cys doses tested (varying between 50% and 75% reduction in parasitemia), although without a clear dose-dependent effect in this Cys dosing range. Testing a lower Cys dose range (20, 40 and 60 mg/kg) revealed a clear dose-dependent effect on synergistic inhibition of parasitemia, with doses as low as 20-40 mg/kg showing potentiation of the ART effect (FIG. 4B). It was also assessed whether Cys could potentiate low doses of artesunate which, given alone, have no significant effect on parasitemia. In this experiment, Cys (170 mg/kg) was administered in combination, or not, with increasing doses of ART (0.05, 0.1, 0.2, 0.4 mg/kg) in the same 4-day experimental protocol. In these experiments, a strong potentiation (minimum of 3-fold) of low-dose artesunate by Cys was detected, with 60-75% inhibition of parasitemia replication for combinations containing low dose ART at 0.1 and 0.2 mg/kg, compared to <10% for these doses of ART used alone (FIG. 4C).

Example 6

Figure 5A:
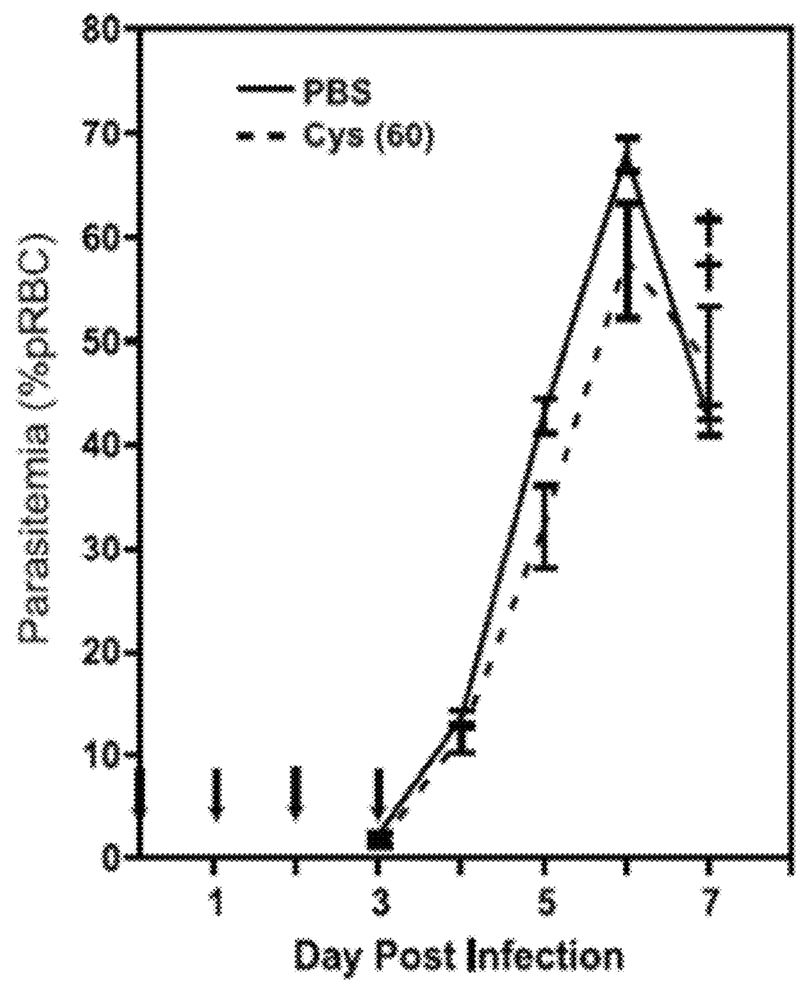
FIGS. 5A to 5D show the effect of cysteamine and artesunate combinations on progression and resolution of *P. chabaudi* infection in vivo. Groups (n=6) of female NJ mice were infected with *P. chabaudi* ($10^6$ pRBC, i.v.) and treated for 4 days (days 0, 1, 2, and 3) with PBS (FIG. 5A), cysteamine (60 mg/kg, FIG. 5A), or cysteamine (60 mg/kg) combined with increasing doses of artesunate (0.5, 1.0, 5, or 10 mg/kg, FIG. 5B), all given i.p. Blood parasitemia was measured daily up to day 20 (expressed as percentage of pRBC), and death was recorded (indicated by a cross). Solid and dashed lines represent mice receiving artesunate doses alone or in combination with cysteamine, respectively; artesunate doses are depicted by the abbreviations "Art0.5", "Art1", "Art5", and "Art10", as indicated. Error bars represent standard deviation of the mean, and arrows represent drug treatment days.
Figure 5B:
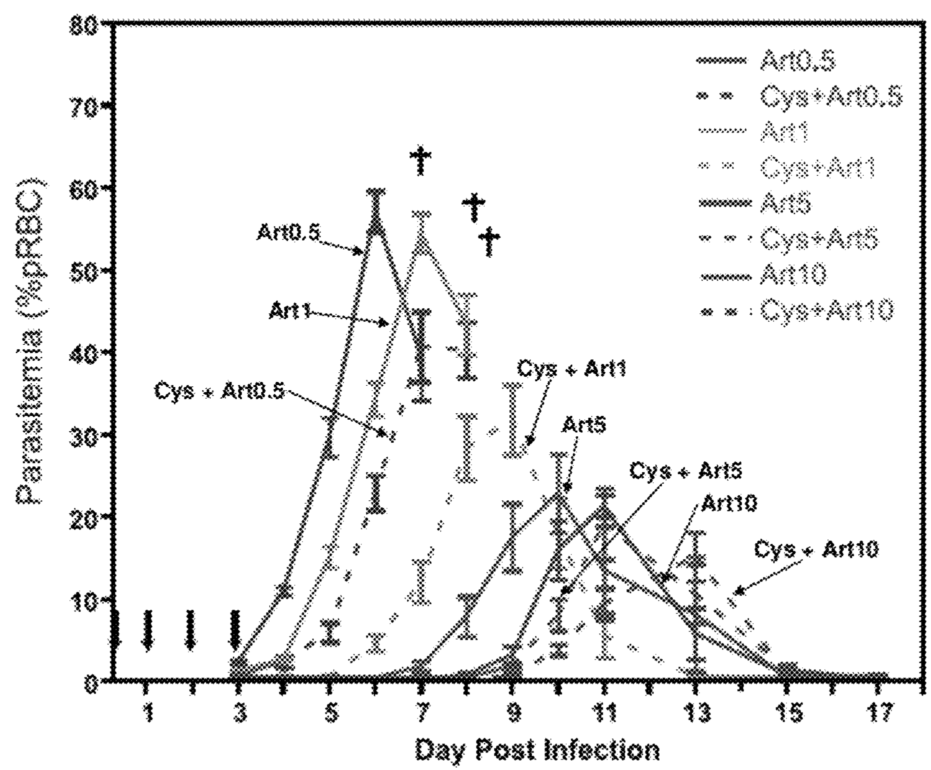
Figure 5C:
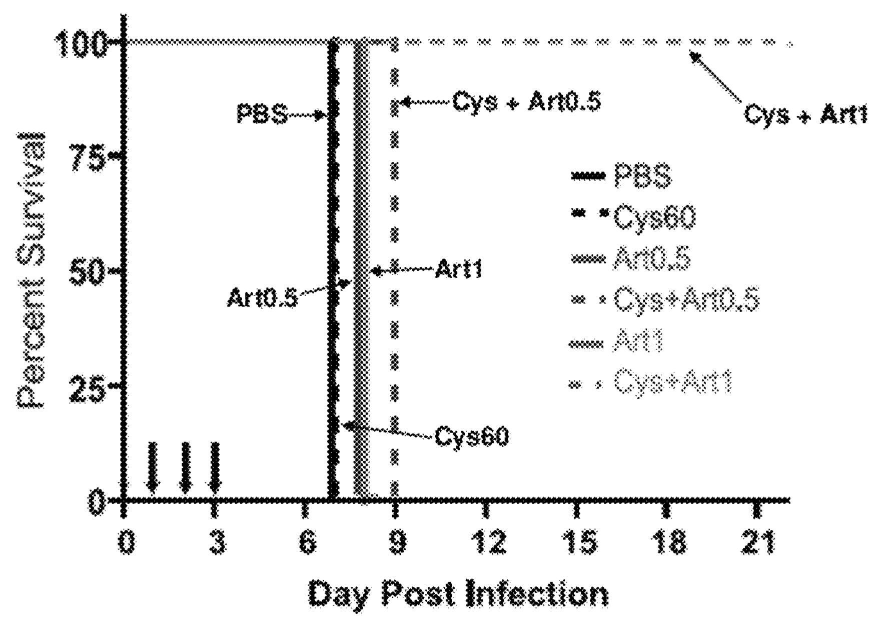
Figure 5D:
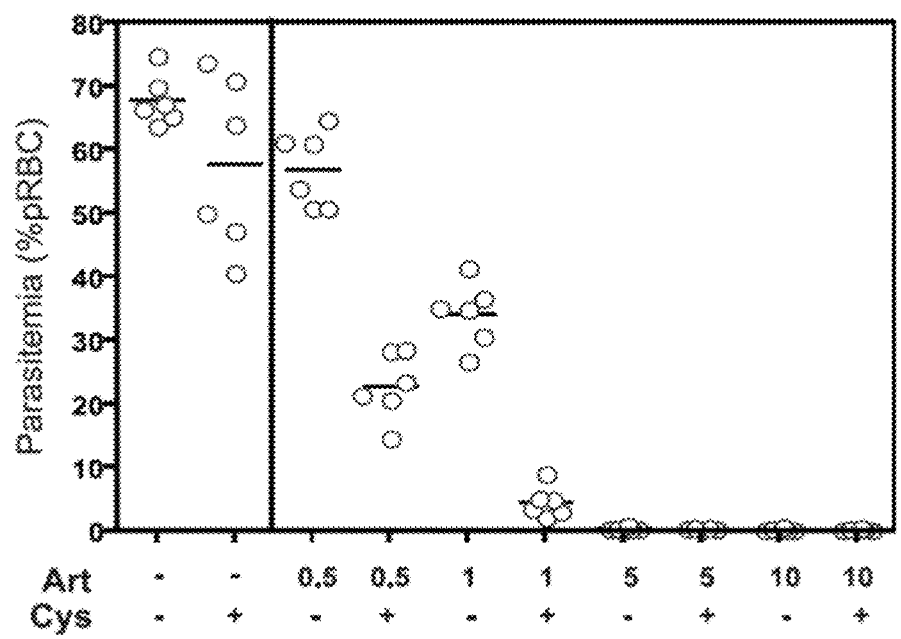

The Impact of Cysteamine and Artesunate in Combination on the Resolution of *P. chabaudi* Infection It was investigated if low dose Cys could potentiate standard doses of ART that show therapeutic activity in vivo and concurrently determined possible long-term effects on patent parasitemia, resolution of infection and survival in a lethal infection model. In this protocol, mice were infected with $10^6$ pRBC *P. chabaudi* (i.v.) and treated with Cys (60 mg/kg) and/or ART (0.5, 1, 2, 5 and 10 mg/kg) for 4 days (days 0-3), while blood parasitemia and survival were followed for 22 days. Control animals treated with either PBS or Cys alone (60 mg/kg) developed high parasite burdens, which peaked at day 6, and all mice succumbed to the infection by day 7 (FIGS. 5A and 5C). In animals receiving ART alone, there was a dose-dependent effect on infection, which manifested as a delay in the onset of parasitemia and a reduction of peak parasitemia. Strikingly, the addition of Cys (60 mg/kg) to all ART doses tested had a beneficial effect on infection kinetics, causing both a further delay in onset (by 2 to 3 days), and a reduction of peak levels of parasitemia relative to mice receiving only the corresponding dose of ART (FIG. 5B). Notably, the addition of Cys to 0.5 mg/kg or 1 mg/kg of ART caused a strong potentiation of the ART effect, with a further 60-70% reduction in parasitemia at day 6 (FIG. 5D). Likewise, although all mice treated with 0.5 mg/kg ART succumbed to the infection early (day 8), mice additionally receiving Cys survived until day 9; moreover, addition of Cys to 1.0 mg/kg ART completely rescued animals from lethality of infection, with 100% survival in this group (FIGS. 5B, 5C). These results indicate that the synergistic effect of low doses of Cys on artemisinin derivatives not only impacts early parasite burdens, but also significantly improves ultimate outcome to infection.

Example 7

Figure 6A:
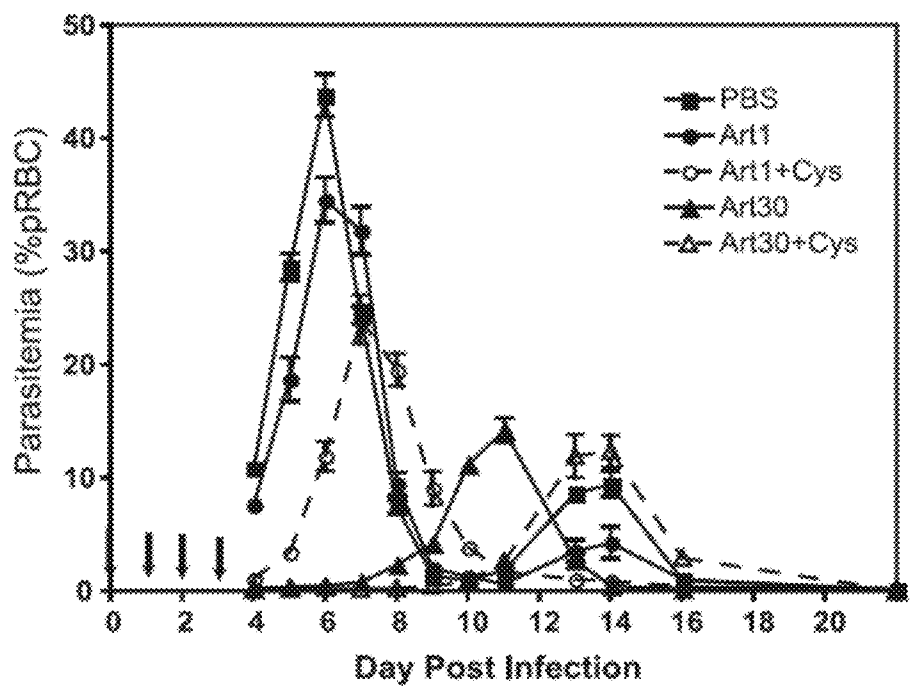
FIGS. 6A and 6B show the effect of cysteamine and artesunate combinations on progression of *P. chabaudi* in pantetheinase-sufficient B6 mice. Groups (n=6) of female B6 mice were infected with *P. chabaudi* ($10^6$ pRBC, i.v.) and treated for 4 days (days 0, 1, 2, and 3) with either PBS or artesunate (1.0 or 30 mg/kg) combined with, or without, cysteamine (60 mg/kg, FIG. 6A), all given i.p. Blood parasitemia was measured daily up to day 22 (expressed as percentage of pRBC). Solid and dashed lines represent mice receiving artesunate doses alone or in combination with cysteamine, respectively. Error bars represent standard deviation of the mean, and arrows represent drug treatment days.
Figure 6B:
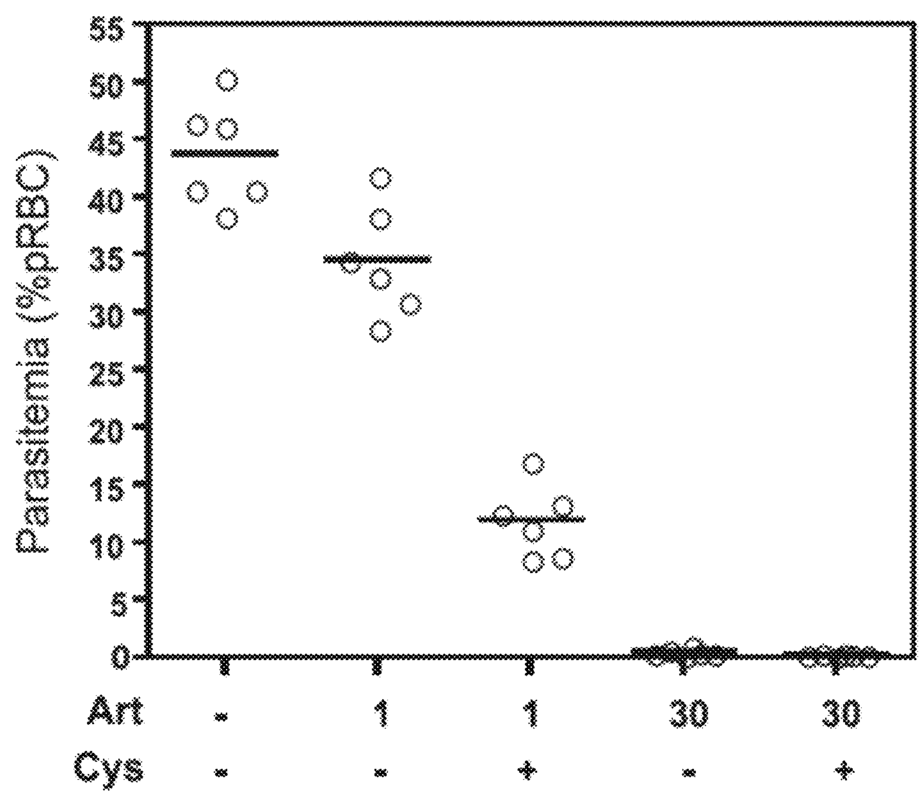

Effect of Cysteamine and Artesunate Combinations on Progression of *P. chabaudi* in Pantetheinase-Sufficient B6 Mice To investigate whether the effects on parasite burden over the course of infection would also be observed with a pantetheinase-sufficient mouse strain, a similar experiment was performed using female B6 mice. Groups of mice were infected with $10^6$ *P. chabaudi* pRBC i.v. and treated with PBS, 1 mg/kg or 30 mg/kg of Art, or 1 mg/kg or 30 mg/kg of Art plus 60 mg/kg of Cys for 4 days. A reduction in parasite levels and a delay in the peak were observed when Cys and Art are given in combination, compared to results with Art administered alone, at both high and low doses (FIG. 6A). As in NJ mice, the effect of Cys addition to 1 mg/kg of Art has a clear effect on early parasite replication at day 6 (FIG. 6B). Although a "curative" dose combination was not achieved with a 4-day treatment regimen, parasite levels remained under 12% pRBC in the 30 mg/kg Art-plus-Cys group, and mice did not display any outward symptoms of disease such as lethargy or ruffled fur. B6 mice were able to completely clear parasite burdens and survive the infection, even in the control PBS-treated group. However, the addition of Cys eliminated the appearance of recrudescent parasitemia around day 14, as seen with the control group (FIG. 6A). These results indicate that the synergistic effect of low doses of Cys on artemisinin derivatives not only impacts early parasite burdens but can also significantly improve ultimate outcome to infection.

Example 8

Effect of Cysteamine and Artesunate Combinations on Progression of *Plasmodium berghei* ANKA Infection Intravenous infection with *Plasmodium berghei* ANKA is an accepted mouse model of cerebral malaria (CM) (Hunt, N. H. et al. 2006, *Int. J. Parasitol.* 36: 569-582). The infection causes the following pathology. First, there is appearance of blood parasitemia, starting at days 3 or 4, which can go up to 10% by day 7-8. Starting at day 5-6, there is emergence of cerebral symptoms caused by permeability of the blood brain barrier, concomitant to trapping of parasitized red cells in the microvasculature and acute pathological host inflammatory response in situ. This cerebral phase quickly progresses from tremors, to paralysis, to coma, and is uniformly lethal in mice by days 8-10. In this model, progress of infection and possibly drug effects may be monitored by a) appearance and intensity of blood parasitemia (between days 5-8), b) appearance of cerebral symptoms, and c) lethality.

Figure 8A:
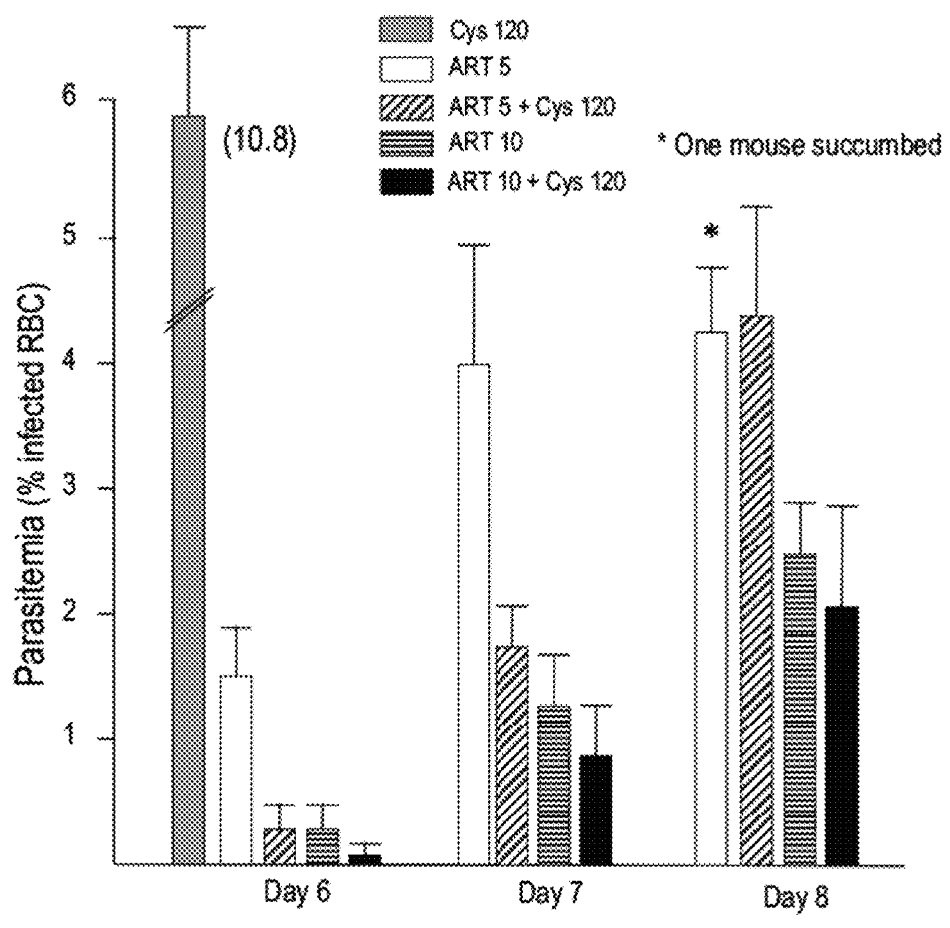
FIGS. 8A and 8B show the results of two independent experiments on the effect of cysteamine and artesunate combinations on the progression of *Plasmodium berghei* ANKA infection (parasitemia). Groups of 5 adult 18-20 g C57BL/6J males and females were infected intravenously with $1\times10^6$ erythrocytes parasitized with *P. berghei* ANKA at time "0". Two hours later, mice were injected i.p with either Artemisinin alone or with Artemisinin/Cysteamine combinations (at the indicated concentrations in mg/kg body weight). In the case of the latter, Artemisinin was injected first in one quadrant, and cysteamine was injected second, 10-15 minutes later in another quadrant. The drug treatment was further repeated at days 1, 2 and 3 post-infection to emulate the standard 4-day test used in anti-malarial drug discovery. Starting at day 5, blood was collected, thin blood smears were prepared, and parasitemia was determined (400 erythrocytes counted, expressed as percentage parasitized erythrocytes). Error bars show standard deviations on the mean.
Figure 8B:
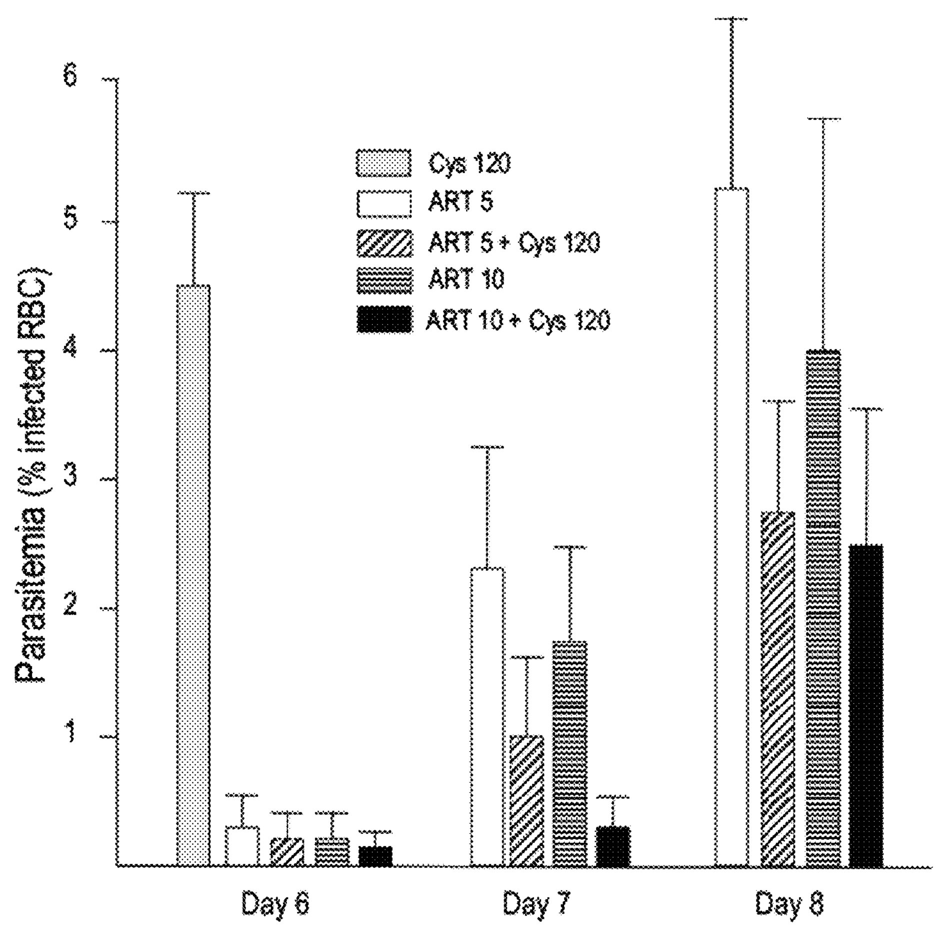

The results depicted in FIGS. 8A and 8B show that addition of Cysteamine to either of the two Artemisinin dosings (5 or 10 mg/kg) causes a delay in the rise of parasitemia and seems to cause a reduction in absolute levels measured at days 6-8 over what is detected in animals treated with Artemisnin alone. Second, the addition of cysteamine to Artemisinin causes an effect which is comparable (FIG. 8A) or superior (FIG. 8B) to that of doubling the dose of Artemisinin.

Figure 9A:
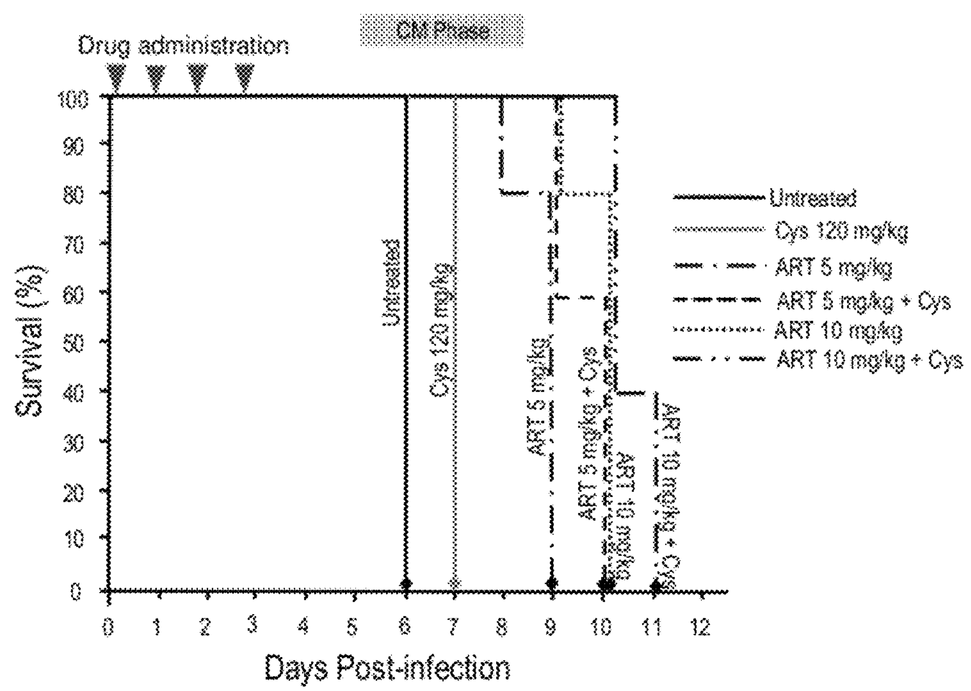
FIGS. 9A and 9B show the results of two independent experiments on the effect of cysteamine and artesunate combinations on the survival of *Plasmodium berghei* ANKA-infected mice. Infection and drug administration were performed as described above for FIGS. 8A and 8B. Animals were monitored for the appearance and severity of cerebral symptoms (CM phase, shown as rectangle in graph), and moribund animals were euthanized, and time of death was recorded.
Figure 9B:
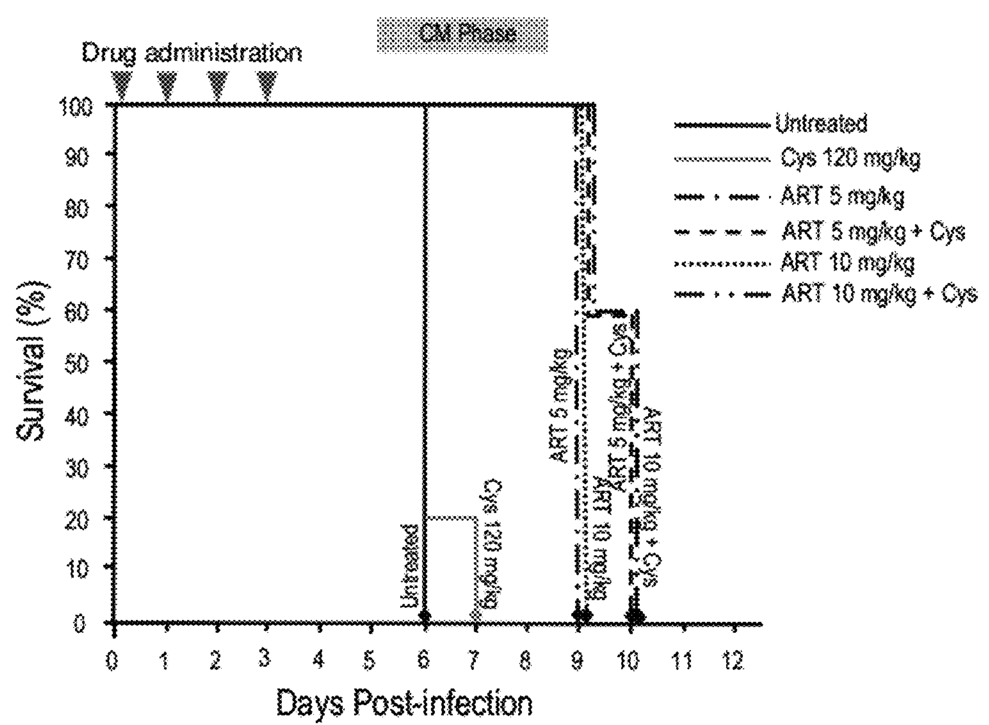

With respect to survival (FIGS. 9A and 9B), Cysteamine alone had a minor positive effect on survival of *P. berghei*-infected animals. Adding cysteamine to Artemisinin prolonged survival of *P. berghei*-infected animals over that measured in animals treated with Artemisinin alone, and this by a factor of 1-2 days.

Although the present invention has been described herein above by way of specific embodiments thereof, it can be modified, without departing from the spirit and nature of the subject invention as defined in the appended claims.

What is claimed is:

1. A method for decreasing susceptibility to parasite infection or disease or treating parasite infection or disease, in a subject in need thereof, said method comprising administering to said subject an effective amount of (i)(a) a compound of formula I:

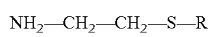

$$NH_2—CH_2—CH_2—S—R \quad (I)$$

wherein R is H or $S—CH_2—CH_2—NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) an artemisinin-related compound.

2. The method of claim 1, wherein said method comprises administering to said subject an effective amount of (i) (a) cystamine; (b) cysteamine; (c) a pharmaceutically acceptable salt of (a) or (b); or (d) any combination of (a) to (c); and (ii) an artemisinin-related compound.

3. The method of claim 2, wherein said method comprises administering to said subject an effective amount of (i) cysteamine or a pharmaceutically acceptable salt thereof; and (ii) an artemisinin-related compound.

4. The method according to claim 1, wherein said artemisinin-related compound is artesunate.

5. The method according to claim 1, wherein said artemisinin-related compound is dihydroartemisinin (DHA).

6. The method according to claim 1, wherein said parasite is of the genus *Plasmodium.*

7. The method according to claim 1, wherein said disease is malaria.

8. The method according to claim 7, wherein said malaria is blood-stage malaria.

9. The method according to claim 7, wherein said malaria is cerebral malaria.

10. The method according to claim 1, wherein said subject is a human.

11. The method according to claim 1 wherein compounds (i) and (ii) act synergistically.

12. The method of claim 11, wherein the synergy results in use of effective doses of compound i) and/or ii) that are lower than doses administered when the compounds are administered in the absence of the other composition.

13. The method of claim 12, wherein the effective dose of compound (i) is lower than a dose of (i) administered in the absence of compound (ii).

14. The method of claim 12, wherein the effective dose of compound (ii) is lower than a dose of (ii) administered in the absence of compound (i).

15. The method of claim 12, wherein the effective dose of (i) and (ii) are lower than a dose of compound (i) or compound (ii) administered in the absence of the other composition.

16. The method of claim 12, wherein the dose of compound (i) and/or (ii) is suboptimal.

17. The method of claim 1, wherein the effective dose of compound (i) is in the range of 1 to 500 mg/kg.

18. The method of claim 1, wherein compound (i) is present in a delayed release composition.

19. The method according to claim 1, wherein the peak level of parisitemia is reduced.

20. The method according to claim 1, wherein the administering prevents parisitemia.

21. The method according to claim 1, wherein compound (i) is administered less than four times a day.

22. The method according to claim 1, wherein compound (i) is administered twice daily.

23. The method of claim 1, wherein compounds (i) and (ii) are administered coextensively.

24. A composition for decreasing susceptibility to parasite infection or disease or treating parasite infection or disease, in a subject, said composition comprising (i) (a) a compound of formula I:

$$NH_2—CH_2—CH_2—S—R \quad (I)$$

wherein R is H or $S—CH_2—CH_2—NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) an artemisinin-related compound.

25. The composition according to claim 24, wherein said composition comprises (i) (a) cystamine; (b) cysteamine; (c) a pharmaceutically acceptable salt of (a) or (b); or (d) any combination of (a) to (c); and (ii) (a) artemisinin, (b) a functional derivative, analog, conjugate, metabolite, prodrug or precursor of artemisinin, (c) a pharmaceutically acceptable salt of (a) or (b), or (d) any combination of (a) to (c).

26. The composition according to claim 25, wherein said composition comprises (a) cysteamine or a pharmaceutically acceptable salt thereof; and (b) an artemisinin-related compound.

27. The composition according to claim 24, wherein said artemisinin-related compound is artesunate.

28. The composition according to claim 24, wherein said an artemisinin-related compound is dihydroartemisinin.

29. The composition according to claim 24, further comprising a pharmaceutically acceptable carrier or excipient.

30. The composition according to claim 24, wherein said parasite is of the genus *Plasmodium.*

31. The composition according to claim 24, wherein said disease is malaria.

32. The composition according to claim 31, wherein said malaria is blood-stage malaria.

33. The composition according to claim 31, wherein said malaria is cerebral malaria.

34. A package comprising (i) (a) a compound of formula I:

$$NH_2—CH_2—CH_2—S—R \quad (I)$$

wherein R is H or $S—CH_2—CH_2—NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) an artemisinin-related compound for decreasing susceptibility to parasite infection or disease or treating parasite infection or disease in a subject.

35. The package of claim 34, wherein i) and ii) are packaged separately.

36. The package of claim 34, wherein i) and ii) are packaged in the same formulation.

37. The package of claim 34 wherein compound i) is present in a delayed release composition.

38. The package of claim 34, further comprising labels and instructions for use.

39. A package comprising (i) a plurality of doses of a compound of formula I:

$$NH_2—CH_2—CH_2—S—R \quad (I)$$

wherein R is H or S—CH2—CH2—NH2; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) a plurality of doses of an artemisinin-related compound for decreasing susceptibility to parasite infection or disease or for preventing or treating parasite infection or disease in a subject.

40. The package of claim 39, wherein (i) and (ii) are packaged separately.

41. The package of claim 39, wherein (i) and (ii) are packaged together.

* * * * *

SEQUENCE LISTING

```
<160> NUMBER OF SEQ ID NOS: 19

<210> SEQ ID NO 1
<211> LENGTH: 2255
<212> TYPE: DNA
<213> ORGANISM: Mus musculus
<220> FEATURE:
<221> NAME/KEY: CDS
<222> LOCATION: (22)..(1560)

<400> SEQUENCE: 1

ttgctgtcgt tggacttcag c atg ggc acg tct tgg tgg ctg gcg tgt gct        51
                        Met Gly Thr Ser Trp Trp Leu Ala Cys Ala
                        1               5                   10

gca gcg ttt tct gcc ctc tgt gtc tta aaa gcc agc tcg ctg gat act        99
Ala Ala Phe Ser Ala Leu Cys Val Leu Lys Ala Ser Ser Leu Asp Thr
                15                  20                  25

ttc ctc gcg gct gtt tac gag cat gct gtg atc ctg cct aag gac acc       147
Phe Leu Ala Ala Val Tyr Glu His Ala Val Ile Leu Pro Lys Asp Thr
            30                  35                  40

ctg ttg cca gtg tct cac ggt gag gct ctg gca tta atg aac cag aat       195
Leu Leu Pro Val Ser His Gly Glu Ala Leu Ala Leu Met Asn Gln Asn
        45                  50                  55

ctg gac ctt ctg gaa gga gcg atc gta tct gca gcg aag cag ggt gcg       243
Leu Asp Leu Leu Glu Gly Ala Ile Val Ser Ala Ala Lys Gln Gly Ala
    60                  65                  70

cac att att gtg act cca gaa gat ggc ata tac ggt gtg cgt ttc acc       291
His Ile Ile Val Thr Pro Glu Asp Gly Ile Tyr Gly Val Arg Phe Thr
75                  80                  85                  90

agg gat acg atc tac cca tac ctg gag gag atc cca gac cct caa gta       339
Arg Asp Thr Ile Tyr Pro Tyr Leu Glu Glu Ile Pro Asp Pro Gln Val
                95                  100                 105
```

-continued

```
aac tgg ata ccc tgt gat aac cct aaa aga ttt ggc tct acc ccg gtg      387
Asn Trp Ile Pro Cys Asp Asn Pro Lys Arg Phe Gly Ser Thr Pro Val
            110                 115                 120

cag gag aga ctc agc tgc ttg gcc aag aac aac tcc atc tat gtt gtg      435
Gln Glu Arg Leu Ser Cys Leu Ala Lys Asn Asn Ser Ile Tyr Val Val
        125                 130                 135

gcg aac atg gga gac aag aag ccg tgt aac acc agc gac tct cac tgt      483
Ala Asn Met Gly Asp Lys Lys Pro Cys Asn Thr Ser Asp Ser His Cys
    140                 145                 150

cca cct gac ggc aga ttc cag tac aac act gat gtg gtg ttt gat tcc      531
Pro Pro Asp Gly Arg Phe Gln Tyr Asn Thr Asp Val Val Phe Asp Ser
155                 160                 165                 170

cag ggt aaa ctg gtt gcg aga tac cat aag caa aac att ttc atg gga      579
Gln Gly Lys Leu Val Ala Arg Tyr His Lys Gln Asn Ile Phe Met Gly
                175                 180                 185

gaa gat cag ttc aat gtc ccc atg gag cct gag ttt gtg act ttc gac      627
Glu Asp Gln Phe Asn Val Pro Met Glu Pro Glu Phe Val Thr Phe Asp
            190                 195                 200

acc ccc ttt gga aag ttt ggc gtc ttc acc tgt ttc gat att ctc ttc      675
Thr Pro Phe Gly Lys Phe Gly Val Phe Thr Cys Phe Asp Ile Leu Phe
        205                 210                 215

cat gat ccc gct gtc acc ctg gtg aca gaa ttc cag gtg gac acc ata      723
His Asp Pro Ala Val Thr Leu Val Thr Glu Phe Gln Val Asp Thr Ile
    220                 225                 230

ctg ttc cca acc gcc tgg atg gac gtc ctt cct cat ttg gca gcc att      771
Leu Phe Pro Thr Ala Trp Met Asp Val Leu Pro His Leu Ala Ala Ile
235                 240                 245                 250

gaa ttc cac tca gct tgg gct atg ggc atg ggg gtc aat ttc cta gca      819
Glu Phe His Ser Ala Trp Ala Met Gly Met Gly Val Asn Phe Leu Ala
                255                 260                 265

gct aat cta cat aat ccc tcg agg aga atg aca gga agt ggt atc tat      867
Ala Asn Leu His Asn Pro Ser Arg Arg Met Thr Gly Ser Gly Ile Tyr
            270                 275                 280

gca ccc gat tct cca agg gtc ttt cac tac gac agg aag acc caa gaa      915
Ala Pro Asp Ser Pro Arg Val Phe His Tyr Asp Arg Lys Thr Gln Glu
        285                 290                 295

gga aaa ctc ctc ttc gct cag ctg aaa tcc cac cca att cac tcc ccg      963
Gly Lys Leu Leu Phe Ala Gln Leu Lys Ser His Pro Ile His Ser Pro
    300                 305                 310

gtg aac tgg act tcc tat gct agc agt gta gaa tca acc cca acc aaa     1011
Val Asn Trp Thr Ser Tyr Ala Ser Ser Val Glu Ser Thr Pro Thr Lys
315                 320                 325                 330

acc cag gaa ttt cag agt att gtc ttt ttt gat gag ttt acc ttt gtg     1059
Thr Gln Glu Phe Gln Ser Ile Val Phe Phe Asp Glu Phe Thr Phe Val
                335                 340                 345

gag ctc aaa ggg atc aaa gga aat tac act gtt tgc cag aat gac ctc     1107
Glu Leu Lys Gly Ile Lys Gly Asn Tyr Thr Val Cys Gln Asn Asp Leu
            350                 355                 360

tgc tgt cac cta agc tac cag atg tct gag aag cga gca gat gag gtt     1155
Cys Cys His Leu Ser Tyr Gln Met Ser Glu Lys Arg Ala Asp Glu Val
        365                 370                 375

tat gcc ttt gga gcc ttt gat ggg ctg cac acc gtg gaa ggg cag tac     1203
Tyr Ala Phe Gly Ala Phe Asp Gly Leu His Thr Val Glu Gly Gln Tyr
    380                 385                 390

tac cta cag atc tgc atc ctg cta aaa tgt aaa act acc aat tta cgc     1251
Tyr Leu Gln Ile Cys Ile Leu Leu Lys Cys Lys Thr Thr Asn Leu Arg
395                 400                 405                 410

acc tgt ggt agt tca gtg gac acg gct ttt acc agg ttt gaa atg ttc     1299
Thr Cys Gly Ser Ser Val Asp Thr Ala Phe Thr Arg Phe Glu Met Phe
                415                 420                 425
```

```
tcg ctc agc ggc act ttt gga acc cgg tat gtc ttc cct gaa gtg ttg     1347
Ser Leu Ser Gly Thr Phe Gly Thr Arg Tyr Val Phe Pro Glu Val Leu
            430                 435                 440

ctg agt gag gtc aag ctc gca cct ggg gag ttt cag gtg tca agt gat     1395
Leu Ser Glu Val Lys Leu Ala Pro Gly Glu Phe Gln Val Ser Ser Asp
        445                 450                 455

ggg cgc ctg gtt agc ctg aag cca acc tcg gga cct gtg tta acc atc     1443
Gly Arg Leu Val Ser Leu Lys Pro Thr Ser Gly Pro Val Leu Thr Ile
    460                 465                 470

ggg ctc ttt ggg agg ttg tat ggg aag gac tgg gca tcc aat gct tcc     1491
Gly Leu Phe Gly Arg Leu Tyr Gly Lys Asp Trp Ala Ser Asn Ala Ser
475                 480                 485                 490

tca gac ttc ata gca cac tcg ctg ata ata atg ctg att gtg acg cct     1539
Ser Asp Phe Ile Ala His Ser Leu Ile Ile Met Leu Ile Val Thr Pro
                495                 500                 505

att ata cat tac ttg tgc tga tggaattttt acattttta ttttatttag        1590
Ile Ile His Tyr Leu Cys
            510

aaaatttaaa attggtggat gcagaaaaaa taactgtttg tcaacagtgg actcgggtgt   1650

aagcaaataa agtgcctctt ctttagaaaa acatatgtac accagataca tttcaggaaa   1710

attaataaaa ctttgagcat tggaacgaga tggagggcca agtaaaggtc gcatgtgttt   1770

tattcagaag aaataaaaat tacagttaaa aggcacttca aaccatcata agatagattt   1830

acaagaggtg taaatctatt atacatctta ctcagttatg cttagaattt ccaatgtgtt   1890

tgttcatttg ggctattaag tatttatctc aacatttccg ttctctcatg gaccagatcc   1950

tgtagtttta attcttcagt tcaagtccca gttcccacaa cctcagaacg tgactgcctt   2010

ggtgtctttg gcaatgaaga cataagaggc atcattagca tggactttaa ttcaatatga   2070

ctgatctcct cagaagaaat caggacaaag acttgcatca agtgaagccc ttgtgaacac   2130

aggaaaagat ggtcatgtac aacaagaaaa ggggcctcag gagaacgcaa acctgctaac   2190

gtgtcaaact tccaggtctc cagaatcatg aggcaataaa tttctgtttt aaatgaaaaa   2250

aaaaa                                                               2255


<210> SEQ ID NO 2
<211> LENGTH: 512
<212> TYPE: PRT
<213> ORGANISM: Mus musculus

<400> SEQUENCE: 2

Met Gly Thr Ser Trp Trp Leu Ala Cys Ala Ala Ala Phe Ser Ala Leu
1               5                   10                  15

Cys Val Leu Lys Ala Ser Ser Leu Asp Thr Phe Leu Ala Ala Val Tyr
            20                  25                  30

Glu His Ala Val Ile Leu Pro Lys Asp Thr Leu Leu Pro Val Ser His
        35                  40                  45

Gly Glu Ala Leu Ala Leu Met Asn Gln Asn Leu Asp Leu Leu Glu Gly
    50                  55                  60

Ala Ile Val Ser Ala Ala Lys Gln Gly Ala His Ile Ile Val Thr Pro
65                  70                  75                  80

Glu Asp Gly Ile Tyr Gly Val Arg Phe Thr Arg Asp Thr Ile Tyr Pro
                85                  90                  95

Tyr Leu Glu Glu Ile Pro Asp Pro Gln Val Asn Trp Ile Pro Cys Asp
            100                 105                 110

Asn Pro Lys Arg Phe Gly Ser Thr Pro Val Gln Glu Arg Leu Ser Cys
```

```
        115                 120                 125

Leu Ala Lys Asn Asn Ser Ile Tyr Val Val Ala Asn Met Gly Asp Lys
    130                 135                 140

Lys Pro Cys Asn Thr Ser Asp Ser His Cys Pro Pro Asp Gly Arg Phe
145                 150                 155                 160

Gln Tyr Asn Thr Asp Val Val Phe Asp Ser Gln Gly Lys Leu Val Ala
                165                 170                 175

Arg Tyr His Lys Gln Asn Ile Phe Met Gly Glu Asp Gln Phe Asn Val
            180                 185                 190

Pro Met Glu Pro Glu Phe Val Thr Phe Asp Thr Pro Phe Gly Lys Phe
        195                 200                 205

Gly Val Phe Thr Cys Phe Asp Ile Leu Phe His Asp Pro Ala Val Thr
    210                 215                 220

Leu Val Thr Glu Phe Gln Val Asp Thr Ile Leu Phe Pro Thr Ala Trp
225                 230                 235                 240

Met Asp Val Leu Pro His Leu Ala Ala Ile Glu Phe His Ser Ala Trp
                245                 250                 255

Ala Met Gly Met Gly Val Asn Phe Leu Ala Ala Asn Leu His Asn Pro
            260                 265                 270

Ser Arg Arg Met Thr Gly Ser Gly Ile Tyr Ala Pro Asp Ser Pro Arg
        275                 280                 285

Val Phe His Tyr Asp Arg Lys Thr Gln Glu Gly Lys Leu Leu Phe Ala
    290                 295                 300

Gln Leu Lys Ser His Pro Ile His Ser Pro Val Asn Trp Thr Ser Tyr
305                 310                 315                 320

Ala Ser Ser Val Glu Ser Thr Pro Thr Lys Thr Gln Glu Phe Gln Ser
                325                 330                 335

Ile Val Phe Phe Asp Glu Phe Thr Phe Val Glu Leu Lys Gly Ile Lys
            340                 345                 350

Gly Asn Tyr Thr Val Cys Gln Asn Asp Leu Cys Cys His Leu Ser Tyr
        355                 360                 365

Gln Met Ser Glu Lys Arg Ala Asp Glu Val Tyr Ala Phe Gly Ala Phe
    370                 375                 380

Asp Gly Leu His Thr Val Glu Gly Gln Tyr Tyr Leu Gln Ile Cys Ile
385                 390                 395                 400

Leu Leu Lys Cys Lys Thr Thr Asn Leu Arg Thr Cys Gly Ser Ser Val
                405                 410                 415

Asp Thr Ala Phe Thr Arg Phe Glu Met Phe Ser Leu Ser Gly Thr Phe
            420                 425                 430

Gly Thr Arg Tyr Val Phe Pro Glu Val Leu Leu Ser Glu Val Lys Leu
        435                 440                 445

Ala Pro Gly Glu Phe Gln Val Ser Ser Asp Gly Arg Leu Val Ser Leu
    450                 455                 460

Lys Pro Thr Ser Gly Pro Val Leu Thr Ile Gly Leu Phe Gly Arg Leu
465                 470                 475                 480

Tyr Gly Lys Asp Trp Ala Ser Asn Ala Ser Ser Asp Phe Ile Ala His
                485                 490                 495

Ser Leu Ile Ile Met Leu Ile Val Thr Pro Ile Ile His Tyr Leu Cys
            500                 505                 510
```

<210> SEQ ID NO 3
<211> LENGTH: 1819
<212> TYPE: DNA
<213> ORGANISM: Mus musculus

```
<220> FEATURE:
<221> NAME/KEY: CDS
<222> LOCATION: (113)..(1615)

<400> SEQUENCE: 3

atatattcac aggcagctgg ctggcatcac gacttgcgtc tgaatatttt tttttcccac     60

tgagatacag tagaagaacc ttctgatttt cagagatcac tctattttaa tt atg gct    118
                                                          Met Ala
                                                          1

tca tta cat ttt cct caa tgg gca gtg agt ttt gtc ttc ttt gcc cag      166
Ser Leu His Phe Pro Gln Trp Ala Val Ser Phe Val Phe Phe Ala Gln
        5                   10                  15

gct gtg ggt tca atg gac act ttt att gct gct gtg tat gaa cat gct      214
Ala Val Gly Ser Met Asp Thr Phe Ile Ala Ala Val Tyr Glu His Ala
    20                  25                  30

gtt ata ctg cca aac aaa act gaa agt cct gtt tcc act gaa gag gct      262
Val Ile Leu Pro Asn Lys Thr Glu Ser Pro Val Ser Thr Glu Glu Ala
35                  40                  45                  50

ttg ctc ctg ata aac aag aac ata gac att ttg gag agt gca atc aag      310
Leu Leu Leu Ile Asn Lys Asn Ile Asp Ile Leu Glu Ser Ala Ile Lys
                55                  60                  65

ctg gca gcc aga cag ggt gca cat atc att gtg acg cca gaa gat gga      358
Leu Ala Ala Arg Gln Gly Ala His Ile Ile Val Thr Pro Glu Asp Gly
            70                  75                  80

atc tat ggt tgg atc ttc acc agg gag acc att tac ccc tac cta gag      406
Ile Tyr Gly Trp Ile Phe Thr Arg Glu Thr Ile Tyr Pro Tyr Leu Glu
        85                  90                  95

gat ata cca gac cct gaa gtg aac tgg att ccc tgt aga gac cct agg      454
Asp Ile Pro Asp Pro Glu Val Asn Trp Ile Pro Cys Arg Asp Pro Arg
    100                 105                 110

agg ttt ggc tac aca cca gta cag gag aga ctg agc tgc ctt gcc aag      502
Arg Phe Gly Tyr Thr Pro Val Gln Glu Arg Leu Ser Cys Leu Ala Lys
115                 120                 125                 130

gag aac tct atc tat att atg gca aat att ggg gac aag aag cca tgc      550
Glu Asn Ser Ile Tyr Ile Met Ala Asn Ile Gly Asp Lys Lys Pro Cys
                135                 140                 145

aat gct act gat cct cat tgt ccc ccg gat ggc cgt tac caa tat aat      598
Asn Ala Thr Asp Pro His Cys Pro Pro Asp Gly Arg Tyr Gln Tyr Asn
            150                 155                 160

acc aat gtg gtc ttc gat tct aag ggt agg cta aca gcc cgc tac cat      646
Thr Asn Val Val Phe Asp Ser Lys Gly Arg Leu Thr Ala Arg Tyr His
        165                 170                 175

aag tac aat ctt ttt gaa cca gag att cag ttt gat ttc ccc aaa gat      694
Lys Tyr Asn Leu Phe Glu Pro Glu Ile Gln Phe Asp Phe Pro Lys Asp
    180                 185                 190

tca gag ctg gtg acc ttt gac acc ccg ttt ggg aag ttt ggc atc ttc      742
Ser Glu Leu Val Thr Phe Asp Thr Pro Phe Gly Lys Phe Gly Ile Phe
195                 200                 205                 210

act tgc ttt gac att ttc tct tat gac cca gct gtg gtg gtt gtg aag      790
Thr Cys Phe Asp Ile Phe Ser Tyr Asp Pro Ala Val Val Val Val Lys
                215                 220                 225

gac acc cag gtc gac agt gtt ctc tta ccc acg gcg tgg tac aac acc      838
Asp Thr Gln Val Asp Ser Val Leu Leu Pro Thr Ala Trp Tyr Asn Thr
            230                 235                 240

ctg ccc ctg ctt tca gca gtt cca ttc cat tcg gtg tgg gcc aga gcc      886
Leu Pro Leu Leu Ser Ala Val Pro Phe His Ser Val Trp Ala Arg Ala
        245                 250                 255

atg ggg gtc aac gtg ctt gct gca aac acc cac aac acc agc atg cat      934
Met Gly Val Asn Val Leu Ala Ala Asn Thr His Asn Thr Ser Met His
    260                 265                 270
```

```
atg aca ggg agt gga atc tac agc ccg gaa gct gtc cga gtg tac cac      982
Met Thr Gly Ser Gly Ile Tyr Ser Pro Glu Ala Val Arg Val Tyr His
275                 280                 285                 290

tat gac atg gag aca gag agt ggc caa ctg ctg ctt tca gag ctg agg     1030
Tyr Asp Met Glu Thr Glu Ser Gly Gln Leu Leu Leu Ser Glu Leu Arg
                295                 300                 305

tct cgg cct cgc cag cac gcc acc cct gca gag gtt aac tgg agc gct     1078
Ser Arg Pro Arg Gln His Ala Thr Pro Ala Glu Val Asn Trp Ser Ala
            310                 315                 320

tat gcc agg act gtg aag ccg ttc tca tcg ggg cag gca gac ttc cca     1126
Tyr Ala Arg Thr Val Lys Pro Phe Ser Ser Gly Gln Ala Asp Phe Pro
        325                 330                 335

gga aag att tat ttt gac gaa ttt agc ttc acc aag ctt aca gga agt     1174
Gly Lys Ile Tyr Phe Asp Glu Phe Ser Phe Thr Lys Leu Thr Gly Ser
    340                 345                 350

gct ggc aat tac aca gtt tgc caa aag gac ctg tgc tgt cac ctg act     1222
Ala Gly Asn Tyr Thr Val Cys Gln Lys Asp Leu Cys Cys His Leu Thr
355                 360                 365                 370

tac aag atg tct gaa agc cga atg gac gag gtg tat gtt ctg ggt gcc     1270
Tyr Lys Met Ser Glu Ser Arg Met Asp Glu Val Tyr Val Leu Gly Ala
                375                 380                 385

ttt gat gga ctc cat aca ggg gaa ggc cag tat tac cta cag ata tgt     1318
Phe Asp Gly Leu His Thr Gly Glu Gly Gln Tyr Tyr Leu Gln Ile Cys
            390                 395                 400

aca ttg ctg aag tgt caa acc acc aac tcg aga act tgt ggg gaa ccc     1366
Thr Leu Leu Lys Cys Gln Thr Thr Asn Ser Arg Thr Cys Gly Glu Pro
        405                 410                 415

gtg ggg tca gct ttt aca aag ttt gaa gaa ttc tct ctc agt ggc acc     1414
Val Gly Ser Ala Phe Thr Lys Phe Glu Glu Phe Ser Leu Ser Gly Thr
    420                 425                 430

ttt cgg aca aaa tat gtt ttc cca cag atc gtg cta agt ggg agt caa     1462
Phe Arg Thr Lys Tyr Val Phe Pro Gln Ile Val Leu Ser Gly Ser Gln
435                 440                 445                 450

ctt gcc ctg gaa aga tat tat gaa gtc tca aga gat gga cgt ctg agg     1510
Leu Ala Leu Glu Arg Tyr Tyr Glu Val Ser Arg Asp Gly Arg Leu Arg
                455                 460                 465

agt cga ggt gga gcc cct ttg cct atc tta gtg atg gcc ctg tat gga     1558
Ser Arg Gly Gly Ala Pro Leu Pro Ile Leu Val Met Ala Leu Tyr Gly
            470                 475                 480

aga gtg ttt gag aga gac cct ccg cgc tta ggg cag gga cct ggg aag     1606
Arg Val Phe Glu Arg Asp Pro Pro Arg Leu Gly Gln Gly Pro Gly Lys
        485                 490                 495

ctg cag tga tcccttcatt ggggacccca cccgcctgcc ctgacacaag             1655
Leu Gln
    500

gggcggggtc tgcacaggat tagcctggca gagagcgggg ctctaagagc aagaacaagg   1715

agctgcaggg ttccattagg agatacgatg taagctgctg aaaaggcaaa gcaagtgaga   1775

ggaaacaata aagtaaaaaa gcaaaaaaaa aaaaaaaaaa aaaa                    1819


<210> SEQ ID NO 4
<211> LENGTH: 500
<212> TYPE: PRT
<213> ORGANISM: Mus musculus

<400> SEQUENCE: 4

Met Ala Ser Leu His Phe Pro Gln Trp Ala Val Ser Phe Val Phe Phe
1               5                   10                  15

Ala Gln Ala Val Gly Ser Met Asp Thr Phe Ile Ala Ala Val Tyr Glu
```

-continued

```
            20                  25                  30

His Ala Val Ile Leu Pro Asn Lys Thr Glu Ser Pro Val Ser Thr Glu
        35                  40                  45

Glu Ala Leu Leu Leu Ile Asn Lys Asn Ile Asp Ile Leu Glu Ser Ala
    50                  55                  60

Ile Lys Leu Ala Ala Arg Gln Gly Ala His Ile Ile Val Thr Pro Glu
65                  70                  75                  80

Asp Gly Ile Tyr Gly Trp Ile Phe Thr Arg Glu Thr Ile Tyr Pro Tyr
                85                  90                  95

Leu Glu Asp Ile Pro Asp Pro Glu Val Asn Trp Ile Pro Cys Arg Asp
            100                 105                 110

Pro Arg Arg Phe Gly Tyr Thr Pro Val Gln Glu Arg Leu Ser Cys Leu
        115                 120                 125

Ala Lys Glu Asn Ser Ile Tyr Ile Met Ala Asn Ile Gly Asp Lys Lys
    130                 135                 140

Pro Cys Asn Ala Thr Asp Pro His Cys Pro Pro Asp Gly Arg Tyr Gln
145                 150                 155                 160

Tyr Asn Thr Asn Val Val Phe Asp Ser Lys Gly Arg Leu Thr Ala Arg
                165                 170                 175

Tyr His Lys Tyr Asn Leu Phe Glu Pro Glu Ile Gln Phe Asp Phe Pro
            180                 185                 190

Lys Asp Ser Glu Leu Val Thr Phe Asp Thr Pro Phe Gly Lys Phe Gly
        195                 200                 205

Ile Phe Thr Cys Phe Asp Ile Phe Ser Tyr Asp Pro Ala Val Val Val
    210                 215                 220

Val Lys Asp Thr Gln Val Asp Ser Val Leu Leu Pro Thr Ala Trp Tyr
225                 230                 235                 240

Asn Thr Leu Pro Leu Leu Ser Ala Val Pro Phe His Ser Val Trp Ala
                245                 250                 255

Arg Ala Met Gly Val Asn Val Leu Ala Ala Asn Thr His Asn Thr Ser
            260                 265                 270

Met His Met Thr Gly Ser Gly Ile Tyr Ser Pro Glu Ala Val Arg Val
        275                 280                 285

Tyr His Tyr Asp Met Glu Thr Glu Ser Gly Gln Leu Leu Leu Ser Glu
    290                 295                 300

Leu Arg Ser Arg Pro Arg Gln His Ala Thr Pro Ala Glu Val Asn Trp
305                 310                 315                 320

Ser Ala Tyr Ala Arg Thr Val Lys Pro Phe Ser Ser Gly Gln Ala Asp
                325                 330                 335

Phe Pro Gly Lys Ile Tyr Phe Asp Glu Phe Ser Phe Thr Lys Leu Thr
            340                 345                 350

Gly Ser Ala Gly Asn Tyr Thr Val Cys Gln Lys Asp Leu Cys Cys His
        355                 360                 365

Leu Thr Tyr Lys Met Ser Glu Ser Arg Met Asp Glu Val Tyr Val Leu
    370                 375                 380

Gly Ala Phe Asp Gly Leu His Thr Gly Glu Gly Gln Tyr Tyr Leu Gln
385                 390                 395                 400

Ile Cys Thr Leu Leu Lys Cys Gln Thr Thr Asn Ser Arg Thr Cys Gly
                405                 410                 415

Glu Pro Val Gly Ser Ala Phe Thr Lys Phe Glu Glu Phe Ser Leu Ser
            420                 425                 430

Gly Thr Phe Arg Thr Lys Tyr Val Phe Pro Gln Ile Val Leu Ser Gly
        435                 440                 445
```

```
Ser Gln Leu Ala Leu Glu Arg Tyr Tyr Glu Val Ser Arg Asp Gly Arg
    450                 455                 460

Leu Arg Ser Arg Gly Gly Ala Pro Leu Pro Ile Leu Val Met Ala Leu
465                 470                 475                 480

Tyr Gly Arg Val Phe Glu Arg Asp Pro Pro Arg Leu Gly Gln Gly Pro
                485                 490                 495

Gly Lys Leu Gln
            500


<210> SEQ ID NO 5
<211> LENGTH: 3109
<212> TYPE: DNA
<213> ORGANISM: Homo sapiens
<220> FEATURE:
<221> NAME/KEY: CDS
<222> LOCATION: (15)..(1556)

<400> SEQUENCE: 5

cattggactt cagc atg act act cag ttg cca gct tac gtg gca att ttg       50
                Met Thr Thr Gln Leu Pro Ala Tyr Val Ala Ile Leu
                1               5                   10

ctt ttc tat gtc tca aga gcc agc tgc cag gac act ttc att gca gct       98
Leu Phe Tyr Val Ser Arg Ala Ser Cys Gln Asp Thr Phe Ile Ala Ala
        15                  20                  25

gtt tat gag cat gca gcg ata ttg ccc aat gcc acc cta aca cca gtg      146
Val Tyr Glu His Ala Ala Ile Leu Pro Asn Ala Thr Leu Thr Pro Val
    30                  35                  40

tct cgt gag gag gct ttg gca tta atg aat cgg aat ctg gac att ttg      194
Ser Arg Glu Glu Ala Leu Ala Leu Met Asn Arg Asn Leu Asp Ile Leu
45                  50                  55                  60

gaa gga gcg atc aca tca gca gca gat cag ggt gcg cat att att gtg      242
Glu Gly Ala Ile Thr Ser Ala Ala Asp Gln Gly Ala His Ile Ile Val
                65                  70                  75

act cca gaa gat gct att tat ggc tgg aac ttc aac agg gac tct ctc      290
Thr Pro Glu Asp Ala Ile Tyr Gly Trp Asn Phe Asn Arg Asp Ser Leu
            80                  85                  90

tac cca tat ttg gag gac atc cca gac cct gaa gta aac tgg atc ccc      338
Tyr Pro Tyr Leu Glu Asp Ile Pro Asp Pro Glu Val Asn Trp Ile Pro
        95                  100                 105

tgt aat aat cgt aac aga ttt ggc cag acc cca gta caa gaa aga ctc      386
Cys Asn Asn Arg Asn Arg Phe Gly Gln Thr Pro Val Gln Glu Arg Leu
    110                 115                 120

agc tgc ctg gcc aag aac aac tct atc tat gtt gtg gca aat att ggg      434
Ser Cys Leu Ala Lys Asn Asn Ser Ile Tyr Val Val Ala Asn Ile Gly
125                 130                 135                 140

gac aag aag cca tgc gat acc agt gat cct cag tgt ccc cct gat ggc      482
Asp Lys Lys Pro Cys Asp Thr Ser Asp Pro Gln Cys Pro Pro Asp Gly
                145                 150                 155

cgt tac caa tac aac act gat gtg gta ttt gat tct caa gga aaa ctg      530
Arg Tyr Gln Tyr Asn Thr Asp Val Val Phe Asp Ser Gln Gly Lys Leu
            160                 165                 170

gtg gca cgc tac cat aag caa aac ctt ttc atg ggt gaa aat caa ttc      578
Val Ala Arg Tyr His Lys Gln Asn Leu Phe Met Gly Glu Asn Gln Phe
        175                 180                 185

aat gta ccc aag gag cct gag att gtg act ttc aat acc acc ttt gga      626
Asn Val Pro Lys Glu Pro Glu Ile Val Thr Phe Asn Thr Thr Phe Gly
    190                 195                 200

agt ttt ggc att ttc aca tgc ttt gat ata ctc ttc cat gat cct gct      674
Ser Phe Gly Ile Phe Thr Cys Phe Asp Ile Leu Phe His Asp Pro Ala
205                 210                 215                 220
```

```
gtt acc ttg gtg aaa gat ttc cac gtg gac acc ata gta ttc cca aca      722
Val Thr Leu Val Lys Asp Phe His Val Asp Thr Ile Val Phe Pro Thr
                225                 230                 235

gct tgg atg aat gtt ttg cca cat ttg tca gct gtt gaa ttc cac tca      770
Ala Trp Met Asn Val Leu Pro His Leu Ser Ala Val Glu Phe His Ser
            240                 245                 250

gct tgg gct atg ggc atg agg gtc aat ttc ctt gca tcc aac ata cat      818
Ala Trp Ala Met Gly Met Arg Val Asn Phe Leu Ala Ser Asn Ile His
        255                 260                 265

tac ccc tca aag aaa atg aca gga agt ggc atc tat gca ccc aat tct      866
Tyr Pro Ser Lys Lys Met Thr Gly Ser Gly Ile Tyr Ala Pro Asn Ser
    270                 275                 280

tca aga gca ttt cat tat gat atg aag aca gaa gag gga aaa ctc ctc      914
Ser Arg Ala Phe His Tyr Asp Met Lys Thr Glu Glu Gly Lys Leu Leu
285                 290                 295                 300

ctc tcg caa ctg gat tcc cac cca tcc cat tct gca gtg gtg aac tgg      962
Leu Ser Gln Leu Asp Ser His Pro Ser His Ser Ala Val Val Asn Trp
                305                 310                 315

act tcc tat gcc agc agt ata gaa gcg ctc tca tca gga aac aag gaa     1010
Thr Ser Tyr Ala Ser Ser Ile Glu Ala Leu Ser Ser Gly Asn Lys Glu
            320                 325                 330

ttt aaa ggc act gtc ttt ttc gat gaa ttc act ttt gtg aag ctc aca     1058
Phe Lys Gly Thr Val Phe Phe Asp Glu Phe Thr Phe Val Lys Leu Thr
        335                 340                 345

gga gtt gca gga aat tat aca gtt tgt cag aaa gat ctc tgc tgt cat     1106
Gly Val Ala Gly Asn Tyr Thr Val Cys Gln Lys Asp Leu Cys Cys His
    350                 355                 360

tta agc tac aaa atg tct gag aac ata cca aat gaa gtg tac gct cta     1154
Leu Ser Tyr Lys Met Ser Glu Asn Ile Pro Asn Glu Val Tyr Ala Leu
365                 370                 375                 380

ggg gca ttt gac gga ctg cac act gtg gaa ggg cgc tat tat cta cag     1202
Gly Ala Phe Asp Gly Leu His Thr Val Glu Gly Arg Tyr Tyr Leu Gln
                385                 390                 395

att tgt acc ctg ttg aaa tgt aaa acg act aat tta aac act tgc ggt     1250
Ile Cys Thr Leu Leu Lys Cys Lys Thr Thr Asn Leu Asn Thr Cys Gly
            400                 405                 410

gac tca gct gaa aca gct tct acc agg ttt gaa atg ttc tcc ctc agt     1298
Asp Ser Ala Glu Thr Ala Ser Thr Arg Phe Glu Met Phe Ser Leu Ser
        415                 420                 425

ggc act ttc gga acc cag tat gtc ttt cct gag gtg ttg ctg agt gaa     1346
Gly Thr Phe Gly Thr Gln Tyr Val Phe Pro Glu Val Leu Leu Ser Glu
    430                 435                 440

aat cag ctt gca cct gga gaa ttt cag gtg tca act gac gga cgc ttg     1394
Asn Gln Leu Ala Pro Gly Glu Phe Gln Val Ser Thr Asp Gly Arg Leu
445                 450                 455                 460

ttt agt ctg aag cca aca tcc gga cct gtc tta aca gta act ctg ttt     1442
Phe Ser Leu Lys Pro Thr Ser Gly Pro Val Leu Thr Val Thr Leu Phe
                465                 470                 475

ggg agg ttg tat gag aag gac tgg gca tca aat gct tca tca ggc ctc     1490
Gly Arg Leu Tyr Glu Lys Asp Trp Ala Ser Asn Ala Ser Ser Gly Leu
            480                 485                 490

aca gca caa gca aga ata ata atg cta ata gtt ata gca cct att gta     1538
Thr Ala Gln Ala Arg Ile Ile Met Leu Ile Val Ile Ala Pro Ile Val
        495                 500                 505

tgc tca tta agt tgg tag aatattgact ttttctcttt tttatttggg            1586
Cys Ser Leu Ser Trp
    510

ataatttaaa aaatgatgga tgagaaaaga aagattggtc cgggttaata ttatcctcta   1646
```

```
gtataagtga attactagtt tctctttatt tagacaaaca cacacacacc agataatata   1706

aacttaataa attatctgtt aatgtagatt ttatttaaaa aactatattt gaacattggt   1766

ctttcttgga cgtgagctaa ttatatcaaa taagtatcac aaatctttta cgcagaagaa   1826

ataaaaacta cgggtagaaa acataagaac tatcataaaa tttacttaca aggaggctgc   1886

tcttgttacc acttttatta tattacgtat cacttattca gctctgctga aaatttccaa   1946

tgactttgtt tgtttgctct tttagttttt tacctaaaca atacattttg attctcttgt   2006

gggttgataa tgtctcccca aaatttacat gttgaagcac ctcagaatgt gactgtattt   2066

ggagacaggg tctttaaaga ggtaaaataa ggtcattagg atagacccta attcaatatg   2126

actgatgatc ataaaagaag aggcgagtag ggcacaacag gcacaaaggg agaccataag   2186

gagacacaga ggaaggacaa ctctttacaa gctaagaaga gagggcctca gaagaaacca   2246

accctgccaa caccttgatc ttggacttcc agcctccaaa actatgagaa ataaatttct   2306

attgtttaag tcacccagtc catggtactt tgttaggcag ccctggcaaa tgaatcaaag   2366

acccattcct gttcctctcc ccaccactac tgttttctac tgtaatctga agcttcaaca   2426

aaaggcttac ctggtaagaa tattcagctg gtctgggtcc tcaagactcc aatagacact   2486

cttaaagaag gattgctgat ggattgatag tgaaaccatt agatcattga attcctctgg   2546

aattagaaaa ccagagagtc ccattttaag aaattagata tttaatatag cattgtgtgt   2606

tctattttag taacagcaga atctcttgac attacacaac tcagtgaaac aacatcattt   2666

aagccaaaat atctcccaac tgactgatag actctgagca ctaatatcat agtgctgtga   2726

tgatggacaa ttacatagta ccgataacag ccatgcactg tgcaaagcat gcccttctgc   2786

acaggagagc aaggcacttg cagtagtgat ctatgccagc aaaacatcat tttgagacaa   2846

acatttttgt ggcagatgtt tttcctaaaa agtactatat catccaagaa atatttgagt   2906

aaaatccctt gttcttttgg gtgacattaa ctgacatttg cttttttttca agacctaata   2966

gaaaataaga aagcccataa tgtatttaga aacaggaatc ctcagagcaa ttctctgtat   3026

tctcatataa tttcaatgta aaacagaaaa catattgatg tgttggtgat aggcttgaat   3086

tattaaaaac ttcaaaaaca aaa                                           3109
```

```
<210> SEQ ID NO 6
<211> LENGTH: 513
<212> TYPE: PRT
<213> ORGANISM: Homo sapiens

<400> SEQUENCE: 6

Met Thr Thr Gln Leu Pro Ala Tyr Val Ala Ile Leu Leu Phe Tyr Val
1               5                   10                  15

Ser Arg Ala Ser Cys Gln Asp Thr Phe Ile Ala Ala Val Tyr Glu His
            20                  25                  30

Ala Ala Ile Leu Pro Asn Ala Thr Leu Thr Pro Val Ser Arg Glu Glu
        35                  40                  45

Ala Leu Ala Leu Met Asn Arg Asn Leu Asp Ile Leu Glu Gly Ala Ile
    50                  55                  60

Thr Ser Ala Ala Asp Gln Gly Ala His Ile Ile Val Thr Pro Glu Asp
65                  70                  75                  80

Ala Ile Tyr Gly Trp Asn Phe Asn Arg Asp Ser Leu Tyr Pro Tyr Leu
                85                  90                  95

Glu Asp Ile Pro Asp Pro Glu Val Asn Trp Ile Pro Cys Asn Asn Arg
            100                 105                 110
```

```
Asn Arg Phe Gly Gln Thr Pro Val Gln Glu Arg Leu Ser Cys Leu Ala
        115                 120                 125

Lys Asn Asn Ser Ile Tyr Val Val Ala Asn Ile Gly Asp Lys Lys Pro
    130                 135                 140

Cys Asp Thr Ser Asp Pro Gln Cys Pro Pro Asp Gly Arg Tyr Gln Tyr
145                 150                 155                 160

Asn Thr Asp Val Val Phe Asp Ser Gln Gly Lys Leu Val Ala Arg Tyr
                165                 170                 175

His Lys Gln Asn Leu Phe Met Gly Glu Asn Gln Phe Asn Val Pro Lys
            180                 185                 190

Glu Pro Glu Ile Val Thr Phe Asn Thr Thr Phe Gly Ser Phe Gly Ile
        195                 200                 205

Phe Thr Cys Phe Asp Ile Leu Phe His Asp Pro Ala Val Thr Leu Val
    210                 215                 220

Lys Asp Phe His Val Asp Thr Ile Val Phe Pro Thr Ala Trp Met Asn
225                 230                 235                 240

Val Leu Pro His Leu Ser Ala Val Glu Phe His Ser Ala Trp Ala Met
                245                 250                 255

Gly Met Arg Val Asn Phe Leu Ala Ser Asn Ile His Tyr Pro Ser Lys
            260                 265                 270

Lys Met Thr Gly Ser Gly Ile Tyr Ala Pro Asn Ser Ser Arg Ala Phe
        275                 280                 285

His Tyr Asp Met Lys Thr Glu Glu Gly Lys Leu Leu Leu Ser Gln Leu
    290                 295                 300

Asp Ser His Pro Ser His Ser Ala Val Val Asn Trp Thr Ser Tyr Ala
305                 310                 315                 320

Ser Ser Ile Glu Ala Leu Ser Ser Gly Asn Lys Glu Phe Lys Gly Thr
                325                 330                 335

Val Phe Phe Asp Glu Phe Thr Phe Val Lys Leu Thr Gly Val Ala Gly
            340                 345                 350

Asn Tyr Thr Val Cys Gln Lys Asp Leu Cys Cys His Leu Ser Tyr Lys
        355                 360                 365

Met Ser Glu Asn Ile Pro Asn Glu Val Tyr Ala Leu Gly Ala Phe Asp
    370                 375                 380

Gly Leu His Thr Val Glu Gly Arg Tyr Tyr Leu Gln Ile Cys Thr Leu
385                 390                 395                 400

Leu Lys Cys Lys Thr Thr Asn Leu Asn Thr Cys Gly Asp Ser Ala Glu
                405                 410                 415

Thr Ala Ser Thr Arg Phe Glu Met Phe Ser Leu Ser Gly Thr Phe Gly
            420                 425                 430

Thr Gln Tyr Val Phe Pro Glu Val Leu Leu Ser Glu Asn Gln Leu Ala
        435                 440                 445

Pro Gly Glu Phe Gln Val Ser Thr Asp Gly Arg Leu Phe Ser Leu Lys
    450                 455                 460

Pro Thr Ser Gly Pro Val Leu Thr Val Thr Leu Phe Gly Arg Leu Tyr
465                 470                 475                 480

Glu Lys Asp Trp Ala Ser Asn Ala Ser Ser Gly Leu Thr Ala Gln Ala
                485                 490                 495

Arg Ile Ile Met Leu Ile Val Ile Ala Pro Ile Val Cys Ser Leu Ser
            500                 505                 510

Trp
```

<210> SEQ ID NO 7

```
<211> LENGTH: 2034
<212> TYPE: DNA
<213> ORGANISM: Homo sapiens
<220> FEATURE:
<221> NAME/KEY: CDS
<222> LOCATION: (12)..(1574)

<400> SEQUENCE: 7

aaaccttggc c atg gtc act tcc tct ttt cca atc tct gtg gca gtt ttt      50
             Met Val Thr Ser Ser Phe Pro Ile Ser Val Ala Val Phe
             1               5                   10

gcc cta ata acc ctg cag gtt ggt act cag gac agt ttt ata gct gca       98
Ala Leu Ile Thr Leu Gln Val Gly Thr Gln Asp Ser Phe Ile Ala Ala
    15                  20                  25

gtg tat gaa cat gct gtc att ttg cca aat aaa aca gaa aca cca gtt      146
Val Tyr Glu His Ala Val Ile Leu Pro Asn Lys Thr Glu Thr Pro Val
30                  35                  40                  45

tct cag gag gat gcc ttg aat ctc atg aac gag aat ata gac att ctg      194
Ser Gln Glu Asp Ala Leu Asn Leu Met Asn Glu Asn Ile Asp Ile Leu
                50                  55                  60

gag aca gcg atc aag cag gca gct gag cag ggt gct cga atc att gtg      242
Glu Thr Ala Ile Lys Gln Ala Ala Glu Gln Gly Ala Arg Ile Ile Val
            65                  70                  75

act cca gaa gat gca ctt tat gga tgg aaa ttt acc agg gaa act gtt      290
Thr Pro Glu Asp Ala Leu Tyr Gly Trp Lys Phe Thr Arg Glu Thr Val
        80                  85                  90

ttc cct tat ctg gag gat atc cca gac cct cag gtg aac tgg att ccg      338
Phe Pro Tyr Leu Glu Asp Ile Pro Asp Pro Gln Val Asn Trp Ile Pro
    95                  100                 105

tgt caa gac ccc cac aga ttt ggt cac aca cca gta caa gca aga ctc      386
Cys Gln Asp Pro His Arg Phe Gly His Thr Pro Val Gln Ala Arg Leu
110                 115                 120                 125

agc tgc ctg gcc aag gac aac tct atc tat gtc ttg gca aat ttg ggg      434
Ser Cys Leu Ala Lys Asp Asn Ser Ile Tyr Val Leu Ala Asn Leu Gly
                130                 135                 140

gac aaa aag cca tgt aat tcc cgt gac tcc aca tgt cct cct aat ggc      482
Asp Lys Lys Pro Cys Asn Ser Arg Asp Ser Thr Cys Pro Pro Asn Gly
            145                 150                 155

tac ttt caa tac aat acc aat gtg gtg tat aat aca gaa gga aaa ctc      530
Tyr Phe Gln Tyr Asn Thr Asn Val Val Tyr Asn Thr Glu Gly Lys Leu
        160                 165                 170

gtg gca cgt tac cat aag tac cac ctg tac tct gag cct cag ttt aat      578
Val Ala Arg Tyr His Lys Tyr His Leu Tyr Ser Glu Pro Gln Phe Asn
    175                 180                 185

gtc cct gaa aag ccg gag ttg gtg act ttc aac acc gca ttt gga agg      626
Val Pro Glu Lys Pro Glu Leu Val Thr Phe Asn Thr Ala Phe Gly Arg
190                 195                 200                 205

ttt ggc att ttc acg tgc ttt gat ata ttc ttc tat gat cct ggt gtt      674
Phe Gly Ile Phe Thr Cys Phe Asp Ile Phe Phe Tyr Asp Pro Gly Val
                210                 215                 220

acc ctg gtg aaa gat ttc cat gtg gac acc ata ctg ttt ccc aca gct      722
Thr Leu Val Lys Asp Phe His Val Asp Thr Ile Leu Phe Pro Thr Ala
            225                 230                 235

tgg atg aac gtt ttg ccc ctt ttg aca gct att gaa ttc cat tca gct      770
Trp Met Asn Val Leu Pro Leu Leu Thr Ala Ile Glu Phe His Ser Ala
        240                 245                 250

tgg gca atg gga atg gga gtt aat ctt ctt gtg gcc aac aca cat cat      818
Trp Ala Met Gly Met Gly Val Asn Leu Leu Val Ala Asn Thr His His
    255                 260                 265

gtc agc cta aat atg aca gga agt ggt att tat gca cca aat ggt ccc      866
Val Ser Leu Asn Met Thr Gly Ser Gly Ile Tyr Ala Pro Asn Gly Pro
```

```
270                 275                 280                 285

aaa gtg tat cat tat gac atg aag aca gag ttg gga aaa ctt ctc ctt      914
Lys Val Tyr His Tyr Asp Met Lys Thr Glu Leu Gly Lys Leu Leu Leu
                290                 295                 300

tca gag gtg gat tca cat ccc cta tcc tcg ctt gcc tac cca aca gct      962
Ser Glu Val Asp Ser His Pro Leu Ser Ser Leu Ala Tyr Pro Thr Ala
            305                 310                 315

gtt aat tgg aat gcc tac gcc acc acc atc aaa cca ttt cca gta cag     1010
Val Asn Trp Asn Ala Tyr Ala Thr Thr Ile Lys Pro Phe Pro Val Gln
        320                 325                 330

aaa aac act ttc agg gga ttt att tcc agg gat ggg ttc aac ttc aca     1058
Lys Asn Thr Phe Arg Gly Phe Ile Ser Arg Asp Gly Phe Asn Phe Thr
    335                 340                 345

gaa ctt ttt gaa aat gca gga aac ctt aca gtc tgt caa aag gag ctt     1106
Glu Leu Phe Glu Asn Ala Gly Asn Leu Thr Val Cys Gln Lys Glu Leu
350                 355                 360                 365

tgc tgt cat tta agc tac aga atg tta caa aaa gaa gag aat gaa gta     1154
Cys Cys His Leu Ser Tyr Arg Met Leu Gln Lys Glu Glu Asn Glu Val
                370                 375                 380

tac gtt cta gga gct ttt aca gga tta cat ggc cga agg aga aga gag     1202
Tyr Val Leu Gly Ala Phe Thr Gly Leu His Gly Arg Arg Arg Arg Glu
            385                 390                 395

tac tgg cag gtc tgc aca atg ctg aag tgc aaa act act aat ttg aca     1250
Tyr Trp Gln Val Cys Thr Met Leu Lys Cys Lys Thr Thr Asn Leu Thr
        400                 405                 410

act tgt gga cgg cca gta gaa act gct tct aca aga ttt gaa atg ttc     1298
Thr Cys Gly Arg Pro Val Glu Thr Ala Ser Thr Arg Phe Glu Met Phe
    415                 420                 425

tcc ctc agt ggc aca ttt gga aca gag tat gtt ttt cct gaa gtg cta     1346
Ser Leu Ser Gly Thr Phe Gly Thr Glu Tyr Val Phe Pro Glu Val Leu
430                 435                 440                 445

ctt acc gaa att cat ctg tca cct gga aaa ttt gag gtg ctg aaa gat     1394
Leu Thr Glu Ile His Leu Ser Pro Gly Lys Phe Glu Val Leu Lys Asp
                450                 455                 460

ggg cgt ttg gta aac aag aat gga tca tct ggg cct ata cta aca gtg     1442
Gly Arg Leu Val Asn Lys Asn Gly Ser Ser Gly Pro Ile Leu Thr Val
            465                 470                 475

tca ctc ttt ggg agg tgg tac aca aag gac tca ctt tac agc tca tgt     1490
Ser Leu Phe Gly Arg Trp Tyr Thr Lys Asp Ser Leu Tyr Ser Ser Cys
        480                 485                 490

ggg acc agc aat tca gca ata act tac ctg cta ata ttc ata tta tta     1538
Gly Thr Ser Asn Ser Ala Ile Thr Tyr Leu Leu Ile Phe Ile Leu Leu
    495                 500                 505

atg atc ata gct ttg caa aat att gta atg tta tag ggcgtctctt          1584
Met Ile Ile Ala Leu Gln Asn Ile Val Met Leu
510                 515                 520

tatcactcag cttctgcatc atatgcttgg ctgaatgtgt ttatcggctt cccaagttta   1644

ctaagaaact ttgaagggct atttcagtag tatagaccag tgagtcctaa atattttttc   1704

tcatcaataa ttattttta agtattatga taatgttgtc catttttttg gctactctga    1764

aatgttgcag tgtggaacaa tggaaagagc ctgggtgttt gggtcagata aatgaagatc   1824

aaactccagc tccagcctca tttgcttgag actttgtgtg tatgggggac ttgtatgtat   1884

gggagtgagg agtttcaggg ccattgcaaa catagctgtg cccttgaaga gaatagtaat   1944

gatgggaatt tagaggttta tgactgaatt ccctttgaca ttaaagacta tttgaattca   2004

aaaaaaaaaa aaaaaaaaaa aaaaaaaaaa                                    2034
```

<210> SEQ ID NO 8
<211> LENGTH: 520
<212> TYPE: PRT
<213> ORGANISM: Homo sapiens

<400> SEQUENCE: 8

```
Met Val Thr Ser Ser Phe Pro Ile Ser Val Ala Val Phe Ala Leu Ile
1               5                   10                  15

Thr Leu Gln Val Gly Thr Gln Asp Ser Phe Ile Ala Ala Val Tyr Glu
            20                  25                  30

His Ala Val Ile Leu Pro Asn Lys Thr Glu Thr Pro Val Ser Gln Glu
        35                  40                  45

Asp Ala Leu Asn Leu Met Asn Glu Asn Ile Asp Ile Leu Glu Thr Ala
    50                  55                  60

Ile Lys Gln Ala Ala Glu Gln Gly Ala Arg Ile Ile Val Thr Pro Glu
65                  70                  75                  80

Asp Ala Leu Tyr Gly Trp Lys Phe Thr Arg Glu Thr Val Phe Pro Tyr
                85                  90                  95

Leu Glu Asp Ile Pro Asp Pro Gln Val Asn Trp Ile Pro Cys Gln Asp
            100                 105                 110

Pro His Arg Phe Gly His Thr Pro Val Gln Ala Arg Leu Ser Cys Leu
        115                 120                 125

Ala Lys Asp Asn Ser Ile Tyr Val Leu Ala Asn Leu Gly Asp Lys Lys
    130                 135                 140

Pro Cys Asn Ser Arg Asp Ser Thr Cys Pro Pro Asn Gly Tyr Phe Gln
145                 150                 155                 160

Tyr Asn Thr Asn Val Val Tyr Asn Thr Glu Gly Lys Leu Val Ala Arg
                165                 170                 175

Tyr His Lys Tyr His Leu Tyr Ser Glu Pro Gln Phe Asn Val Pro Glu
            180                 185                 190

Lys Pro Glu Leu Val Thr Phe Asn Thr Ala Phe Gly Arg Phe Gly Ile
        195                 200                 205

Phe Thr Cys Phe Asp Ile Phe Phe Tyr Asp Pro Gly Val Thr Leu Val
    210                 215                 220

Lys Asp Phe His Val Asp Thr Ile Leu Phe Pro Thr Ala Trp Met Asn
225                 230                 235                 240

Val Leu Pro Leu Leu Thr Ala Ile Glu Phe His Ser Ala Trp Ala Met
                245                 250                 255

Gly Met Gly Val Asn Leu Leu Val Ala Asn Thr His His Val Ser Leu
            260                 265                 270

Asn Met Thr Gly Ser Gly Ile Tyr Ala Pro Asn Gly Pro Lys Val Tyr
        275                 280                 285

His Tyr Asp Met Lys Thr Glu Leu Gly Lys Leu Leu Leu Ser Glu Val
    290                 295                 300

Asp Ser His Pro Leu Ser Ser Leu Ala Tyr Pro Thr Ala Val Asn Trp
305                 310                 315                 320

Asn Ala Tyr Ala Thr Thr Ile Lys Pro Phe Pro Val Gln Lys Asn Thr
                325                 330                 335

Phe Arg Gly Phe Ile Ser Arg Asp Gly Phe Asn Phe Thr Glu Leu Phe
            340                 345                 350

Glu Asn Ala Gly Asn Leu Thr Val Cys Gln Lys Glu Leu Cys Cys His
        355                 360                 365

Leu Ser Tyr Arg Met Leu Gln Lys Glu Glu Asn Glu Val Tyr Val Leu
    370                 375                 380
```

```
Gly Ala Phe Thr Gly Leu His Gly Arg Arg Arg Arg Glu Tyr Trp Gln
385                 390                 395                 400

Val Cys Thr Met Leu Lys Cys Lys Thr Thr Asn Leu Thr Thr Cys Gly
                405                 410                 415

Arg Pro Val Glu Thr Ala Ser Thr Arg Phe Glu Met Phe Ser Leu Ser
            420                 425                 430

Gly Thr Phe Gly Thr Glu Tyr Val Phe Pro Glu Val Leu Leu Thr Glu
        435                 440                 445

Ile His Leu Ser Pro Gly Lys Phe Glu Val Leu Lys Asp Gly Arg Leu
    450                 455                 460

Val Asn Lys Asn Gly Ser Ser Gly Pro Ile Leu Thr Val Ser Leu Phe
465                 470                 475                 480

Gly Arg Trp Tyr Thr Lys Asp Ser Leu Tyr Ser Ser Cys Gly Thr Ser
                485                 490                 495

Asn Ser Ala Ile Thr Tyr Leu Leu Ile Phe Ile Leu Leu Met Ile Ile
            500                 505                 510

Ala Leu Gln Asn Ile Val Met Leu
        515                 520


<210> SEQ ID NO 9
<211> LENGTH: 1976
<212> TYPE: DNA
<213> ORGANISM: Homo sapiens
<220> FEATURE:
<221> NAME/KEY: CDS
<222> LOCATION: (113)..(1516)

<400> SEQUENCE: 9

gactggagga gcacaggcct tggaaaggaa agcagctgag atccagagga gtggaaggct      60

ccccttgac taaagctaaa caccagtttc tcaggaggat gccttgaatc tc atg aac     118
                                                          Met Asn
                                                          1

gag aat ata gac att ctg gag aca gcg atc aag cag gca gct gag cag      166
Glu Asn Ile Asp Ile Leu Glu Thr Ala Ile Lys Gln Ala Ala Glu Gln
        5                   10                  15

ggt gct cga atc att gtg act cca gaa gat gca ctt tat gga tgg aaa      214
Gly Ala Arg Ile Ile Val Thr Pro Glu Asp Ala Leu Tyr Gly Trp Lys
    20                  25                  30

ttt acc agg gaa act gtt ttc cct tat ctg gag gat atc cca gac cct      262
Phe Thr Arg Glu Thr Val Phe Pro Tyr Leu Glu Asp Ile Pro Asp Pro
35                  40                  45                  50

cag gtg aac tgg att ccg tgt caa gac ccc cac aga ttt ggt cac aca      310
Gln Val Asn Trp Ile Pro Cys Gln Asp Pro His Arg Phe Gly His Thr
                55                  60                  65

cca gta caa gca aga ctc agc tgc ctg gcc aag gac aac tct atc tat      358
Pro Val Gln Ala Arg Leu Ser Cys Leu Ala Lys Asp Asn Ser Ile Tyr
            70                  75                  80

gtc ttg gca aat ttg ggg gac aaa aag cca tgt aat tcc cgt gac tcc      406
Val Leu Ala Asn Leu Gly Asp Lys Lys Pro Cys Asn Ser Arg Asp Ser
        85                  90                  95

aca tgt cct cct aat ggc tac ttt caa tac aat acc aat gtg gtg tat      454
Thr Cys Pro Pro Asn Gly Tyr Phe Gln Tyr Asn Thr Asn Val Val Tyr
    100                 105                 110

aat aca gaa gga aaa ctc gtg gca cgt tac cat aag tac cac ctg tac      502
Asn Thr Glu Gly Lys Leu Val Ala Arg Tyr His Lys Tyr His Leu Tyr
115                 120                 125                 130

tct gag cct cag ttt aat gtc cct gaa aag ccg gag ttg gtg act ttc      550
Ser Glu Pro Gln Phe Asn Val Pro Glu Lys Pro Glu Leu Val Thr Phe
                135                 140                 145
```

```
aac acc gca ttt gga agg ttt ggc att ttc acg tgc ttt gat ata ttc      598
Asn Thr Ala Phe Gly Arg Phe Gly Ile Phe Thr Cys Phe Asp Ile Phe
            150                 155                 160

ttc tat gat cct ggt gtt acc ctg gtg aaa gat ttc cat gtg gac acc      646
Phe Tyr Asp Pro Gly Val Thr Leu Val Lys Asp Phe His Val Asp Thr
        165                 170                 175

ata ctg ttt ccc aca gct tgg atg aac gtt ttg ccc ctt ttg aca gct      694
Ile Leu Phe Pro Thr Ala Trp Met Asn Val Leu Pro Leu Leu Thr Ala
    180                 185                 190

att gaa ttc cat tca gct tgg gca atg gga atg gga gtt aat ctt ctt      742
Ile Glu Phe His Ser Ala Trp Ala Met Gly Met Gly Val Asn Leu Leu
195                 200                 205                 210

gtg gcc aac aca cat cat gtc agc cta aat atg aca gga agt ggt att      790
Val Ala Asn Thr His His Val Ser Leu Asn Met Thr Gly Ser Gly Ile
                215                 220                 225

tat gca cca aat ggt ccc aaa gtg tat cat tat gac atg aag aca gag      838
Tyr Ala Pro Asn Gly Pro Lys Val Tyr His Tyr Asp Met Lys Thr Glu
            230                 235                 240

ttg gga aaa ctt ctc ctt tca gag gtg gat tca cat ccc cta tcc tcg      886
Leu Gly Lys Leu Leu Leu Ser Glu Val Asp Ser His Pro Leu Ser Ser
        245                 250                 255

ctt gcc tac cca aca gct gtt aat tgg aat gcc tac gcc acc acc atc      934
Leu Ala Tyr Pro Thr Ala Val Asn Trp Asn Ala Tyr Ala Thr Thr Ile
    260                 265                 270

aaa cca ttt cca gta cag aaa aac act ttc agg gga ttt att tcc agg      982
Lys Pro Phe Pro Val Gln Lys Asn Thr Phe Arg Gly Phe Ile Ser Arg
275                 280                 285                 290

gat ggg ttc aac ttc aca gaa ctt ttt gaa aat gca gga aac ctt aca     1030
Asp Gly Phe Asn Phe Thr Glu Leu Phe Glu Asn Ala Gly Asn Leu Thr
                295                 300                 305

gtc tgt caa aag gag ctt tgc tgt cat tta agc tac aga atg tta caa     1078
Val Cys Gln Lys Glu Leu Cys Cys His Leu Ser Tyr Arg Met Leu Gln
            310                 315                 320

aaa gaa gag aat gaa gta tac gtt cta gga gct ttt aca gga tta cat     1126
Lys Glu Glu Asn Glu Val Tyr Val Leu Gly Ala Phe Thr Gly Leu His
        325                 330                 335

ggc cga agg aga aga gag tac tgg cag gtc tgc aca atg ctg aag tgc     1174
Gly Arg Arg Arg Arg Glu Tyr Trp Gln Val Cys Thr Met Leu Lys Cys
    340                 345                 350

aaa act act aat ttg aca act tgt gga cgg cca gta gaa act gct tct     1222
Lys Thr Thr Asn Leu Thr Thr Cys Gly Arg Pro Val Glu Thr Ala Ser
355                 360                 365                 370

aca aga ttt gaa atg ttc tcc ctc agt ggc aca ttt gga aca gag tat     1270
Thr Arg Phe Glu Met Phe Ser Leu Ser Gly Thr Phe Gly Thr Glu Tyr
                375                 380                 385

gtt ttt cct gaa gtg cta ctt acc gaa att cat ctg tca cct gga aaa     1318
Val Phe Pro Glu Val Leu Leu Thr Glu Ile His Leu Ser Pro Gly Lys
            390                 395                 400

ttt gag gtg ctg aaa gat ggg cgt ttg gta aac aag aat gga tca tct     1366
Phe Glu Val Leu Lys Asp Gly Arg Leu Val Asn Lys Asn Gly Ser Ser
        405                 410                 415

ggg cct ata cta aca gtg tca ctc ttt ggg agg tgg tac aca aag gac     1414
Gly Pro Ile Leu Thr Val Ser Leu Phe Gly Arg Trp Tyr Thr Lys Asp
    420                 425                 430

tca ctt tac agc tca tgt ggg acc agc aat tca gca ata act tac ctg     1462
Ser Leu Tyr Ser Ser Cys Gly Thr Ser Asn Ser Ala Ile Thr Tyr Leu
435                 440                 445                 450

cta ata ttc ata tta tta atg atc ata gct ttg caa aat att gta atg     1510
Leu Ile Phe Ile Leu Leu Met Ile Ile Ala Leu Gln Asn Ile Val Met
```

```
                455                 460                 465

tta tag ggcgtctctt tatcactcag cttctgcatc atatgcttgg ctgaatgtgt      1566
Leu

ttatcggctt cccaagttta ctaagaaact ttgaagggct atttcagtag tatagaccag   1626

tgagtcctaa atattttttc tcatcaataa ttattttttta agtattatga taatgttgtc   1686

catttttttg gctactctga aatgttgcag tgtggaacaa tggaaagagc ctgggtgttt   1746

gggtcagata aatgaagatc aaactccagc tccagcctca tttgcttgag actttgtgtg   1806

tatgggggac ttgtatgtat gggagtgagg agtttcaggg ccattgcaaa catagctgtg   1866

cccttgaaga gaatagtaat gatgggaatt tagaggttta tgactgaatt ccctttgaca   1926

ttaaagacta tttgaattca aaaaaaaaaa aaaaaaaaaa aaaaaaaaaa              1976


<210> SEQ ID NO 10
<211> LENGTH: 467
<212> TYPE: PRT
<213> ORGANISM: Homo sapiens

<400> SEQUENCE: 10

Met Asn Glu Asn Ile Asp Ile Leu Glu Thr Ala Ile Lys Gln Ala Ala
1               5                   10                  15

Glu Gln Gly Ala Arg Ile Ile Val Thr Pro Glu Asp Ala Leu Tyr Gly
            20                  25                  30

Trp Lys Phe Thr Arg Glu Thr Val Phe Pro Tyr Leu Glu Asp Ile Pro
        35                  40                  45

Asp Pro Gln Val Asn Trp Ile Pro Cys Gln Asp Pro His Arg Phe Gly
    50                  55                  60

His Thr Pro Val Gln Ala Arg Leu Ser Cys Leu Ala Lys Asp Asn Ser
65                  70                  75                  80

Ile Tyr Val Leu Ala Asn Leu Gly Asp Lys Lys Pro Cys Asn Ser Arg
                85                  90                  95

Asp Ser Thr Cys Pro Pro Asn Gly Tyr Phe Gln Tyr Asn Thr Asn Val
            100                 105                 110

Val Tyr Asn Thr Glu Gly Lys Leu Val Ala Arg Tyr His Lys Tyr His
        115                 120                 125

Leu Tyr Ser Glu Pro Gln Phe Asn Val Pro Glu Lys Pro Glu Leu Val
    130                 135                 140

Thr Phe Asn Thr Ala Phe Gly Arg Phe Gly Ile Phe Thr Cys Phe Asp
145                 150                 155                 160

Ile Phe Phe Tyr Asp Pro Gly Val Thr Leu Val Lys Asp Phe His Val
                165                 170                 175

Asp Thr Ile Leu Phe Pro Thr Ala Trp Met Asn Val Leu Pro Leu Leu
            180                 185                 190

Thr Ala Ile Glu Phe His Ser Ala Trp Ala Met Gly Met Gly Val Asn
        195                 200                 205

Leu Leu Val Ala Asn Thr His His Val Ser Leu Asn Met Thr Gly Ser
    210                 215                 220

Gly Ile Tyr Ala Pro Asn Gly Pro Lys Val Tyr His Tyr Asp Met Lys
225                 230                 235                 240

Thr Glu Leu Gly Lys Leu Leu Leu Ser Glu Val Asp Ser His Pro Leu
                245                 250                 255

Ser Ser Leu Ala Tyr Pro Thr Ala Val Asn Trp Asn Ala Tyr Ala Thr
            260                 265                 270

Thr Ile Lys Pro Phe Pro Val Gln Lys Asn Thr Phe Arg Gly Phe Ile
```

```
        275                 280                 285

Ser Arg Asp Gly Phe Asn Phe Thr Glu Leu Phe Glu Asn Ala Gly Asn
    290                 295                 300

Leu Thr Val Cys Gln Lys Glu Leu Cys Cys His Leu Ser Tyr Arg Met
305                 310                 315                 320

Leu Gln Lys Glu Glu Asn Glu Val Tyr Val Leu Gly Ala Phe Thr Gly
                325                 330                 335

Leu His Gly Arg Arg Arg Arg Glu Tyr Trp Gln Val Cys Thr Met Leu
            340                 345                 350

Lys Cys Lys Thr Thr Asn Leu Thr Thr Cys Gly Arg Pro Val Glu Thr
        355                 360                 365

Ala Ser Thr Arg Phe Glu Met Phe Ser Leu Ser Gly Thr Phe Gly Thr
    370                 375                 380

Glu Tyr Val Phe Pro Glu Val Leu Leu Thr Glu Ile His Leu Ser Pro
385                 390                 395                 400

Gly Lys Phe Glu Val Leu Lys Asp Gly Arg Leu Val Asn Lys Asn Gly
                405                 410                 415

Ser Ser Gly Pro Ile Leu Thr Val Ser Leu Phe Gly Arg Trp Tyr Thr
            420                 425                 430

Lys Asp Ser Leu Tyr Ser Ser Cys Gly Thr Ser Asn Ser Ala Ile Thr
        435                 440                 445

Tyr Leu Leu Ile Phe Ile Leu Leu Met Ile Ile Ala Leu Gln Asn Ile
    450                 455                 460

Val Met Leu
465


<210> SEQ ID NO 11
<211> LENGTH: 1733
<212> TYPE: DNA
<213> ORGANISM: Homo sapiens
<220> FEATURE:
<221> NAME/KEY: CDS
<222> LOCATION: (73)..(897)

<400> SEQUENCE: 11

atgtaaagtt tttccagtga aacaaaacgt aagaatctga gtttgttttt caaagatcac      60

taaattttag tt atg att ata tca cat ttt cca aaa tgt gtg gca gtt ttt     111
              Met Ile Ile Ser His Phe Pro Lys Cys Val Ala Val Phe
              1               5                   10

gcc ctc ctt gct ctg agt gtt ggt gca ctg gac act ttt att gct gca       159
Ala Leu Leu Ala Leu Ser Val Gly Ala Leu Asp Thr Phe Ile Ala Ala
    15                  20                  25

gta tat gag cat gcg gtg ata tta cca aac aga aca gaa aca cct gtt       207
Val Tyr Glu His Ala Val Ile Leu Pro Asn Arg Thr Glu Thr Pro Val
30                  35                  40                  45

tca aaa gaa gaa gct ttg ctc ctg atg aac aag aac ata gat gtt ttg       255
Ser Lys Glu Glu Ala Leu Leu Leu Met Asn Lys Asn Ile Asp Val Leu
                50                  55                  60

gag aaa gca gtt aag ctg gca gcg aag cag ggt gca cat atc att gtg       303
Glu Lys Ala Val Lys Leu Ala Ala Lys Gln Gly Ala His Ile Ile Val
            65                  70                  75

acc cca gaa gat gga atc tat ggt tgg atc ttc acc agg gag agc att       351
Thr Pro Glu Asp Gly Ile Tyr Gly Trp Ile Phe Thr Arg Glu Ser Ile
        80                  85                  90

tac ccc tat cta gag gat ata cca gac cct gga gtg aac tgg att cca       399
Tyr Pro Tyr Leu Glu Asp Ile Pro Asp Pro Gly Val Asn Trp Ile Pro
    95                  100                 105
```

```
tgt aga gac ccc tgg aga ttc ggc aac aca cca gtg caa caa aga ctc      447
Cys Arg Asp Pro Trp Arg Phe Gly Asn Thr Pro Val Gln Gln Arg Leu
110                 115                 120                 125

agc tgc ctg gcc aag gac aac tct atc tat gtc gtg gct aat att ggg      495
Ser Cys Leu Ala Lys Asp Asn Ser Ile Tyr Val Val Ala Asn Ile Gly
                130                 135                 140

gac aag aag cca tgc aat gcc agt gac tct cag tgt ccc cct gat ggc      543
Asp Lys Lys Pro Cys Asn Ala Ser Asp Ser Gln Cys Pro Pro Asp Gly
            145                 150                 155

cgt tac caa tac aac act gat gtg gtg ttt gat tct cag gga aaa ctg      591
Arg Tyr Gln Tyr Asn Thr Asp Val Val Phe Asp Ser Gln Gly Lys Leu
        160                 165                 170

ttg gca cgc tac cat aag tac aat ctt ttt gca cct gaa att cag ttt      639
Leu Ala Arg Tyr His Lys Tyr Asn Leu Phe Ala Pro Glu Ile Gln Phe
    175                 180                 185

gat ttc ccc aag gat tca gaa ctt gtg act ttt gac act ccc ttt ggg      687
Asp Phe Pro Lys Asp Ser Glu Leu Val Thr Phe Asp Thr Pro Phe Gly
190                 195                 200                 205

aag ttt ggc att ttt act tgc ttt gac att ttt tct cat gac cca gct      735
Lys Phe Gly Ile Phe Thr Cys Phe Asp Ile Phe Ser His Asp Pro Ala
                210                 215                 220

gtg gtg gtg gtg gat gag ttt caa ttg aca gca ttc tct acc cca cag      783
Val Val Val Val Asp Glu Phe Gln Leu Thr Ala Phe Ser Thr Pro Gln
            225                 230                 235

cat ggt aca aca cgc tgc ccc tcc tct cgg ctg ttc cct tcc att cag      831
His Gly Thr Thr Arg Cys Pro Ser Ser Arg Leu Phe Pro Ser Ile Gln
        240                 245                 250

cat ggg cca agg cca tgg gag tca atc tac ttg ctg caa ata ccc aca      879
His Gly Pro Arg Pro Trp Glu Ser Ile Tyr Leu Leu Gln Ile Pro Thr
    255                 260                 265

aca cca gca tgc aca tga cagggagtgg aatctacgcc ccagaagcag             927
Thr Pro Ala Cys Thr
270

tcaaggtgta ccactatgac atggaaacag agagtggtca gctgttgcta tcagaactga    987

agtctcggcc ccgccgtgag cccacctacc ctgcagctgt tgactggcat gcgtatgcca   1047

gcagtgtcaa gccattttcc tctgaacagt cagattttct ggggatgatt tattttgatg   1107

agtttacctt caccaagctt aagagaaata caggaaatta cacagcttgc cagaaagatc   1167

tgtgttgtca cttaacttac aagatgtctg agaagcgaac agacgagatc tatgccctag   1227

gtgcttttga tggactgcac acagtagaag gccaatatta cttacagata tgtgcattac   1287

tgaagtgtca aaccactgac ctggaaacgt gtggagaacc tgtggggtca gcttttacca   1347

agtttgaaga cttctccctc agtggcacat ttggaacgcg ttatgttttc ccacagatca   1407

ttctaagtgg gagtcagctt gcccctgaaa gacattatga gatttcaaga gatggacgct   1467

tgaggagccg aagtggagcc cctttgcctg tcttagttat ggccctgtat ggaagagtgt   1527

ttgagaagga ccctccacgc ttagggcagg gatctgggaa attccagtga tctcctttag   1587

cagagccctt ttaggattag cctggctaag aaaggaagaa aaaaaagaga tccgttagtg   1647

tctgtttaga aaagatgtta taaacttaca gaaacaaata taataaactg aagcagattt   1707

gaaaagcaaa aaaaaaaaaa aaaaaa                                        1733
```

```
<210> SEQ ID NO 12
<211> LENGTH: 274
<212> TYPE: PRT
<213> ORGANISM: Homo sapiens

<400> SEQUENCE: 12
```

```
Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
            100                 105                 110

Pro Trp Arg Phe Gly Asn Thr Pro Val Gln Gln Arg Leu Ser Cys Leu
        115                 120                 125

Ala Lys Asp Asn Ser Ile Tyr Val Val Ala Asn Ile Gly Asp Lys Lys
    130                 135                 140

Pro Cys Asn Ala Ser Asp Ser Gln Cys Pro Pro Asp Gly Arg Tyr Gln
145                 150                 155                 160

Tyr Asn Thr Asp Val Val Phe Asp Ser Gln Gly Lys Leu Leu Ala Arg
                165                 170                 175

Tyr His Lys Tyr Asn Leu Phe Ala Pro Glu Ile Gln Phe Asp Phe Pro
            180                 185                 190

Lys Asp Ser Glu Leu Val Thr Phe Asp Thr Pro Phe Gly Lys Phe Gly
        195                 200                 205

Ile Phe Thr Cys Phe Asp Ile Phe Ser His Asp Pro Ala Val Val Val
    210                 215                 220

Val Asp Glu Phe Gln Leu Thr Ala Phe Ser Thr Pro Gln His Gly Thr
225                 230                 235                 240

Thr Arg Cys Pro Ser Ser Arg Leu Phe Pro Ser Ile Gln His Gly Pro
                245                 250                 255

Arg Pro Trp Glu Ser Ile Tyr Leu Leu Gln Ile Pro Thr Thr Pro Ala
            260                 265                 270

Cys Thr
```

<210> SEQ ID NO 13
<211> LENGTH: 1932
<212> TYPE: DNA
<213> ORGANISM: Homo sapiens
<220> FEATURE:
<221> NAME/KEY: CDS
<222> LOCATION: (73)..(516)

<400> SEQUENCE: 13

```
atgtaaagtt tttccagtga aacaaaacgt aagaatctga gtttgttttt caaagatcac      60

taaattttag tt atg att ata tca cat ttt cca aaa tgt gtg gca gtt ttt     111
              Met Ile Ile Ser His Phe Pro Lys Cys Val Ala Val Phe
              1               5                   10

gcc ctc ctt gct ctg agt gtt ggt gca ctg gac act ttt att gct gca       159
Ala Leu Leu Ala Leu Ser Val Gly Ala Leu Asp Thr Phe Ile Ala Ala
    15                  20                  25

gta tat gag cat gcg gtg ata tta cca aac aga aca gaa aca cct gtt       207
Val Tyr Glu His Ala Val Ile Leu Pro Asn Arg Thr Glu Thr Pro Val
30                  35                  40                  45
```

```
tca aaa gaa gaa gct ttg ctc ctg atg aac aag aac ata gat gtt ttg      255
Ser Lys Glu Glu Ala Leu Leu Leu Met Asn Lys Asn Ile Asp Val Leu
                50                  55                  60

gag aaa gca gtt aag ctg gca gcg aag cag ggt gca cat atc att gtg      303
Glu Lys Ala Val Lys Leu Ala Ala Lys Gln Gly Ala His Ile Ile Val
            65                  70                  75

acc cca gaa gat gga atc tat ggt tgg atc ttc acc agg gag agc att      351
Thr Pro Glu Asp Gly Ile Tyr Gly Trp Ile Phe Thr Arg Glu Ser Ile
        80                  85                  90

tac ccc tat cta gag gat ata cca gac cct gga gtg aac tgg att cca      399
Tyr Pro Tyr Leu Glu Asp Ile Pro Asp Pro Gly Val Asn Trp Ile Pro
    95                  100                 105

tgt aga gac ccc tgg agg aag agt aaa aag atg aat gag cct gtt tcc      447
Cys Arg Asp Pro Trp Arg Lys Ser Lys Lys Met Asn Glu Pro Val Ser
110                 115                 120                 125

aaa gag ctt tgc tat cac tgt cat tca gaa tgc aat caa tat ggc caa      495
Lys Glu Leu Cys Tyr His Cys His Ser Glu Cys Asn Gln Tyr Gly Gln
                130                 135                 140

tgg aaa ttg tat agg act tga aaaaggaagc cctacttctg ggaccacatt         546
Trp Lys Leu Tyr Arg Thr
            145

ttacgaccac ctagctgagt gataaatcac taaaatatag taagtttgag gaaatgtcta    606

ttgaattaga ttcggcaaca caccagtgca acaaagactc agctgcctgg ccaaggacaa    666

ctctatctat gtcgtggcta atattgggga caagaagcca tgcaatgcca gtgactctca    726

gtgtccccct gatggccgtt accaatacaa cactgatgtg gtgtttgatt ctcagggaaa    786

actgttggca cgctaccata agtacaatct ttttgcacct gaaattcagt ttgatttccc    846

caaggattca gaacttgtga cttttgacac tccctttggg aagtttggca tttttacttg    906

ctttgacatt ttttctcatg acccagctgt ggtggtggtg gatgagtttc aattgacagc    966

attctctacc ccacagcatg gtacaacacg ctgcccctcc tctcggctgt tcccttccat   1026

tcagcatggg ccaaggccat gggagtcaat ctacttgctg caaataccca caacaccagc   1086

atgcacatga cagggagtgg aatctacgcc ccagaagcag tcaaggtgta ccactatgac   1146

atggaaacag agagtggtca gctgttgcta tcagaactga agtctcggcc ccgccgtgag   1206

cccacctacc ctgcagctgt tgactggcat gcgtatgcca gcagtgtcaa gccattttcc   1266

tctgaacagt cagattttct ggggatgatt tattttgatg agtttacctt caccaagctt   1326

aagagaaata caggaaatta cacagcttgc cagaaagatc tgtgttgtca cttaacttac   1386

aagatgtctg agaagcgaac agacgagatc tatgccctag gtgcttttga tggactgcac   1446

acagtagaag gccaatatta cttacagata tgtgcattac tgaagtgtca aaccactgac   1506

ctggaaacgt gtggagaacc tgtggggtca gcttttacca agtttgaaga cttctccctc   1566

agtggcacat ttggaacgcg ttatgttttc ccacagatca ttctaagtgg gagtcagctt   1626

gcccctgaaa gacattatga gatttcaaga gatggacgct tgaggagccg aagtggagcc   1686

cctttgcctg tcttagttat ggccctgtat ggaagagtgt ttgagaagga ccctccacgc   1746

ttagggcagg gatctgggaa attccagtga tctcctttag cagagcccct ttaggattag   1806

cctggctaag aaaggaagaa aaaaaagaga tccgttagtg tctgtttaga aaagatgtta   1866

taaacttaca gaaacaaata taataaactg aagcagattt gaaaagcaaa aaaaaaaaaa   1926

aaaaaa                                                               1932
```

<210> SEQ ID NO 14
<211> LENGTH: 147

```
<212> TYPE: PRT
<213> ORGANISM: Homo sapiens

<400> SEQUENCE: 14

Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
            100                 105                 110

Pro Trp Arg Lys Ser Lys Lys Met Asn Glu Pro Val Ser Lys Glu Leu
        115                 120                 125

Cys Tyr His Cys His Ser Glu Cys Asn Gln Tyr Gly Gln Trp Lys Leu
    130                 135                 140

Tyr Arg Thr
145


<210> SEQ ID NO 15
<211> LENGTH: 1779
<212> TYPE: DNA
<213> ORGANISM: Homo sapiens
<220> FEATURE:
<221> NAME/KEY: CDS
<222> LOCATION: (73)..(426)

<400> SEQUENCE: 15

atgtaaagtt tttccagtga aacaaaacgt aagaatctga gtttgttttt caaagatcac      60

taaattttag tt atg att ata tca cat ttt cca aaa tgt gtg gca gtt ttt     111
              Met Ile Ile Ser His Phe Pro Lys Cys Val Ala Val Phe
              1               5                   10

gcc ctc ctt gct ctg agt gtt ggt gca ctg gac act ttt att gct gca      159
Ala Leu Leu Ala Leu Ser Val Gly Ala Leu Asp Thr Phe Ile Ala Ala
    15                  20                  25

gta tat gag cat gcg gtg ata tta cca aac aga aca gaa aca cct gtt      207
Val Tyr Glu His Ala Val Ile Leu Pro Asn Arg Thr Glu Thr Pro Val
30                  35                  40                  45

tca aaa gaa gaa gct ttg ctc ctg atg aac aag aac ata gat gtt ttg      255
Ser Lys Glu Glu Ala Leu Leu Leu Met Asn Lys Asn Ile Asp Val Leu
                50                  55                  60

gag aaa gca gtt aag ctg gca gcg aag cag ggt gca cat atc att gtg      303
Glu Lys Ala Val Lys Leu Ala Ala Lys Gln Gly Ala His Ile Ile Val
            65                  70                  75

acc cca gaa gat gga atc tat ggt tgg atc ttc acc agg gag agc att      351
Thr Pro Glu Asp Gly Ile Tyr Gly Trp Ile Phe Thr Arg Glu Ser Ile
        80                  85                  90

tac ccc tat cta gag gat ata cca gac cct gga gtg aac tgg att cca      399
Tyr Pro Tyr Leu Glu Asp Ile Pro Asp Pro Gly Val Asn Trp Ile Pro
    95                  100                 105

tgt aga gac ccc tgg aga aat cac taa aatatagtaa gtttgaggaa            446
Cys Arg Asp Pro Trp Arg Asn His
110                 115
```

```
atgtctattg aattagattc ggcaacacac cagtgcaaca aagactcagc tgcctggcca    506

aggacaactc tatctatgtc gtggctaata ttggggacaa gaagccatgc aatgccagtg    566

actctcagtg tccccctgat ggccgttacc aatacaacac tgatgtggtg tttgattctc    626

agggaaaact gttggcacgc taccataagt acaatctttt tgcacctgaa attcagtttg    686

atttccccaa ggattcagaa cttgtgactt ttgacactcc ctttgggaag tttggcattt    746

ttacttgctt tgacattttt tctcatgacc cagctgtggt ggtggtggat gagtttcaat    806

tgacagcatt ctctacccca cagcatggta caacacgctg cccctcctct cggctgttcc    866

cttccattca gcatgggcca aggccatggg agtcaatcta cttgctgcaa atacccacaa    926

caccagcatg cacatgacag ggagtggaat ctacgcccca gaagcagtca aggtgtacca    986

ctatgacatg gaaacagaga gtggtcagct gttgctatca gaactgaagt ctcggccccg   1046

ccgtgagccc acctaccctg cagctgttga ctggcatgcg tatgccagca gtgtcaagcc   1106

attttcctct gaacagtcag attttctggg gatgatttat tttgatgagt ttaccttcac   1166

caagcttaag agaaatacag gaaattacac agcttgccag aaagatctgt gttgtcactt   1226

aacttacaag atgtctgaga agcgaacaga cgagatctat gccctaggtg cttttgatgg   1286

actgcacaca gtagaaggcc aatattactt acagatatgt gcattactga agtgtcaaac   1346

cactgacctg gaaacgtgtg gagaacctgt ggggtcagct tttaccaagt ttgaagactt   1406

ctccctcagt ggcacatttg gaacgcgtta tgttttccca cagatcattc taagtgggag   1466

tcagcttgcc cctgaaagac attatgagat ttcaagagat ggacgcttga ggagccgaag   1526

tggagcccct ttgcctgtct tagttatggc cctgtatgga agagtgtttg agaaggaccc   1586

tccacgctta gggcagggat ctgggaaatt ccagtgatct cctttagcag agccctttta   1646

ggattagcct ggctaagaaa ggaagaaaaa aaagagatcc gttagtgtct gtttagaaaa   1706

gatgttataa acttacagaa acaaatataa taaactgaag cagatttgaa aagcaaaaaa   1766

aaaaaaaaaa aaa                                                      1779
```

<210> SEQ ID NO 16
<211> LENGTH: 117
<212> TYPE: PRT
<213> ORGANISM: Homo sapiens

<400> SEQUENCE: 16

```
Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
            100                 105                 110

Pro Trp Arg Asn His
        115
```

<210> SEQ ID NO 17
<211> LENGTH: 36369
<212> TYPE: DNA
<213> ORGANISM: Homo sapiens

<400> SEQUENCE: 17
gttaccttgg caattgcaga ataaatgcat tatagttact aaagtaaaaa attagatatg 60
cctgtttgca gattgaacta taaaaatacc attcaaagac aaatagatct aaaaataaaa 120
tggaaaaaca taaacactaa ttctgtaaat attatactta atgcacaact gaaacaaaat 180
ttgccagctt actcaatatc aaaatctatg aacagttttt ctattttata taatttccct 240
ctcctctctc tggatctcgc tccccagctc attttttctt ttttttgctc tgattcttta 300
tacacctctg ttgcctctgt gataagcagc ttcaaagatg gttcctaatg ctttattgga 360
tagaatacaa caaaagcgat gaggtgttgc ttccccaatt acattacgaa gcatccgtgg 420
cttccatctc cagtgggttc acttgctgtc tggctctaag ggaatccaga taccataatg 480
cgggctgccc tatggtgagg tttgcatcac taggaactca tgtctctggg caacaaccaa 540
tgaggtcttg atccctgccg tcagccacat gagggagctt ggagctcgga agtgaatcct 600
cctggagtca agccttgata tagctagccc tggcagctgc ttgactgcag ccttgtgaaa 660
gagaccttgg gccagaggca ccagctaaac tgcccctgga ttcctgaccc agagaaagtg 720
ggagatgatg tatttttgct ttttgaagct gctgaatttg gggataattt gttatatagc 780
aatagaaaat gagtaactct tttgtattcc tctttgtcct ggcttcccca ttttgaggaa 840
aataaagtaa atcaaagtgt agagctgaaa tattcacatg aaaataataa taaagtttta 900
aaattatttg aatgtcttgt gttgacattc caaaatatat gaattccaaa aatttatatg 960
ttgaagtcct aactgtcagt atcttagaat gtaacttttt tggaaaaggg gtcatttcag 1020
atctaattag ttaagatgaa gttatactgg agtacagtgg gcactaaatc gaattggtcc 1080
tatgattgag tctcagtctt tcagtgagcc tgtacccctg ggtttatgac cttcagttgg 1140 ctttttttctt ctgcccttat ttggcataaa aacaaagcag gtggatcacc tgaggtcagc 1200
aatttgagac cagcctgccc aacacggcga aaccctgtct ctactaaaaa tacaaaaaat 1260
tagcctggcg tggtggcggg cgcctgtaat cccagctact tgggaggctg aggcaggaga 1320
atcacatgaa cccgagaggc ggaggttgca gtgagccaag atttcgccac tgcactctag 1380
cctgggtgac aagagtgaaa ctccatctca aacaacaaca acaataaaca aacaacaacg 1440
atgacaaaaa aagctagagc tgggattttc cctttccctg tgttaaagat tagagtggtg 1500
tcctcacaaa aagggaaaac ttggatacag gcacacacat ggggagaata gcatatgaag 1560
agacacaggg agaaggcagc catctatggg tcaaggagag aggcctggaa cacatctttc 1620
cttcaccgcc ctcaggagga accaactctg ctgacacctt catctgggac tcccaccctc 1680
cagaactgca aagcaataaa ttttttattt tttacaccac ccagtttatt gtattttgtt 1740
aggcagccct agcgaactaa tgtacataga gttcttgagt taatcttcac aaattactgc 1800
aataagggag ggtcttttgt tatgtaacaa tgctatgaaa tcatagcgtt ttcttaatta 1860
acttccgtag tttaaggtac taagttctgg acaccacgtg tcttctttct ataaatacca 1920
ggacatgctc tgtttttcag cactcattgg acttcagcat gactactcag ttgccagctt 1980
acgtggcaat tttgcttttc tatgtctcaa gagccagctg ccaggacact ttcattgcag 2040
ctgtttatga gcatgcagcg atattgccca atgccaccct aacaccagtg tctcgtgagg 2100
aggctttggc attaatgaat cggaatctgg acattttgga aggagcgatc acatcagcag 2160

```
cagatcaggt accatctcta ccatctctcc agtgtactgg attctatgag aaaggagggg   2220
gtcctaggag acagggccac tgtcagggtc agttacactt ttagatgata tatgtatcag   2280
agtagccaag aacctttatt ttacagttag aattctactt tcctctcaaa attagagcaa   2340
ggacttccct aaaagtaaga acaaagttaa gaaaagaaca atttgctcat tatcaagaag   2400
cagcagacct ttgaggaact ggccataaat tcaacatctt tgttcccctt ttctggtaca   2460
gatggaggat ggaggataaa tgggtcaggg actaggtgct attttcagag tattagtggc   2520
cttcatgtac tcatgtgcta ttaaggcttt gcaggttttc gaataaattt ataatctgaa   2580
aacaaattta agttttcaat tccttgccag catgcattat atacttcaca cttcattcta   2640
attacaagat aaaagtatat gtaatgcatt gtgagtcctt aagtttagtg aaggtttcag   2700
tttgaagtta atcatacagt ataaattgtg gtttacacaa atattatttt aaaagctatt   2760
gatcgattag gtgtagacca ggaatacatg aagtgtgata aaagtcatgg ataaatgtgt   2820
attacatata tctataaata tatattcttt tgtgttgttg agttaaggtc tcactctgtc   2880
acccaggatg gagtatagtg gtgtgatcac gtctcactgc agccttgact tcccgggctc   2940
aggtgattct cccactacag tctccagagt agctgggacc acagatgcat gccaccgtgc   3000
ccagctaagt tttgtatttt ttgtagagat gggattttgc catgttgccc acgctggact   3060
tgaactcctg acctcaggtg atccacctgc cttgggctcc caaagtgctg ggattacagg   3120
catgagctac cgtgactgcc ctatattctt atatatacta atatttaaaa ggttatcagg   3180
agttctgatg ttctttttca tccttagtcc aactatttcc ttgaaggtca cagagctttt   3240
taaggtgact ctctaattgg aaggtgccca ggttagctca ggcagtactt gtaggcatgg   3300
gacagttcaa gtaaccagtt tgtggctcct ctttttctga gaagcaggaa tcatgtttgc   3360
aggggaaagc tagggcagag gaggaaataa acagaatatt taagttatta atcagtcttg   3420
acacaggcac agtcatcagc gaaagttcaa ggagaggctt ggttccagga taagctaggt   3480
ttatagttaa cgactgccat aggaaacaac aatggcagga ttagaaaatt aaaatgcttg   3540
actaagccag gtgcggtggc tcatgtctgt aattccaaca ctttgggagg ctgaagcagg   3600
cggatcacct gaggttggga gttcaagacc atcctgacca atatggagaa accccatctc   3660
tactaaaaat acaaaaatta gccaggcgtg gtggcagatg cctgtgatcc tagctactta   3720
tgaggctgag gcgggagaat cgcttgaacc cgggaggtgg agattgtggt aagccgagat   3780
ctagccattg cactccagcc tgggcagcag agcgaaactc catctgaaaa aaaaaaaaaa   3840
gagagaaaaa aaaatgcttg actagaagcc caaacctcac cattatgtaa catatccatg   3900
caacaaacct gcatttgtac cctttgaatc taaaattaga aataaagaaa agaaaagaaa   3960
aagaaaaaga agtgacagtg cactgaaaaa aaaggaaatt aaaatgcttt ggaaaagaaa   4020
ataaattata aaaatataga aaacaaaata agatttaagg ggtgtggggg aagcccaaat   4080
agttgttact cagccactca gctcctcagc tcctcttgca ggcccccctt tggattaagt   4140
tgcattttta acagggtgcg catattattg tgactccaga agatgctatt tatggctgga   4200
acttcaacag ggactctctc tacccatatt tggaggacat cccagaccct gaagtaaact   4260
ggatcccctg taataatcgt aacaggtaaa gaaacaactt gtgaaaaatt cactagtaaa   4320
catcaacttg atttacctgg gaaaactttg ttgatgatca ttgcatagat ccacgatcaa   4380
ttcttaagtt tcagtatagc ttatttttca tctactatgg gtatatttac tgggagagca   4440
aatatgaatt atgaagtcac agaaatcaga gctagaaagt agcttagaaa tcatcacatt   4500
```

```
cagtgtgaac atctctggtc tctgactcct caccagtgaa cagaaaaata tttccctgtg   4560
taggtctgtg atttgaaaac tatatgagta aatggcaaaa gagagtcaca tcagtttaag   4620
attaatagtt ttcctttctc attgctaaga tagctgatga ggttaatgta gtaaaagtcc   4680
ttaaagtgta agctgattgt aatctaagag gtgatatggc aggattttaa gtggtttaag   4740
tcaggtctcg gctacagaga tattaagtgt ggtgaaagca gcactattaa ttttaatgta   4800
aggaaaccaa tatcttatac acctaagaaa atcatgtcga ttcacatact tctttctgaa   4860
tacacatggc taaaattatt ttaggaattc ctcttttgga actattctca aaaccgcaca   4920
acgccagtta gaatggtgat cattaaaaag tcaggaaaca acagatgctg gagaggatgt   4980
ggagaaaggg gaactctttt acactgttgg tgggagtata aattagttca accattgtgg   5040
aagacagtgt ggtgattcct caaggatcta gaaccagaaa taccatttga cccaccaatc   5100
ccattactgg gtatatacca aaggatcata aatcatttta ctataaagac acatgcatgc   5160
atatgtttat tgcagcactg ttcacaatag caaagacttg gaaccaaccc aaatacccat   5220
caatggtaga ctggataaag aaaatgtggc acatatatac cacagaacac tacacagctg   5280
taaaaaagga taagttcatg tcctttgcag ggacatggat aaagctggaa accatcattc   5340
tcagcaaact aacacaggaa cagaaaacaa aacactgcat gttctcgctc ataagtggga   5400
gttgaacaac gagaatacat ggacacaagg aggggaacat cacacaccgg ggcctgtcgg   5460
ggagtcgggg gctaagggag ggatggcatt aggagaaata cctaatgtag atgatgggtt   5520
ggtgggtgca gcaaaccacc atggcacgtg tatacctatg taacaagcct gcatgttctg   5580
cacatgtatc tcagaactta aagtataata ataataatac taaaattaaa aatcccacag   5640
aaactggctg ggtgtggtga ctcatgcctg taattccaac actttgggag gccgaggcag   5700
gaggatcacc tgaggtcagg agtttgagac cagcctggcc aatttggcaa aaccccatct   5760
ctactaaaaa tacaaaaatt agtggggcgt ggtggtgggc acctataatc ccagctactt   5820
ggaaggctga ggcagggaga actgcttgaa cctgggaggc agaggttgca gtgagccaag   5880
atagtgacac tgcactccag cctgggtaac agagctagac tctgtctcaa aaacaaacaa   5940
acaaacaaac ccacaaaaac tacttacaga gacaccttga ttttgacaag gtggattttg   6000
ataaattcca gtgttattta tcgtaatcat ttactctatt cttatttaat tgtaccataa   6060
ttatttctta tttaatcatg tcatatgtca gtgcttcagt ttctaaaagg caagcactct   6120
attatcactt ccactatgaa ttgaattgac ttatttctga atggcctttc cctagaacct   6180
catctccaag ggcctcctga acatccccac aaggatgtcc cattcacttc atttcaagga   6240
acacggttgc ccatttatgt tttccatcaa ctaatgatgt ctgaatgtct tgccttaatt   6300
ctctctgtct ctctctctct tttttttttt tttgagagag agactctgtg tcgcccaagc   6360
tggagtgcag tggcgtgatc tcagctcact gcaacctcta tcccccaggt ccaagcaatt   6420
cttgtgcctc agcctcccga agatgacaag tgtgagccac aacacccagc tagtttttttg  6480
tattttcagt agagatgggt ttcaccatgt tggccaggct ggtcttgaac tcctggcctc   6540
aagtgatcca cctgctcggc ctcccaaagt gctgggatta caggtatgag tcatcacgcc   6600
cagctgcctt aatttattaa ctctgcaaat tttttttgag tacctattat gtctaaacat   6660
tgttctgggc aatgaagtga acaaaacaga ttaaaaattc ctgtcccctt gaaatttata   6720
ttctagtgtg gggaggtaat aaatgtttta aaaagataat tatctatcta tctatcatct   6780
atctatcatc tatctattat ctatctacct atctttatat aggtatcttt catctgtcta   6840
cctatctatg atatgaggtg gaagtaaatg ttatggaaaa aataaagtgg ggaaggtgaa   6900
```

```
tagggtggca agcgtggggc tgaaatttta aaaggtcgtc tgagggcatc acagtgagat   6960
ttcagcaaag acctgaaaga aatgaggcaa tagatcatgt gagtatctga aaaaagtgca   7020
ttccaggctg aaggaattct aaattccaag atcctgtggt cagagtatgt gtctaaccta   7080
tggaacagaa aaagggttag tgtggttaca gtgatgtgac agaagaggag aaaagtagga   7140
aatggaggca gaagggcagg aggagcgcaa tgttgagaat agactccagg gtataggtca   7200
ccaaagaagc agagggcagt tcaaaagctg ttgtgatcat tatggcatag agatgatggg   7260
tctgagacca agaaatggta gaagtttagg tattgagaag tggacagatt ccgaataaag   7320
tttgaaagta gcactggcag gttttgttga aagactggat gtaggatgtg agagaaaagg   7380
aggactcaat atccttccct gctctcatag aatcagatct catcttattg agtatgtttg   7440
aagtatgcac atagttgatt gctttctctt ctcatattca ccaaactttt gggacctaca   7500
tcacctctta gactgagcgt taaaggaaca ggctctcatc acttttcttt tttatttaat   7560
ttatttagca tttatatgtc atatcgttcc agaaggattt gaagtttcta attatatcta   7620
atataattaa aaataggata ctttagttct aacaacaaac tagaacccat atgaatagag   7680
gaagcagttg ttatgaggca tcatggtaaa gagctgctca ttacaactgg atgttaagta   7740
tagttctaag agtttctgag cagctaagag aagtacaatt ttgttcagac actttgattg   7800
catcatagaa gaaagcttgc atatttcttc agagacaaac tatgtctaat aacctaactt   7860
aaagatgaat ttacttattc aactgttttt gttaattatt ttatttttaa ctttcatggg   7920
tacatagtag atgtatatat ttatagggta catgagatgt tttgatgttt gtacacaagc   7980
atgcaatggt aacaatcaca tcatgaagaa tggggtttcc atcccctcaa gcatttatcc   8040
tttgtattac aaaccattca attatgctct tttaggtatt taaaaatgta caattaagtt   8100
attattgatt atagtcaccc tgttgtgcta ttgaatacta gaccttattc attcattcta   8160
actatttttt tgtacccatt aatctcctca ctttctcccc actcctcccc taactaccct   8220
tcccagcctc tggtaaccat ctttctattc tctatctcta tctccatgag ttcaattgtt   8280
ttgattttca gatcccacaa ataagtgaga acatgtgatg tttgcctttc tgtgcctaac   8340
ttacgttatt tcacataacc taatgatctc cagttccatt catattgttg caaatgactg   8400
gatctcattc tttttgtagc tgaatagtac tttattgtgt acatgtacca cacggttgtt   8460
tccaaatttt ggctattgtg aacagagttg caataaacat gaaagtgcag atatcttttc   8520
tatatactga ttttcttttt gaggagtata tacccagcag tgggattgct ggatcgtatg   8580
gtggctctat ttttagtttt ttgagaaacc ttcaaactgt tctctacagt gactgtacta   8640
atttgcattc ccactaacag tgtatgaggg ttccctttc tccacatcct caccagcatt   8700
tgttataagt cattttaaca ggtgtgagat gatataattg tacttttgat ttgctttttt   8760
ttttttttga gacagagcct ccctcttgtt gcccaggctg aagtgcaatg gtgccatctt   8820
ggctcactgc aacctctgcc tcctgggttc aagcaattct cctgcctcag cctcacgagt   8880
agctgggatt acaggtgcct gccactacac ccagctattt ttgtattttt ggtagagacg   8940
gggttccacc atgttgtcca ggctgatctc aaactcctga cctcaggtga tcctcttgcc   9000
tcagcctcca gaaatgctgg gattacaggt gtgaatcacc atgcccggtt gatttgcagt   9060
tttctgatga tcagtgatgt tgagcaactt ttcacatgcc tgtttgccat ttgtataact   9120
tcttttgaga aatgtctgtt caaatctttt gcccattttt ggattggatt attagatttt   9180
ttttcctata gagttgtttg gacttcttac atattccggt tatgaatccc ttataagatg   9240
```

```
gatagtttgc acatatttta tcccaatctg tgggttgtct cttcactttc ttgatagttt   9300
cccctgctgt gcagaagctt tttaccttca tgtgattcca tttgtccatt tttgctttgg   9360
ttgcctgtgc ctgtggggta ttactcaaga aatctttgtc cagaccaatg tcctggagag   9420
tttccccaaa gttttctttt agtagtttca tagtttgagg tcaaatattt aagtatataa   9480
ttcattttta tttgattttt gtatatggtg agagataggg gtctactttc attcttccgc   9540
atatgggtat ctggttttcc cagcaccatt tattgaaaaa actgtccttt ccccaatata   9600
tgctcttggc atctttgttg aagacgagtt cactgtagat atttgggttt atttctgggt   9660
tctctcttct gtttcattgg tctatgtgtc tgtttttatg ccagtaccat gcagttttgg   9720
ttactagagc tctgtagtat aatttaaagt caggtaatgt gatttctcca gtttttttc    9780
tttttgctta ggagggcttc tggatcttct gtgtttccac gtaaatttca gaattttttt   9840
ttctatgtct gtgaagaatg acattggtat tttgatggag attgcattga atctgtagaa   9900
tgctttggat agtatgggca ttttaacaat attgattctt ccaatctatg aacatggaat   9960
atctttccat gttttgtgtc ctcttcaatt tcttacatca atgttttaca gacttcattg  10020
tagagagctt tctcttcttt ggataaatta attcctaggt attgtatttt atttatagct  10080
ataacaaatg ctattccttt cttgatttct ttttcagatt gcttgctgtt ggcacagaaa  10140
tgctactgat tttttatgtt gattttgtat cctgcaactt tactgaattt gtttgtcagt  10200
tctattagtt ttttggtgga gtctttaggg ttttccaagt ataagataat aacatctgca  10260
aacaaaaata attttcctcc tttccaattt ggatgcattt tatttctttc tcttgtctga  10320
ttactttagt gagaacctcc actactatgt tgaataatag tggtgaaaat ggacattctt  10380
gtcttttcta gatcttagag aaaagctttc agttttccct cattcagtat gataccagcc  10440
atgggtctgt cataaatggc tattattgtg ttgaggtatg ttccttctat atccagtcat  10500
tgagggtttt tattatgaag gaatgttgaa ttttaccaaa tattttttca gtgtcaattg  10560
aaatgaccat ttggtttttg ttcttcattc tgttgatatg atgtgccaca tcaattgatt  10620
tgtgcatgtt gaaccatcct tgcacccttg ggataaatcc gacttggtca tgatgaataa  10680
ttttttaatg tgtcgttgca tttggtttgc tagtattttg ttgaggtttt tttgcatcaa  10740
tgttcatcag ggatgttggg ctgtagtttt ctttttttatg tgtctttgcc tggttttggt  10800
atagtataat actagcctca ttgaatgagt ttggaagcat tcctttctct attttttgga  10860
atagtttgaa taggatttgt attagttctt taattgtttg gtaaaattca gcactgaagc  10920
ctttaagtcc tgggcttttt tttgctggga gatcttttat tacagcttca atcttattat  10980
ttgttatctg tctattcagg ttttggattt ctttgtggtt caatcttggt aggctgtatg  11040
tgtctaggaa tttattcatg tcttttaggt tttccaattt atcggcatgt agttgctcat  11100
agtaatctct aatgatcttt tgaatttctg cagtattggt tataatgtct catttttcat  11160
ctctgagttt atttttcttc tatctttttt tcttagtctc actaaaagtc aattttatct  11220
tttcaaaaag aaacttttta gtttttttttg gatgtttttt atttcaattt catttatttc  11280
tgttcagatg tttattattt ttcttctact aatttcaggt ttggtttgct cttccttttc  11340
tagtttaaaa aaatatatca ttaggctgtt tacttgaagg ttttcttctt tgttagtgta  11400
ggcacttata gctataaact ttcctcttag aacgattttg ctgtatccca taagttttga  11460
tatgttgcat atccattttc atttgtttca ataaaaattt taaatttctt cttaatttct  11520
tcattaacct gctggtaatt caggagcaca ttgtttaaat tctgtatgtt tgtatagttt  11580
tcaaaattcc ctttgctatt gatttctagt actattccac tgtggtcaga gaagatactt  11640
```

```
gatatgatct caattttttt taatgtttta agatttgttt tgtgacctaa catatggtct  11700
ctccttgaga atgatccatg tgctggggag aagaatgttt attctgtagc cattggatga  11760
aattttctgt aactatctat taagcccact tggtctgtaa tgcagattaa gtccaatgtt  11820
tctttatttt ttttttcctt ctggatgatc tgtccaatgc tgaaagtagg atgttgaaat  11880
ctccagctat tattgcattg ggatctatct ctctctttag ctctagtaat atgtccttta  11940
tatatctgtg tgctcaagtg ttagcacact tgtgtgctca attgttatat cctctgacag  12000
aattgacctc tttatcatta tataattaat ttctttgtct ccttttatgg tttttgtcct  12060
gaaatctatt ctgtctgata aaaatatagc taccccctgct ccttttgttt tccatttgca  12120
tggaaatctt tgctatccct ttattttctg tctgtgtgtg tctttataag tgaagtgtgt  12180
ttcttgtaca caatcgacca ttgccattga ttttttttct tttttatcca tttagccact  12240
ctatgtcttt tgattggaga gtttagacca tttacattca atgttttatt gttaagtaag  12300
gacatactcc tgccattttg tttttttgtt ttctggttgt tttgtggtgt tgtcttcctt  12360
tcttcctgtc ttcctttttg tgaaggtgtt tttctctgat ggtatgtttt aatttttgct  12420
tttcattttt tgtgtatctg ttgtaggttt tttgatttga tgttatgcag cttgtaaata  12480
acaacttata gttcattatt ttaaagtgat gacaacttaa cattgattgt ataaactaac  12540
aagcaaagag aaagctaata aaagcttcat actttaactt catcccccat acttttaatt  12600
tttaatactt tctatttata tcttatactg tctatgtctt aaaaagcttt tataattatt  12660
atttttgatt ggttcatctt ttagtttttc tactcaagat atgagaagtt tacaccacaa  12720
ttacagagtt ataacactcc atgtttgtct gtgtacttac tagtgagttt tgtaccttaa  12780
gatgctttct tattggttat tgatgtcttt ttctttcaga ttgaagaaat ttctttagca  12840
tttcttataa gagaaggcag tgggttcttt tctggctcag ggtgggtcta gaaatgccat  12900
ccaggagcta agtcctggaa ttgaggactt taggagtctg cttggtgctt catgttactg  12960
tggctaagtt ggtacccaat ttgtaagaca aagtcctttt actcttccct ctcctttcct  13020
ccccatgcct ccccatggct acaacagctg ggaatgtgct gggtcacacc tgaaaccagc  13080
atggtactgg gtcccaccca agcctcgtgg tgagtactgc ctggctatca ctgatgttta  13140
ttcaaagccc aagggctctt tagttagcag gtgatgattc ttgccaggac tgggtccttc  13200
catttaaggc aagaagttcc cttatagcct agtgtatgtc tagaaatatc atcagggagc  13260
tagggcctgg gttgggggat tcagtactct acttggtgct ttattttact gtggttgagc  13320
tgttatccaa gttgcaagac aaagtcctct ttatgctcct gtctcctttc ttaaggcaga  13380
gggacggagt ctctcaaagc tgtgagctgt gctgcctgga gttggaggag ggttgatgca  13440
accactcctt tgactactcc agctggtgtc tcactaggtt atgtgcgctc caaggctact  13500
ggttctgagc tcagtacagc actaggactt gcctaggaat tgtagtcctt gtggcctaaa  13560
tcagctgtcc ccaacgtttt tggcaccagg gactggtttt gtggaagaca attttttaat  13620
ggacagggtg gagtatgctt tctggataaa actgttccac cttagatcat caggcattag  13680
ttaaattctc ataaggaaca tgcaacctag attcctcaga tgcacagttc acaacaggct  13740
tccattccta tgagaatcta atgctgcaac tgatctgaca ggaggcagag ctcaggcagt  13800
aatgtcactc atctcctact gtgcagccag tttctaacag gccatggact ggtactgccg  13860
tgcagcccaa ttcctaacag gccacagtcc atggcatagg gattgggaac ccctggccta  13920
gactgccttt caagtttatt tagaacccca gagaacttta tcccacattg gtgatccttg  13980
```

-continued

```
gtagaactca ggttctgact gctgggtagg acaattcctc tctgacaaga gctgttctaa  14040
atgtgccctc tgtgggcact ggctgaattc tgtgccatgt tgctttctgc tgttacatgg  14100
caacactgac ttccaatgta aagtcccaca atcactgtac tttccttccc ccaagggcac  14160
aaattttctc tccacaccat gtggtaacct ggaggatggg ggagagtggt attggcaatt  14220
aaagactttc tttcttacct ccttcagtgc ctctttcctt gatatgattt taaaacaagg  14280
tactgtgatt actcttctga tttttggttc ttatgaaggt tcattcttgt tgtggatggt  14340
tgttcagttt ggtgatcctg caggaagaca attgctggaa ggttctattt ggccatcttc  14400
ctctgcttcc tcctcatctt ttatttcttc ctcttgcctg attgctctgg ctaggacttc  14460
cagtatgatg ttgaatagaa gtggtgaagg tgggcttcct tgtcttgtta cagttcttag  14520
aacaaaggct ttcagctttt ccccattcca taggatgtta gctgtaggtg ctgacatata  14580
cgccatctat agcctttatt atgttgaggt atattccttc tgtataataa agtgcacatg  14640
tctgaattat atattacttg ccttgagggt gccaagaaac tatttatact gcctagaata  14700
ttaaccttta ttatgcctaa agagttcatt agtcaaatgt tggttttgat gtagacctca  14760
tagtttaaaa tttaacattt aaattaaatg ggttataatt tttaatacca cctaaataca  14820
atatattgat ccaatataga aagttagatc aatgttagaa ataaagagtc acagtgtacc  14880
tttccagact tgtcattagc atttcatatt tatagtttta gctttgattt gaatgtctca  14940
cagatgaact taaatcaaca cataattcca ccatagcata atagtaatta ggcagtttcc  15000
ctaaatttga gaacattgcc ttaatgtagt tgtgatgttt tgaggcttca tagcttaaat  15060
ccattatacc attatggaat ctatagagca gggctatgga gaaaggcttc agagaagttt  15120
tttttgctac tataacctta tttaaagaaa caaacagaaa aaaacccaaa cgtatttgaa  15180
gtctgcttaa atattactgt taaatgtgaa gtgtttatat ctaacattca taatcatatg  15240
aatgtcaaca tttagtttcg agtagaaaaa gataaatcat tactgtgagt taagaaattt  15300
aaatggagat gtgtgaggga gcatgtccat ttcatccttc ccatctccac cctccccaga  15360
gtttcatccc cagggtgccc ttcttggttt ccagcctctg gtgttctgct tggggtcttg  15420
acttcttccc atgccactca ggctcagccc cagactagaa cagggtttgg gaagcagtgg  15480
ggatagccaa gatgggtgtc agtgggtggc ccagcagttt ctgtcccagg agtggccaca  15540
ggccaggggt agtggtggct gtgcatgtgg ccagcctgct gccattgtcc catccttgtc  15600
agggccctct ctttcacctt acagcatctg aggggcagag ctctagagtg tttgggcaga  15660
caatgcctct gaaaattttt ttttaaataa aatttagatg acaagtatat atcatatatg  15720
cagtgaccaa gcatataact actttacagt catctaactg ctgtagcaat gatatgtaac  15780
tacagtgtca aaacaccctg acagttttca gaaacccaat gtggagacca tctgccatat  15840
cttacttttt ctttaggtac aatattcaaa ttcatattga ttttgcttac atatgaatag  15900
tttcaaattt gttcacatat ggtttaaact ttttgtccct attgtcttac tcaggcttgt  15960
gtaacttaaa atgagcctga gcatgggtct acacacagca agatgtgtaa taaaaacaca  16020
attttagtgc tactttcaaa attcatgcta ttaagaaaga tgctgttttc aaagctgaaa  16080
agatcatgaa atggctaact tacatatcag aggttggata attccttact attgaggtgt  16140
tatattttct gtgtagtaaa tgccttcaaa tattaactga aagatcagtg aagtcatttt  16200
ccccttttgtg attccaactt cattttgttt attttgaaga taattaatat tttaattgca  16260
aaagaaaatt atagcattgg aaaattttct gtatatggag aataacaatg aaccaaattt  16320
accaattagg gaaccatttc aggaattgtt ggatggtgaa tttttcttca gtaactatgc  16380
```

```
tttagttgca atgcagtatg cccagaaaca atccatttca acttctgaat gtttgatttg  16440
gaacatttgt ttgatgagta ttcagttaaa cacttggata caaactcttt ccagaaggtc  16500
acatctctac catttatctt ggaatgtttc tgaagacatt ctactcattt tattaactgt  16560
atacacttct gtttttggat ctccaatatg attatagaca atatcaacat agaaggcttt  16620
gatttagact ccaaagttta gagcatttga tcttgacatg ccttaaattg ggcttccagt  16680
caaaattgag gccacttctc ctttcaaatg gcaagttctc ttgaatgagt gaatagtgga  16740
gttgtagaaa ttgaaaggca gtagtagctt tcactttaca ttacaacttc tccaatgcaa  16800
tcttttccat tctcatcaag tctgaaaccg tgaacctata ttcacctatt tggaacacat  16860
cagttgccaa tgggacatcc ctttcctctt ctattgattt tacagccgaa tagaagaagc  16920
tcagttcaac acatccaagg tgcttgggct gcaccttcat ttaacacagg aatctgtcca  16980
gtaaattcac agagaaaatg cctttgtgtt aaagccaaag aactgaatta gactaacatc  17040
ttgtacttca aagtcctgta gccttgcagt cattctgagg ctattgtcta tcatgtgcaa  17100
actcaattag tctcaaacca cagatcttta actgacatct agacttcagt tccaacaagg  17160
cattcagctg gtgtagcagt ttctgacagt caggtttcag tacctctatc atcttgatag  17220
tgattgagcc tcagtggtaa ccacccttct tgggcctgca ctcacctcac cccacgaaat  17280
ccaatctcag aggcctagga aacaaagcaa acagagaggc ccagggaggg gaagccttcc  17340
tgggtggatg tctctgcaga gccaccaaga tcatattgcc ctcatcaggg tcagcttgga  17400
gctgaagggc tgaaaaggca ttttgatatt tgattgcata ttatttcata ctgttatttc  17460
agagttttgt gtgcacacat tgtttcttca gtaagcctaa tgctttataa gcatagcaac  17520
cacatctgac atttctatgt ctctcacatt gtatgcttgg acagctctgc ctggaatatt  17580
cttcccccag ttgcccacat gtccaatata gtgctttgtg ttgtgtcaaa acctaatgca  17640
tatttgttga atatttaaca tgtgctgatt ttagattagt aaatatcttt ccgataattg  17700
atgatttttg ttatacctaa agattgaaca ctttgaaagc agccttagaa aatgcatttc  17760
aattattctc tttcacctcc tccttctgtg cccagggcaa aactctgcat ggattaagga  17820
ctcagcaaat atcatggatg aagcaacagg cagatttcag gcaccataag caaactgaat  17880
ttttaaaccc taaattagga catgtggtct aattttggag cattttatgt gtacgccaaa  17940
cagcctgaga aatgtagctt gaattgaaat atattagaat acatgaagac taatagagtc  18000
agtaggaaaa tatgtttgtc atcagaactg tttcagaaat ccaaaacacc aacctactta  18060
ttccaccact taaggtgatc caaaaagact gggggtaaac atgtttcaag tggttcaatg  18120
tgttgtaatt tatatctatg catttcagat atcaattgaa gcaaaggtgg gttaaactat  18180
tgaacggttg ttctttctta caaacacatt gaaataataa ttttctatat gtattattat  18240
atccttttcc aatctttttc aaggatatgt tttatagatg attgctatgg ctttccttat  18300
attcattata caaatttgtt tgtagatcta gtagccaata tttgatgtca ccaaattttt  18360
attcatacaa cagttatctc agccttctca gctattcttc aataaccatt tatcatttca  18420
gagttgtgca atagaggata aatatagcaa tatgttaaat attattttca aaattgtatt  18480
ttaattgctt tactgggaca attattggta actttgtaaa agaataaaaa aatcaggcat  18540
taacaaatgc tccaggattt ccattgtttc atactagctg gtactgccct agccaatcct  18600
tgttacctct tatttgaaca atggcaacag cttcctaatg aatcccctgc atttagtctc  18660
tcactgttcc agtacattct acactccgtg ttctatttat ctttatgaag aaaattttga  18720
```

ccaggttgct tctgtcttca aaggctttaa tagtacctat ttattactaa atttggaaca 18780
aatcttagcc tcttgtgcaa agctcaatat ccatccttcc ttccttcctt cctccctgcc 18840
tcccttcttt ctttcttttt ttaaaatatt tttaaacttt ttattttttt gagacagagt 18900
ctcactctgt cacccaggct ggagtgcagg ggcgcaatct cagctcactg caagctccac 18960
ctcccgagtt cacgccattc tgctgcctca gcctcctgag tagctggaac tacaggcacc 19020
tgccaccacg cctggctaat tttttgtatt tttagtggag acggggtttc accgtgttag 19080
ccaggatggt ctcgatctcc tgacctcagg tgttccactg gcctcagtct tgcaaagtgc 19140
taggattaca ggcgtgagcc actgtgccct ctcctctcct ctcctcccct cccctcctct 19200
cccctcccct cccttctctc tttcctttct tctcaaatct gagaatgtct tcatttctcc 19260
ctcccttttg aagggcagtt ctgatggata tagaattctt ggttgtcaga tttttttttc 19320
tttcagtact ttaaatatat cagctcaatg ctttgtggtc tccaaagtta ttgatgagaa 19380
atctgccgat aatcttattg gggatccctt gtatgtatga gtcacttctg tcttgctgct 19440
ttcaagattc tcattttgtc tttggctctc tacaatttga ttatagtgtg tcttagtgtg 19500
agtctctttg aattcattct cttggagttt gttgagcttc ttggatcttt atattcatat 19560
ctttcttcaa gtttgggaag ttttcagcca ttatttcttc aaataatctc tcttctcctt 19620
ctgagactcc cacagtgcat gtgttggaca ctcaatggtg ttcctaaggc tctgttcaat 19680
tttctttaat atttttgtt gttgttctgc agactcaata atttcaatgg tcctgtcttc 19740
cagttcactg tttctttttt ctacatgcct gaattggtct tcgaatcctc ctataaaata 19800
ttcatttcag ttattgtaat tttcagctcc agattctttt taggttttct atctttttat 19860
tgatatttct actttgtttt gtttttgat tttctccaca tcttccttta ttttcttaag 19920
cttctgtaaa accattgttt taaagtctgt gtttagtagg tctgtcatgt ggtccttttc 19980
agggatgatt ttcgttggtt tatttttcct ttcttttgag tgagtcatac tttcctgttt 20040
ctttgtatga tttgtgattt ttttggttga taactagaca tttgaatctt atcacatggt 20100
tactctggga atcagattct ctgggtttgc tatgtttgtt tgtttgtttg ttttgttgtt 20160
gtaggatgtt tgtgttgagg atcagcttga gatgtaaatt taaggtcttc ttagaccttt 20220
tatgagtctg tacctttccc tgggcatgta tggcgacttt ctaaatttcc ctgtatattt 20280
aattgcttat tccttaaatg tctcactatc caaaggagaa aaagagaaaa taaataaata 20340
aataagacac tggttcttta aatctcctgg aagccacttc agccagaaag agggcctgca 20400
aaaatggtgt gtctgtatgt atacacaaca atagctgctt gcctttgcat ttgtacctcc 20460
atgatcagaa gcaacaatta gtgatcagaa tgcagatctc gtatatttga aagacaaggt 20520
cattattgtc caccctgctc ccataagctg cctgcaagct gctttaggaa cacagacatg 20580
gcagcctgtc acagggacag gggatgagga attggtaacc actattgagc taagagctaa 20640
aatggactga aattaactgt aagttacctt ccaagcattc ttctggaagt tgcaagcact 20700
agagctccaa aatagtaata ttagacagat tccaacagtg caattgttat ctaggtgggg 20760
agaaaaattc cctgctctgc tatcttccca gcatccctct acctctaaat ttttgttaac 20820
tcattcaaaa aaattttttt ttgagatgga gtctcactct tgttgcctag gatggagtgc 20880
aatggcatga tctcagctca ccacaacctc tgcctcccaa gatcaagcaa ttctcccacc 20940
tcagcctctt gagtagctgg gattataggc gcacgccacc aggcccagct aattttgtat 21000
ttttagtaga gacggggttt cttcatgttg gtctggctgg tctcgaactc ctgacctcag 21060
ctgatccacc cacctcggcc tcccaaaatg ttgggattac aggcatgagc taccacacct 21120

```
ggccccccaa aatttgtttt ttgagacagg gttttgctct gttgcccagg ttggaatgca  21180
gtggaactca ctgtagcctc aaaatcccaa gttcaagcaa tcatcccacc tcagtctccc  21240
aaatatctga gactacaggc acacaccact atgcctggct attttttttt tttttcattt  21300
tttgtagaga gacagtcttg ctttgttgcc caggctggtc tcaaactcct gggctcaagc  21360
aatccttcct ccttggactc ccaaagtgct ggaattacag gcatgagcaa ccacacccac  21420
cccaagatat tttttaatgc ctctcttctg ttagacataa ttttagtaaa cgggatatgt  21480
aagtcattga tctatgatat ccacaggatg ctgcagacat tataagacaa acacgtaagt  21540
gaaaatatga ctatagatta cgataaatgc tatgaagaaa aaatacgtgg tctggaatct  21600
tatcctacag taggttccta caaccaattt tactcaagca tgggcttcct ctgaactcct  21660
ttcttgtctt aatacttctc ttctaattat tgttatttag aatttacttt tgcatatatc  21720
aaataatagg tttaggcaac tatcattcag gattttgttg agagttaaga ttgatttaca  21780
aagatttttt tcctccaata aacatgtatc agatttggcc agaccccagt acaagaaaga  21840
ctcagctgcc tggccaagaa caactctatc tatgttgtgg caaatattgg ggacaagaag  21900
ccatgcgata ccagtgatcc tcagtgtccc cctgatggcc gttaccaata caacactgat  21960
gtggtatttg attctcaagg aaaactggtg gcacgctacc ataaggtaaa attaatttgc  22020
aaataatcca attagttaat gcctaatgaa ataaagtggg caaggagaaa aatatgttat  22080
tgataatgat aagcacactt tagaaatcga gtagggggcaa agcatagaaa gtaatgataa  22140
agtgtggaaa gctcctataa agaggcttaa ggggttccgt gtacatataa gaacacagga  22200
gtgtgttttc aggagtgtgt agcagtcaga aagtgccgca tgcattatgt tgcctaatgt  22260
tgccttttgg actttgtcct tttaaaggca taccctggca atgggtcaag gctagaatga  22320
aaaactgctt accacataga ctctgtcttg aggagaatgg aacaaacaaa gttccttgcc  22380
aaggaaaaca gttaagtcta cttggcaaac agaagtaatc tattttatgt cttataagat  22440
tccagtgggt ctttatagat aaagataccc atgtacatat ttgtaatgtg gagactgaac  22500
taaaggccca atttagctag aatggcctct gattctctaa agcaaactca tttcccatga  22560
aaacactgat catagatgaa attggcacta agatgtgagc ttgtactttt tcccacactg  22620
tgatgtccag atcaacttcc taaaataatt tttttctctt tatcttctgt ttattgcagc  22680
aaaacctttt catgggtgaa aatcaattca atgtacccaa ggagcctgag attgtgactt  22740
tcaataccac ctttggaagt tttggcattt tcacatgctt tgatatactc ttccatgatc  22800
ctgctgttac cttggtgaaa gatttccacg tggacaccat agtattccca acagcttgga  22860
tgaatgtttt gccacatttg tcagctgttg aattccactc agcttgggct atgggcatga  22920
gggtcaattt ccttgcatcc aacatacatt accccctcaaa gaaaatgaca ggtaatgtgt  22980
gatcttaaag atatgcaggc tgatgtaatc agaaaagaaa agaaaaaaaa aacatgtttt  23040
tctagctaac gcatactcct taatacaatg ttttccagct cttaattttt gaacatctag  23100
ctgttaatat gctatagaat caatctcagt ctaaattgtt ttgtagattt atttggtttt  23160
atttaacttg attttttttt caaaatatat gacttcttac atacaactct cccttcttgg  23220
cttcttggtt tcatacttta attgatttcc tctcacttct ctgtctttat cagcatgttt  23280
tactgaaatt aataaaacat ataacttaga gagagtaaaa tgtgaatatg aggttaaaat  23340
agtaataaca attatgaaat cccttttttac tttccaattt caaatgatgt tttcaactta  23400
ttacttccag gaagtggcat ctatgcaccc aattcttcaa gagcatttca ttatgatatg  23460
```

```
aagacagaag agggaaaact cctcctctcg caactggatt cccacccatc ccattctgca  23520
gtggtgaact ggacttccta tgccagcagt atagaagcgc tctcatcagg aaacaaggaa  23580
tttaaaggca ctgtcttttt cgatgaattc acttttgtga agctcacagg agttgcagga  23640
aattatacag tttgtcagaa agatctctgc tgtcatttaa gctacaaaat gtctgagaac  23700
ataccaaatg aagtgtacgc tctaggggca tttgacggac tgcacactgt ggaagggcgc  23760
tattatctac aggtaatatt ttgatgtcag aagagttact ggataaaata aagacactca  23820
gttaaatata cagtttagat aaataatgaa tgatttttta gtataagcat atcacacttt  23880
tggggattta tgtatgctaa aaattttgtt gtttatttga aattcaactt tagctgggaa  23940
gcctacaaat acaggctaaa tttatttgct aaatcttttt tttttttttt tgagacagag  24000
tctcactctg tagcccaagc tggagtgcag tggtgcatca gctcactgca agctctgcct  24060
cctcggccaa gcaattctca cgcctcagcc tcccaagtag ctgggactac aggcgagtgc  24120
caccacgcct ggctaatttt tttgttgttg ttgtatttta gtagagacag agtttcacca  24180
tattggccag ggtggtctca aactccccga gctcaggtga tccgcccacc tcagcctccc  24240
aaagtgttga gattataggc atgagccacc gtgccctgcc tatttgctaa accttgaaac  24300
cttagatgtc agttcaattt taagctgatt gggaaaaggc aggacattta cttgcagtag  24360
cagtattaaa aataaatatt caaattacag atcattataa caggagttca ttgaaaaccc  24420
attttatttc ctgcctgaac aaattaagcc attttcctta tatgttcaca aatgcctatc  24480
ttgctttata aagagtttga cactaagtat atcctggata tgaatggggt tgaccaccaa  24540
gatagttcaa tggaatggtt tattgctgca aagatccaat ctctcattgc tcgcaagtgg  24600
cctccatggt cctctcattc ttctcttctc ttccttggtc tggcccccat cttatctcac  24660
ttaacagggc ttcctattga cagtctgaca atctcagctc catccagtca gttctccata  24720
ttgtagttac agaaatcaca aaaagctgtt tttgattata atactgtctg gcttaaaatt  24780
cttcactgac ttctaattga caaatcaaat ttcttaacat gaaagacaca caaagtctag  24840
atgtgtggtc ccttcctatt ctctatcctc taatctcact tctacttaca aatatcctgg  24900
gcttctgcaa tattgaaata ttttcccatc tcctatttgc tagcatatgc agaacctcaa  24960
ggtgtttgca cagattgttt ggtcctttat ccgtggcgag ccccacctac taatctttca  25020
tagcactttt ctggtgttat cgtcaccaag aggggttcct ggatatttcc cacagagcta  25080
ctcctacctc tccagatgag ttaagtacat cctttatgtg ctcccaggac accctatgct  25140
tagctttatc aaagacatat tatgtcatag tattcactta cttatttgag actgagaacc  25200
ccttgagtgc tgaaattatg ccaactgcac agtattttgt ttgctctatg ataactaccc  25260
taacaatact ttttcgtttt agcaaatgaa ggcctactat atgccaggta tttatttagt  25320
gttaatgata tgaagataaa taagcataga tcctcctctt gaagaattca gtctttagta  25380
atggagaaag acatttgaac agataatttc agcataggtt ggcatgtgat tgtccgtaga  25440
atgcacattt tgctggagga gtactaaaga gctctactta gattaatttg ggaatgcagg  25500
gaagtttctg gagctgatgc tattatccag gtgaaaaaga gtaggagggg attctttgtg  25560
gtgtgaagag catgaacaag ggtgtggatg caggcaggag cagggtctgc agggaacagc  25620
aacaggtcag tgctactaag gcaactgagg catggcttgc gaagctgggt ttggtgggaa  25680
ataagcctgg aagcaacatc ctgtcctgca ggatcttacc tagcacactt aagattcagc  25740
ctttattctg tgggtgatgg tcagctggtg gaagtggtcc agtgaaggaa tgatgtggtc  25800
agatctacct ttgaatatat catttttact actctgtaga tgatggagca aagacccaaa  25860
```

```
agactagatt attaaaatag tcttattaag ggtctggacc aagactgtgt ttgttggaat  25920
aaaagcaggg catggagtct agacatattt agaaaatgga actcagtggc caatttgatg  25980
tggaacagga aaacggaatg gagagtccag aatgtggcag atttctggca agaatggctg  26040
ggtgggtgag atgcatctga cagatcagga ggcaagagag gagcagactc actgacagtg  26100
ggtagaggct gagttcagtt atagatgtgc tggttttgaa gtagttatga gacattcagc  26160
tggacccagc cagttgtctg ttgaatactt tggtctgatg cttaagggag atactagaat  26220
tagaaatatt gtttcaaaaa tcagcaagat acaaggggca attaagcaaa caacagtgaa  26280
tgatacgaca aaggagactg tactgacagt aaagaactat tgacaaagta gaacctttgg  26340
gagcttcggt atttggggca ggaaaggaca gaggacaaga aacctgcaaa tacaattaag  26400
aaataaagga aaatttaaaa agagaacatc tggtagatgc caaggaagta gagactcttg  26460
gaggaaagaa atcatgaggt gtattaacac aatacgttga ccattattag catttttgag  26520
tataattttg gcagaatttt ctgagctcat aatgatagga tgatgggcag attatattgg  26580
gttgaaaagt caaagggaag tgaatgcact tttttcccca agaaatctta tctgagacaa  26640
gaagaagaga agcaagacaa tggtttaaca gagactcatg gtcaggagaa atgtgtgtgt  26700
atgtgtgtat gtgtgtgtgt gtgtttctca acaaacgaga gagccttgat tgcctttgta  26760
ggtctaagag aaagagctac aaaaggaaaa aatacataaa atatgagagg aatcaggtcc  26820
agtgcagtgg cctgtaatcc cagcactttg ggaggtcaag gcgggcagat catctgagat  26880
caggagtttg tgacccctgt ccaacatggt gaaacctgtc tctactaaaa atacaaaaat  26940
tagccaggca tggtggcagg cgcctgcaat cccagctact tggaaggctg agacaggaga  27000
attgcttgat cctgggagat agaggttgca gtgagctgaa attgtgccac tgcactccag  27060
cctaggcaac agagtgagac tctgtctcaa aataaaataa aatatacaag gaatcattac  27120
tcctactcag tgttccaagg tgctggagga aagagggaaa aatagtatca tgaacacagg  27180
tacaaaatgt ccaacaactg gaaattaaat gaatcatatt gtagaagaac atttattgcc  27240
ataaaattat taccatatac catatgttat attaacatat atagccttat atatgtgaca  27300
ttcatatggt attatattgc tatataaatt tttaaaatta aaatataaat tgtgatgtat  27360
tatttttaag ttaaaaaaag ttggtcacaa aacaagagag taatctctta gctcttcttc  27420
cctccttttc cttcctgcct cctcaatctt ttcctacctt tttacctcct ccagagtctt  27480
ggctctacct aaagagagtt gtgggaagtt ctttcttagt gttgtgaggt aggttagctt  27540
tgtcaagtaa aaccaagctt tctgtttatc ttgctagacg gtgatatttc atctaaacga  27600
ttggtaccag atatgttttg gaatcttcct atttaaagat aataatacat attacttgat  27660
attaccagca gagtctggga aaatacccag aatcaaacat attaatatat ctattggaaa  27720
acatgggatt attcacctta aatagcttga ataaaaatgt tatagcctta tgttaattca  27780
agttaggtct taatgccaat gtgccagtgg gttacaaaaa tcctttattt tcagaagatt  27840
ttggattttt gtattgaaga taaggaattt tggtataata ttatatttat aatttttcat  27900
agtctaactg tgatgatata ttatgcttga aaaatctcga ttatcaccaa aagctacctc  27960
caaaccaagg gaagagacac aaagagaggt aaaagtgaaa taaaccccta tcttgccaca  28020
cagattttcc aagcatttta tagcaaatat gcataatttt gtttatatca gtatgtcatt  28080
gcaaacatca ctcagagttt tgcttttata gtttttcttt gtttttccta aagttattaa  28140
ttgccttatt tttttaaatt tcgttaattt tctttgactt tttgttaaaa ccccatatct  28200
```

```
tccaacagca tctcagaata atttttccac aatatcattt tcataagttt atcttgagct  28260
aaaaataata acctttctct gcactggttt ccctctagtc attctgcaca gttgtcatat  28320
tgagatttcc tttactgtca tcctaggaat gctctcttag ctatttcctt gttttaggtt  28380
ctctgttttt ctccttctac ctttatttgc tcctttgttc tgttgtagtc aacgctgtct  28440
agtcacattg ctctaatctg aactggctgc tctccatgcc ttgtatacga taggagtcat  28500
cctggaatct ccctttatcc tcatggtgaa gatttttctt taccacttcc ctgtgtggat  28560
ttcctgtttt ctgttccccg tcttccttgt tttgggcttg tgccctcttt cttgttgtta  28620
acagtttccg gaaagagagt gatcgggatg caagattttt gagactcact ggtctgaaac  28680
tgcctttcct cttaaattta gttaagtatt tccctgggca tggaattcaa aggtggttat  28740
gacttttctt caggattgtg aatgtattta tatcctccca tcttacgttg ctattgagaa  28800
ttctgaagtt cttctgattc ctgattcttt gtatgtgtat tcctcattcc acaccttccc  28860
cagaatgcat gcagaatttc ttcctttcta ttttcttttc tctttttctg aaactcttat  28920
tattgggatc ttctgcctct tggattaggg ctctaatttt ccgacatttt ctctgctatt  28980
ttttactact ttatttttct cctctacttt ctgagagatt tcctcctctt gatcttccaa  29040
atcttgtact gaatctttta tttttgttaa catgttctta atttccaaga actctttttt  29100
cttgtcttcg gagtttcaac acttattgtt gttttgtgca tgtattattt tttcttctct  29160
ctctgaggct atttaggaaa ttttttattg aagctcctcc cccctgcttc cttcaagttg  29220
cttttatctg ctttttttatt tgctttttca tgcaataagt ttttctcaca tgtctggtaa  29280
ctcttgggga ttaccaaaaa ctcatagaaa attctgacca tgtgagtaac acttgccaat  29340
tttgagcttc atgatagaat gatctagctg gaccttttgc tgcggggaaa tcggaggtaa  29400
gtgtctttgg agacttcctc ttgggatggt caggtctccc aggtttcaag attcttctaa  29460
tttccttctt gaatcagttg cctaatttag gaaataaaaa tacaggatct ccaggtaaat  29520
ttgaagttca gataaacttt gttttttttg agagagtctc tttctgttgc caaggctgga  29580
gtgcagtggc atgatttccg ctcactgcaa cctctgcctc ccgggttcaa gcaattctcc  29640
tgcctcagcc tcccgagtag ctgggattac aggttcatgc caccactccc agctaatttt  29700
ttatattttt ggtacagatg gggtttcccc atgttggcca ggctggtctc gaactcctga  29760
cctcaagtga tccgcctgcc tcggcctccc aaagtgctgg gattacaggt gggagccact  29820
gctcccagcc cagataaaca ttttttttaa aaagtgtaag tatgtcccat tcaatattta  29880
agacatactt atactaaaaa attatttgtt gtgtatctga acttcacatt taactgggag  29940
tcttgtcctg tgttttacct ggcaacccta ttcctgaaag ataaatcctt gctgacagca  30000
ttagggatcc aagtgaggaa aatggccttg caaggtgtgg gtgggggtgg agggggaacg  30060
ttttcaacat tcagtgttat ttattcaggt aatccccttc aactatgtct cttaaacttt  30120
catctaaaga ccatccactt taccctctct ggaaacattc tccgttattt actggagtag  30180
gggaggatca gttatctggt tttttggaggg acttagtatc caaggcatcc ttcacaactt  30240
tctgctcatt tattttcctt tgactgccac aactttactc ctagctctag gtatagagca  30300
gtcccagtga ttaatttgag tgctttgcag tgtagatagg gattcttggc tctttctact  30360
gctagtttag gacctggttt tcttgggtct gctgaatcaa ttactacttt ttgtatcaac  30420
atcctagttt ttaaaactgt gttgtggtct atcctcctat tttcctacct ttgtgggtta  30480
aaaaaaatag tgttcttttg aaggattgta ggaaataaaa ttgaagcata tgttcattct  30540
acctttacct gaaagttact tctatcccat cttaatacac ttgcactgaa gtgattactt  30600
```

tccacctgca aagtggaaac aataagacca gttagcggct gctgctttag tcaagcaaga 30660
gatgaaggtg acttggaata tgctgtacag atggcattaa atgaatatgg atctcctttt 30720
ggaaactttt catctgcatg gtgagatgac tcacatactt agattttata ttcaaatagc 30780
tacgtactat agtggaagaa aaacttaatg gagaagtgtt tcagttcttg cgcagtatag 30840
aggatatgac ttttccagat tacaggggtt gcctctaggt caactctagg gctcattaca 30900
actctgaagc tcttttattg tgtgaaacag gcaataagat atgatttaca caggtgccta 30960
aattaaacct ttaaacacat tttaaattct tgataattaa aatcattagt aacttgagaa 31020
caatgaagat atagctgttc atggctatag gccaaggatc tgattgcttt tacagggcta 31080
atctttttga cagtgaattg caggaggcac tggggcttaa agccctttat ttttattatt 31140
agttgtatta attattcagt gataaactgg atgactctaa tgaagaagta acattatttt 31200
accaaataaa gtggcatagg catttttcta gatcaagaga gtatttcagt tgactttctc 31260
atgttttttt tttaagagca tctagcagtt tatttaatta ttttattcta ttttttatct 31320
ttaaaattta tcctagcttt attgtcatta acaaatgaaa attgtatatc tttacagtgt 31380
atgatgtgac gttttgatat gtgtacacac cgtgaaatga ttaaatcaag caaattcaca 31440
tatcccacat gactttctta tgacttactg gttttcatga cttccctaga tttgtaccct 31500
gttgaaatgt aaaacgacta atttaaacac ttgcggtgac tcagctgaaa cagcttctac 31560
caggtttgaa atgttctccc tcagtggcac tttcggaacc cagtatgtct ttcctgaggt 31620
gttgctgagt gaaaatcagc ttgcacctgg agaatttcag gtaagaatct tcgaatattg 31680
ccaattagtt tcatgtaaga ggaagcactt tttgatataa aaatctgctc aagtgcttac 31740
aaatatcata aaatttccat ttagaaaggt taagattatc cttggggatc atgaaggaca 31800
ttgagcaggc tgcatttctt gtctggaaat tcttaacata ataattactg tgtccttcag 31860
aataaaaaaa tatatatctt attttgggga ttatagggag tttaaagtct tccaagtaga 31920
aagaagattc aacgagagta gtttcagaac cagtgccatt ggagcccctt aggaccactg 31980
gggagtgatg gcctagggaa gttgaaagga gtccctctcg tcgagtgagt caaggctctg 32040
tgtgatggta gaaggaaaag agacaaggaa aagctgaaga agagagaatt tgacagtggc 32100
ggatgttagc aaaaaagcaa aaacttttta aagttcagaa ataatccctt gcttcacatg 32160
tgctctgccc agccacattc tttcgctgac ttcctgcaag ttctcctccc actccccgtt 32220
cctggtagaa accactgctg gggtgtggga ggacaatgga atggtgagga ggttgtggtg 32280
agcaagagac aggagatgac agatgctcag ttcaaatccc tgttagtcaa ttgcttcggg 32340
ccattgtggg gagtctttat cttgtctgag aggactaggt ttctcttctg tatactgcca 32400
aatccactgg tttgtgttta ttaactctta cggcgcttcc acaggtaagt aaattagaag 32460
acattgatta cgggcatctc actaataaat gaatcagtgc cagtttcata gctccaattt 32520
ttcttgtact tggcaacatt tcaaattttt ctgatagaat ggaatttggc cagtattttt 32580
gtttcttcat tctgttatag taaattttaa aagtgattta tgggattgta aaacttgaag 32640
gtagcctttg cctacttttt tgttttaatc aggtgtcaac tgacggacgc ttgtttagtc 32700
tgaagccaac atccggacct gtcttaacag taactctgtt tgggaggttg tatgagaagg 32760
actgggcatc aaatgcttca tcaggcctca cagcacaagc aagaataata atgctaatag 32820
ttatagcacc tattgtatgc tcattaagtt ggtagaatat tgactttttc tcttttttat 32880
ttgggataat ttaaaaaatg atggatgaga aaagaaagat tggtccgggt taatattatc 32940

```
ctctagtata agtgaattac tagtttctct ttatttagac aaacacacac acaccagata  33000
atataaactt aataaattat ctgttaatgt agattttatt taaaaaacta tatttgaaca  33060
ttggtctttc ttggacgtga gctaattata tcaaataagt atcacaaatc ttttacgcag  33120
aagaaataaa aactacgggt agaaaacata agaactatca taaaatttac ttacaaggag  33180
gctgctcttg ttaccacttt tattatatta cgtatcactt attcagctct gctgaaaatt  33240
tccaatgact ttgtttgttt gctctttttg ttttttacct aaacaataca ttttgattct  33300
cttgtgggtt gataatgtct ccccaaaatt tacatgttga agcacctcag aatgtgactg  33360
tatttggaga cagggtcttt aaagaggtaa aataaggtca ttaggataga ccctaattca  33420
atatgactga tgatcataaa agaagaggcg agtagggcac aacaggcaca aagggagacc  33480
ataaggagac acagaggaag gacaactctt tacaagctaa gaagagaggg cctcagaaga  33540
aaccaaccct gccaacacct tgatcttgga cttccagcct ccaaaactat gagaaataaa  33600
tttctattgt ttaagtcacc cagtccatgg tactttgtta ggcagccctg gcaaatgaat  33660
caaagaccca ttcctgttcc tctccccacc actactgttt tctactgtaa tctgaagctt  33720
caacaaaagg cttacctggt aagaatattc agctggtctg ggtcctcaag actccaatag  33780
acactcttag agaaggattg ctgatggatt gatagtgaaa ccattagatc attgaattcc  33840
tctggaatta gaaaaccaga gagtcccatt ttaagaaatt agatatttaa tatagcattg  33900
tgtgttctat tttagtaaca gcagaatctc ttgacattac acaactcagt gaaacaacat  33960
catttaagcc aaaatatctc ccaactgact gatagactct gagcactaat atcatagtgc  34020
tgtgatgatg gacaattaca tagtaccgat aacagccatg cactgtgcaa agcatgccct  34080
tctgcacagg agagcaaggc acttgcagta gtgatctatg ccagcaaaac atcattttga  34140
gacaaacatt tttgtggcag atgtttttcc taaaaagtac tatatcatcc aagaaatatt  34200
tgagtaaaat cccttgttct tttgggtgac attaactgac atttgctttt tttcaagacc  34260
taatagaaaa taagaaagcc cataatgtat ttagaaacag gaatcctcag agcaattctc  34320
tgtattctca tataatttca atgtaaaaca gaaaacatat tgatgtgttg gtgataggct  34380
tgaattatta aaaacttcaa aaacatccta agtgtttctt ttttgctcaa cgttgtcaac  34440
tatagtaggt ctcccttgtg gtgtaatgaa ttgcccccaa actattatct taaaacaaca  34500
aacatttatt atcttatagc atttctgagg gtcaggatct gggactggct tagtggagtt  34560
gttctggatc agggcctttg gaaagttgta gttaacttgt ccccagggct gccatcatct  34620
caaggctcgg gtggggctgg agaaaatctg cttctcagct cactcacggc ggttgccagg  34680
cctccattct ttaggatgct agaaaaactt tcataaaatg tcatctggct tctcctagag  34740
caatgatact gagagagaaa gcacatgaga gaaagagcga gggaacttgg atgtaagcca  34800
cagtctttga aaacctaatc acagaagtga catctcttct tccacatgat gttggtcaca  34860
tggaccaaca atggcacaac gtggacagaa tcaaacagag ttgagaatat caggaggtgg  34920
ggcttcatgg gggccatttt ggatgctatc atagtgaata tatgtattta tatttatatc  34980
tgtatatatt gcaatgtaat ttaaaaaata ggattgtttt ccttttcttt ttgctatatg  35040
tgatatgtat ttcaaaatac actcccaata gttacgtctg aaaagcacta cactaaaaaa  35100
ctttctatac attgaataat taaattaaat aatctaataa tctctacttt tggtccatag  35160
taaatttaag ttaactgttt gccttaacta cagtttgtgg caaaaccatc tccttttaat  35220
atacacaagg gacttttttt ttttttttg agacggagtt ttgctcttgt tgcccaggct  35280
ggaatgcgat ggtgtgatct cagctcactg caacctctgt ctcctgggtt taagcgattc  35340
```

```
tcctgccaga gcctcctgtg tagctgggat tacaggctgg gattacaggc atgcgccacc  35400

atgcctgcct aattttgtat ttttagtaga gatggggttt ctccatgttg gtcaggttgg  35460

tctcgaaacc cgagctcagg tgatccaccc gtctaggcct cccaaagtgc tgggattaca  35520

ggcgtgagcc accatgcccg gcccgtggga cttttgcatt catttttcag aagcttactt  35580

tgtaggggaa catacattaa aaggtaacaa aataaacagc ataagttcca gaattattaa  35640

ttcatgaagt gcaaccacta ggaaaagggg tcttaaaaac atcaccctct ttactggatt  35700

ctttgaagaa accaagattt ttttcctaat aatctgtttt atacacaata tataccaaaa  35760

atatataaat atataagtat ataacaaaag tgaaagaaac tgactcttaa tcacaatgtt  35820

ctgaatagca agaggaatac taaaaaagtc aactagaaag tcatgtcaac gtcaaaatct  35880

gttctgaaac acatcacttt gattttatac tgaaagccga tacctcgaat ttcctctgct  35940

tcgctgtcct gtggttgtac tgggcatgtt ccaaatgtat cacttttatt tttatttcaa  36000

taatttcaag tgttatttta gattcaggag gcccatgtgc aggtttgtta catgggtata  36060

ttcagtaatg ctgaggtttg gggtacaaat gatcctgtca cccaggtgat aagcataata  36120

cccaaaaggt agttttcagc cctttccccc tccctgtttc ccagctgtag tagccgctag  36180

tgtctgttgt taccatcttt atatctatgt gtaccaaatg tttagcttcc atttaaaagt  36240

gagaatatgc agtatttggt tttctgttcc tgccttaact tgcttaggat aatggcctcc  36300

agctgcatcc atgttgctgc aaaagacatg attttgttct tttttatggc tctgtggtat  36360

tctatggtg                                                         36369
```

<210> SEQ ID NO 18
<211> LENGTH: 18023
<212> TYPE: DNA
<213> ORGANISM: Homo sapiens

<400> SEQUENCE: 18

```
atactaacag tctattatac aatctgctaa aaattcataa aaatatctat ccctttacat     60

tttccacaaa agggcttgac catttttcct gaattatttt tagttttctg ctctatagag    120

ataagaaaag ttattccttt aatagaaact tctattcaaa gcagaaaata tgagcagatc    180

ttatttatag cccctaggcc ccattcttaa caaaacattt atctcagtaa gaaggaaagc    240

acagaataaa ctttgtttaa tcgtacctac tcttctatgc tgtctaaaag catttccgtg    300

acttttacca aagggctgga taaaaataaa acaaatcctt tatttggcag gattgggcct    360

ggggaaggga gaatatgaat gtcctaagaa ggcatctgag atcacatcct gtatttgttg    420

ttattattgt tttttttttt tttttttttt ttgagacgga gtttcgctct gtcgcccagc    480

ctggagcgca atggtgtgat ctcagctcac tgcagcctct gcctcctggg ttccagcgat    540

tctcctgcct cagcctcccg agtagctggg attacaggcg cccaccacca cgaccagcta    600

ctttttgtgt ttttggtaga gatggggggt tccactatgt tggccaggct ggtcttgaac    660

tcctgacctc aggtgatctg cctgcctcgg cctcccaaag tgctaggatt acaggcatga    720

gccactgcac ctggcctgtt agcattgttt ttaaactcat tgttgttatt tgctgctaac    780

aaaaatgtaa gttacatctt ctccttatta caacacagat gatctttatc accaatcctg    840

gactcttccc cttccctggc atcttcctcc aaagcagggg gtggggaggg aggaaaaaga    900

aggaggagaa ggagtaggag gagaaggaga agtaggggga ggatggggag ggaagggtga    960

aagagagaaa gaaggaaaga agcggagtat cctgaggcct ggggccccct gagctgagat   1020
```

```
tcctcctctg gcctaggtgc ctcggggtat tgttgctgta ggcactaact atacagcagt   1080
gaacaaacca gacacaaaat cctgcttttc tggagcacat gttttcagtc cttaatagca   1140
ataagtaagt cagagtgtag atttgggtaa attttgttat caatattgtc ctgtgttaca   1200
ttttcttagt agtaagtatt taatattttc ccccccgtct aaaaataaac acaatgtaag   1260
tgactcaaca gaaccaaaaa aattgttgtc aatttttaaa tttaataaat gagatatttg   1320
ttgggatgtg atttttttac acgagagtta gttatgagtt tctattaaca aaagctggaa   1380
ttgttctata tttgaattcg ggtgtctttt ggaaattcaa tattaaatct tagtactaat   1440
agtacatgct gttcaatccc tgtaatactt tctgattgtc ttaaatggac tgcaactttt   1500
ctttctttaa aagtggtcag atatattgcg ttcttaagat tataaagtag gccaagtgca   1560
gtggctcacg cctgtaatcc cagcactttg agaggctgag gtggatggat cacaagatca   1620
ggagtttgag accagcctgg ccaatattgt gaaaccccat ctctactaaa aatacaaaaa   1680
ttagctggac gtggtggcgc gcacctgtag tcctagctgt ttcagaggct gaagaaggac   1740
aatcgcttga acctgggagg tggaagttgt agtgagctga gcttgcgcca ctgcattcca   1800
gcctgggtga cagagcaaac tccgcctcaa aaaaaaaaaa aaaaaaaaaa aagaagaaga   1860
agaagaagaa gaagaagaag aagaagaaga aaaaagatga taaagtaaaa ggccagtaac   1920
tggcagccac atgttatgca aacattctcc cctctgtaaa tactacatga atgttatttt   1980
tgctttcaga aatcactaaa ccttggccat ggtcacttcc tcttttccaa tctctgtggc   2040
agtttttgcc ctaataaccc tgcaggttgg tactcaggac agttttatag ctgcagtgta   2100
tgaacatgct gtcattttgc caaataaaac agaaacacca gtttctcagg aggatgcctt   2160
gaatctcatg aacgagaata tagacattct ggagacagcg atcaagcagg cagctgagca   2220
ggtattctct tatttctgtt aatcataatg tacacgaggg gcatgggagc tggtggaaga   2280
cgagagagct gaattgtctg tgttgtacat ggaaaaaatca tttttatttt gcttgttttg   2340
aacagggtgc tcgaatcatt gtgactccag aagatgcact ttatggatgg aaatttacca   2400
gggaaactgt tttcccttat ctggaggata tcccagaccc tcaggtgaac tggattccgt   2460
gtcaagaccc ccacaggtat tttaactatc ttagtctttt gtgcaaaagt aactctctaa   2520
aatgcgcacg ttcaccaaag caaaatgatt gctcttgaat taccatatat gtggtatatg   2580
ttatggttat atttatctca acatttgtca gattttaaaa aattgtactt agatactatt   2640
taacaatctt ttgtgattga aaatctttat taaattttga gaaaatgtgt aaatagggta   2700
ttcctgcaag aaaaactaag ggaagagatc tcatagatac aagtagtaac ttaatttctg   2760
aagtagacag tggattgtgt taggaataca ttccaaagcc tctgctgaag ggacaccctt   2820
tcaatgttat agagtctctc cattccagag ttgcttctta ggcagaaaga cttcaccatg   2880
tattttcaag tgaatcataa gaccttatgc tttgaaactg cattttccta ggctcacaaa   2940
tctaattttc ctgggaaaag gttatctaga aaccttctaa tatatattaa aaatctgggt   3000
cctactgtca tcctggaggt gtcaacgtgg cagttgcatg gacaagtctg gcatgaaaag   3060
acaaaattat atctggagat agaaaatcaa atgtcagcat atagatggtg ttaaacacca   3120
tgatgagttc acctgtggag tgagttagag aagagtttag gtataaggct tgagcactag   3180
gaaattctag tgtttagact cggaagaaaa cgaggaatca gcagaagagt cgaagaagag   3240
caaccaataa ataggaaaat gagagggtgg gtccaataga gaagtgaggt gtttccagaa   3300
ggaggtgtaa ttaactgtgc caactgctgt tgaaaagtta agatgagatc aggtaaaatg   3360
tgggggtcac tgctggcatt agtaagagtt tgggtgatag agatacaagt tggagtgctc   3420
```

```
tgaaagggaa tgggagagga ggaactggca acagcaagag ggactgatct tttgaggagt   3480

tttgctttaa gagagagatg aggattaaag caatatttgg aagggcatgt ttggaaaggt   3540

caaaagaggt tttaatttta ttttttaaag atgggaggta ctagaggata tttcattgct   3600

gatgggatgt ttcagtagag aggagaccct tgatgaggca ggagaccgaa taatgaattt   3660

ctggagcaat agataccgtg tgggaagcat tcatcaagtg tataatcatc tgtggctttt   3720

aaagtatgat atttttaggc atagtttttg tattaactta agttccactt aagtggttac   3780

agttgctatc gtttccatat aaagtgacta aaatattttt ttaaaattga aatttcttaa   3840

ttataatttg gtttagattt ggtcacacac cagtacaagc aagactcagc tgcctggcca   3900

aggacaactc tatctatgtc ttggcaaatt tgggggacaa aaagccatgt aattcccgtg   3960

actccacatg tcctcctaat ggctactttc aatacaatac caatgtggtg tataatacag   4020

aaggaaaact cgtggcacgt taccataagg taagagagag tgacggacgt gtaaaatgga   4080

gcgtgttgtg agtggtcaat gctgggttta ggagtttgaa tttcattccc tatatgatac   4140

aatattacta gagggttttt ttgttttgtt ttgtttttttg tttttgaaa gtgggcaata   4200

aagaaaatga cacttttggc tgggcgtgga ggcttatgcc tgtaagccca gcactttggg   4260

aggctgaggc aggtggatca cttgaggcca ggaatttgag accagtctgg ccaacattgt   4320

gaaaccccgt ctctactaaa aaatacaaaa attagcgggg cgtgatggca catgcctgta   4380

gtcccagcta tgtgggagct gaagcaggag acttgcttga acccaggagg tggaggctgc   4440

agtgagccga gattgtgtca ctgcactcca gcctgggtga cagagggaga ctctcaaaaa   4500

aaaaaaaaga aaaaaaagaa aaagaaaaaa gaaaatgaca cgttgtaaaa aactactcag   4560

aaaaacatgt aggcagagaa ctgttaaaaa aaaaaaaaag tagcatgatg gtccaggatt   4620

gagataaact ttttgcacat ataaaacaaa taattttaac ataaaaaaag atactaaggt   4680

gactataatc tgggcactgt ttcaataatt ttatattttt ttagagacag ggtctcactg   4740

ttgcccaggc tggagtgcag tggagccatc atggctcact gttaacctca aactcctggg   4800

ctctagtgat cctcctgcct cagcctccca agtagctgag actgtaggca tgtgccacca   4860

tgctaatttt taaatatttt tttggaaaca gagtctcact acattgccca ggctgtcttt   4920

gaactcttca cctcaagcag tcctcccacc ttggcctccc aaaatgctga gattagaggc   4980

atgagccact gagcacagcc ataatctaaa tactatttaa tattgaaatg gtagaaagat   5040

gtttcaaaat tgtatgaatc agctttgcat aagttaattt gctatcaaac cacaaaatac   5100

cttattttct acaccagcta atttaattac catcttatag atttaagatc aaaccataaa   5160

atgtttactt taaattctga attgaaaaaa ggaatcaaat aacctttaag tcataatttt   5220

atactaaact aggtagagaa agaagcctgg ccttttaaat ggatatgtgt gatgtacagg   5280

cagtatgaat gtcccttctc cacacccaga tattttgtaa gcatcttaaa ctgtagcctc   5340

agaatctttg gagtggagaa attatctcct ggcagtctca gttaaaatat aaatattaat   5400

taagaggagg gatgttaaac caatggtttt caaatgattt cgatcatgga cccctattgg   5460

aaaaaatcgt taacataagt cctcaatata tgtatttttg tgtgtgtatt tataaagtgc   5520

aacaatttca aaatgctttc ttcataattt tgtggatttt gacagcttct tttcatatat   5580

atcactgcac ttcactttct tcttaaaatg tgtctcatag taaaaataga aaggtcagtg   5640

cttccatttt cttgcttggg agattgtttg cattatttgt attatctttc aatgcagttt   5700

atttgcagta atcatttgaa gctattctgc cattctgtaa atatgcagga tggcacagtg   5760
```

```
cactgaatgt ggacaaacta gcaaggaacc tgcagtcacc ctgtctaagt tgaaaggctc   5820
tcactcttcc ctgagggtac ctcagggacc gtttgtaacc catgacctct gacatatgtg   5880
aacctaatga gaataccttt gtcgatcaat tcctttttt tttttttttt ttttttttt   5940
aggcagagtc tggctctgtc atcccggctg gagtgcaatg gcacgatctc agctcactgc   6000
aacctctgac tcccaggttc aacccattct cctgcctcag cctcctgagt agctgggatt   6060
acaggtgcat accaccacac ccggctaatt tttggatttt ttagtagaga tggggtttct   6120
ccatgttggc caggctggtc ttgagctcct ggcctcaagt tatctgcctg ccttggcctc   6180
ccaaagtgct tggattacag gcatgagcca ccttgcctgg cctgtcaatt cttaaaatag   6240
tagtaaagcc caatttcttt tctatttttt agatattttt tctacactgc agaccatttt   6300
attaactgtt gattccattt attatattag actaagtttt tttttagttt acctagaagg   6360
aatcggggaa ttaaatacat ttctatggta attttgaaag gtgggcaaga gtcactgaga   6420
ttactttgga tgggacacta aagagagaga tgacatctct cacctgactt acaggtattt   6480
attatgcatc tattaatatt acgtttctag gcaccaagga ttcaaagaag aataatgcat   6540
gtttttaac ttttaagaag cttatagggc caggtgctgt ggttcattcc tgtaatccca   6600
gcactttggg aggcccaggt gggtggatca tgaggtcagg agattgagat catcctggct   6660
gacacggtga aaccccgact ctactaaaaa tacgaaaaaa ttagccgggc atagtggcac   6720
gtgcctgtaa tcccagctac tcgcttgaac tcaggaggtg gagattgcag tgagccgaaa   6780
tcatgccact gcactccagc ctgggtgata gagcgaggct ccgtctcaga aaaataaaat   6840
taaattaaat ttaaaaaaag cttacggact ttggggttta tgggggggt atttggctct   6900
taactgagag agagggaaag agagagaagg gagagagagg agatgagaga tgctatggac   6960
gtatgttaca tattcctcca cattttcctt agaaatttac ttccaattgc cagatttatc   7020
cgcttcctag gagattccct gcagttgacc atagccaaat ctgttaccaa cttagagggt   7080
ttttatgagt catttcttca acaaataagg ttttactggt tttctcctat ccatttgttg   7140
tagtaccacc tgtactctga gcctcagttt aatgtccctg aaaagccgga gttggtgact   7200
ttcaacaccg catttggaag gtttggcatt ttcacgtgct ttgatatatt cttctatgat   7260
cctggtgtta ccctggtgaa agatttccat gtggacacca tactgtttcc cacagcttgg   7320
atgaacgttt tgcccctttt gacagctatt gaattccatt cagcttgggc aatgggaatg   7380
ggagttaatc ttcttgtggc caacacacat catgtcagcc taaatatgac aggtaattca   7440
tgaccaggtt aggtttcatc ttatattttt aagtgcagag aaatgaatgc ctcagttatg   7500
acttgtatta attttttgct tattggaaat tcttactgtg tttgtcatag tttcacaata   7560
gaaaaaaaaa gctagcactt gattataagc tatggttata ctaagacctt tatgtgtatt   7620
attcatttaa ttattacaat aattatatga gatagatagt gtcatcccaa ttttgcagat   7680
gagaaaattg acatacagag agtgcaagta atttgccaaa tgctacccag ctactacttt   7740
cctcagtggc catggaagcc tctatatctt gccctttgtc tcctcctatg gctgcatggc   7800
atatcctcgt gacatggctg ctgtcttcct ctagagcaat taatgagagg ggacaagaga   7860
gaaaaggaaa gaagccacat tgctatttat gactagttac ccaccatcac ttctgccatg   7920
ttctattcat tggaagtgag tcactaagtc cagcccctct tcaaggggaa aggaattaga   7980
tcctcccacc agaaagaaga attttaagga atttttggat atatttgaaa accaccacaa   8040
tgaggaatag gggagaattt ttattccctt tccccacctt tcaggaactc ctgactacaa   8100
agatttttgt agttggttta attttccata atgctaataa ataatgctat tatatttaag   8160
```

```
gtttaattga aatgagacca aggaatgttt attttaatct cttccattag agaatagaag   8220
tagttaggtg ttcagtgcaa ttagaagcat gtatcctctc tcatcgtgac taatatggtg   8280
gcgtgatcac atgcccaatt ctgatgggga aattggcagt tttggttttt ttgtgtgtgg   8340
tgttgttttt agaagacttg tctttcattc acaggaagtg gtatttatgc accaaatggt   8400
cccaaagtgt atcattatga catgaagaca gagttgggaa aacttctcct ttcagaggtg   8460
gattcacatc ccctatcctc gcttgcctac ccaacagctg ttaattggaa tgcctacgcc   8520
accaccatca aaccatttcc agtacagaaa aacactttca ggggatttat ttccagggat   8580
gggttcaact tcacagaact ttttgaaaat gcaggaaacc ttacagtctg tcaaaaggag   8640
ctttgctgtc atttaagcta cagaatgtta caaaaagaag agaatgaagt atacgttcta   8700
ggagctttta caggattaca tggccgaagg agaagagagt actggcaggt aatttcagtt   8760
caaatgaaag ggcattcaag tgaaaggtaa attccaggtt aactttttat atttgttcca   8820
gaaaaccagg tgcttttcct tggcttgact ccatgcattg atggcaacac acacacacac   8880
aacacacaca cacacacgtg catttatgca cgtacataca ctgggataaa atatttacaa   8940
tgggaattaa gtataatctt attgcttgct ttaagcatat ttaaaaaatt attaacctaa   9000
ccatgatgag tttcgatttg actaataaac cagcctactg tggagaacat caagaagact   9060
tccttaagtg ggtttgccaa catatctaaa ttataaacag tcttattttc acttgcaaaa   9120
ctaacagtaa atagagatac tacttttatt ttagtttctc ttctaatcag atgtcccggg   9180
ttttgtatag ctttcttttt cttttctttt ctttttcttt tttttttttt tgagacaatt   9240
tcactctgtc accctggcta gagtgcagta gcatgatctc ggctcactac aacctctgcc   9300
tcccaggttc aagcgattct catgcctcag cctcctgagt agctgggact acaggcatgt   9360
gccaccacac ctggaaaaat atatatatat atatacacat atacaaaata tttttagtag   9420
agacagggtt tcaccatgtt ggccaggctg gtctccaact cctcacctct gctgatccga   9480
ctgcctcggc ctcccaaatt gctgggataa catgtgtgaa ccaccacacc tggccttgta   9540
ttgctttcaa atgacaaatt ttaaagatga aactttttat agaatgttgg ctctgaattt   9600
gtattttcct attatactcc atgtcccact gccttcttct aaagaaaagg attgggaaga   9660
gaggtgagat taaagggtgg aaaaaatttt aatatccttt cagcttcagt actcttcagt   9720
actattgttg cccaaagatc tccacttcat tgagctcgat gccatcatct gacataccaa   9780
actaatggtt taactctaat tctaaactga cttctttctc ttaatccgct tgttatttag   9840
gaagtgggtt gattctcaag tcactggcca tttttaataa agcagttaat tataagacac   9900
atgatccaaa tccctttca gagaaagata atgtttgctt cgctgtagtt aaaaactaag   9960
gcaacatttc tggtatgagt aacttcaatg taaggcattg cgttttatct gcgtttgttc  10020
cacataggtc tgcacaatgc tgaagtgcaa aactactaat ttgacaactt gtggacggcc  10080
agtagaaact gcttctacaa gatttgaaat gttctccctc agtggcacat ttggaacaga  10140
gtatgttttt cctgaagtgc tacttaccga aattcatctg tcacctggaa aatttgaggt  10200
aagaggactt ttataagagt attttcattt tatatgttct ctgaagtcaa gtaaaacaag  10260
ctatagccac tctgccagtt aacttctgct gtgtaacaaa tttcctcaaa accatttctt  10320
tagccctggt tctgtgggtt ggcaatttga acttggggta ggtaggctgt ttttctggtc  10380
tgagataggc tcagttgacg ttggctgggc tcattgtgtc tgccattggc tagtgggttg  10440
attaggactg accagtttgt gattgccttg tcctggacag ctgggattat taaggccatc  10500
```

-continued

```
tctccccgtg gtctctcatc tttcagcaaa cctgagcttg ttcacatgtt agctgaatga  10560
gtccaggagc atcaagagaa aaacaaatct ttgcaagttc tttgcaaatc tctgcttgca  10620
ccgtgtttgc aaatgttgca tcaacacagg aagttacatg agcagtggtg attcaaatgg  10680
tagagaaatg aagaactcag acctctcaat gggaagagct ataaaatcac acggcaaaag  10740
gacatgggtc aaggagggga aaatattgtg atcatttttt caatttataa caactaatta  10800
taaaatgatg atacttcatt ggaagaacat aataaagaac atacctagaa ctgtgagtct  10860
gagataccat tcattgaaga atgtttgttt atagattttt aatttccttt tgtcactagt  10920
gaagacaaac agaaaatcag atgtttattt cacatttttt tttaaacaga gtcttgctct  10980
gtcacccagg ttagagtgca gtggcatgat catagctcac tgaagcctca aactcctggg  11040
ctcaagcaat cctcctgcct cagcctcctg agtagctagg atttaaaggc atgtgccact  11100
gcacccagca tttgttcata aattacagtg gctgtagcta attaattcac aaattaagct  11160
ggcttcaaat tagaattatg actctgcagg cttatatctg ctaatataca acacttgcac  11220
acatgcacat acacgcatac atacacatat tccagtggtt tgaatattaa tgtcttctct  11280
gaattgtggc aaacagtggc agggtttcag taactagggt gaaatcattg catattctat  11340
aaaatagggt ccaagttaat tcaatcaagg catcaagtaa ggaagtcttt aaaattgcag  11400
attgcttatg gtcatgtatc tgtatctgct gtgttatcag agtggaatat atcatactta  11460
taaaaatgct taattctatg aaaccaacaa tttaacatac agtgtaacct taaggccata  11520
aaatccaaag atcaggaatg ctttgctgcc atagaacctg tttaggcaga atctcatgag  11580
caaattgagg ctggaataaa agctgaagtg ccaactacag aaaatcatga ttaaatctac  11640
agcaaggagt ctggggctaa aatccagtag ctaaaaggtg gctggactga cataaatatc  11700
tatctgagat cacttcaagg aagtgagaga gagaaatcag ggtcaccaag gtaaacttag  11760
gaggacatag ggtctagcca tattgatgca ttatattctg taagcctgaa gatttaaact  11820
gagcacacaa tctaatttc tcgtactact ttgccacttt ttccatgtct tgtactcata  11880
gaaatctatc tctttgagga attgtcccat agtaggactg aacatttacc tgatgaaact  11940
acttcatcca tgggagaagg acaaaaaaat gctagagttt tccaaactag gttaaaggtc  12000
caaagccaga aataccattt cactcttact ctgaaccaca taagtgtttg aaggtggatg  12060
gtgatagtgc atgaagagtt ggagaacgta aataatttat tccattacta cttcctttct  12120
ttgttttaaa aatttcatcc caaatgtctt caggcagtta agaagagtta gagaatgata  12180
caagagaata catgtttaaa tgcttaactc catagtattt gtacatctca actcttaaac  12240
atttttttaa attattttta attattatta ttatttgaga tggcgtctcg ctgtgttgcc  12300
cagactggag tgcagtggtg caatctcagc tcactgcaaa ctctgcctct tgggttcaag  12360
cgattctcct gcctcagcct cataagtagc tgggactaca ggtgcatgcc accacgccca  12420
gctactttt gtatttttag tggagatggg gtttcaccat attggccagg ctggtctcga  12480
actcctaaca tctagtgatc tgccacctcg acctcccaaa gttctggaat tacaggcatg  12540
agccaccatg cctggccttg tttttaattt ttgtgggtac atagtaggtg tatatattta  12600
tgggttacag gagatatttt gatacagaca tgcaatgtgt aataatcaca ttagggtaaa  12660
tatggtatca gtaggtctca acttttaatg attctgtgaa cttgtcatgc tgtatcccat  12720
ctctggttcc ttcttagatg gaaggaagga gggaaggggg catagcacct accgtttaaa  12780
ttgggcacct gtaatcatta tttggatctt gtcttacctg ctccagacca tttgcagaag  12840
aaggaaatga gatatagatt gtattacacc aaaaaagata tgaaagagcc atgtgacagc  12900
```

tggcagggag ggtctttgga attgtagtcc cttggaggga gcatcatgat gagggtgagg 12960
caggtcttta ttttgtaagt gtagattctc tgtggcatga ctttcactga agttcatcag 13020
gttctaagga acagatacta atcaaatttg caagatagat aagcgagaac accaacttgt 13080
tattttaaaa aataggttcc cttagctggg aacaatgaac tgtatgtcaa ggagactctt 13140
cattggcaaa tcctctcaaa agtacaaatg atagatcagt ttgttttgtg agtgcagaat 13200
taaaacaaaa ggagttgggc attcttggaa aagatttcca agaacccacg gaagcctgag 13260
gcaatgtgat tcttctcttt agggctggtg atctgaagac catgtaggat caaggtgccc 13320
actttcctca aaaagagcca aaaaaaaagt ccaataaccc attcttggtt tttttagtgc 13380
ttcttttctc tagagacctt gcagggcatg gcccttctgt gaatatgttg tttctagaaa 13440
cagcagtcat aatattgaag atgacaaatg ttttacatca gtcatgctca ttatggcttc 13500
ttgagtagct tctcagttct gttgatggat gcacactctc tccatagata tttacacgtt 13560
atcttagagg atcactattg cagagatttc aacacacttg ttgtgtatcc tcaacccccca 13620
ccaccacttt agttttatgt taaaagggtg gtgttactca ccatgcccac aaatgtggaa 13680
acatcttgct ttagcacctt aggcaactct ggtgtattgt cagaagcact ggcagagtct 13740
gttctctgta actaactagt tagataacct tgggaaagtc acttaacctc tgaatttcct 13800
actcatagaa gagaatattt tcctcactga tttggtgagg atcaaatatg ataatgcatg 13860
tgaagacact ttgtgaatgg tgaagtacaa tcattatctt ctaggatatt tagtcatttt 13920
ctcctcccag ttgtaaagca tctgttttcc taattttcaa tttcttctcc actccaacta 13980
atttcccaat tttcaatttc ttctccattc caactccatt tccacaacta atgggttcat 14040
tttcttttat tcttgttctg tttattgact gtctatgcat gtttccttct gttcttgttc 14100
aattgctttg tacatattcc tctcttatga aaactccact gtggcttcag gctagatcta 14160
gtcattaatg cctttcacag tctgatctcc accttcctct gatcatattc cttcttctct 14220
tcttcactaa tcttcagcgc tagccagtgg tgtgatgtaa ctttaaacaa ttccttctct 14280
gaggtagaaa acaaaaagcc ctgacttatg gaatttgcca gttttcattg tgtcaatatt 14340
cccgccatga tcccaccagc ttcaagaatg gatctgttgg cagagtttga tagctcacgc 14400
ctgtaatccc agcactttgg gaggctgagt tgggaggacc atttgaggcc aggagttcga 14460
gaacagcctg ggcaacatgg tgaagccctg tctctactaa aaatacaaaa attagctggg 14520
cttggtggca cgcccctgta atcccagcta ctggggagct tgaggcagga gaatcacttg 14580
aacccagcag gcggaggttg cagtgagcca agatcatgcc actgcactcc agcctgggtg 14640
acagagcgag actccatctc aaaaaagggg gaaaaaaaga atggctgtgt ttaacagcca 14700
gctgtccaat ttcctggaaa tttaacaatc tgttctcatg agcctgtgca ccactagctc 14760
cagcacacca ctggttttaa ccaatctaga atgagaactc acattgcctt gatctgtcac 14820
acacacttct gtctcagaat gagcctttgc tggttcaatg tccacttccc acaatgtctt 14880
ccaccataca gcccttgaaa gaaattccta acagcttgag tttttggcag cttgtgtccc 14940
actccgtgaa acagaccagt tcagtttttt ttttctcaga cctcctagca cttacctgtt 15000
ctcttctctg atacactgat aaactgattt ctctctttat gtttagaatc cgctccattt 15060
caccattagc tctttagctt cttgagggaa ggatgtgatg tataactctc tggttcctga 15120
ttgtcttgca cataatcgaa ctcaatgaat tgctgctgct gattttgact ttccattaat 15180
ggttacattt gattgttgaa actaaaatct tgggccctct tgaattgctc tagtcttcat 15240

```
tatgtagtaa atggctgtcc cctgcctggc ctacttgctg catcctccta aatcagaaat  15300
gatttgacta tacattatat ctaggatggt ttcaaaatga ttaatttgct tttaacttct  15360
atgttaagaa agctgactgt acttttccca ccttttcttt aggtgctgaa agatgggcgt  15420
ttggtaaaca agaatggatc atctgggcct atactaacag tgtcactctt tgggaggtgg  15480
tacacaaagg actcacttta cagctcatgt gggaccagca attcagcaat aacttacctg  15540
ctaatattca tattattaat gatcatagct ttgcaaaata ttgtaatgtt atagggcgtc  15600
tctttatcac tcagcttctg catcatatgc ttggctgaat gtgtttatcg gcttcccaag  15660
tttactaaga aactttgaag ggctatttca gtagtataga ccagtgagtc ctaaatattt  15720
tttctcatca ataattattt tttaagtatt atgataatgt tgtccatttt tttggctact  15780
ctgaaatgtt gcagtgtgga acaatggaaa gagcctgggt gtttgggtca gataaatgaa  15840
gatcaaactc cagctccagc ctcatttgct tgagactttg tgtgtatggg ggacttgtat  15900
gtatgggagt gaggagtttc agggccattg caaacatagc tgtgcccttg aagagaatag  15960
taatgatggg aatttagagg tttatgactg aattcccttt gacattaaag actatttgaa  16020
ttcacctagt tttctgtgct aatgtttatc aggagattta ctttccaatc aaaaggcaat  16080
gtcgacattt atttctacag tgaacgtagt tttgagtgct agaagaattg atggctattc  16140
caagttcata tcaaaggaga cctgacccag ggcactcata gccccagctg tcccacctta  16200
aggctatggc gtaatttaac aggcagaaat ctcataacac aaagaccatg acagttaaaa  16260
gttacactat tttcagcatt tggttgactt tttacaaaat acacatattc catgctactt  16320
gaagtaaact agtatatttg ttattgatca tttaattcag atactcttaa aattaaagaa  16380
ctgattttga attttcagat ttattttctg atttttatct cccaaagtat ttttaagttc  16440
aatactttta cataaaaaaa cacaattgaa gcatttatct tttgttttta catattgtca  16500
taaacctact tatggatttg attttaaaat tctactaaaa tacactagaa aagtaagatt  16560
ccttttataa tctcgtggtt agtattaaga gaagaaatat ggaagttaag ccacactttg  16620
tatttaattt tgagaagagc atacatattc cctatgttca gcattgggac atcaaagatg  16680
gcaattttaa agctgtaatg aacgtgcatt tgtgtatata gtccaaatca tataatcatc  16740
aaagttttat gctctttttt ctttttcttt ttcttttttt tttttgaga cagagtctca  16800
ctctgtcacc caagctggag tgcaatggtg ggagttcagc tcattgcaac ctccgcctcc  16860
tgggttcaag tgcttctcct gcctcaacct cccaagtagc tggaattaca ggcacccacc  16920
accatgcccg gctaattttt gtatttttag tagagatgga gtttcgccat gttggccagg  16980
ctggtctcga actcctgacc aggtgatcca cccactttgg cctcccgatg tgctgggatt  17040
acaggcatga gccaccatgc ctggcttctt tttccttttc ataaagtatg ggacatttaa  17100
aatttgccaa gttttgcttg aggaagttag atgttgtgca gtggttttgc agcatgtatt  17160
ttggctcttg ggcaatgacg tttcatttgc agaagtttag atgttgattg aaaatcaaca  17220
gctgacgtta aacaaactgg tttgagtaag atacaagcaa ggagctcctt tcacagaaag  17280
ggacagttct gattcaagct tggagctctc agctgtacct cagtttgtta aaaataaaaa  17340
caaaaaacga aagcaccaag tgccaaggaa attaaagagc acttaatgct ctactgtaaa  17400
attgcctgca ccacatttta acccatctcc accgtggttt ctcacataca ttttatttta  17460
tcaaacaacc caagcatagt ttcatttggc ctttatattt ctttgataac tatctttcat  17520
cccattttat tttattttta cttatttatt tatttatttt ttgagataga gtctcgctct  17580
gttgcccagg ccggagtgca gtggtgcgat ctcggctcac ttcaagctcc gcctcccggg  17640
```

```
ttcacgccat tctcctgcct cagcctcctg agtagctggg actacaggcg cccgccacca  17700
cgcctggcta attttttgta tttttagtag agacggggtt tcaccatgtt agccaggatg  17760
gtctcgaact cctgacctca tgatccgccc acctcggcct cccaaagtgc tggaattaca  17820
ggcgtgagcc accgcgcccg gcctcatccc attctaaaat ttcatgttag ttcttgagtc  17880
ccttgtggtt ctggagatag taaacaaagc tcttattttc tcctatttgg ctttcattag  17940
gctttttcc tgaaatgctc ttttacaact tcctggttac agccccctgt attacaaagt  18000
cacatgctca gcagcagcct tct                                          18023
```

<210> SEQ ID NO 19
<211> LENGTH: 14616
<212> TYPE: DNA
<213> ORGANISM: Homo sapiens

<400> SEQUENCE: 19

```
cgccttatac acctaggaag caaagacatt actaacaaca ttgggtaatc aaatatttaa     60
ctcaagtttc tattgatttc aacacacaaa aaaagctggt acatttcctg gaactagggg    120
ctgggagaat gaaggggaat tcccatatgt ttccttttga ttctattcag aaagtcaggt    180
gaaccaagaa aagagttaga atttcaactt gaaatatgaa aattattttc ttctcatccc    240
agatcaatcc atctgtttta catagtttcc ctcttctcct cagaaatttt tttggaaaag    300
aacttatgtc tgatgtctga tgaaaacaat ttatgtcaga cataaactca gaatttaggg    360
ctgaatttat gttcatatgt ccttatttcc tgaaatggta tcagggcata aggacatatg    420
gaaacactgt ggggtatctg ggagcagaaa tatttggata atggaaaagt ttattgaaac    480
caagggactt tgaattatag aaacaaacca aacccaaaat agacacaaat ctccataact    540
tacaattttc cttagatctt agaaagaatc tcaagaggga gaagcagtgt taattgttct    600
agaatcagag atttaaacct taaaaaatat tctacatttt aaattaactg atattcaaac    660
aaggagattc aatccaaaat tgggcgaggg aagtgaattt aactaatcaa aaaacattta    720
cagagcttag cacagtataa aattctatag aagcagcaga gaattataat gtgaccctgc    780
ccttaaggga cttataagga tgatatgttt aaaaaataaa agaattaaag gagaacttaa    840
cactttttga attattgatt agtcttcata tggaagcggg tttaaactgt agaagacagg    900
taaagtaaat tgcatctcaa taacaagaat gttcttaaaa ttggcaatgt tcaaaggtgg    960
aatagactgg cccatcaggt agtagattcc gtcattcaac attcattcat atattgagct   1020
ttcaccatct gtcacacatg tgctggggtg atgaggttca acagtgagca ggacacttcc   1080
cttaccctcc aggggccaca tcccaggata catcatctct gtctagatgt ttattggaca   1140
tggatgttct gaaagaaaac agcaagtttc tttttaatct ctttaagaag acaaaacata   1200
catatataat attaagtatt ggtataatat ttaaattaaa ggtcaagaca acagcaagga   1260
gtgagagaca ttcagcagca cagaaaaaaa tgctatagga gttcagaaat atcacttagg   1320
actggagtgg atttgggagg actctagggg gagctggaac ttagacggat ggagaacaag   1380
ggcttttcaa atagaaatgg ccatacaaat atgtaagtag agtgctcaac aaattgttgc   1440
tatgatgact accttccaat attggcccta ttaatagaaa tgttggctta ccaggaaaat   1500
tttttttat tagaaaagac ttcaactgcc agtgtgtttt ggactggggt gaattcatct   1560
ggttggctca atcttttagt gttgacttga ctctgaacaa tgtcaacaac tgcactgtac   1620
acttgaatca atccaattac gtcctggctg tcagttttct tgcacaacat cctttctcaa   1680
```

-continued

```
tgctgtgttg tgtaatatat gtgcaagaaa atataaacag ctgattgcca ggagggattt   1740
aatgtaaagt ttttccagtg aaacaaaacg taagaatctg agtttgtttt tcaaagatca   1800
ctaaatttta gttatgatta tatcacattt tccaaaatgt gtggcagttt ttgccctcct   1860
tgctctgagt gttggtgcac tggacacttt tattgctgca gtatatgagc atgcggtgat   1920
attaccaaac agaacagaaa cacctgtttc aaaagaagaa gctttgctcc tgatgaacaa   1980
gaacatagat gttttggaga aagcagttaa gctggcagcg aagcaggtat taccatttta   2040
tacttgtaaa ggagacttgc agtttggtca aagagtattt ggaattcatg acaaactttt   2100
ttgccccact tgtttcgagc agggtgcaca tatcattgtg accccagaag atggaatcta   2160
tggttggatc ttcaccaggg agagcattta cccctatcta gaggatatac cagaccctgg   2220
agtgaactgg attccatgta gagacccctg gaggtaatat catatcatta atttctaaac   2280
aaaaagttgt gatttggtaa aacaccaaca gtaaactcac tgaatttgac tggtaattgt   2340
gttgataaat agtcaatctg tggcatagga tgtagatgct ttttttccc tgtaatttca   2400
acttttagtt tagattgagg gagtacatgt gcaggtttgt tacatgggca aattgcatga   2460
cgctgaggat tgggttacaa tgattgcacc acccagcata gtatacaaca ggaaggtttt   2520
cagcccttgc cttcctctct ctctctcccc tctattagtt cccagtgtct attgctgtca   2580
tctttatggc catgagttcc caatgcttag ctcccactta taagtgagaa catgcagtat   2640
ttggttttct gttcctgtgt taacttgctg aggataatgt cctttggtgc tgcaaaagac   2700
atgattttgt tccttcttgt gggcacctag gttaattcca tatctttgct gttgtgaaaa   2760
gtgctgcgat gaacatacaa gtgcacgagt ctttttggta gaatgatttc ctttcctttg   2820
ggtatatacc tagtaatggg attgtgagtc gaatggttgc tgtgttttaa gttctctgag   2880
aaatctccaa actgctttcc acaatggctg aactaattta catttccacc aatagtgtgt   2940
aagtgttccc ctttctccat agcatctttt attatttgac tttttgttaa cagtcattct   3000
gactggtgtg agatgatatc tcattgtggt tttgcttggc atttctctga tgataagtga   3060
tgttgagtgt ttgttcacgt gttttttggc cacttgtatg tcctcttttg agaagtgtct   3120
gttcatgtct tttgcccact tttcaatggg gttatttgtt ttgtttttgc ttattgattt   3180
aagttcctta tggattctag atagtagacc tttgttagat gcctagtttg caaatatttt   3240
ctcccattct gtaggttgtc tatttactct gttgatagtt gcttttgctg tacagagctc   3300
tttagttaaa ttaggtccta catgtcaagt tttgtttttg ttgcaattgc ttttgaggac   3360
ttagtcataa attattttcc aaggttcatg tccagaatgg tgcttcttag attttcttct   3420
aggattctta tagtttgagg tcatacattt aaatctttaa tccatcttga gttaattttt   3480
gtacatggtg aaagataggg gtccagtttc aatcttctgc atatggctag ccagatattc   3540
cagcaccttt tgttgaataa ggagtccttt ccccatactt atttttgtga actttgtttg   3600
agctacagat ggctgtaggt gtgcggcttt gtttctaggc tctctattct gttctattgg   3660
tctatgtgtc tgtttttcta acagtaccat gttgttttga ttactgtagc cttgggtaat   3720
gtgatgcctc aggctttgtt ctttttgttt aggattggtt tggcgattca ggctcttttt   3780
tggttccata tgaattttag aaattttgtt tataaatctg tgaaaaaatg acattggtag   3840
tttgttagaa atagtgttga ggctgggtgc tgtgggtcat gcctataatc ccagcacttt   3900
gggaggccaa ggcaggtgga ttacttgaga ttaggagttt gagaccagcc tggccaacgt   3960
ggtaaaaccc catctctact aaaatacaaa aattagctgg gtgtggtggt gtgtgcctgt   4020
aatcccagct actcgggagg ctaaggcatg agaattgctt gaacgataga gtgagactct   4080
```

```
gtctcaaaaa aaaaaaaaaa aaaaaaagaa gaaaagaaat agtgttgaat ctgcagatac   4140

tgcttatgtt tcatagtgta tatcatctgg catatctcct gtttggtaaa tgacttgaga   4200

tactgatgac tagttggtta tttgttgcaa ttgtctttca acaatagtag gtgtgaccag   4260

gcgtggtggc tcacacttgt aatcccatca ctgtgggaag ccaaagcagg aggactgctt   4320

gaagccagaa gtttgagacc agcctgcgca gcaaagccag accctatttc ggcaaataaa   4380

aaatttagcc aggtgtggtg gctcacacct ataatcccag ctactcgaga ggctgaagca   4440

ggaggatcac tggggcccag gagtttgagg ctgcagtgag ctatgattgc accactgcac   4500

tccagcctgg gtgacagtaa gaccttgtct taaaaaaata gtaggtatag gccgggtgtg   4560

gtggctcacg cctgtaatcc cggaacttta ggaggtggag gtgggcaaat cacctgaggt   4620

caggagttcg agaccagcct ggccaacatg gtgaaacccc atctctacta aaaaatacaa   4680

acattagctg ggtgtggttg tgcatgccta taatcccagc tactcgggag actgaggcag   4740

gagaactact tgaacccagg aggcagaggt tgcagtgagc cgagatcacg ccactgcact   4800

ccagactggg caacagagtg agactccatc tcgaaaaaaa aatagtaggt atatacacaa   4860

tttttatagt aaatgtgttt aattgggttt gaacaaagtg aaaaagttgg aatatctaga   4920

acctgtgtcc caaatacaag taagttggtt catccatgga cacctgcctc cttcacagga   4980

agagtaaaaa gatgaatgag cctgtttcca aagagctttg ctatcactat cattcagaat   5040

gcaatcaata tggccaatgg aaattgtata ggacttgaaa aaggaagccc tacttctggg   5100

accacatttt acgaccacct agctgagtga tgtaagcgta taacctaaat gcttaacatt   5160

tctgtttcat tatctgtaaa acagggataa tagagtccct taattctctt acagatcaga   5220

caagagtaat gaagtaatac acatggaatt tgtacattgt aatgcactct ccaatgctag   5280

ctgtcactat tcctttttttt tttttgttaa cagaagggac tgagtctgaa cttctttgtg   5340

ttcttgtcct ttgagagact ttagtaatta ttagtagatg taatttaggc ataactttct   5400

taaagaaaat atgcataata aatatgatat ctgtgaaata gattatttta gttgtattaa   5460

cttttaaaaa tagtttaaga ttatttcttt aaatggcaaa attgatgggt taagaagtca   5520

tttaacttgc taattttaaa tttacatgca cctgtttaga actacaccta ttgtgcaaaa   5580

agagaaactt ctttgataat tttacctatg tgaaattaag tggaaagtca tgcttaatgg   5640

tacaacattc aggctcagct atgtgagtca aacctcactc tgggattttg ccctttggaa   5700

aaatattctc taaacattgc atggtctgtg tttacagaaa ccatgtcact atgattcaac   5760

atctacttgc ttatgaggcg tttcccagaa caggaaggaa tcattatttg ctgcagttga   5820

tgaggcttac acgaaaatgt actgtatttg actgggctaa tgaaactgac ttttccaggg   5880

aaaagatatc cataaatttg ataattagct atcgataaat tattttaagt tgggaaagta   5940

ggtgactgat gaaatgtcaa cattatgaac tcttacacct acttattcaa atgacaacct   6000

ttcagttttg tgttacaaaa aggagaaatc cagtatttaa tataatgata atattggaaa   6060

agaaagtcag ttttctccct ggtgatattt atccctgaag agaatagtag agaggcatgc   6120

ggtcatcctt gtgcatttaa atatttagaa tgctgacatg tcaaacagtt ccatgggctt   6180

ttttcatgag taactagtag gaaatattaa ataactcaaa ttatttagtc aagaaaagaa   6240

aaattaaaca aagtacatga taaagttatt aaaggtctta atgaatatga atattaatag   6300

tacttctctg tttttttag aagaaaataa aaagaaaagg tctaaaccag taggccatta   6360

atctgtcctt tttattcaaa ggttagttta acctcaattg cagaggggct gtgagttcat   6420
```

```
agagagacat ggaatggcct ctaatcacac aatccataat agcaattttc atttactgag   6480
cacttacttg gtcccaagaa ctgtacctgg tatactatac ccattattac attcaattta   6540
tgtagttggc attactattt gcattacaaa tatgtgaaaa aaggaaggct tatgatctca   6600
tgattgatca ttagattggc tggaattaaa acagctatgt catttaactg tgctaacgga   6660
atggactcta agggcctaga tgaaccatat tataataaaa tttttagtga ctagcaaatc   6720
cacttattta acagagtgag ctggttgcta aacatttttt gtcttatttt ctgctgaaat   6780
ctgcctcact ttaacttcct ttcgtctttt tcctgcattc tatgctatgt tcacacatat   6840
gacccatctc ctataaatta agcctttcaa atatttgaag ccagctatca ccatgctaca   6900
ttctcttctt ataccaagga taaatatctt taatatggat ggacttggta aaacaatttc   6960
atgtctgtac ttatctcagg atttctcatg tggatccact aaggcagaaa ggaagctatt   7020
gttttacatt tgacagatga agaaactgag tcagtacagt gaagtgcttt ttattttta   7080
ttttaatttt taacatttcc actacttaca gctatatttg ttttttata gagacaatct   7140
ggagggtaca aactatttac tgtcacctgg catttctgtt tccaaccaca tctcgtatca   7200
gcaaccttgt acaaattatg gcttggatta tagaaaaggt cctctccatt agcagaatct   7260
gctaaatttc aagtgcttca tatatcttcc tgggagcact tcataagaga atgtgctgct   7320
tcttttcatc ctcctcttcc tcttccatct tttctttcct tcagtcttgt actgtaatct   7380
ggagtttggc atagtaaatt aggttagctt tcaggaagat aaacactgta tcacatgaga   7440
gttttaaaat attttctgtt gattcttgac ctagagctgt tgtgttatgg gcaatgggca   7500
aataaagtat cactttggta tttcagaaat cactaaaata tagtaagttt gaggaaatgt   7560
ctattgaatt agattcggca acacaccagt gcaacaaaga ctcagctgcc tggccaagga   7620
caactctatc tatgtcgtgg ctaatattgg ggacaagaag ccatgcaatg ccagtgactc   7680
tcagtgtccc cctgatggcc gttaccaata caacactgat gtggtgtttg attctcaggg   7740
aaaactgttg gcacgctacc ataaggtgag catcacttgt gccttagctc aacttgttac   7800
ttcttctgtg tgcttgtggt atgtatgtgt gtttgtttgt tgaatgttgg ggagagaact   7860
gttatagatg catcttataa ttattacatc atagttgaaa aggagattta attcagttcc   7920
atataaccgt tctgggtttg catttatcat aaaacagaat atggtagagt atttaaatgg   7980
atgtgacaat agccacacaa agcttttaat gttctctgaa aaagaagtaa acattctgtt   8040
tcattcatga tttaatatca ggttcatttt ttagcccaat ttgttagcat ttcatactaa   8100
gctaccatgt attccattag gacttttttg attgcaatga aaacaaaacc tcaaatgaaa   8160
atggctttaa aaagatggaa atttccttgc ttatgcacat gtaaaaatgt gtatcataga   8220
aaggacaggt ctcatttcag tgcagtctga cactcagagg ctccaaagtt atcatccacc   8280
cctctagctc tcctagccct ttgttacagc ttctttctca ggggaactct ccttttagaa   8340
gccacattgc tggagcaaca cgaaattcac atctttatca acaaaatcta caggaagggt   8400
gtatttctcc ctcctagaac cttgcaaagg ccttatcgct ccttgattca attaggtgac   8460
gtgcctttcc tgagctaatc accaaaggat gagggatagg ctgccacatg ggaggagaaa   8520
ggaggagcaa gaggcctcca tggaccacag aggtgggaag tagctctccc cagagcacac   8580
acatgcacac aacaggccaa acaaaaacct gagcaaaaca tatgctgtac tcctgagccc   8640
aggttaagtg gagttttgga aaaagaatca ggctgaaaaa taaaataaaa ttatgaatgg   8700
cttactaatt aataatatgt agcaactgca ttgtctaaat taattttcaa tggacttcac   8760
ttctataaac ctggcagtat cattgggaca catgacaaag tttattttat taacatagta   8820
```

```
gtgctgttga aatttaaaga atatagtgga aaacaatctg agaagtgtag gattcaagat   8880
ttcaacctgt gattttaaga tacacatttt cacattttaa atatcatttg tacatgtggt   8940
ttcattcatt ggttgtaaaa aaaataaagt ttttttatta atgtcacagt aagaaaatgt   9000
atagatggtg gtatagtggg gatgattttt acaaatgtat gtgtaacagt tttattttgt   9060
tgttgttgtt gattttggaa atggaatctt gctctgttgc ccaggctgga gtgcagtggc   9120
gcgatctcgg ctcactgcaa cctcggcctc ctgggttcag ggctccccc tgcctcagcc    9180
tatgagtagc tgggattaca ggcatatgcc atcatgcctg gctaattttt tttgatattt   9240
gtagtagaga cagggtttta ccacattggc caggctggtc tcgaactcct gacctcaagt   9300
gatccacccg cctcagcctc ctaacatgct gggattacag gcgtaagcca ccacacctgg   9360
cctatgtgta acacttttaa acctgcatgt caacatacat gagaggaaag atttaacggg   9420
gaaagactta attgatcaca tctatttggc agttttctta ttaattttct tcttctttgc   9480
tttttattaa cagtacaatc tttttgcacc tgaaattcag tttgatttcc ccaaggattc   9540
agaacttgtg acttttgaca ctccctttgg gaagtttggc atttttactt gctttgacat   9600
tttttctcat gacccagctg tggtggtggt ggatgagttt caattgacag cattctctac   9660
cccacagcat ggtacaacac gctgcccctc ctctcggctg ttcccttcca ttcagcatgg   9720
gccaaggcca tgggagtcaa tctacttgct gcaaataccc acaacaccag catgcacatg   9780
acaggtaact cacgcgggcc tgcaccaagt gggagtgaca gtcttaggaa ggcttcattg   9840
attttcaagc cacaaacttt tgtttaataa ctttattacc aattttaaca tcacaaaatt   9900
aataatagca tttgttccta cttaaggaac gttcattgtc cttgtgaata aaagaggcaa   9960
acattattat ctcaatttta cttgaaagga aattggagct ggaggaagtc atgtaaaaaa  10020
atcaaagaga gttctaagaa acttcctagc caatgtgcat tagtaatatc gaaataagtc  10080
tggttgttta aagagataac ctacagagca gaagaaaata tttgcaaact atgcatttca  10140
taaaaatcta atatctagaa tccataagga acttaaacaa atcaacaaac aaaaaacaaa  10200
ctatcccatt aaaaaatgga caaaggacat gaacagacac ttctcaaaag aagacataca  10260
tgtggccaac aagcatgtaa aaatgcttaa catcactaat cattacagaa atgcaaatca  10320
aaaccacaat gagataccac ctcgctccag tcagaatggc tatgattaaa aaataaaaaa  10380
caaacagatg ctggcgaggt tgtgaagaaa aaggaaacac ttatacactg ctggtgaaaa  10440
tgtaaattag ttcagccaca gtggaaagca gtttggcgat ttctcagaga acttaaaaca  10500
gaactgccat tcgactcagc aatcccatta ataggtatat accagaagga atataaatca  10560
ttctaccata aagacacatg cacttgtatg ttaattgcag cagttttagc aatagcaata  10620
acgtggaatc aacccaggtg ctcatcaacg gtgaagtgga taaagaaaat gtgatacata  10680
tacaccatag aatactacat agccataaca aagaatgaaa taatgtcctt tgcaacaaga  10740
tggatgcaac tggaggtcat tatcctcagc gaatgaacac aggaacagaa aatcaaatac  10800
ctcgtgttct cacgagttga agttaaacat tgagtacaca tgaacacaaa gaggggaaca  10860
atagacacca gggtttactt gaggggggat ggtgggagga gggtgaggat tgaaaaacta  10920
cctattggat actgtgctca ctacctgggt gacaaaatcg tttgcacacc aaaccccagc  10980
aacatgcaat ttacccatgt aacaaacctt cacacgttcc ccttctatac ctaaaataac  11040
agttggaaga aaaaaataca aacaaataaa aatatttcaa gcattaaaaa aaaacttgtt  11100
gaagtgataa aaatctcttt tgacttaatc aggtttttag agtttctcct ttatcatatc  11160
```

-continued

```
catgttcaaa gtaatgcagg cttccttttt aactgttctg ttatttgttg aataacaaat  11220
cccaaacaca aataaactaa atcgtcagtg gagagctaaa attattcttc acgttggggg  11280
attttctagt ttgttgctaa gttagcttaa aactatgccc cccaagtcaa atgataattt  11340
cagtgcaagt agtaccttat ggaggacaca gagtcaaatt ggaacttagg ccaatgtaac  11400
agctatctcc ttaactatct tgaaaatatg ctttaataac tttgtattta acttcacatg  11460
ggaatattct attagttggt caccataaca aatctgaaac caatgtttgt atttatgttg  11520
cttgtaggga gtggaatcta cgccccagaa gcagtcaagg tgtaccacta tgacatggaa  11580
acagagagtg gtcagctgtt gctatcagaa ctgaagtctc ggccccgccg tgagcccacc  11640
taccctgcag ctgttgactg gcatgcgtat gccagcagtg tcaagccatt ttcctctgaa  11700
cagtcagatt ttctggggat gatttatttt gatgagttta ccttcaccaa gcttaagaga  11760
aatacaggaa attacacagc ttgccagaaa gatctgtgtt gtcacttaac ttacaagatg  11820
tctgagaagc gaacagacga gatctatgcc ctaggtgctt ttgatggact gcacacagta  11880
gaaggccaat attacttaca ggtagaaatg ctttaatatg ttaaagtggc cttattatca  11940
gtttttcttc taggtcatca ttgcctttct ttgaaaattg ggctggattt agctaatttt  12000
ataattagta atgttatatt tatctctgaa ttttgtcccc agaacacatt atttgttcag  12060
tcttagcaag aacagaatta gttcttttag ttgaaaggca aaaacataaa gcaaattgat  12120
tagttctcag caggccaggt tcaggtttca aaagctgcaa tttctgtgta ttctcttttc  12180
ccgtcaggtt actttagagc agtgtttttc aaattgtctt caactaaatc cagagaaaga  12240
aggatatttt acctcataac ccagtgtagc caagtggatg tgtgactgaa taaaaaaaaa  12300
gatatttaat tgaaatagtt tatgaaataa tttaaaatag aattagaaat agctattatt  12360
atgtgcaatg cactctgatt tttaaaatcc tagtctattc tatttgactt cagtataaaa  12420
agtgttaatc ctgacccact atattgattt taggattcat taataagttg ttacctgcag  12480
tttgaaaaat acttcttatg aggcaattta aatatgcatt tatagtttga aattgcatta  12540
tttagctgag aaaatatttg caagttttct gactccttct cttttctttt cttccataga  12600
tatgtgcatt actgaagtgt caaaccactg acctggaaac gtgtggagaa cctgtggggt  12660
cagcttttac caagtttgaa gacttctccc tcagtggcac atttggaacg cgttatgttt  12720
tcccacagat cattctaagt gggagtcagc ttgcccctga aagacattat gaggtaggag  12780
gtgtgcagga tgataaattc ctttgagcag agtagatggg tagagcagca taatgaaaat  12840
ctttgaaata atgagagtat agcaatatcg tggttcacat tctacaagaa acaccttaaa  12900
tatgtggaaa ctatgatatg gaatataaat tgtggtttta gattgccatt aggctgtgat  12960
ggagaatttg gggttcattt ttttaacata aatgtgatgt tgatattcaa ggcaacagga  13020
aattcacaga gaagctaaaa taaaaatgtt gactgctgat aatggcaata atgttgtcat  13080
ttgcatggtg tagaaggtgc aaattaaata cattaaataa tgcatctaca acttattttc  13140
tgggtatact attttgagaa gttgttataa ttatagtaat aactaatatt ttgtatagtg  13200
tttcatgagt ttgaagaaca tatttttata catattattt gaccacctgt gcaacaaatt  13260
tgttggctgc actttcgcac aaagtccctc tactttcaga cttgaaacat gaacctgggt  13320
cttccaacac caaatcctgt gtgattttta ccattctaca ctgctttagg agggagtgat  13380
cttgcctgag aagggctcta ggttgtaacc taaactctgc actgaagtta accctttgct  13440
ttctttgacc agatttcaag agatggacgc ttgaggagcc gaagtggagc ccctttgcct  13500
gtcttagtta tggccctgta tggaagagtg tttgagaagg accctccacg cttagggcag  13560
```

-continued

```
ggatctggga aattccagtg atctccttta gcagagccct tttaggatta gcctggctaa  13620

gaaaggaaga aaaaaaagag atccgttagt gtctgtttag aaaagatgtt ataaacttac  13680

agaaacaaat ataataaact gaagcagatt tgaaaagcaa caagtgtgtg tgcaaatttc  13740

acattttaca tgtttggtat agcacaggtt catttatggg agccgcattc atcctccatg  13800

tatgtgagtt taagtatatg taagtatgta tatgtatagt ggagcgtata tttaaatagg  13860

aggaggtcct agaaaaatcc ttttgcagta actgcactaa tgtatgcaag tgttgtttcc  13920

atcatatgat ggttaatttt atgtgttgat ttgactgggt catgagatgc ccagatagct  13980

ggttaaccat tgtttctggg tgtgtctgtg agggtgtttc aaggaagaga acagcatttg  14040

aattggtgga ctgagtaaag cagacggtcc tccccagtgt ggatggtcat cgtccagtcc  14100

cttgagggcc tgcagagaaa aacaagaagg aggaggtttg aattcatttt ctgccagact  14160

acttgagctg gatagagatc ttctcctgcc ttcatgtgct cctggttctc aggccttcag  14220

gcctggactg gaattgacac catcaactct tcagctctca ggccttcgaa tgacacccct  14280

ggctttcctg catctccagc ttgcaaatgg cagaccagac tgtgggattt ctcagccttc  14340

ataactgtct gagccaatac cttatcataa atctctttct ctctctctct cctgttggtt  14400

ctctttctct ggagaaccct gactaatgca cttcatttgt aaatacatag gatgaacttt  14460

gaatatgcag agggtatttg attccagcca attaagatac aggaaattaa agaataagga  14520

catcttttaa agtaactatg aacaactttt tagctagtat tgtcccttta gtcatgacta  14580

atttgactcc taagttctat ttatatggaa attgga                            14616
```